(12) United States Patent
Loyall et al.

(10) Patent No.: US 10,072,269 B2
(45) Date of Patent: Sep. 11, 2018

(54) SYNTHETIC PROMOTER AND METHODS OF USE THEREOF

(71) Applicant: BASF PLANT SCIENCE COMPANY GMBH, Ludwigshafen (DE)

(72) Inventors: Linda Patricia Loyall, Limburgerhof (DE); Josef Martin Kuhn, Ludwigshafen (DE); Malte Siebert, Heidelberg (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 0 days.

(21) Appl. No.: 15/805,676

(22) Filed: Nov. 7, 2017

(65) Prior Publication Data

US 2018/0119161 A1 May 3, 2018

Related U.S. Application Data

(63) Continuation of application No. 13/991,566, filed as application No. PCT/IB2011/055412 on Dec. 1, 2011, now Pat. No. 9,834,778.

(60) Provisional application No. 61/419,895, filed on Dec. 6, 2010.

(30) Foreign Application Priority Data

Dec. 6, 2010 (EP) .................................... 10193800

(51) Int. Cl.
  *C12N 15/82* (2006.01)
  *C12N 15/113* (2010.01)
  *C12N 15/63* (2006.01)

(52) U.S. Cl.
  CPC ........ *C12N 15/8234* (2013.01); *C12N 15/113* (2013.01); *C12N 15/63* (2013.01); *C12N 15/82* (2013.01); *C12N 15/8201* (2013.01); *C12N 15/8216* (2013.01); *C12N 15/8241* (2013.01)

(58) Field of Classification Search
  None
  See application file for complete search history.

(56) References Cited

U.S. PATENT DOCUMENTS

| | | | |
|---|---|---|---|
| 6,927,321 B2 | 8/2005 | Wang et al. | |
| 9,428,757 B2 * | 8/2016 | Senger ............... | C12N 15/8216 |
| 9,834,778 B2 | 12/2017 | Loyall et al. | |
| 2010/0199365 A1 | 8/2010 | Senger et al. | |

FOREIGN PATENT DOCUMENTS

| | | |
|---|---|---|
| CA | 2721879 A1 | 10/2009 |
| CN | 1489631 A | 4/2004 |
| WO | WO-02/50295 | 12/2001 |
| WO | WO-2006/131490 A1 | 12/2006 |
| WO | WO-2009/016202 A2 | 2/2009 |
| WO | WO-2009/117417 A2 | 9/2009 |
| WO | WO-2009/133145 A1 | 11/2009 |
| WO | WO-2010/127969 A1 | 11/2010 |

OTHER PUBLICATIONS

Rombauts et al. PlantCARE, a plant cis-activing regulatory element database. Nucleic Acids Research. 1999. 27(1): 295-296.*
Baek et al., "Human Mediator Enhances Basal Transcription by Facilitating Recruitment of Transcription Factor IIB During Preinitiation Complex Assembly," Journal of Biological Chemistry, vol. 281, (2006), pp. 1517215181.
Buckwold et al. Effects of a naturally occurring mutation in the Hepatitis B Virus Basal Core Promoter on Precore gene expression and viral replication. Journal of Virology. 1996. 70(9): 5845-5851.
Cartharius et al., "MatInspector and Beyond: Promoter Analysis Based on Transcription Factor Biding Sites," Bioinformatics, vol. 21, No. 13, (2005), pp. 2933-2942.
Cartharius, "MatInspector: Analysing Promoters for Transcription Factor Binding Sites," Analytical Tools for DNA, Genes and Genomes, (2005), pp. 161-184.
Dare et al., "Identification of a Cis-Regulatory Element by Transient Analysis of Co-ordinately Regulated Genes," Plant Methods, vol. 4, No. 17, (2008).
DePater et al., "The Promoter of the Rice Gene GOS2 is Active in Various Different Monocot Tissues and Binds Rice Nuclear Factor ASF-1," Plant Journal, vol. 2, No. 6, (1992), pp. 837-844.
Donald et al. Mutation of either G box or I box sequences profoundly affects expression from the Arabidopsis rbcS-1A promoter. The EMBO Journal. 1990. 9(6): 1717-1726.
Extended European Search Report, issued in co-assigned application No. 11846949.3, dated Apr. 23, 2014.
Goossens et al. The arcelin-5 Gene of Phaseolus vulgarisDirects High Seed-Specific Expression in TransgenicPhaseolus acutifolius and Arabidopsis Plants. Molecular Genetis and Genomics. 1999. 120(4): 1095-1103.
Hamilton et al., "A Monocot Pollen-Specific Promoter Contains Separable Pollen-Specific and Quantitative Elements," Plant Molecular Biology, vol. 38, No. 4, (1998), pp. 663-669.
Hehl and Bulow, "Internet Resources for Gene Expression Analysis in *Arabidopsis thaliana*," Current Genomics, vol. 9, No. 6, (2008), pp. 375-380.
Hehl and Wingender, "Database-Assisted Promoter Analysis," Trends in Plant Science, vol. 6, No. 6, (2001), pp. 251-255.
International Preliminary Report on Patentability, issued in PCT/I132011/055412, dated Jun. 20, 2013.
International Search Report, issued in PCT/162011/055412, dated Apr. 12, 2012.
Ito et al. A novel cis-acting element in promoters of plant b-type cyclin genes activates M phase-specific transcription. The Plant Cell. 1998. 10: 331-341.

(Continued)

*Primary Examiner* — Ashley Kate Buran
(74) *Attorney, Agent, or Firm* — Marshall, Gerstein & Borun LLP

(57) ABSTRACT

The present invention relates to methods for the design and production of synthetic promoters with a defined specificity and promoters produced with these methods.

9 Claims, 3 Drawing Sheets

Specification includes a Sequence Listing.

(56) References Cited

OTHER PUBLICATIONS

Jensen et al., "The Sequence of Spacers Between the Consensus Sequences Modulates the Strength of Prokaryotic Promoters," Applied and Environmental Microbiology, vol. 64, No. 1, (1998), pp. 82-87.
Kaplan et al., "Rapid Transcriptome Changes Induced by Cytosolic Cal* Transients Reveal Abre-Related Sequences as CA2+-Responsive cis Elements in *Arabidopsis*," Plant Cell, vol. 18, No. 10, (2006), pp. 2733-2748.
Kim et al. A 20 nucleotide upstream element is essential for the nopaline synthase (nos) promoter activity. Plant Molecular Biology. 1994. 24: 105-117.
Konishi and Yanagisawa, "Identification of a Nitrate-Responsive cis-Element in the *Arabidopsis* NIR1 Promoter Defines the Presence of Multiple cis-Regulatory Elements for Nitrogen Response," The Plant Journal, vol. 62, (2010), pp. 269-282.
Kramvis et al., The core promoter of hepatitis B virus. Journal of Viral Hepatitis. 1999. 6: 415-427.
Kutach et al. The downstream promoter element DPE appears to be as widely used as the TATA box in *Drosphila* core promoters. Molecular and Cellular Biology. 2000. 4754-4764.
Matys et al., "TRANSFACGD: Transcriptional Regulation, from Patterns to Profiles," Nucleic Acids Research, vol. 31, No. 1, (2003), pp. 374-378.
Montgomery et al., "Positive and Negative Regulatory Regions Control the Spatial-Distribution of Polygalacturonase Transcription in Tomato Fruit Pericarp," Plant Cell, vol. 5, No. 9, (1993), pp. 1049-1062.
Quandt et al., "MatInd and MatInspector New Fast and Versatile Tools for Detection of Consensus Matches in Nucleotide Sequence Data," Nucleic Acids Research, vol. 23, (1995), pp. 4878-4884.
Que and Jorgensen, "Homology-Based Control of Gene Expression Patterns in Transgenic Petunia Flowers," Developmental Genetics, vol. 22, No. 1, (1998), pp. 100-109.
Roeder, "The Role of General Initiation Factors in Transcription by RNA Polymerase II," Trends in Biochemical Science, vol. 21, No. 9, (1996), pp. 327-335.
Rombauts et al. PlantCARE, a plant cis-acting regulatory element database. Nucleic Acids Research. 1999. 27(1): 295-296.
Ross et al. Activation of the *Oryza sativa* non-symbiotic haemoglobin-2 promoter by the cytokinin-regulated transcription factor, ARR1. Journal of Experimental Biology. 2004. 55(403): 1721-1731.
Rossi et al., "Biological Expression of an *Escherichia coli* Consensus Sequence Promoter and Some Mutant Derivatives," Proc. Natl. Acad. Sci. USA, vol. 80, (1983), pp. 3203-3207.
Roychoudhury et al., "Trans-acting Factor Designated OSBZB Interacts with Both Typical Abscisic Acid Responsive Elements as well as Abscisic Acid Responsive Element-Like Sequences in the Vegetative Tissues of Indica Rice Cultivars," Plant Cell Rep., vol. 27, (2008), pp. 779-794.
Wu et al., "Quantitative Nature of the Prolamin-box, ACGT and AACA Motifs in a Rice Glutelin Gene Promoter: Minimal cis-Element Requirements for Endosperm-Specific Gene Expression," The Plant Journal, vol. 23, No. 3, (2000), pp. 415-421.

* cited by examiner

SYNTHETIC PROMOTER AND METHODS OF USE THEREOF

This Application is a continuation of U.S. application Ser. No. 13/991,566, which is a U.S. National Stage Application of PCT/IB2011/055412, filed Dec. 1, 2011, which claims the benefit of U.S. Provisional Application No. 61/419,895, filed Dec. 6, 2010, and which also claims priority under 35 U.S.C. § 119 to European Patent Application No. 10193800.9, filed Dec. 6, 2010; the entire contents of these applications are hereby incorporated by reference herein in their entirety.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "70392A_Seqlisting.txt", which was created on Nov. 7, 2017 and is 99,055 bytes in size. The subject matter of the Sequence Listing is incorporated herein in its entirety by reference.

FIELD OF THE INVENTION

The present invention relates to methods for the design and production of synthetic promoters with a defined specificity and promoters produced with these methods.

BACKGROUND OF THE INVENTION

Manipulation of plants to alter and/or improve phenotypic characteristics such as productivity or quality requires expression of heterologous genes in plant tissues. Such genetic manipulation relies on the availability of a means to drive and to control gene expression as required. For example, genetic manipulation relies on the availability and use of suitable promoters which are effective in plants and which regulate gene expression so as to give the desired effect(s) in the transgenic plant.

Advanced traits often require the coordinated expression of more than one gene in a transgenic plant. For example, to achieve the production of polyunsaturated fatty acids such as archachidonic acid in a plant requires expression of at least 5 genes. There is also increasing demand of trait stacking which requires the combination of more than one gene in transgenic plants.

The availability of suitable promoters for such coordinated expression is limited. Promoters would often need to have the same tissue and/or developmental specificity and preferably comparable expression strength. One solution has been to use the same promoter for the expression of several genes. Expression constructs comprising more than one expression cassette with tandem or inverted sequence repeats of for example a promoter cause various problems. When located on one vector, handling of the vector in bacteria for cloning, amplification and transformation is difficult due to recombination events which lead to the loss and/or rearrangement of part of the expression construct. Moreover, sequence verification of constructs comprising repeated sequences is difficult and sometimes impossible. A further problem of such expression constructs comprising repeats of the same promoter sequence is that recombination may also occur after introduction into the genome of the target organism such as a plant.

Additionally it is well known that repeated promoter sequences in the genome of organisms such as a plant may induce silencing of expression derived from these promoters, for example by methylation of the promoter or increase of chromatin density at the site of the promoters which makes the promoter inaccessible for transcription factors.

The use of different promoters in expression constructs comprising more than one expression cassette is one possibility to circumvent these problems. Isolation and analysis of promoters is laborious and time consuming. It is unpredictable what expression pattern and expression strength an isolated promoter will have and hence a high number of promoters need to be tested in order to find at least two promoters with comparable expression pattern and optionally comparable expression strength.

There is, therefore, a great need in the art for the availability of new sequences that may be used for expression of selected transgenes in economically important plants. It is thus an objective of the present invention to provide new methods for the production of synthetic promoters with identical and/or overlapping expression pattern or expression specificity and optionally similar expression strength. This objective is solved by the present invention.

DETAILED DESCRIPTION OF THE INVENTION

Figure 1:
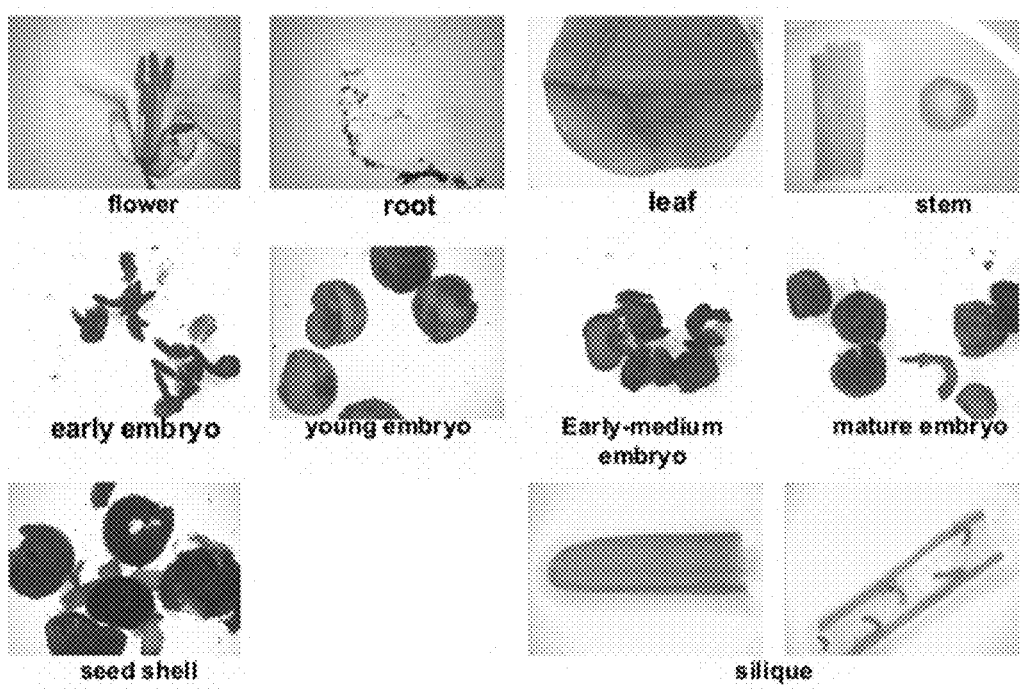
FIG. 1 shows the gene expression activity conferred by p-PvArc5_perm as described in Example 2.

A first embodiment of the invention is a method for the production of one or more synthetic regulatory nucleic acid molecules of a defined specificity comprising the steps of
a) identifying at least one naturally occurring nucleic acid molecule of the defined specificity (starting molecule) and
b) identifying conserved motives in the at least one nucleic acid sequence (starting sequence) of the starting molecule of the defined specificity as defined in a) and
c) mutating the starting sequence while
  i) leaving at least 70%, preferably 80%, 85%, 90%, more preferably at least 95%, even more preferably at least 98% or at least 99% for example 100% of the motives unaltered known to be involved in regulation of the respective defined specificity (also called preferentially associated motives) and
  ii) leaving at least 80%, preferably at least 90%, 95% for example 100% of the motives unaltered involved in transcription initiation (also called essential motives) and
  iii) leaving at least 10%, preferably at least 20%, 30%, 40% or 50%, more preferably at least 60%, 70% or 80%, even more preferably at least 90% or 95% of other identified motives (also called non exclusively associated) unaltered and
  iv) keeping the arrangement of the identified motives substantially unchanged and
  v) avoiding the introduction of new motives known to influence expression with another specificity than said defined specificity and
  vi) avoiding identical stretches of more than 50 basepairs, preferably 45 basepairs, more preferably 40 basepairs, most preferably 35 basepairs, for example 30 basepairs between each of the starting sequence and the one or more mutated sequences and d) producing a nucleic acid molecule comprising the mutated sequence and e) optionally testing the specificity of the mutated sequence in the respective organism.

In one embodiment of the invention, additional preferably associated motives may be introduced into the sequence of the synthetic nucleic acid molecule.

Production of the nucleic acid molecule comprising the mutated sequence could for example be done by chemical synthesis or by oligo ligation whereby smaller oligos comprising parts of the sequence of the invention are stepwise annealed and ligated to form the nucleic acid molecule of the invention.

In a preferred embodiment of the invention, the synthetic regulatory nucleic acid molecule is a synthetic promoter, in a more preferred embodiment the synthetic regulatory nucleic acid molecule is a synthetic promoter functional in a plant, plant tissue or plant cell.

The at least one starting molecule comprising the starting sequence may for example be identified by searches in literature or internet resources such as sequence and/or gene expression data bases. The at least one starting molecule comprising the starting sequence may in another example be identified by isolation and characterization of a natural occurring promoter from the respective organism, for example plants, algae, fungi, animals and the like. Such methods are well known to a person skilled in the art and for example described in Back et al., 1991, Keddie et al., 1992, Keddie et al., 1994.

Motives in a series of nucleic acid molecules may be identified by a variety of bioinformatic tools available in the art. For example see Hehl and Wingender, 2001, Hehl and Bulow, 2002, Cartharius et al., 2005, Kaplan et al., 2006, Dare at al., 2008.

In addition, there are various databases available specialized in promoter analysis and motif prediction in any given sequence. For example as reviewed in Hehl and Wingender, 2001.

It is also possible to identify motives necessary for regulation of expression of the defined specificity with experimental methods known to a skilled person. Such methods are for example deletion or mutation analysis of the respective starting sequence as for example described in Montgomery et al., 1993.

Essential motives known to be involved in transcription initiation for example by being bound by general initiation factors and/or RNA polymerases as described above under ii) are for example the TATA box, the CCAAT box, the GC box or other functional similar motives as for example identified in Roeder (1996, Trends in Biochemical Science, 21(9)) or Baek et al. (2006, Journal of Biological Chemistry, 281). These motives allow a certain degree of degeneration or variation of their sequence without changing or destroying their functionality in initiation of transcription. The skilled person is aware of such sequence variations that leave the respective motives functional. Such variations are for example given in the Transfac database as described by Matys et al, ((2003) NAR 31 (1)) and literature given therein. The Transfac database may for example be accessed via ftp://ftp.ebi.ac.uk/pub/databases/transfac/transfac32.tar.Z. Hence it is to be understood that the term "leaving motives unaltered involved in transcription initiation" means that the respective motives may be mutated, hence altered in their sequence as long as their respective function which is enabling initiation of transcription is not altered, hence as long as the essential motives are functional. In another embodiment of the invention the first 49, preferably 44, more preferably 39, even more preferably 34, most preferably 29 bp directly upstream of the transcription initiation site are kept unaltered.

The term "keeping the arrangement of the motives unchanged" as used above under iv) means, that the order of the motives and/or the distance between the motives are kept substantially unchanged, preferably unchanged. Substantially unchanged means, that the distance between two motives in the starting sequence does not differ from the distance between these motives in the synthetic regulatory nucleic acid sequence, hence the distance between said motives is not longer or shorter, by more than 100%, for example 90%, 80% or 70%, preferably 60%, 50% or 40%, more preferably not more than 30% or 20%, most preferably not more than 10% in the synthetic regulatory nucleic acid sequence as compared to the starting sequence. Preferably the distance between two motives in the starting sequence differs by not more than 10, preferably 9, more preferably 8 or 7 or 6 or 5 or 4, even more preferably not more than 3 or 2, most preferably not more than 1 basepairs from the distance in the permutated sequence.

Inverted and/or direct stretches of repeated sequences may lead to the formation of secondary structures in plasmids or genomic DNA. Repeated sequences may lead to recombination, deletion and/or rearrangement in the plasmid both in E. coli and Agrobacterium. In eukaryotic organisms, for example plants, repeated sequences also tend to be silenced by methylation. Recombination events which lead to deletions or rearrangements of one or more expression cassettes and/or T-DNAs are likely to lead to loss of function for example loss of expression of such constructs in the transgenic plant (Que and Jorgensen, 1998, Hamilton et al., 1998). It is therefore a critical feature of the invention at hand to avoid identical stretches of 50 basepairs, preferably 45 basepairs, more preferably 40 basepairs, most preferably 35 basepairs, for example 30 basepairs between each of the starting sequence and the one or more permutated sequences. In case of the production of more than one permutated sequences said identical stretches must be avoided between the starting sequence and each of the permutated sequences in a pair wise comparison. In another embodiment, such identical stretches must be avoided between all permutated sequences and the starting sequence; hence none of the permutated and starting sequences shares such identical stretches with any of the other sequences.

The skilled person is aware that regulatory nucleic acids may comprise promoters and functionally linked to said promoters 5'UTR the latter may comprise at least one intron. It has been shown, that introns may be lead to increased expression levels derived from the promoter to which the 5'UTR comprising the intron is functionally linked. The 5' UTR and the intron may be altered in their sequence as described, wherein the splice sites and putative branching point are not altered in order to ensure correct splicing of the intron after permutation. No nucleotide exchanges are introduced into sequences at least 2, preferably at least 3, more preferably at least 5, even more preferably at least 10 bases up- and downstream of the splice sites (5' GT; 3' CAG) are kept unchanged. In addition, "CURAY" and "TNA" sequence elements being potential branching points of the intron are kept unchanged within the last 200 base pairs, preferably the last 150 base pairs, more preferably the last 100 base pairs, even more preferably the last 75 base pairs of the respective intron.

The 5'UTR may be permutated according to the rules as defined above, wherein preferably at least 25, more preferably at least 20, even more preferably at least 15, for example at least 10, most preferably at least 5 base pairs up- and downstream of the transcription start are kept unchanged. The AT content of both the 5' UTR and the intron is not changed by more than 20%, preferably not more than 15%, for example 10% or 5% compared to the AT content of the starting sequence.

A further embodiment of the invention is a synthetic regulatory nucleic acid molecule produced according to the method of the invention.

An expression construct comprising the said synthetic regulatory nucleic acid molecule is another embodiment of the invention.

A vector comprising the regulatory nucleic acid molecule or the expression construct of the invention is also comprised in this invention, as well as microorganisms, plant cells or animal cells comprising the regulatory nucleic acid molecule, the expression construct and/or the vector of the invention.

A further embodiment of the invention is a plant, plant seed, plant cell or part of a plant comprising the regulatory nucleic acid molecule, the expression construct and/or the vector of the invention.

A further embodiment of the invention are exemplary recombinant seed specific or seed preferential synthetic regulatory nucleic acid molecules produced according to the method of the invention wherein the regulatory nucleic acid molecule is comprised in the group consisting of I) a nucleic acid molecule represented by SEQ ID NO: 2, 4 or 6 and II) a nucleic acid molecule comprising at least 1000 consecutive base pairs, for example 1000 base pairs, preferably at least 800 consecutive base pairs, for example 800 base pairs, more preferably at least 700 consecutive base pairs, for example 700 base pairs, even more preferably at least 600 consecutive base pairs, for example 600 base pairs, most preferably at least 500 consecutive base pairs, for example 500 base pairs or at least 400, at least 300, at least 250 for example 400, 300 or 250 base pairs of a sequence described by SEQ ID NO: 2, 4 or 6 and III) a nucleic acid molecule having an identity of at least 70%, for example at least 75%, 76%, 77%, 78%, 79% preferably at least 80%, for example at least 81%, 82%, 83%, 84%, 85%, 86%, 87%, 88%, 89%, more preferably 90%, for example at least 91%, 92%, 93%, 94%, 95%, 96%, 97%, even more preferably 98% most preferably 99% over a sequence of at least 250, 300, 400, 500, 600 preferably 700, more preferably 800, even more preferably 900, most preferably 1000 consecutive nucleic acid base pairs to a sequences described by SEQ ID NO: 2, 4 or 6 and IV) a nucleic acid molecule having an identity of at least 70%, for example at least 75%, 76%, 77%, 78%, 79% preferably at least 80%, for example at least 81%, 82%, 83%, 84%, 85%, 86%, 87%, 88%, 89%, more preferably 90%, for example at least 91%, 92%, 93%, 94%, 95%, 96%, 97%, even more preferably 98% most preferably 99% to a sequence consisting of at least 50%, 60%, 70%, 80%, 90% or 100% of any of the sequences described by SEQ ID NO: 2, 4 or 6 and V) a nucleic acid molecule hybridizing under high stringent, preferably very high stringent conditions with a nucleic acid molecule of at least 250, 300, 400, 500, 600, 700, 800, 900, 1000 or the complete consecutive base pairs of a nucleic acid molecule described by any of SEQ ID NO: 2, 4 or 6 and VI) a complement of any of the nucleic acid molecules as defined in I) to V).

Another embodiment of the invention are exemplary recombinant seed specific or seed preferential synthetic regulatory nucleic acid molecules produced according to the method of the invention wherein the regulatory nucleic acid molecule is comprised in the group consisting of i) a nucleic acid molecule represented by SEQ ID NO: 2, 4 or 6 and ii) a nucleic acid molecule comprising at least 1000 consecutive base pairs, for example 1000 base pairs, preferably at least 800 consecutive base pairs, for example 800 base pairs, more preferably at least 700 consecutive base pairs, for example 700 base pairs, even more preferably at least 600 consecutive base pairs, for example 600 base pairs, most preferably at least 500 consecutive base pairs, for example 500 base pairs or at least 400, at least 300, at least 250 for example 400, 300 or 250 base pairs of a sequence described by SEQ ID NO: 2, 4 or 6 and iii) a nucleic acid molecule having an identity of at least 75% over a sequence of at least 250, 300, 400, 500, 600 preferably 700, more preferably 800, even more preferably 900, most preferably 1000 or the complete consecutive nucleic acid base pairs to a sequences described by SEQ ID NO: 6, iv) a nucleic acid molecule having an identity of at least 90% over a sequence of at least 250, 300, 400, 500, 600 preferably 700, more preferably 800, even more preferably 900, most preferably 1000 or the complete consecutive nucleic acid base pairs to a sequences described by SEQ ID NO: 2 or 4 and v) a nucleic acid molecule hybridizing under high stringent, preferably very high stringent conditions with a nucleic acid molecule of at least 250, 300, 400, 500, 600, 700, 800, 900, 1000 or the complete consecutive base pairs of a nucleic acid molecule described by any of SEQ ID NO: 2, 4 or 6 and vi) a complement of any of the nucleic acid molecules as defined in i) to v).

Further embodiments of the invention are exemplary recombinant constitutive regulatory nucleic acid molecules produced according to the method of the invention wherein the regulatory nucleic acid molecule is comprised in the group consisting of I) a nucleic acid molecule represented by SEQ ID NO: 14 or 15 and II) a nucleic acid molecule comprising at least 1750, 1500, 1250 or 1000 consecutive base pairs, for example 1000 base pairs, preferably at least 800 consecutive base pairs, for example 800 base pairs, more preferably at least 700 consecutive base pairs, for example 700 base pairs, even more preferably at least 600 consecutive base pairs, for example 600 base pairs, most preferably at least 500 consecutive base pairs, for example 500 base pairs or at least 400, at least 300, at least 250 for example 400, 300 or 250 base pairs of a sequence described by SEQ ID NO: 14 or 15 and III) a nucleic acid molecule having an identity of at least 70%, for example at least 75%, 76%, 77%, 78%, 79% preferably at least 80%, for example at least 81%, 82%, 83%, 84%, 85%, 86%, 87%, 88%, 89%, more preferably 90%, for example at least 91%, 92%, 93%, 94%, 95%, 96%, 97%, even more preferably 98% most preferably 99% over a sequence of at least 250, 300, 400, 500, 600 preferably 700, more preferably 800, even more preferably 900, for example 1000, most preferably 1250, for example 1500 or 1750 or 2000 consecutive nucleic acid base pairs to a sequences described by SEQ ID NO: 14 or 15 and IV) a nucleic acid molecule having an identity of at least 70%, for example at least 75%, 76%, 77%, 78%, 79% preferably at least 80%, for example at least 81%, 82%, 83%, 84%, 85%, 86%, 87%, 88%, 89%, more preferably 90%, for example at least 91%, 92%, 93%, 94%, 95%, 96%, 97%, even more preferably 98% most preferably 99% to a sequence consisting of at least 50%, 60%, 70%, 80%, 90% or 100% of any of the sequences described by SEQ ID NO: 14 or 15 and V) a nucleic acid molecule hybridizing under high stringent, preferably very high stringent conditions with a nucleic acid molecule of at least 250, 300, 400, 500, 600, 700, 800, 900, 1000, 1250, 1500, 1750 or 2000 or the complete consecutive base pairs of a nucleic acid molecule described by any of SEQ ID NO: 14 or 15 and VI) a complement of any of the nucleic acid molecules as defined in I) to V).

Another embodiment of the invention are exemplary recombinant constitutive synthetic regulatory nucleic acid molecules produced according to the method of the invention wherein the regulatory nucleic acid molecule is comprised in the group consisting of i) a nucleic acid molecule represented by SEQ ID NO: 14 or 15 and ii) a nucleic acid molecule comprising at least 2000, 1750, 1500, 1250 or 1000 consecutive base pairs, for example 1000 base pairs, preferably at least 800 consecutive base pairs, for example 800 base pairs, more preferably at least 700 consecutive base pairs, for example 700 base pairs, even more preferably at least 600 consecutive base pairs, for example 600 base pairs, most preferably at least 500 consecutive base pairs, for example 500 base pairs or at least 400, at least 300, at least 250 for example 400, 300 or 250 base pairs of a sequence described by SEQ ID NO: 14 or 15 and iii) a nucleic acid molecule having an identity of at least 95%, preferably 97%, more preferably 98%, most preferably 99% over a sequence of at least 250, 300, 400, 500, 600 preferably 700, more preferably 800, even more preferably 900, fore example 1000, most preferably 1500, for example 2000 or the complete consecutive nucleic acid base pairs to a sequences described by SEQ ID NO: 14 or 15, iv) a nucleic acid molecule hybridizing under high stringent, preferably very high stringent conditions with a nucleic acid molecule of at least 250, 300, 400, 500, 600, 700, 800, 900, 1000, 1250. 1500, 1750, 2000 or the complete consecutive base pairs of a nucleic acid molecule described by any of SEQ ID NO: 14 or 15 and v) a complement of any of the nucleic acid molecules as defined in i) to v).

It is to be understood, that the group of exemplary recombinant seed specific or seed preferential or constitutive synthetic regulatory nucleic acid molecules produced according to the method of the invention as defined above under I) to V) and i) to vi) does not comprise the starting molecules as defined by SEQ ID NO: 1, 3, 5 and 13 or a complement thereof or a nucleic acid molecule having at least 250 consecutive base pairs of a sequence described by SEQ ID NO: 1, 3, 5 or 13 or a complement thereof or any other nucleic acid molecule occurring in a wild type plant as such nucleic acid molecules are molecules that are not produced according to the invention but are naturally present in wild type plants.

An expression construct comprising any of said synthetic regulatory nucleic acid molecules as defined above under I) to VI) and i) to vi) is another embodiment of the invention.

A vector comprising the regulatory nucleic acid molecule or the expression construct of the invention is also comprised in this invention, as well as microorganisms, plant cells or animal cells comprising the regulatory nucleic acid molecule, the expression construct and/or the vector of the invention.

A further embodiment of the invention is a plant, plant seed, plant cell or part of a plant comprising the regulatory nucleic acid molecule, the expression construct and/or the vector of the invention.

Definitions

Abbreviations: GFP—green fluorescence protein, GUS—beta-Glucuronidase, BAP—6-benzylaminopurine; 2,4-D—2,4-dichlorophenoxyacetic acid; MS—Murashige and Skoog medium; NAA—1-naphtaleneacetic acid; MES, 2-(N-morpholino-ethanesulfonic acid, IAA indole acetic acid; Kan: Kanamycin sulfate; GA3—Gibberellic acid; Timentin™: ticarcillin disodium/clavulanate potassium.

It is to be understood that this invention is not limited to the particular methodology or protocols. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Antiparallel: "Antiparallel" refers herein to two nucleotide sequences paired through hydrogen bonds between complementary base residues with phosphodiester bonds running in the 5'-3' direction in one nucleotide sequence and in the 3'-5' direction in the other nucleotide sequence.

Antisense: The term "antisense" refers to a nucleotide sequence that is inverted relative to its normal orientation for transcription or function and so expresses an RNA transcript that is complementary to a target gene mRNA molecule expressed within the host cell (e.g., it can hybridize to the target gene mRNA molecule or single stranded genomic DNA through Watson-Crick base pairing) or that is complementary to a target DNA molecule such as, for example genomic DNA present in the host cell.

"Box" or as synonymously used herein "motif" or "cis-element" of a promoter means a transcription factor binding sequence defined by a highly conserved core sequence of approximately 4 to 6 nucleotides surrounded by a conserved matrix sequence of in total up to 20 nucleotides within the plus or minus strand of the promoter, which is able of interacting with the DNA binding domain of a transcription factor protein. The conserved matrix sequence allows some variability in the sequence without loosing its ability to be bound by the DNA binding domain of a transcription factor protein.

One way to describe transcription factor binding sites (TFBS) is by nucleotide or position weight matrices (NWM or PWM) (for review see Stormo, 2000). A weight matrix pattern definition is superior to a simple IUPAC consensus sequence as it represents the complete nucleotide distribution for each single position. It also allows the quantification of the similarity between the weight matrix and a potential TFBS detected in the sequence (Cartharius et al. 2005).

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine and on the 3'-side by one of the three triplets which specify stop codons (i.e., TAA, TAG, TGA). In addition to containing introns, genomic forms of a gene may also include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Conserved motives: A conserved motif as used herein means a sequence motif or box found in various promoters having the same or overlapping specificity. Overlapping specificity means the specificity of at least two promoters wherein the expression derived from one promoter is in part or completely in the same for example tissue as the other promoter, wherein the latter one may drive expression in additional tissues in which the first promoter may not drive expression. Motives may be grouped in three classes:

Essential: motives present in the promoters of most genes that are transcribed by RNA Polymerase II and which are preferentially localized close to the transcription start side. Such motives must not be made dysfunctional by mutations according to the method of the invention. Hence they must not be altered in a way that prevents them from being bound by the respective DNA binding domain of the transcription factor protein that would have bound to the unaltered sequence.

non exclusively associated: motives present in the promoters of genes that are associated with certain tissues/physiological states/treatments but not exclusively, they may be expressed also in other tissues/physiological states/treatments. According to the method of the invention, such motives should preferably not be made dysfunctional by mutations or at least only a certain percentage of such motives present in one particular promoter or starting sequence. Hence they should preferably not be altered in a way that prevents them from being bound by the respective DNA binding domain of the transcription factor protein that would have bound to the unaltered sequence.

preferentially associated: motives present in the promoters of genes that are expressed preferentially in specific tissues/physiological states/treatments. The vast majority of such motives identified in a starting sequence must not be made dysfunctional by mutations according to the method of the invention. Hence they must not be altered in a way that prevents them from being bound by the respective DNA binding domain of the transcription factor protein that would have bound to the unaltered sequence.

Defined specificity: the term "defined specificity" means any expression specificity of a promoter, preferably a plant specific promoter, which is beneficial for the expression of a distinct coding sequence or RNA. A defined specificity may for example be a tissue or developmental specificity or the expression specificity could be defined by induction or repression of expression by biotic or abiotic stimuli or a combination of any of these.

Double-stranded RNA: A "double-stranded RNA" molecule or "dsRNA" molecule comprises a sense RNA fragment of a nucleotide sequence and an antisense RNA fragment of the nucleotide sequence, which both comprise nucleotide sequences complementary to one another, thereby allowing the sense and antisense RNA fragments to pair and form a double-stranded RNA molecule.

Endogenous: An "endogenous" nucleotide sequence refers to a nucleotide sequence, which is present in the genome of the untransformed plant cell.

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In other cases, expression may refer only to the transcription of the DNA harboring an RNA molecule. Expression may also refer to the change of the steady state level of the respective RNA in a plant or part thereof due to change of the stability of the respective RNA.

Similar expression strength: Two or more regulatory nucleic acid molecules have a similar expression strength when the expression derived from any of the regulatory nucleic acid molecule in a distinct cell, tissue or plant organ does not deviate by more than factor 2.

Expression construct: "Expression construct" as used herein mean a DNA sequence capable of directing expression of a particular nucleotide sequence in an appropriate part of a plant or plant cell, comprising a promoter functional in said part of a plant or plant cell into which it will be introduced, operatively linked to the nucleotide sequence of interest which is—optionally—operatively linked to termination signals. If translation is required, it also typically comprises sequences required for proper translation of the nucleotide sequence. The coding region may code for a protein of interest but may also code for a functional RNA of interest, for example RNAa, siRNA, snoRNA, snRNA, microRNA, ta-siRNA or any other noncoding regulatory RNA, in the sense or antisense direction. The expression construct comprising the nucleotide sequence of interest may be chimeric, meaning that one or more of its components is heterologous with respect to one or more of its other components. The expression construct may also be one, which is naturally occurring but has been obtained in a recombinant form useful for heterologous expression. Typically, however, the expression construct is heterologous with respect to the host, i.e., the particular DNA sequence of the expression construct does not occur naturally in the host cell and must have been introduced into the host cell or an ancestor of the host cell by a transformation event. The expression of the nucleotide sequence in the expression construct may be under the control of a constitutive promoter or of an inducible promoter, which initiates transcription only when the host cell is exposed to some particular external stimulus. In the case of a plant, the promoter can also be specific to a particular tissue or organ or stage of development.

Expression pattern or expression specificity of a regulatory nucleic acid molecule as used herein defines the tissue and/or developmental and/or environmentally modulated expression of a coding sequence or RNA under the control of a distinct regulatory nucleic acid molecule.

Foreign: The term "foreign" refers to any nucleic acid molecule (e.g., gene sequence) which is introduced into the genome of a cell by experimental manipulations and may include sequences found in that cell so long as the introduced sequence contains some modification (e.g., a point mutation, the presence of a selectable marker gene, etc.) and is therefore distinct relative to the naturally-occurring sequence.

Functional linkage: The term "functional linkage" or "functionally linked" is to be understood as meaning, for example, the sequential arrangement of a regulatory element (e.g. a promoter) with a nucleic acid sequence to be expressed and, if appropriate, further regulatory elements (such as e.g., a terminator or an enhancer) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly is preferably less than 200 base pairs, especially preferably less than 100 base pairs, very especially preferably less than 50 base pairs. In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form and be inserted into a plant genome, for example by transformation.

Gene: The term "gene" refers to a region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleus (also referred to as chromosomal DNA) but also the DNA of the plastids (e.g., chloroplasts) and other cellular organelles (e.g., mitochondria). Preferably the terms genome or genomic DNA is referring to the chromosomal DNA of the nucleus.

Heterologous: The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. A heterologous expression construct comprising a nucleic acid molecule and one or more regulatory nucleic acid molecule (such as a promoter or a transcription termination signal) linked thereto for example is a constructs originating by experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural chromosomal locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenization. Such methods have been described (U.S. Pat. No. 5,565,350; WO 00/15815). For example a protein encoding nucleic acid molecule operably linked to a promoter, which is not the native promoter of this molecule, is considered to be heterologous with respect to the promoter. Preferably, heterologous DNA is not endogenous to or not naturally associated with the cell into which it is introduced, but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

Hybridization: The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

Medium stringency conditions when used in reference to nucleic acid hybridization comprise conditions equivalent to binding or hybridization at 68° C. in a solution consisting of 5×SSPE (43.8 g/L NaCl, 6.9 g/L NaH2PO4.H2O and 1.85 g/L EDTA, pH adjusted to 7.4 with NaOH), 1% SDS, 5×Denhardt's reagent [50×Denhardt's contains the following per 500 mL 5 g Ficoll (Type 400, Pharmacia), 5 g BSA (Fraction V; Sigma)] and 100 µg/mL denatured salmon sperm DNA followed by washing (preferably for one times 15 minutes, more preferably two times 15 minutes, more preferably three time 15 minutes) in a solution comprising 1×SSC (1×SSC is 0.15 M NaCl plus 0.015 M sodium citrate) and 0.1% SDS at room temperature or—preferably 37° C.—when a DNA probe of preferably about 100 to about 500 nucleotides in length is employed.

High stringency conditions when used in reference to nucleic acid hybridization comprise conditions equivalent to binding or hybridization at 68° C. in a solution consisting of 5×SSPE (43.8 g/L NaCl, 6.9 g/L NaH2PO4.H2O and 1.85 g/L EDTA, pH adjusted to 7.4 with NaOH), 1% SDS, 5×Denhardt's reagent [50×Denhardt's contains the following per 500 mL 5 g Ficoll (Type 400, Pharmacia), 5 g BSA (Fraction V; Sigma)] and 100 µg/mL denatured salmon sperm DNA followed by washing (preferably for one times 15 minutes, more preferably two times 15 minutes, more preferably three time 15 minutes) in a solution comprising 0.1×SSC (1×SSC is 0.15 M NaCl plus 0.015 M sodium citrate) and 1% SDS at room temperature or—preferably 37° C.—when a DNA probe of preferably about 100 to about 500 nucleotides in length is employed.

Very high stringency conditions when used in reference to nucleic acid hybridization comprise conditions equivalent to binding or hybridization at 68° C. in a solution consisting of 5×SSPE, 1% SDS, 5×Denhardt's reagent and 100 µg/mL denatured salmon sperm DNA followed by washing (preferably for one times 15 minutes, more preferably two times 15 minutes, more preferably three time 15 minutes) in a solution comprising 0.1×SSC, and 1% SDS at 68° C., when a probe of preferably about 100 to about 500 nucleotides in length is employed.

"Identity": "Identity" when used in respect to the comparison of two or more nucleic acid or amino acid molecules means that the sequences of said molecules share a certain degree of sequence similarity, the sequences being partially identical.

To determine the percentage identity (homology is herein used interchangeably) of two amino acid sequences or of two nucleic acid molecules, the sequences are written one underneath the other for an optimal comparison (for example gaps may be inserted into the sequence of a protein or of a nucleic acid in order to generate an optimal alignment with the other protein or the other nucleic acid).

The amino acid residues or nucleic acid molecules at the corresponding amino acid positions or nucleotide positions are then compared. If a position in one sequence is occupied by the same amino acid residue or the same nucleic acid molecule as the corresponding position in the other sequence, the molecules are homologous at this position (i.e. amino acid or nucleic acid "homology" as used in the present context corresponds to amino acid or nucleic acid "identity". The percentage identity between the two sequences is a function of the number of identical positions shared by the sequences (i.e. % homology=number of identical positions/total number of positions×100). The terms "homology" and "identity" are thus to be considered as synonyms.

For the determination of the percentage identity of two or more amino acids or of two or more nucleotide sequences several computer software programs have been developed. The identity of two or more sequences can be calculated with for example the software fasta, which presently has been used in the version fasta 3 (W. R. Pearson and D. J. Lipman, PNAS 85, 2444(1988); W. R. Pearson, Methods in Enzymology 183, 63 (1990); W. R. Pearson and D. J. Lipman, PNAS 85, 2444 (1988); W. R. Pearson, Enzymology 183, 63 (1990)). Another useful program for the calculation of identities of different sequences is the standard blast program, which is included in the Biomax pedant software (Biomax, Munich, Federal Republic of Germany). This leads unfortunately sometimes to suboptimal results since blast does not always include complete sequences of the subject and the query. Nevertheless as this program is very efficient it can be used for the comparison of a huge number of sequences. The following settings are typically used for such a comparisons of sequences:
-p Program Name [String]; -d Database [String]; default=nr; -i Query File [File In]; default=stdin; -e Expectation value (E) [Real]; default=10.0; -m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; -o BLAST report Output File [File Out] Optional; default=stdout; -F Filter query sequence (DUST with blastn, SEG with others) [String]; default=T; -G Cost to open a gap (zero invokes default behavior) [Integer]; default=0; -E Cost to extend a gap (zero invokes default behavior) [Integer]; default=0; -X X dropoff value for gapped alignment (in bits) (zero invokes default behavior); blastn 30, megablast 20, tblastx 0, all others 15 [Integer]; default=0; -I Show GI's in defines [T/F]; default=F; -q Penalty for a nucleotide mismatch (blastn only) [Integer]; default=−3; -r Reward for a nucleotide match (blastn only) [Integer]; default=1; -v Number of database sequences to show one-line descriptions for (V) [Integer]; default=500; -b Number of database sequence to show alignments for (B) [Integer]; default=250; -f Threshold for extending hits, default if zero; blastp 11, blastn 0, blastx 12, tblastn 13; tblastx 13, megablast 0 [Integer]; default=0; -g Perform gapped alignment (not available with tblastx) [T/F]; default=T; -Q Query Genetic code to use [Integer]; default=1; -D DB Genetic code (for tblast[nx] only) [Integer]; default=1; -a Number of processors to use [Integer]; default=1; -O SeqAlign file [File Out] Optional; -J Believe the query defline [T/F]; default=F; -M Matrix [String]; default=BLOSUM62; -W Word size, default if zero (blastn 11, megablast 28, all others 3) [Integer]; default=0; -z Effective length of the database (use zero for the real size) [Real]; default=0; -K Number of best hits from a region to keep (off by default, if used a value of 100 is recommended) [Integer]; default=0; -P 0 for multiple hit, 1 for single hit [Integer]; default=0; -Y Effective length of the search space (use zero for the real size) [Real]; default=0; -S Query strands to search against database (for blast[nx], and tblastx); 3 is both, 1 is top, 2 is bottom [Integer]; default=3; -T Produce HTML output [T/F]; default=F; -I Restrict search of database to list of GI's [String] Optional; -U Use lower case filtering of FASTA sequence [T/F] Optional; default=F; -y X dropoff value for ungapped extensions in bits (0.0 invokes default behavior); blastn 20, megablast 10, all others 7 [Real]; default=0.0; -Z X dropoff value for final gapped alignment in bits (0.0 invokes default behavior); blastn/megablast 50, tblastx 0, all others 25 [Integer]; default=0; -R PSI-TBLASTN checkpoint file [File In] Optional; -n MegaBlast search [T/F]; default=F; -L Location on query sequence [String] Optional; -A Multiple Hits window size, default if zero (blastn/megablast 0, all others 40 [Integer]; default=0; -w Frame shift penalty (OOF algorithm for blastx) [Integer]; default=0; -t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution., 25, 351 (1987), Higgins et al., CABIOS 5, 151 (1989)) or preferably with the programs "Gap" and "Needle", which are both based on the algorithms of Needleman and Wunsch (J. Mol. Biol. 48; 443 (1970)), and "BestFit", which is based on the algorithm of Smith and Waterman (Adv. Appl. Math. 2; 482 (1981)). "Gap" and "BestFit" are part of the GCG software-package (Genetics Computer Group, 575 Science Drive, Madison, Wis., USA 53711 (1991); Altschul et al., (Nucleic Acids Res. 25, 3389 (1997)), "Needle" is part of the The European Molecular Biology Open Software Suite (EMBOSS) (Trends in Genetics 16 (6), 276 (2000)). Therefore preferably the calculations to determine the percentages of sequence identity are done with the programs "Gap" or "Needle" over the whole range of the sequences. The following standard adjustments for the comparison of nucleic acid sequences were used for "Needle": matrix: EDNAFULL, Gap_penalty: 10.0, Extend_penalty: 0.5. The following standard adjustments for the comparison of nucleic acid sequences were used for "Gap": gap weight: 50, length weight: 3, average match: 10.000, average mismatch: 0.000.

For example a sequence, which is said to have 80% identity with sequence SEQ ID NO: 1 at the nucleic acid level is understood as meaning a sequence which, upon comparison with the sequence represented by SEQ ID NO: 1 by the above program "Needle" with the above parameter set, has a 80% identity. The identity is calculated on the complete length of the query sequence, for example SEQ ID NO:1.

Isogenic: organisms (e.g., plants), which are genetically identical, except that they may differ by the presence or absence of a heterologous DNA sequence.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring polynucleotide or polypeptide present in a living plant is not isolated, but the same polynucleotide or polypeptide, separated from some or all of the coexisting materials in the natural system, is isolated. Such polynucleotides can be part of a vector and/or such polynucleotides or polypeptides could be part of a composition, and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO:1 where the nucleic acid sequence is in a chromosomal or extrachromosomal location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

Minimal Promoter: promoter elements, particularly a TATA element, that are inactive or that have greatly reduced promoter activity in the absence of upstream activation. In the presence of a suitable transcription factor, the minimal promoter functions to permit transcription.

Naturally occurring as used herein means a cell or molecule, for example a plant cell or nucleic acid molecule that occurs in a plant or organism which is not manipulated by man, hence which is for example neither mutated nor genetically engineered by man.

Non-coding: The term "non-coding" refers to sequences of nucleic acid molecules that do not encode part or all of an expressed protein. Non-coding sequences include but are not limited to introns, enhancers, promoter regions, 3' untranslated regions, and 5' untranslated regions.

Nucleic acids and nucleotides: The terms "Nucleic Acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used interchangeably herein with "gene", "cDNA, "mRNA", "oligonucleotide," and "polynucleotide". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 7-position sugar modifications, including but not limited to, sugar-modified ribonucleotides in which the 2'-OH is replaced by a group selected from H, OR, R, halo, SH, SR, NH2, NHR, NR2, or CN. Short hairpin RNAs (shRNAs) also can comprise non-natural elements such as non-natural bases, e.g., ionosin and xanthine, non-natural sugars, e.g., 7-methoxy ribose, or non-natural phosphodiester linkages, e.g., methylphosphonates, phosphorothioates and peptides.

Nucleic acid sequence: The phrase "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Overhang: An "overhang" is a relatively short single-stranded nucleotide sequence on the 5'- or 3'-hydroxyl end of a double-stranded oligonucleotide molecule (also referred to as an "extension," "protruding end," or "sticky end").

Overlapping specificity: The term "overlapping specificity" when used herein related to expression specificity of two or more promoters means that the expression regulated by these promoters occur partly in the same plant tissues, developmental stages or conditions. For example, a promoter expressed in leaves and a promoter expressed in root and leaves have an overlap in expression specificity in the leaves of a plant.

Plant: is generally understood as meaning any eukaryotic single- or multi-celled organism or a cell, tissue, organ, part or propagation material (such as seeds or fruit) of same which is capable of photosynthesis. Included for the purpose of the invention are all genera and species of higher and lower plants of the Plant Kingdom. Annual, perennial, monocotyledonous and dicotyledonous plants are preferred. The term includes the mature plants, seed, shoots and seedlings and their derived parts, propagation material (such as seeds or microspores), plant organs, tissue, protoplasts, callus and other cultures, for example cell cultures, and any other type of plant cell grouping to give functional or structural units. Mature plants refer to plants at any desired developmental stage beyond that of the seedling. Seedling refers to a young immature plant at an early developmental stage. Annual, biennial, monocotyledonous and dicotyledonous plants are preferred host organisms for the generation of transgenic plants. The expression of genes is furthermore advantageous in all ornamental plants, useful or ornamental trees, flowers, cut flowers, shrubs or lawns. Plants which may be mentioned by way of example but not by limitation are angiosperms, bryophytes such as, for example, Hepaticae (liverworts) and Musci (mosses); Pteridophytes such as ferns, horsetail and club mosses; gymnosperms such as conifers, cycads, ginkgo and Gnetatae; algae such as Chlorophyceae, Phaeophpyceae, Rhodophyceae, Myxophyceae, Xanthophyceae, Bacillariophyceae (diatoms), and Euglenophyceae. Preferred are plants which are used for food or feed purpose such as the families of the Leguminosae such as pea, alfalfa and soya; Gramineae such as rice, maize, wheat, barley, sorghum, millet, rye, triticale, or oats; the family of the Umbelliferae, especially the genus *Daucus*, very especially the species *carota* (carrot) and *Apium*, very especially the species *Graveolens dulce* (celery) and many others; the family of the Solanaceae, especially the genus *Lycopersicon*, very especially the species *esculentum* (tomato) and the genus *Solanum*, very especially the species *tuberosum* (potato) and *melongena* (egg plant), and many others (such as tobacco); and the genus *Capsicum*, very especially the species *annuum* (peppers) and many others; the family of the Leguminosae, especially the genus *Glycine*, very especially the species max (soybean), alfalfa, pea, lucerne, beans or peanut and many others; and the family of the Cruciferae (Brassicacae), especially the genus *Brassica*, very especially the species *napus* (oil seed rape), *campestris* (beet), *oleracea* cv Tastie (cabbage), *oleracea* cv Snowball Y (cauliflower) and *oleracea* cv Emperor (broccoli); and of the genus *Arabidopsis*, very especially the species *thaliana* and many others; the family of the Compositae, especially the genus *Lactuca*, very especially the species *sativa* (lettuce) and many others; the family of the Asteraceae such as sunflower, *Tagetes*, lettuce or *Calendula* and many other; the family of the Cucurbitaceae such as melon, pumpkin/squash or zucchini, and linseed. Further preferred are cotton, sugar cane, hemp, flax, chillies, and the various tree, nut and wine species.

Polypeptide: The terms "polypeptide", "peptide", "oligopeptide", "polypeptide", "gene product", "expression product" and "protein" are used interchangeably herein to refer to a polymer or oligomer of consecutive amino acid residues.

Pre-protein: Protein, which is normally targeted to a cellular organelle, such as a chloroplast, and still comprising its transit peptide.

Primary transcript: The term "primary transcript" as used herein refers to a premature RNA transcript of a gene. A "primary transcript" for example still comprises introns and/or is not yet comprising a polyA tail or a cap structure and/or is missing other modifications necessary for its correct function as transcript such as for example trimming or editing.

Promoter: The terms "promoter", or "promoter sequence" are equivalents and as used herein, refer to a DNA sequence which when ligated to a nucleotide sequence of interest is capable of controlling the transcription of the nucleotide sequence of interest into RNA. Such promoters can for example be found in the following public databases http://www.grassius.org/grasspromdb.html, http://mendel.cs.rhul.ac.uk/mendel.php?topic=plantprom, http://ppdb.gene.nagoya-u.ac.jp/cgibin/index.cgi. Promoters listed there may be addressed with the methods of the invention and are herewith included by reference. A promoter is located 5' (i.e., upstream), proximal to the transcriptional start site of a nucleotide sequence of interest whose transcription into mRNA it controls, and provides a site for specific binding by RNA polymerase and other transcription factors for initiation of transcription. Said promoter comprises for example the at least 10 kb, for example 5 kb or 2 kb proximal to the transcription start site. It may also comprise the at least 1500 bp proximal to the transcriptional start site, preferably the at least 1000 bp, more preferably the at least 500 bp, even more preferably the at least 400 bp, the at least 300 bp, the at least 200 bp or the at least 100 bp. In a further preferred embodiment, the promoter comprises the at least 50 bp proximal to the transcription start site, for example, at least 25 bp. The promoter does not comprise exon and/or intron regions or 5' untranslated regions. The promoter may for example be heterologous or homologous to the respective plant. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host cells (e.g., plants or plant pathogens like plant viruses). A plant specific promoter is a promoter suitable for regulating expression in a plant. It may be derived from a plant but also from plant pathogens or it might be a synthetic promoter designed by man. If a promoter is an inducible promoter, then the rate of transcription increases in response to an inducing agent. Also, the promoter may be regulated in a tissue-specific or tissue preferred manner such that it is only or predominantly active in transcribing the associated coding region in a specific tissue type(s) such as leaves, roots or meristem. The term "tissue specific" as it applies to a promoter refers to a promoter that is capable of directing selective expression of a nucleotide sequence of interest to a specific type of tissue (e.g., petals) in the relative absence of expression of the same nucleotide sequence of interest in a different type of tissue (e.g., roots). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., GUS activity staining, GFP protein or immunohistochemical staining. The term "constitutive" when made in reference to a promoter or the expression derived from a promoter means that the promoter is capable of directing transcription of an operably linked nucleic acid molecule in the absence of a stimulus (e.g., heat shock, chemicals, light, etc.) in the majority of plant tissues and cells throughout substantially the entire lifespan of a plant or part of a plant. Typically, constitutive promoters are capable of directing expression of a transgene in substantially any cell and any tissue.

Promoter specificity: The term "specificity" when referring to a promoter means the pattern of expression conferred by the respective promoter. The specificity describes the tissues and/or developmental status of a plant or part thereof, in which the promoter is conferring expression of the nucleic acid molecule under the control of the respective promoter. Specificity of a promoter may also comprise the environmental conditions, under which the promoter may be activated or down-regulated such as induction or repression by biological or environmental stresses such as cold, drought, wounding or infection.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated. A purified nucleic acid sequence may be an isolated nucleic acid sequence.

Recombinant: The term "recombinant" with respect to nucleic acid molecules refers to nucleic acid molecules produced by recombinant DNA techniques. Recombinant nucleic acid molecules as such do not exist in nature but are modified, changed, mutated or otherwise manipulated by man. A "recombinant nucleic acid molecule" is a non-naturally occurring nucleic acid molecule that differs in sequence from a naturally occurring nucleic acid molecule by at least one nucleic acid. The term "recombinant nucleic acid molecule" may also comprise a "recombinant construct" which comprises, preferably operably linked, a sequence of nucleic acid molecules, which are not naturally occurring in that order wherein each of the nucleic acid molecules may or may not be a recombinant nucleic acid molecule. Preferred methods for producing said recombinant nucleic acid molecule may comprise cloning techniques, directed or non-directed mutagenesis, synthesis or recombination techniques.

Sense: The term "sense" is understood to mean a nucleic acid molecule having a sequence which is complementary or identical to a target sequence, for example a sequence which binds to a protein transcription factor and which is involved in the expression of a given gene. According to a preferred embodiment, the nucleic acid molecule comprises a gene of interest and elements allowing the expression of the said gene of interest.

Starting sequence: The term "starting sequence" when used herein defines the sequence of a promoter of a defined specificity which is used as a reference sequence for analysis of the presence of motives. The starting sequence is referred to for the definition of the degree of identity to the sequences of the promoters of the invention. The starting sequence could be any wild-type, naturally occurring promoter sequence or any artificial promoter sequence. The sequence of a synthetic promoter sequence produced with the method of the invention may also be used as a starting sequence.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the later being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with a recombinant DNA molecule that preferably comprises a suitable promoter operatively linked to a DNA sequence of interest.

Vector: As used herein, the term "vector" refers to a nucleic acid molecule capable of transporting another nucleic acid molecule to which it has been linked. One type of vector is a genomic integrated vector, or "integrated vector", which can become integrated into the chromosomal DNA of the host cell. Another type of vector is an episomal vector, i.e., a nucleic acid molecule capable of extra-chromosomal replication. Vectors capable of directing the expression of genes to which they are operatively linked are referred to herein as "expression vectors". In the present specification, "plasmid" and "vector" are used interchangeably unless otherwise clear from the context. Expression vectors designed to produce RNAs as described herein in vitro or in vivo may contain sequences recognized by any RNA polymerase, including mitochondrial RNA polymerase, RNA pol I, RNA pol II, and RNA pol III. These vectors can be used to transcribe the desired RNA molecule in the cell according to this invention. A plant transformation vector is to be understood as a vector suitable in the process of plant transformation.

Wild-type: The term "wild-type", "natural" or "natural origin" means with respect to an organism, polypeptide, or nucleic acid sequence, that said organism is naturally occurring or available in at least one naturally occurring organism which is not changed, mutated, or otherwise manipulated by man.

EXAMPLES

Chemicals and Common Methods

Unless indicated otherwise, cloning procedures carried out for the purposes of the present invention including restriction digest, agarose gel electrophoresis, purification of nucleic acids, Ligation of nucleic acids, transformation, selection and cultivation of bacterial cells were performed as described (Sambrook et al., 1989). Sequence analyses of recombinant DNA were performed with a laser fluorescence DNA sequencer (Applied Biosystems, Foster City, Calif., USA) using the Sanger technology (Sanger et al., 1977). Unless described otherwise, chemicals and reagents were obtained from Sigma Aldrich (Sigma Aldrich, St. Louis, USA), from Promega (Madison, Wis., USA), Duchefa (Haarlem, The Netherlands) or Invitrogen (Carlsbad, Calif., USA). Restriction endonucleases were from New England Biolabs (Ipswich, Mass., USA) or Roche Diagnostics GmbH (Penzberg, Germany). Oligonucleotides were synthesized by Eurofins MWG Operon (Ebersberg, Germany).

Example 1

1.1 Directed Permutation of the Promoter Sequence

Using publicly available data, two promoters showing seed specific expression in plants were selected for analyzing the effects of sequence permutation in periodic intervals throughout the full length of the promoter DNA sequence (WO2009016202, WO2009133145). The wildtype or starting sequences of the *Phaseolus vulgaris* p-PvARC5 (SEQ ID NO 1) (with the prefix p- denoting promoter) and the *Vicia faba* p-VfSBP (SEQ ID NO 3) promoters were analyzed and annotated for the occurrence of motives, boxes, cis-regulatory elements using e.g. the GEMS Launcher Software (www.genomatix.de) with default parameters (Core similarity 0.75, matrix similarity 0.75)

The "core sequence" of a matrix is defined as the usually 4 consecutive highest conserved positions of the matrix.

The core similarity is calculated as described here and in the papers related to MatInspector (Cartharius K, et al. (2005) Bioinformatics 21; Cartharius K (2005), DNA Press; Quandt K, et al (1995) Nucleic Acids Res. 23.

The maximum core similarity of 1.0 is only reached when the highest conserved bases of a matrix match exactly in the sequence. More important than the core similarity is the matrix similarity which takes into account all bases over the whole matrix length. The matrix similarity is calculated as described here and in the MatInspector paper. A perfect match to the matrix gets a score of 1.00 (each sequence position corresponds to the highest conserved nucleotide at that position in the matrix), a "good" match to the matrix has a similarity of >0.80.

Mismatches in highly conserved positions of the matrix decrease the matrix similarity more than mismatches in less conserved regions.

Opt gives the Optimized matrix threshold: This matrix similarity is the optimized value defined in a way that a minimum number of matches is found in non-regulatory test sequences (i.e. with this matrix similarity the number of false positive matches is minimized). This matrix similarity is used when the user checks "Optimized" as the matrix similarity threshold for MatInspector.

In the following, the DNA sequences of the promoters were permutated according to the method of the invention to yield p-PvArc5_perm (SEQ ID NO 2) and p-VfSBP_perm (SEQ ID NO 4). In case of the p-PvArc5 promoter 6.6% of the motives not associated with seed specific/preferential expression and transcription initiation have been altered, in case of the p-VfSBP 7.8%. DNA permutation was conducted in a way to not affect cis regulatory elements which have been associated previously with seed specific gene expression or initiation of transcription and permutations were distributed periodically over the full promoter DNA sequence with less than 46 nucleotides between permutated nucleotide positions and within a stretch of 5 nucleotides having at least one nucleotide permutated. Permutations were carried out with the aim to keep most of the cis regulatory elements, boxes, motives present in the native promoter and to avoid creating new putative cis regulatory elements, boxes, motives.

The list of motives, boxes, cis regulatory elements in the PvARC5 promoters before and after the permutation are shown in Table 1 and 2.

The list of motives, boxes, cis regulatory elements in the VfSBP promoters before and after the permutation are shown in Table 3 and 4.

Empty lines resemble motives, boxes, cis regulatory elements not found in one sequence but present in the corresponding sequence, hence, motives, boxes, cis regulatory elements that were deleted from the starting sequence or that were introduced into the permutated sequence.

TABLE 1

Boxes and Motifs identified in the starting sequence of the PvARC5 promoter

| Family | Further Family Information | Matrix | Opt. | Position from-to | Strand | Core sim. | Matrix sim. |
|---|---|---|---|---|---|---|---|
| P$PSRE | Pollen-specific regulatory elements | P$GAAA.01 | 0.83 | 9-25 | (+) | 1 | 0.862 |
| P$IDDF | ID domain factors | P$ID1.01 | 0.92 | 36-48 | (−) | 1 | 0.922 |
| P$MYBL | MYB-like proteins | P$ATMYB77.01 | 0.87 | 47-63 | (+) | 1 | 0.887 |
| P$RAV5 | 5'-part of bipartite RAV1 binding site | P$RAV1-5.01 | 0.96 | 48-58 | (+) | 1 | 0.96 |
| P$MYBL | MYB-like proteins | P$GAMYB.01 | 0.91 | 52-68 | (−) | 1 | 0.932 |
| O$INRE | Core promoter initiator elements | O$DINR.01 | 0.94 | 75-85 | (+) | 0.97 | 0.988 |
| P$AHBP | *Arabidopsis* homeobox protein | P$WUS.01 | 0.94 | 84-94 | (−) | 1 | 0.963 |
| P$MIIG | MYB IIG-type binding sites | P$PALBOXL.01 | 0.80 | 87-101 | (+) | 0.84 | 0.806 |
| P$NCS1 | Nodulin consensus sequence 1 | P$NCS1.01 | 0.85 | 106-116 | (+) | 1 | 0.99 |
| P$GAPB | GAP-Box (light response elements) | P$GAP.01 | 0.88 | 108-122 | (+) | 0.81 | 0.884 |
| P$AHBP | *Arabidopsis* homeobox protein | P$WUS.01 | 0.94 | 110-120 | (−) | 1 | 0.963 |
| P$TEFB | TEF-box | P$TEF1.01 | 0.76 | 111-131 | (−) | 0.96 | 0.761 |
| P$CCAF | Circadian control factors | P$CCA1.01 | 0.85 | 113-127 | (+) | 0.77 | 0.856 |
| P$IBOX | Plant I-Box sites | P$GATA.01 | 0.93 | 121-137 | (−) | 1 | 0.964 |
| P$GAGA | GAGA elements | P$GAGABP.01 | 0.75 | 125-149 | (−) | 0.75 | 0.768 |

TABLE 1-continued

Boxes and Motifs identified in the starting sequence of the PvARC5 promoter

| Family | Further Family Information | Matrix | Opt. | Position from-to | Strand | Core sim. | Matrix sim. |
|---|---|---|---|---|---|---|---|
| P$NCS2 | Nodulin consensus sequence 2 | P$NCS2.01 | 0.79 | 126-140 | (+) | 1 | 0.799 |
| P$AHBP | *Arabidopsis* homeobox protein | P$HAHB4.01 | 0.87 | 144-154 | (−) | 1 | 0.923 |
| P$AHBP | *Arabidopsis* homeobox protein | P$BLR.01 | 0.90 | 147-157 | (−) | 1 | 0.928 |
| O$VTBP | Vertebrate TA-TA binding protein factor | O$LTATA.01 | 0.82 | 151-167 | (+) | 1 | 0.839 |
| P$NCS1 | Nodulin consensus sequence 1 | P$NCS1.01 | 0.85 | 164-174 | (−) | 1 | 0.898 |
| P$L1BX | L1 box, motif for L1 layer-specific expression | P$ATML1.01 | 0.82 | 175-191 | (+) | 0.75 | 0.872 |
| P$AHBP | *Arabidopsis* homeobox protein | P$ATHB5.01 | 0.89 | 177-187 | (+) | 0.83 | 0.902 |
| P$AHBP | *Arabidopsis* homeobox protein | P$ATHB5.01 | 0.89 | 177-187 | (−) | 1 | 1 |
| O$VTBP | Vertebrate TA-TA binding protein factor | O$ATATA.01 | 0.78 | 184-200 | (+) | 0.75 | 0.797 |
| P$TELO | Telo box (plant interstitial telomere motifs) | P$ATPURA.01 | 0.85 | 186-200 | (−) | 0.75 | 0.857 |
| P$NCS2 | Nodulin consensus sequence 2 | P$NCS2.01 | 0.79 | 213-227 | (−) | 1 | 0.826 |
| P$SUCB | Sucrose box | P$SUCROSE.01 | 0.81 | 233-251 | (+) | 0.75 | 0.824 |
| P$MYBL | MYB-like proteins | P$MYBPH3.02 | 0.76 | 238-254 | (+) | 0.82 | 0.798 |
| P$NCS1 | Nodulin consensus sequence 1 | P$NCS1.01 | 0.85 | 261-271 | (−) | 1 | 0.851 |
| P$MYBL | MYB-like proteins | P$MYBPH3.02 | 0.76 | 264-280 | (+) | 1 | 0.774 |
| O$VTBP | Vertebrate TA-TA binding protein factor | O$ATATA.01 | 0.78 | 267-283 | (+) | 1 | 0.872 |
| P$SPF1 | Sweet potato DNA-binding factor with two WRKY-domains | P$SP8BF.01 | 0.87 | 298-310 | (−) | 1 | 0.872 |
| P$BRRE | Brassinosteroid (BR) response element | P$BZR1.01 | 0.95 | 303-319 | (−) | 1 | 0.953 |
| P$L1BX | L1 box, motif for L1 layer-specific expression | P$ATML1.02 | 0.76 | 319-335 | (+) | 0.89 | 0.762 |
| P$GBOX | Plant G-box/C-box bZIP proteins | P$TGA1.01 | 0.90 | 327-347 | (−) | 1 | 0.909 |
| P$GTBX | GT-box elements | P$GT1.01 | 0.85 | 337-353 | (+) | 1 | 0.854 |
| P$IBOX | Plant I-Box sites | P$GATA.01 | 0.93 | 337-353 | (−) | 1 | 0.935 |
| P$OPAQ | Opaque-2 like transcriptional activators | P$O2.01 | 0.87 | 351-367 | (−) | 1 | 0.919 |
| P$GTBX | GT-box elements | P$S1F.01 | 0.79 | 362-378 | (−) | 0.75 | 0.797 |
| P$AHBP | *Arabidopsis* homeobox protein | P$ATHB9.01 | 0.77 | 367-377 | (−) | 1 | 0.788 |
| P$AHBP | *Arabidopsis* homeobox protein | P$HAHB4.01 | 0.87 | 367-377 | (+) | 1 | 0.926 |
| P$GTBX | GT-box elements | P$SBF1.01 | 0.87 | 367-383 | (+) | 1 | 0.894 |
| P$L1BX | L1 box, motif for L1 layer-specific expression | P$ATML1.01 | 0.82 | 369-385 | (+) | 1 | 0.827 |
| P$AHBP | *Arabidopsis* homeobox protein | P$WUS.01 | 0.94 | 371-381 | (−) | 1 | 1 |
| O$VTBP | Vertebrate TATA binding protein factor | O$LTATA.01 | 0.82 | 396-412 | (−) | 1 | 0.857 |
| P$LREM | Light responsive element motif, not modulated by different light qualities | P$RAP22.01 | 0.85 | 397-407 | (+) | 1 | 0.921 |

TABLE 1-continued

Boxes and Motifs identified in the starting sequence of the PvARC5 promoter

| Family | Further Family Information | Matrix | Opt. | Position from-to | Strand | Core sim. | Matrix sim. |
|---|---|---|---|---|---|---|---|
| P$AHBP | *Arabidopsis* homeobox protein | P$HAHB4.01 | 0.87 | 401-411 | (−) | 1 | 0.916 |
| P$MYBL | MYB-like proteins | P$WER.01 | 0.87 | 403-419 | (−) | 1 | 0.9 |
| P$MYBS | MYB proteins with single DNA binding repeat | P$OSMYBS.01 | 0.82 | 416-432 | (+) | 0.75 | 0.837 |
| P$TELO | Telo box (plant interstitial telomere motifs) | P$ATPURA.01 | 0.85 | 440-454 | (−) | 0.75 | 0.854 |
| P$SUCB | Sucrose box | P$SUCROSE.01 | 0.81 | 461-479 | (−) | 0.75 | 0.826 |
| P$AHBP | *Arabidopsis* homeobox protein | P$HAHB4.01 | 0.87 | 468-478 | (+) | 1 | 0.892 |
| O$VTBP | Vertebrate TATA binding protein factor | O$VTATA.01 | 0.90 | 473-489 | (−) | 1 | 0.913 |
| O$PTBP | Plant TATA binding protein factor | O$PTATA.01 | 0.88 | 476-490 | (−) | 1 | 0.889 |
| P$PSRE | Pollen-specific regulatory elements | P$GAAA.01 | 0.83 | 482-498 | (+) | 1 | 0.831 |
| P$HMGF | High mobility group factors | P$HMG_IY.01 | 0.89 | 499-513 | (−) | 1 | 0.91 |
| P$SUCB | Sucrose box | P$SUCROSE.01 | 0.81 | 499-517 | (−) | 1 | 0.878 |
| P$GTBX | GT-box elements | P$SBF1.01 | 0.87 | 509-525 | (−) | 1 | 0.885 |
| P$GARP | Myb-related DNA binding proteins (Golden2, ARR, Psr) | P$ARR10.01 | 0.97 | 540-548 | (+) | 1 | 0.976 |
| P$AHBP | *Arabidopsis* homeobox protein | P$ATHB9.01 | 0.77 | 558-568 | (−) | 1 | 0.775 |
| P$L1BX | L1 box, motif for L1 layer-specific expression | P$PDF2.01 | 0.85 | 558-574 | (−) | 1 | 0.865 |
| P$NCS1 | Nodulin consensus sequence 1 | P$NCS1.01 | 0.85 | 558-568 | (−) | 0.88 | 0.927 |
| P$EINL | Ethylen insensitive 3 like factors | P$TEIL.01 | 0.92 | 572-580 | (+) | 1 | 0.921 |
| P$AHBP | *Arabidopsis* homeobox protein | P$ATHB5.01 | 0.89 | 583-593 | (+) | 0.94 | 0.977 |
| P$AHBP | *Arabidopsis* homeobox protein | P$ATHB5.01 | 0.89 | 583-593 | (−) | 0.83 | 0.94 |
| P$L1BX | L1 box, motif for L1 layer-specific expression | P$HDG9.01 | 0.77 | 607-623 | (+) | 1 | 0.772 |
| P$IBOX | Plant I-Box sites | P$IBOX.01 | 0.81 | 610-626 | (+) | 0.75 | 0.824 |
| P$MYBS | MYB proteins with single DNA binding repeat | P$MYBST1.01 | 0.90 | 613-629 | (−) | 1 | 0.953 |
| P$IBOX | Plant I-Box sites | P$GATA.01 | 0.93 | 616-632 | (+) | 1 | 0.942 |
| P$TEFB | TEF-box | P$TEF1.01 | 0.76 | 616-636 | (+) | 0.96 | 0.778 |
| P$MYBS | MYB proteins with single DNA binding repeat | P$TAMYB80.01 | 0.83 | 625-641 | (−) | 1 | 0.859 |
| O$PTBP | Plant TATA binding protein factor | O$PTATA.02 | 0.90 | 631-645 | (+) | 1 | 0.927 |
| O$PTBP | Plant TATA binding protein factor | O$PTATA.02 | 0.90 | 632-646 | (−) | 1 | 0.929 |
| O$VTBP | Vertebrate TATA binding protein factor | O$ATATA.01 | 0.78 | 646-662 | (−) | 0.75 | 0.825 |
| P$L1BX | L1 box, motif for L1 layer-specific expression | P$HDG9.01 | 0.77 | 648-664 | (+) | 1 | 0.791 |
| P$HMGF | High mobility group factors | P$HMG_IY.01 | 0.89 | 649-663 | (−) | 1 | 0.902 |

TABLE 1-continued

Boxes and Motifs identified in the starting sequence of the PvARC5 promoter

| | PvARC5 promotor | | | Position | | | |
|---|---|---|---|---|---|---|---|
| Family | Further Family Information | Matrix | Opt. | Position from-to | Strand | Core sim. | Matrix sim. |
| P$DOFF | DNA binding with one finger (DOF) | P$PBF.01 | 0.97 | 654-670 | (+) | 1 | 0.979 |
| P$LREM | Light responsive element motif, not modulated by different light qualities | P$RAP22.01 | 0.85 | 682-692 | (−) | 1 | 0.975 |
| P$TEFB | TEF-box | P$TEF1.01 | 0.76 | 696-716 | (−) | 0.84 | 0.78 |
| P$MYBL | MYB-like proteins | P$CARE.01 | 0.83 | 699-715 | (−) | 1 | 0.88 |
| P$LEGB | Legumin Box family | P$RY.01 | 0.87 | 704-730 | (+) | 1 | 0.94 |
| P$GBOX | Plant G-box/C-box bZIP proteins | P$BZIP910.01 | 0.77 | 716-736 | (−) | 0.75 | 0.856 |
| P$GBOX | Plant G-box/C-box bZIP proteins | P$ROM.01 | 0.85 | 717-737 | (+) | 1 | 1 |
| P$ABRE | ABA response elements | P$ABF1.03 | 0.82 | 719-735 | (−) | 0.75 | 0.857 |
| P$GBOX | Plant G-box/C-box bZIP proteins | P$BZIP910.02 | 0.84 | 722-742 | (−) | 0.75 | 0.862 |
| P$MYCL | Myc-like basic helix-loop-helix binding factors | P$MYCRS.01 | 0.93 | 739-757 | (−) | 0.86 | 0.943 |
| P$OPAQ | Opaque-2 like transcriptional activators | P$GCN4.01 | 0.81 | 745-761 | (−) | 1 | 0.85 |
| P$AREF | Auxin response element | P$ARE.01 | 0.93 | 747-759 | (+) | 1 | 0.941 |
| P$TEFB | TEF-box | P$TEF1.01 | 0.76 | 783-803 | (−) | 0.84 | 0.78 |
| P$MYBL | MYB-like proteins | P$CARE.01 | 0.83 | 786-802 | (−) | 1 | 0.876 |
| P$LEGB | Legumin Box family | P$RY.01 | 0.87 | 788-814 | (−) | 1 | 0.929 |
| P$LEGB | Legumin Box family | P$RY.01 | 0.87 | 791-817 | (+) | 1 | 0.984 |
| P$ROOT | Root hair-specific cis-elements in angiosperms | P$RHE.01 | 0.77 | 796-820 | (+) | 1 | 0.812 |
| P$GBOX | Plant G-box/C-box bZIP proteins | P$CPRF.01 | 0.95 | 803-823 | (−) | 1 | 0.989 |
| P$GBOX | Plant G-box/C-box bZIP proteins | P$CPRF.01 | 0.95 | 804-824 | (+) | 1 | 0.98 |
| P$MYCL | Myc-like basic helix-loop-helix binding factors | P$MYCRS.01 | 0.93 | 804-822 | (−) | 1 | 0.956 |
| P$ABRE | ABA response elements | P$ABRE.01 | 0.82 | 805-821 | (+) | 1 | 0.874 |
| P$MYCL | Myc-like basic helix-loop-helix binding factors | P$PIF3.01 | 0.82 | 805-823 | (+) | 1 | 0.914 |
| P$OPAQ | Opaque-2 like transcriptional activators | P$RITA1.01 | 0.95 | 805-821 | (−) | 1 | 0.992 |
| P$ABRE | ABA response elements | P$ABF1.03 | 0.82 | 806-822 | (−) | 1 | 0.977 |
| P$OPAQ | Opaque-2 like transcriptional activators | P$RITA1.01 | 0.95 | 806-822 | (+) | 1 | 0.973 |
| P$OCSE | Enhancer element first identified in the promoter of the octopine synthase gene (OCS) of the *Agrobacterium tumefaciens* T-DNA | P$OCSTF.01 | 0.73 | 809-829 | (−) | 0.85 | 0.747 |
| P$GTBX | GT-box elements | P$S1F.01 | 0.79 | 823-839 | (−) | 1 | 0.794 |
| P$LFYB | LFY binding site | P$LFY.01 | 0.93 | 839-851 | (−) | 0.91 | 0.935 |

TABLE 1-continued

Boxes and Motifs identified in the starting sequence of the PvARC5 promoter

| Family | Further Family Information | Matrix | Opt. | Position from-to | Strand | Core sim. | Matrix sim. |
|---|---|---|---|---|---|---|---|
| P$LEGB | Legumin Box family | P$RY.01 | 0.87 | 840-866 | (−) | 1 | 0.948 |
| P$LEGB | Legumin Box family | P$RY.01 | 0.87 | 843-869 | (+) | 1 | 0.966 |
| P$LEGB | Legumin Box family | P$IDE1.01 | 0.77 | 847-873 | (+) | 1 | 0.779 |
| P$GBOX | Plant G-box/C-box bZIP proteins | P$BZIP910.01 | 0.77 | 855-875 | (−) | 0.75 | 0.856 |
| P$GBOX | Plant G-box/C-box bZIP proteins | P$ROM.01 | 0.85 | 856-876 | (+) | 1 | 1 |
| P$ABRE | ABA response elements | P$ABF1.03 | 0.82 | 858-874 | (−) | 0.75 | 0.857 |
| P$GBOX | Plant G-box/C-box bZIP proteins | P$BZIP910.02 | 0.84 | 861-881 | (−) | 0.75 | 0.862 |
| P$SALT | Salt/drought responsive elements | P$ALFIN1.02 | 0.95 | 871-885 | (−) | 1 | 0.963 |
| P$LEGB | Legumin Box family | P$RY.01 | 0.87 | 895-921 | (+) | 1 | 0.927 |
| P$GBOX | Plant G-box/C-box bZIP proteins | P$BZIP910.01 | 0.77 | 907-927 | (−) | 0.75 | 0.856 |
| P$GBOX | Plant G-box/C-box bZIP proteins | P$ROM.01 | 0.85 | 908-928 | (+) | 1 | 0.938 |
| P$ABRE | ABA response elements | P$ABF1.03 | 0.82 | 910-926 | (−) | 0.75 | 0.857 |
| P$GBOX | Plant G-box/C-box bZIP proteins | P$BZIP910.02 | 0.84 | 913-933 | (−) | 0.75 | 0.871 |
| P$MADS | MADS box proteins | P$SQUA.01 | 0.90 | 960-980 | (−) | 1 | 0.908 |
| P$L1BX | L1 box, motif for L1 layer-specific expression | P$PDF2.01 | 0.85 | 963-979 | (+) | 1 | 0.856 |
| P$LREM | Light responsive element motif, not modulated by different light qualities | P$RAP22.01 | 0.85 | 972-982 | (+) | 1 | 0.858 |
| O$PTBP | Plant TATA binding protein factor | O$PTATA.01 | 0.88 | 974-988 | (−) | 0.83 | 0.886 |
| O$VTBP | Vertebrate TATA binding protein factor | O$ATATA.01 | 0.78 | 974-990 | (+) | 0.75 | 0.83 |
| O$VTBP | Vertebrate TATA binding protein factor | O$MTATA.01 | 0.84 | 976-992 | (+) | 1 | 0.843 |
| P$MYBL | MYB-like proteins | P$MYBPH3.02 | 0.76 | 983-999 | (−) | 1 | 0.787 |
| P$SUCB | Sucrose box | P$SUCROSE.01 | 0.81 | 984-1002 | (−) | 1 | 0.818 |
| P$AHBP | *Arabidopsis* homeobox protein | P$ATHB1.01 | 0.90 | 991-1001 | (+) | 1 | 0.989 |
| P$AHBP | *Arabidopsis* homeobox protein | P$HAHB4.01 | 0.87 | 991-1001 | (−) | 1 | 0.943 |
| P$HMGF | High mobility group factors | P$HMG_IY.01 | 0.89 | 992-1006 | (+) | 1 | 0.913 |
| P$SPF1 | Sweet potato DNA-binding factor with two WRKY-domains | P$SP8BF.01 | 0.87 | 1003-1015 | (+) | 1 | 0.881 |
| P$OCSE | Enhancer element first identified in the promoter of the octopine synthase gene (OCS) of the *Agrobacterium tumefaciens* T-DNA | P$OCSTF.01 | 0.73 | 1004-1024 | (+) | 1 | 0.776 |
| P$GBOX | Plant G-box/C-box bZIP proteins | P$UPRE.01 | 0.86 | 1009-1029 | (−) | 1 | 0.974 |

TABLE 1-continued

Boxes and Motifs identified in the starting sequence of the PvARC5 promoter

| | PvARC5 promotor | | | Position | | | |
|---|---|---|---|---|---|---|---|
| Family | Further Family Information | Matrix | Opt. | Position from-to | Strand | Core sim. | Matrix sim. |
| P$GBOX | Plant G-box/C-box bZIP proteins | P$TGA1.01 | 0.90 | 1010-1030 | (+) | 1 | 0.991 |
| P$ABRE | ABA response elements | P$ABF1.03 | 0.82 | 1011-1027 | (+) | 1 | 0.828 |
| P$OPAQ | Opaque-2 like transcriptional activators | P$O2.01 | 0.87 | 1011-1027 | (−) | 1 | 0.99 |
| P$OPAQ | Opaque-2 like transcriptional activators | P$O2_GCN4.01 | 0.81 | 1012-1028 | (+) | 0.95 | 0.893 |
| P$ROOT | Root hair-specific cis-elements in angiosperms | P$RHE.01 | 0.77 | 1013-1037 | (−) | 1 | 0.771 |
| P$LEGB | Legumin Box family | P$LEGB.01 | 0.65 | 1025-1051 | (+) | 1 | 0.656 |
| P$AHBP | *Arabidopsis* homeobox protein | P$ATHB5.01 | 0.89 | 1042-1052 | (+) | 0.83 | 0.902 |
| P$AHBP | *Arabidopsis* homeobox protein | P$ATHB5.01 | 0.89 | 1042-1052 | (−) | 1 | 1 |
| P$GTBX | GT-box elements | P$SBF1.01 | 0.87 | 1045-1061 | (+) | 1 | 0.904 |
| O$INRE | Core promoter initiator elements | O$DINR.01 | 0.94 | 1070-1080 | (−) | 0.97 | 0.949 |
| P$CCAF | Circadian control factors | P$CCA1.01 | 0.85 | 1093-1107 | (−) | 1 | 0.952 |
| P$L1BX | L1 box, motif for L1 layer-specific expression | P$ATML1.01 | 0.82 | 1098-1114 | (−) | 0.75 | 0.843 |
| P$CARM | CA-rich motif | P$CARICH.01 | 0.78 | 1102-1120 | (−) | 1 | 0.791 |
| P$MADS | MADS box proteins | P$SQUA.01 | 0.90 | 1108-1128 | (−) | 1 | 0.928 |
| O$PTBP | Plant TATA binding protein factor | O$PTATA.01 | 0.88 | 1111-1125 | (+) | 1 | 0.961 |
| O$VTBP | Vertebrate TATA binding protein factor | O$VTATA.01 | 0.90 | 1112-1128 | (+) | 1 | 0.968 |
| P$LEGB | Legumin Box family | P$RY.01 | 0.87 | 1130-1156 | (−) | 1 | 0.922 |
| P$AHBP | *Arabidopsis* homeobox protein | P$WUS.01 | 0.94 | 1135-1145 | (+) | 1 | 1 |
| P$LEGB | Legumin Box family | P$RY.01 | 0.87 | 1138-1164 | (−) | 1 | 0.914 |
| P$ROOT | Root hair-specific cis-elements in angiosperms | P$RHE.01 | 0.77 | 1138-1162 | (+) | 0.75 | 0.794 |
| P$L1BX | L1 box, motif for L1 layer-specific expression | P$ATML1.01 | 0.82 | 1141-1157 | (+) | 0.75 | 0.833 |

TABLE 2

Boxes and Motifs identified in the permutated sequence of the PvARC5 promoter.

| | PvARC5 promotor permutated | | | Position | | | |
|---|---|---|---|---|---|---|---|
| Family | Further Family Information | Matrix | Opt. | Position from-to | Strand | Core sim. | Matrix sim. |
| P$PSRE | Pollen-specific regulatory elements | P$GAAA.01 | 0.83 | 9-25 | (+) | 1 | 0.862 |
| P$IDDF | ID domain factors | P$ID1.01 | 0.92 | 36-48 | (−) | 1 | 0.922 |
| P$MYBL | MYB-like proteins | P$ATMYB77.01 | 0.87 | 47-63 | (+) | 1 | 0.887 |
| P$RAV5 | 5'-part of bipartite RAV1 binding site | P$RAV1-5.01 | 0.96 | 48-58 | (+) | 1 | 0.96 |
| P$MYBL | MYB-like proteins | P$GAMYB.01 | 0.91 | 52-68 | (−) | 1 | 0.932 |
| P$STKM | Storekeeper motif | P$STK.01 | 0.85 | 58-72 | (+) | 0.79 | 0.894 |

TABLE 2-continued

Boxes and Motifs identified in the permutated sequence of the PvARC5 promoter.

PvARC5 promotor permutated

| Family | Further Family Information | Matrix | Opt. | Position from-to | Strand | Core sim. | Matrix sim. |
|---|---|---|---|---|---|---|---|
| P$MYBL | MYB-like proteins | P$MYBPH3.01 | 0.80 | 59-75 | (+) | 0.75 | 0.806 |
| P$L1BX | L1 box, motif for L1 layer-specific expression | P$ATML1.02 | 0.76 | 62-78 | (+) | 0.89 | 0.791 |
| O$INRE | Core promoter initiator elements | O$DINR.01 | 0.94 | 75-85 | (+) | 0.97 | 0.988 |
| P$AHBP | *Arabidopsis* homeobox protein | P$WUS.01 | 0.94 | 84-94 | (−) | 1 | 0.963 |
| P$MIIG | MYB IIG-type binding sites | P$PALBOXL.01 | 0.80 | 87-101 | (+) | 0.84 | 0.806 |
| P$NCS1 | Nodulin consensus sequence 1 | P$NCS1.01 | 0.85 | 106-116 | (+) | 1 | 0.99 |
| P$GAPB | GAP-Box (light response elements) | P$GAP.01 | 0.88 | 108-122 | (+) | 0.81 | 0.884 |
| P$AHBP | *Arabidopsis* homeobox protein | P$WUS.01 | 0.94 | 110-120 | (−) | 1 | 0.963 |
| P$IBOX | Plant I-Box sites | P$GATA.01 | 0.93 | 121-137 | (−) | 1 | 0.939 |
| P$GAGA | GAGA elements | P$GAGABP.01 | 0.75 | 125-149 | (−) | 0.75 | 0.764 |
| P$NCS2 | Nodulin consensus sequence 2 | P$NCS2.01 | 0.79 | 126-140 | (+) | 1 | 0.799 |
| P$AHBP | *Arabidopsis* homeobox protein | P$HAHB4.01 | 0.87 | 144-154 | (−) | 1 | 0.923 |
| P$AHBP | *Arabidopsis* homeobox protein | P$BLR.01 | 0.90 | 147-157 | (−) | 1 | 0.928 |
| O$VTBP | Vertebrate TATA binding protein factor | O$ATATA.01 | 0.78 | 149-165 | (+) | 1 | 0.78 |
| O$VTBP | Vertebrate TATA binding protein factor | O$LTATA.01 | 0.82 | 151-167 | (+) | 1 | 0.825 |
| P$NCS1 | Nodulin consensus sequence 1 | P$NCS1.01 | 0.85 | 164-174 | (−) | 1 | 0.898 |
| P$L1BX | L1 box, motif for L1 layer-specific expression | P$ATML1.01 | 0.82 | 175-191 | (+) | 0.75 | 0.872 |
| P$AHBP | *Arabidopsis* homeobox protein | P$ATHB5.01 | 0.89 | 177-187 | (+) | 0.83 | 0.902 |
| P$AHBP | *Arabidopsis* homeobox protein | P$ATHB5.01 | 0.89 | 177-187 | (−) | 1 | 1 |
| O$VTBP | Vertebrate TATA binding protein factor | O$ATATA.01 | 0.78 | 184-200 | (+) | 0.75 | 0.797 |
| P$TELO | Telo box (plant interstitial telomere motifs) | P$ATPURA.01 | 0.85 | 186-200 | (−) | 0.75 | 0.857 |
| P$PSRE | Pollen-specific regulatory elements | P$GAAA.01 | 0.83 | 188-204 | (−) | 1 | 0.843 |
| P$NCS2 | Nodulin consensus sequence 2 | P$NCS2.01 | 0.79 | 213-227 | (−) | 1 | 0.826 |
| P$IBOX | Plant I-Box sites | P$GATA.01 | 0.93 | 221-237 | (+) | 1 | 1 |
| P$SUCB | Sucrose box | P$SUCROSE.01 | 0.81 | 233-251 | (+) | 0.75 | 0.824 |
| P$MYBL | MYB-like proteins | P$MYBPH3.02 | 0.76 | 238-254 | (+) | 0.82 | 0.798 |
| P$SUCB | Sucrose box | P$SUCROSE.01 | 0.81 | 243-261 | (−) | 0.75 | 0.824 |
| P$AHBP | *Arabidopsis* homeobox protein | P$HAHB4.01 | 0.87 | 250-260 | (+) | 1 | 0.892 |
| P$PSRE | Pollen-specific regulatory elements | P$GAAA.01 | 0.83 | 257-273 | (+) | 1 | 0.881 |
| P$NCS1 | Nodulin consensus sequence 1 | P$NCS1.01 | 0.85 | 261-271 | (−) | 1 | 0.851 |
| P$MYBL | MYB-like proteins | P$MYBPH3.02 | 0.76 | 264-280 | (+) | 1 | 0.774 |
| O$VTBP | Vertebrate TATA binding protein factor | O$ATATA.01 | 0.78 | 267-283 | (+) | 1 | 0.872 |
| P$MYBL | MYB-like proteins | P$GAMYB.01 | 0.91 | 289-305 | (−) | 1 | 0.919 |
| P$SPF1 | Sweet potato DNA-binding factor with two WRKY-domains | P$SP8BF.01 | 0.87 | 298-310 | (−) | 1 | 0.872 |

TABLE 2-continued

Boxes and Motifs identified in the permutated sequence of the PvARC5 promoter.

PvARC5 promotor permutated

| Family | Further Family Information | Matrix | Opt. | Position from-to | Strand | Core sim. | Matrix sim. |
|---|---|---|---|---|---|---|---|
| P$BRRE | Brassinosteroid (BR) response element | P$BZR1.01 | 0.95 | 303-319 | (−) | 1 | 0.953 |
| P$GBOX | Plant G-box/C-box bZIP proteins | P$TGA1.01 | 0.90 | 327-347 | (−) | 1 | 0.909 |
| P$GTBX | GT-box elements | P$GT1.01 | 0.85 | 337-353 | (+) | 1 | 0.854 |
| P$IBOX | Plant I-Box sites | P$GATA.01 | 0.93 | 337-353 | (−) | 1 | 0.935 |
| P$PSRE | Pollen-specific regulatory elements | P$GAAA.01 | 0.83 | 342-358 | (−) | 1 | 0.896 |
| P$AHBP | *Arabidopsis* homeobox protein | P$ATHB9.01 | 0.77 | 343-353 | (−) | 1 | 0.869 |
| P$NCS1 | Nodulin consensus sequence 1 | P$NCS1.01 | 0.85 | 343-353 | (−) | 0.88 | 0.915 |
| P$GTBX | GT-box elements | P$S1F.01 | 0.79 | 344-360 | (−) | 0.75 | 0.827 |
| O$INRE | Core promoter initiator elements | O$DINR.01 | 0.94 | 345-355 | (+) | 0.97 | 0.945 |
| P$OPAQ | Opaque-2 like transcriptional activators | P$O2.01 | 0.87 | 351-367 | (−) | 1 | 0.919 |
| P$GTBX | GT-box elements | P$S1F.01 | 0.79 | 362-378 | (−) | 0.75 | 0.797 |
| P$AHBP | *Arabidopsis* homeobox protein | P$ATHB9.01 | 0.77 | 367-377 | (−) | 1 | 0.788 |
| P$AHBP | *Arabidopsis* homeobox protein | P$HAHB4.01 | 0.87 | 367-377 | (+) | 1 | 0.926 |
| P$GTBX | GT-box elements | P$SBF1.01 | 0.87 | 367-383 | (+) | 1 | 0.894 |
| P$L1BX | L1 box, motif for L1 layer-specific expression | P$ATML1.01 | 0.82 | 369-385 | (+) | 1 | 0.827 |
| P$AHBP | *Arabidopsis* homeobox protein | P$WUS.01 | 0.94 | 371-381 | (−) | 1 | 1 |
| P$MYBL | MYB-like proteins | P$ATMYB77.01 | 0.87 | 376-392 | (−) | 0.86 | 0.924 |
| P$CCAF | Circadian control factors | P$CCA1.01 | 0.85 | 387-401 | (+) | 1 | 0.851 |
| P$SUCB | Sucrose box | P$SUCROSE.01 | 0.81 | 392-410 | (+) | 1 | 0.864 |
| O$VTBP | Vertebrate TATA binding protein factor | O$LTATA.01 | 0.82 | 396-412 | (−) | 1 | 0.852 |
| P$LREM | Light responsive element motif, not modulated by different light qualities | P$RAP22.01 | 0.85 | 397-407 | (+) | 1 | 0.911 |
| P$AHBP | *Arabidopsis* homeobox protein | P$HAHB4.01 | 0.87 | 401-411 | (−) | 1 | 0.916 |
| P$MYBL | MYB-like proteins | P$WER.01 | 0.87 | 403-419 | (−) | 1 | 0.9 |
| P$MYBS | MYB proteins with single DNA binding repeat | P$OSMYBS.01 | 0.82 | 416-432 | (+) | 0.75 | 0.829 |
| P$L1BX | L1 box, motif for L1 layer-specific expression | P$ATML1.01 | 0.82 | 420-436 | (−) | 0.75 | 0.821 |
| O$VTBP | Vertebrate TA-TA binding protein factor | O$ATATA.01 | 0.78 | 426-442 | (+) | 0.75 | 0.819 |
| P$GTBX | GT-box elements | P$SBF1.01 | 0.87 | 426-442 | (−) | 1 | 0.902 |
| P$MYBL | MYB-like proteins | P$MYBPH3.02 | 0.76 | 428-444 | (−) | 1 | 0.772 |
| P$OCSE | Enhancer element first identified in the promoter of the octopine synthase gene (OCS) of the *Agrobacterium tumefaciens* T-DNA | P$OCSL.01 | 0.69 | 428-448 | (+) | 0.77 | 0.692 |
| P$TELO | Telo box (plant interstitial telomere motifs) | P$ATPURA.01 | 0.85 | 440-454 | (−) | 0.75 | 0.854 |

TABLE 2-continued

Boxes and Motifs identified in the permutated sequence of the PvARC5 promoter.

PvARC5 promotor permutated

| Family | Further Family Information | Matrix | Opt. | Position from-to | Strand | Core sim. | Matrix sim. |
|---|---|---|---|---|---|---|---|
| P$AHBP | Arabidopsis homeobox protein | P$ATHB5.01 | 0.89 | 455-465 | (+) | 0.83 | 0.902 |
| P$AHBP | Arabidopsis homeobox protein | P$HAHB4.01 | 0.87 | 455-465 | (−) | 1 | 0.979 |
| P$SUCB | Sucrose box | P$SUCROSE.01 | 0.81 | 461-479 | (−) | 0.75 | 0.815 |
| P$AHBP | Arabidopsis homeobox protein | P$HAHB4.01 | 0.87 | 468-478 | (+) | 1 | 0.901 |
| O$VTBP | Vertebrate TA-TA binding protein factor | O$VTATA.01 | 0.90 | 473-489 | (−) | 1 | 0.913 |
| O$PTBP | Plant TATA binding protein factor | O$PTATA.01 | 0.88 | 476-490 | (−) | 1 | 0.889 |
| O$VTBP | Vertebrate TA-TA binding protein factor | O$ATATA.01 | 0.78 | 489-505 | (−) | 0.75 | 0.825 |
| P$L1BX | L1 box, motif for L1 layer-specific expression | P$HDG9.01 | 0.77 | 491-507 | (+) | 1 | 0.791 |
| P$HMGF | High mobility group factors | P$HMG_IY.01 | 0.89 | 492-506 | (−) | 1 | 0.902 |
| P$CCAF | Circadian control factors | P$CCA1.01 | 0.85 | 498-512 | (+) | 0.76 | 0.862 |
| P$HMGF | High mobility group factors | P$HMG_IY.01 | 0.89 | 499-513 | (−) | 1 | 0.909 |
| P$SUCB | Sucrose box | P$SUCROSE.01 | 0.81 | 499-517 | (−) | 1 | 0.827 |
| P$GTBX | GT-box elements | P$SBF1.01 | 0.87 | 509-525 | (−) | 1 | 0.885 |
| P$SPF1 | Sweet potato DNA-binding factor with two WRKY-domains | P$SP8BF.01 | 0.87 | 520-532 | (−) | 1 | 0.905 |
| P$WBXF | W Box family | P$WRKY.01 | 0.92 | 526-542 | (−) | 1 | 0.936 |
| P$GARP | Myb-related DNA binding proteins (Golden2, ARR, Psr) | P$ARR10.01 | 0.97 | 540-548 | (+) | 1 | 0.976 |
| P$AHBP | Arabidopsis homeobox protein | P$ATHB9.01 | 0.77 | 558-568 | (−) | 1 | 0.775 |
| P$L1BX | L1 box, motif for L1 layer-specific expression | P$PDF2.01 | 0.85 | 558-574 | (−) | 1 | 0.865 |
| P$NCS1 | Nodulin consensus sequence 1 | P$NCS1.01 | 0.85 | 558-568 | (−) | 0.88 | 0.927 |
| P$EINL | Ethylen insensitive 3 like factors | P$TEIL.01 | 0.92 | 572-580 | (+) | 1 | 0.921 |
| P$SBPD | SBP-domain proteins | P$SBP.01 | 0.88 | 573-589 | (+) | 1 | 0.885 |
| P$AHBP | Arabidopsis homeobox protein | P$ATHB5.01 | 0.89 | 583-593 | (+) | 0.94 | 0.977 |
| P$AHBP | Arabidopsis homeobox protein | P$ATHB5.01 | 0.89 | 583-593 | (−) | 0.83 | 0.94 |
| P$MYCL | Myc-like basic helix-loop-helix binding factors | P$MYCRS.01 | 0.93 | 591-609 | (−) | 0.86 | 0.958 |
| P$OPAQ | Opaque-2 like transcriptional activators | P$O2_GCN4.01 | 0.81 | 593-609 | (+) | 1 | 0.838 |
| O$VTBP | Vertebrate TA-TA binding protein factor | O$VTATA.02 | 0.89 | 603-619 | (+) | 1 | 0.89 |
| P$L1BX | L1 box, motif for L1 layer-specific expression | P$HDG9.01 | 0.77 | 607-623 | (+) | 1 | 0.772 |
| P$IBOX | Plant I-Box sites | P$IBOX.01 | 0.81 | 610-626 | (+) | 0.75 | 0.824 |
| P$MYBS | MYB proteins with single DNA binding repeat | P$MYBST1.01 | 0.90 | 613-629 | (−) | 1 | 0.953 |
| P$IBOX | Plant I-Box sites | P$GATA.01 | 0.93 | 616-632 | (+) | 1 | 0.942 |

TABLE 2-continued

Boxes and Motifs identified in the permutated sequence of the PvARC5 promoter.

PvARC5 promotor permutated

| Family | Further Family Information | Matrix | Opt. | Position from-to | Strand | Core sim. | Matrix sim. |
|---|---|---|---|---|---|---|---|
| P$TEFB | TEF-box | P$TEF1.01 | 0.76 | 616-636 | (+) | 0.96 | 0.778 |
| P$MYBS | MYB proteins with single DNA binding repeat | P$TAMYB80.01 | 0.83 | 625-641 | (−) | 1 | 0.861 |
| O$PTBP | Plant TATA binding protein factor | O$PTATA.02 | 0.90 | 631-645 | (+) | 1 | 0.927 |
| O$PTBP | Plant TATA binding protein factor | O$PTATA.02 | 0.90 | 632-646 | (−) | 1 | 0.929 |
| P$L1BX | L1 box, motif for L1 layer-specific expression | P$HDG9.01 | 0.77 | 648-664 | (+) | 1 | 0.822 |
| P$HMGF | High mobility group factors | P$HMG_IY.01 | 0.89 | 649-663 | (−) | 1 | 0.923 |
| P$DOFF | DNA binding with one finger (DOF) | P$PBF.01 | 0.97 | 654-670 | (+) | 1 | 0.979 |
| P$LREM | Light responsive element motif, not modulated by different light qualities | P$RAP22.01 | 0.85 | 682-692 | (−) | 1 | 0.975 |
| P$MYBL | MYB-like proteins | P$CARE.01 | 0.83 | 689-705 | (+) | 1 | 0.884 |
| P$TEFB | TEF-box | P$TEF1.01 | 0.76 | 696-716 | (−) | 0.84 | 0.779 |
| P$MYBL | MYB-like proteins | P$CARE.01 | 0.83 | 699-715 | (−) | 1 | 0.88 |
| P$LEGB | Legumin Box family | P$RY.01 | 0.87 | 704-730 | (+) | 1 | 0.94 |
| P$GBOX | Plant G-box/C-box bZIP proteins | P$BZIP910.01 | 0.77 | 716-736 | (−) | 0.75 | 0.856 |
| P$GBOX | Plant G-box/C-box bZIP proteins | P$ROM.01 | 0.85 | 717-737 | (+) | 1 | 1 |
| P$ABRE | ABA response elements | P$ABF1.03 | 0.82 | 719-735 | (−) | 0.75 | 0.857 |
| P$GBOX | Plant G-box/C-box bZIP proteins | P$BZIP910.02 | 0.84 | 722-742 | (−) | 0.75 | 0.862 |
| P$GBOX | Plant G-box/C-box bZIP proteins | P$HBP1B.01 | 0.83 | 734-754 | (+) | 0.77 | 0.852 |
| P$MYCL | Myc-like basic helix-loop-helix binding factors | P$MYCRS.01 | 0.93 | 739-757 | (−) | 0.86 | 0.953 |
| P$ABRE | ABA response elements | P$ABF1.01 | 0.79 | 741-757 | (−) | 0.75 | 0.796 |
| P$OPAQ | Opaque-2 like transcriptional activators | P$O2_GCN4.01 | 0.81 | 741-757 | (+) | 1 | 0.871 |
| P$OPAQ | Opaque-2 like transcriptional activators | P$GCN4.01 | 0.81 | 745-761 | (−) | 1 | 0.85 |
| P$AREF | Auxin response element | P$ARE.01 | 0.93 | 747-759 | (+) | 1 | 0.941 |
| P$MYBL | MYB-like proteins | P$GAMYB.01 | 0.91 | 754-770 | (+) | 1 | 0.933 |
| O$INRE | Core promoter initiator elements | O$DINR.01 | 0.94 | 757-767 | (+) | 1 | 0.943 |
| P$WBXF | W Box family | P$WRKY.01 | 0.92 | 780-796 | (+) | 1 | 0.942 |
| P$TEFB | TEF-box | P$TEF1.01 | 0.76 | 783-803 | (−) | 0.84 | 0.779 |
| P$MYBL | MYB-like proteins | P$CARE.01 | 0.83 | 786-802 | (−) | 1 | 0.876 |
| P$LEGB | Legumin Box family | P$RY.01 | 0.87 | 788-814 | (−) | 1 | 0.929 |
| P$LEGB | Legumin Box family | P$RY.01 | 0.87 | 791-817 | (+) | 1 | 0.984 |
| P$ROOT | Root hair-specific cis-elements in angiosperms | P$RHE.01 | 0.77 | 796-820 | (+) | 1 | 0.812 |
| P$GBOX | Plant G-box/C-box bZIP proteins | P$CPRF.01 | 0.95 | 803-823 | (−) | 1 | 0.989 |
| P$GBOX | Plant G-box/C-box bZIP proteins | P$CPRF.01 | 0.95 | 804-824 | (+) | 1 | 0.98 |

TABLE 2-continued

Boxes and Motifs identified in the permutated sequence of the PvARC5 promoter.

PvARC5 promotor permutated

| Family | Further Family Information | Matrix | Opt. | Position from-to | Strand | Core sim. | Matrix sim. |
|---|---|---|---|---|---|---|---|
| P$MYCL | Myc-like basic helix-loop-helix binding factors | P$MYCRS.01 | 0.93 | 804-822 | (−) | 1 | 0.956 |
| P$ABRE | ABA response elements | P$ABRE.01 | 0.82 | 805-821 | (+) | 1 | 0.874 |
| P$MYCL | Myc-like basic helix-loop-helix binding factors | P$PIF3.01 | 0.82 | 805-823 | (+) | 1 | 0.922 |
| P$OPAQ | Opaque-2 like transcriptional activators | P$RITA1.01 | 0.95 | 805-821 | (−) | 1 | 0.992 |
| P$ABRE | ABA response elements | P$ABF1.03 | 0.82 | 806-822 | (−) | 1 | 0.977 |
| P$OPAQ | Opaque-2 like transcriptional activators | P$RITA1.01 | 0.95 | 806-822 | (+) | 1 | 0.973 |
| P$OCSE | Enhancer element first identified in the promoter of the octopine synthase gene (OCS) of the *Agrobacterium tumefaciens* T-DNA | P$OCSL.01 | 0.69 | 809-829 | (−) | 1 | 0.819 |
| P$GTBX | GT-box elements | P$S1F.01 | 0.79 | 823-839 | (−) | 1 | 0.802 |
| P$LFYB | LFY binding site | P$LFY.01 | 0.93 | 839-851 | (−) | 0.91 | 0.936 |
| P$LEGB | Legumin Box family | P$RY.01 | 0.87 | 840-866 | (−) | 1 | 0.948 |
| P$LEGB | Legumin Box family | P$RY.01 | 0.87 | 843-869 | (+) | 1 | 0.966 |
| P$LEGB | Legumin Box family | P$IDE1.01 | 0.77 | 847-873 | (+) | 1 | 0.779 |
| P$GBOX | Plant G-box/C-box bZIP proteins | P$BZIP910.01 | 0.77 | 855-875 | (−) | 0.75 | 0.856 |
| P$GBOX | Plant G-box/C-box bZIP proteins | P$ROM.01 | 0.85 | 856-876 | (+) | 1 | 1 |
| P$ABRE | ABA response elements | P$ABF1.03 | 0.82 | 858-874 | (−) | 0.75 | 0.857 |
| P$GCCF | GCC box family | P$ERE_JERE.01 | 0.85 | 870-882 | (−) | 0.81 | 0.86 |
| P$HEAT | Heat shock factors | P$HSE.01 | 0.81 | 880-894 | (−) | 1 | 0.827 |
| P$MYBS | MYB proteins with single DNA binding repeat | P$ZMMRP1.01 | 0.79 | 881-897 | (+) | 0.81 | 0.867 |
| P$LEGB | Legumin Box family | P$RY.01 | 0.87 | 895-921 | (+) | 1 | 0.924 |
| P$GBOX | Plant G-box/C-box bZIP proteins | P$BZIP910.01 | 0.77 | 907-927 | (−) | 0.75 | 0.856 |
| P$GBOX | Plant G-box/C-box bZIP proteins | P$ROM.01 | 0.85 | 908-928 | (+) | 1 | 0.938 |
| P$ABRE | ABA response elements | P$ABF1.03 | 0.82 | 910-926 | (−) | 0.75 | 0.864 |
| P$GBOX | Plant G-box/C-box bZIP proteins | P$BZIP910.02 | 0.84 | 913-933 | (−) | 0.75 | 0.871 |
| P$SBPD | SBP-domain proteins | P$SBP.01 | 0.88 | 939-955 | (+) | 1 | 0.887 |
| P$EINL | Ethylen insensitive 3 like factors | P$TEIL.01 | 0.92 | 942-950 | (+) | 0.84 | 0.922 |
| P$MADS | MADS box proteins | P$SQUA.01 | 0.90 | 960-980 | (−) | 1 | 0.908 |
| P$L1BX | L1 box, motif for L1 layer-specific expression | P$PDF2.01 | 0.85 | 963-979 | (+) | 1 | 0.856 |
| P$LREM | Light responsive element motif, not modulated | P$RAP22.01 | 0.85 | 972-982 | (+) | 1 | 0.858 |

TABLE 2-continued

Boxes and Motifs identified in the permutated sequence of the PvARC5 promoter.

PvARC5 promotor permutated

| Family | Further Family Information | Matrix | Opt. | Position from-to | Strand | Core sim. | Matrix sim. |
|---|---|---|---|---|---|---|---|
| | by different light qualities | | | | | | |
| O$PTBP | Plant TATA binding protein factor | O$PTATA.01 | 0.88 | 974-988 | (−) | 0.83 | 0.905 |
| O$VTBP | Vertebrate TA-TA binding protein factor | O$ATATA.01 | 0.78 | 974-990 | (+) | 0.75 | 0.83 |
| O$VTBP | Vertebrate TA-TA binding protein factor | O$MTATA.01 | 0.84 | 976-992 | (+) | 1 | 0.855 |
| P$MYBL | MYB-like proteins | P$MYBPH3.02 | 0.76 | 983-999 | (−) | 1 | 0.867 |
| P$SUCB | Sucrose box | P$SUCROSE.01 | 0.81 | 984-1002 | (−) | 1 | 0.81 |
| P$AHBP | *Arabidopsis* homeobox protein | P$ATHB1.01 | 0.90 | 991-1001 | (+) | 1 | 0.989 |
| P$AHBP | *Arabidopsis* homeobox protein | P$HAHB4.01 | 0.87 | 991-1001 | (−) | 1 | 0.943 |
| P$HMGF | High mobility group factors | P$HMG_IY.01 | 0.89 | 992-1006 | (+) | 1 | 0.913 |
| P$OCSE | Enhancer element first identified in the promoter of the octopine synthase gene (OCS) of the *Agrobacterium tumefaciens* T-DNA | P$OCSL.01 | 0.69 | 1004-1024 | (+) | 1 | 0.827 |
| P$GBOX | Plant G-box/C-box bZIP proteins | P$UPRE.01 | 0.86 | 1009-1029 | (−) | 1 | 0.974 |
| P$GBOX | Plant G-box/C-box bZIP proteins | P$TGA1.01 | 0.90 | 1010-1030 | (+) | 1 | 0.991 |
| P$ABRE | ABA response elements | P$ABF1.03 | 0.82 | 1011-1027 | (+) | 1 | 0.828 |
| P$OPAQ | Opaque-2 like transcriptional activators | P$O2.01 | 0.87 | 1011-1027 | (−) | 1 | 0.99 |
| P$OPAQ | Opaque-2 like transcriptional activators | P$O2_GCN4.01 | 0.81 | 1012-1028 | (+) | 0.95 | 0.893 |
| P$ROOT | Root hair-specific cis-elements in angiosperms | P$RHE.01 | 0.77 | 1013-1037 | (−) | 1 | 0.771 |
| P$LEGB | Legumin Box family | P$LEGB.01 | 0.65 | 1025-1051 | (+) | 1 | 0.656 |
| P$AHBP | *Arabidopsis* homeobox protein | P$ATHB5.01 | 0.89 | 1042-1052 | (+) | 0.83 | 0.902 |
| P$AHBP | *Arabidopsis* homeobox protein | P$ATHB5.01 | 0.89 | 1042-1052 | (−) | 1 | 1 |
| P$GTBX | GT-box elements | P$SBF1.01 | 0.87 | 1045-1061 | (+) | 1 | 0.888 |
| P$GTBX | GT-box elements | P$SBF1.01 | 0.87 | 1046-1062 | (−) | 1 | 0.888 |
| P$IBOX | Plant I-Box sites | P$GATA.01 | 0.93 | 1060-1076 | (+) | 1 | 0.949 |
| O$INRE | Core promoter initiator elements | O$DINR.01 | 0.94 | 1070-1080 | (−) | 0.97 | 0.949 |
| P$NACF | Plant specific NAC [NAM (no apical meristem), ATAF172, CUC2 (cup-shaped cotyledons 2)] transcription factors | P$TANAC69.01 | 0.68 | 1078-1100 | (+) | 1 | 0.775 |
| P$CCAF | Circadian control factors | P$CCA1.01 | 0.85 | 1093-1107 | (−) | 1 | 0.949 |
| P$MADS | MADS box proteins | P$SQUA.01 | 0.90 | 1097-1117 | (+) | 1 | 0.908 |
| P$CARM | CA-rich motif | P$CARICH.01 | 0.78 | 1102-1120 | (−) | 1 | 0.791 |
| P$MADS | MADS box proteins | P$SQUA.01 | 0.90 | 1108-1128 | (−) | 1 | 0.928 |

TABLE 2-continued

Boxes and Motifs identified in the permutated sequence of the PvARC5 promoter.

PvARC5 promotor permutated

| Family | Further Family Information | Matrix | Opt. | Position from-to | Strand | Core sim. | Matrix sim. |
|---|---|---|---|---|---|---|---|
| O$PTBP | Plant TATA binding protein factor | O$PTATA.01 | 0.88 | 1111-1125 | (+) | 1 | 0.961 |
| O$VTBP | Vertebrate TA-TA binding protein factor | O$VTATA.01 | 0.90 | 1112-1128 | (+) | 1 | 0.968 |
| P$LEGB | Legumin Box family | P$RY.01 | 0.87 | 1130-1156 | (−) | 1 | 0.932 |
| P$LEGB | Legumin Box family | P$RY.01 | 0.87 | 1138-1164 | (−) | 1 | 0.914 |
| P$ROOT | Root hair-specific cis-elements in angiosperms | P$RHE.01 | 0.77 | 1138-1162 | (+) | 0.75 | 0.794 |
| P$L1BX | L1 box, motif for L1 layer-specific expression | P$ATML1.01 | 0.82 | 1141-1157 | (+) | 0.75 | 0.833 |

Preferably associated boxes are annotated in line 38, 43, 116, 121, 124, 128, 129, 137, 138, 143, 145, 146, 147, 151, 152, 153, 156, 162, 165, 175, 184, 186, 188, 203 and 205 of tables 1 and 2. Essential boxes are annotated in line 83, 111, 112, 172 and 201 of tables 1 and 2.

TABLE 3

Boxes and Motifs identified in the starting sequence of the VfSBP promoter p-VfSBP (nativ)

| Family | Further Family Information | Matrix | Opt. | Position from-to | Strand | Core sim. | Matrix sim. |
|---|---|---|---|---|---|---|---|
| P$MYBS | MYB proteins with single DNA binding repeat | P$MYBST1.01 | 0.90 | 12-28 | (+) | 1 | 0.918 |
| P$GAGA | GAGA elements | P$BPC.01 | 1.00 | 25-49 | (−) | 1 | 1 |
| P$LEGB | Legumin Box family | P$IDE1.01 | 0.77 | 80-106 | (−) | 1 | 0.805 |
| P$GTBX | GT-box elements | P$GT3A.01 | 0.83 | 85-101 | (−) | 1 | 0.843 |
| P$PSRE | Pollen-specific regulatory elements | P$GAAA.01 | 0.83 | 101-117 | (−) | 1 | 0.883 |
| P$SPF1 | Sweet potato DNA-binding factor with two WRKY-domains | P$SP8BF.01 | 0.87 | 118-130 | (+) | 1 | 0.897 |
| P$GBOX | Plant G-box/C-box bZIP proteins | P$HBP1B.01 | 0.83 | 138-158 | (+) | 1 | 0.834 |
| P$MYBL | MYB-like proteins | P$MYBPH3.02 | 0.76 | 165-181 | (−) | 0.78 | 0.788 |
| P$NACF | Plant specific NAC [NAM (no apical meristem), ATAF172, CUC2 (cup-shaped cotyledons 2)] transcription factors | P$TANAC69.01 | 0.68 | 173-195 | (−) | 0.81 | 0.729 |
| P$MADS | MADS box proteins | P$AGL1.01 | 0.84 | 174-194 | (−) | 0.98 | 0.862 |
| P$MADS | MADS box proteins | P$AGL1.01 | 0.84 | 175-195 | (+) | 0.98 | 0.863 |
| P$TCPF | DNA-binding proteins with the plant specific TCP-domain | P$ATTCP20.01 | 0.94 | 189-201 | (+) | 1 | 0.968 |

TABLE 3-continued

Boxes and Motifs identified in the starting sequence of the VfSBP promoter p-VfSBP
(nativ)

| Family | Further Family Information | Matrix | Opt. | Position from-to | Strand | Core sim. | Matrix sim. |
|---|---|---|---|---|---|---|---|
| P$L1BX | L1 box, motif for L1 layer-specific expression | P$ATML1.02 | 0.76 | 194-210 | (−) | 0.89 | 0.8 |
| P$AHBP | *Arabidopsis* homeobox protein | P$BLR.01 | 0.90 | 198-208 | (+) | 0.83 | 0.936 |
| O$VTBP | Vertebrate TATA binding protein factor | O$ATATA.01 | 0.78 | 207-223 | (+) | 0.75 | 0.811 |
| P$EINL | Ethylen insensitive 3 like factors | P$TEIL.01 | 0.92 | 215-223 | (−) | 0.96 | 0.924 |
| P$GBOX | Plant G-box/C-box bZIP proteins | P$HBP1A.01 | 0.88 | 217-237 | (−) | 1 | 0.908 |
| P$GBOX | Plant G-box/C-box bZIP proteins | P$GBF1.01 | 0.94 | 218-238 | (+) | 1 | 0.963 |
| P$GTBX | GT-box elements | P$S1F.01 | 0.79 | 218-234 | (+) | 1 | 0.821 |
| P$ABRE | ABA response elements | P$ABF1.03 | 0.82 | 219-235 | (+) | 1 | 0.825 |
| P$ROOT | Root hair-specific cis-elements in angiosperms | P$RHE.01 | 0.77 | 221-245 | (−) | 1 | 0.803 |
| P$CE1F | Coupling element 1 binding factors | P$SBOX.01 | 0.87 | 222-234 | (−) | 0.78 | 0.916 |
| O$VTBP | Vertebrate TATA binding protein factor | O$VTATA.01 | 0.90 | 233-249 | (−) | 1 | 0.916 |
| O$PTBP | Plant TATA binding protein factor | O$PTATA.02 | 0.90 | 236-250 | (−) | 1 | 0.9 |
| P$AHBP | *Arabidopsis* homeobox protein | P$ATHB5.01 | 0.89 | 256-266 | (+) | 0.94 | 0.896 |
| P$NCS1 | Nodulin consensus sequence 1 | P$NCS1.01 | 0.85 | 256-266 | (−) | 0.88 | 0.871 |
| P$LREM | Light responsive element motif, not modulated by different light qualities | P$RAP22.01 | 0.85 | 290-300 | (−) | 1 | 0.931 |
| P$AGP1 | Plant GATA-type zinc finger protein | P$AGP1.01 | 0.91 | 292-302 | (−) | 1 | 0.984 |
| P$LREM | Light responsive element motif, not modulated by different light qualities | P$RAP22.01 | 0.85 | 306-316 | (+) | 1 | 0.938 |
| P$MYBL | MYB-like proteins | P$CARE.01 | 0.83 | 308-324 | (−) | 1 | 0.854 |
| P$CCAF | Circadian control factors | P$CCA1.01 | 0.85 | 354-368 | (+) | 1 | 0.895 |
| P$HEAT | Heat shock factors | P$HSE.01 | 0.81 | 375-389 | (−) | 1 | 0.861 |
| P$MYBL | MYB-like proteins | P$WER.01 | 0.87 | 392-408 | (−) | 1 | 0.87 |
| P$MYBL | MYB-like proteins | P$WER.01 | 0.87 | 394-410 | (+) | 1 | 0.95 |
| P$MSAE | M-phase-specific activator elements | P$MSA.01 | 0.80 | 395-409 | (−) | 0.75 | 0.808 |
| P$HEAT | Heat shock factors | P$HSE.01 | 0.81 | 415-429 | (+) | 1 | 0.811 |
| P$SUCB | Sucrose box | P$SUCROSE.01 | 0.81 | 421-439 | (−) | 0.75 | 0.852 |
| P$WBXF | W Box family | P$WRKY.01 | 0.92 | 426-442 | (+) | 1 | 0.939 |
| P$DOFF | DNA binding with one finger (DOF) | P$PBOX.01 | 0.75 | 431-447 | (−) | 0.76 | 0.782 |
| P$WBXF | W Box family | P$WRKY.01 | 0.92 | 453-469 | (+) | 1 | 0.958 |
| P$MYBL | MYB-like proteins | P$MYBPH3.02 | 0.76 | 468-484 | (−) | 0.82 | 0.849 |
| P$OPAQ | Opaque-2 like transcriptional activators | P$O2_GCN4.01 | 0.81 | 486-502 | (+) | 1 | 0.818 |

TABLE 3-continued

Boxes and Motifs identified in the starting sequence of the VfSBP promoter p-VfSBP (nativ)

| Family | Further Family Information | Matrix | Opt. | Position from-to | Strand | Core sim. | Matrix sim. |
|---|---|---|---|---|---|---|---|
| P$OPAQ | Opaque-2 like transcriptional activators | P$O2.01 | 0.87 | 498-514 | (−) | 1 | 0.919 |
| P$HEAT | Heat shock factors | P$HSE.01 | 0.81 | 512-526 | (−) | 1 | 0.85 |
| P$WBXF | W Box family | P$WRKY.01 | 0.92 | 533-549 | (−) | 1 | 0.966 |
| P$WBXF | W Box family | P$WRKY.01 | 0.92 | 543-559 | (+) | 1 | 0.966 |
| P$WBXF | W Box family | P$ERE.01 | 0.89 | 562-578 | (+) | 1 | 0.972 |
| P$DOFF | DNA binding with one finger (DOF) | P$PBOX.01 | 0.75 | 614-630 | (+) | 0.76 | 0.766 |
| P$GTBX | GT-box elements | P$S1F.01 | 0.79 | 630-646 | (+) | 1 | 0.819 |
| P$AGP1 | Plant GATA-type zinc finger protein | P$AGP1.01 | 0.91 | 636-646 | (−) | 1 | 0.913 |
| P$AGP1 | Plant GATA-type zinc finger protein | P$AGP1.01 | 0.91 | 637-647 | (+) | 1 | 0.915 |
| P$HEAT | Heat shock factors | P$HSE.01 | 0.81 | 649-663 | (+) | 0.78 | 0.87 |
| P$HEAT | Heat shock factors | P$HSE.01 | 0.81 | 654-668 | (−) | 1 | 0.815 |
| O$INRE | Core promoter initiator elements | O$DINR.01 | 0.94 | 660-670 | (−) | 1 | 0.944 |
| P$GAPB | GAP-Box (light response elements) | P$GAP.01 | 0.88 | 702-716 | (−) | 1 | 0.897 |
| P$GTBX | GT-box elements | P$GT1.01 | 0.85 | 723-739 | (−) | 1 | 0.925 |
| P$AHBP | *Arabidopsis* homeobox protein | P$WUS.01 | 0.94 | 726-736 | (−) | 1 | 1 |
| P$MYBL | MYB-like proteins | P$GAMYB.01 | 0.91 | 773-789 | (+) | 1 | 0.951 |
| P$GTBX | GT-box elements | P$GT3A.01 | 0.83 | 775-791 | (+) | 1 | 0.899 |
| P$MYBL | MYB-like proteins | P$CARE.01 | 0.83 | 801-817 | (−) | 1 | 0.837 |
| O$VTBP | Vertebrate TATA binding protein factor | O$ATATA.01 | 0.78 | 803-819 | (−) | 1 | 0.811 |
| O$VTBP | Vertebrate TATA binding protein factor | O$ATATA.01 | 0.78 | 819-835 | (−) | 0.75 | 0.874 |
| P$MADS | MADS box proteins | P$AGL15.01 | 0.79 | 827-847 | (−) | 0.83 | 0.791 |
| P$MADS | MADS box proteins | P$AGL15.01 | 0.79 | 828-848 | (+) | 1 | 0.895 |
| P$CCAF | Circadian control factors | P$CCA1.01 | 0.85 | 843-857 | (−) | 1 | 0.883 |
| P$GTBX | GT-box elements | P$SBF1.01 | 0.87 | 844-860 | (−) | 1 | 0.948 |
| P$CARM | CA-rich motif | P$CARICH.01 | 0.78 | 845-863 | (+) | 1 | 0.806 |
| P$PSRE | Pollen-specific regulatory elements | P$GAAA.01 | 0.83 | 858-874 | (+) | 0.75 | 0.831 |
| P$MYBL | MYB-like proteins | P$NTMYBAS1.01 | 0.96 | 867-883 | (+) | 1 | 0.963 |
| P$GTBX | GT-box elements | P$SBF1.01 | 0.87 | 869-885 | (+) | 1 | 0.883 |
| P$RAV5 | 5'-part of bipartite RAV1 binding site | P$RAV1-5.01 | 0.96 | 882-892 | (+) | 1 | 0.96 |
| P$AHBP | *Arabidopsis* homeobox protein | P$WUS.01 | 0.94 | 888-898 | (−) | 1 | 1 |
| P$GTBX | GT-box elements | P$SBF1.01 | 0.87 | 897-913 | (+) | 1 | 0.886 |
| P$AHBP | *Arabidopsis* homeobox protein | P$BLR.01 | 0.90 | 906-916 | (+) | 1 | 1 |
| P$AHBP | *Arabidopsis* homeobox protein | P$BLR.01 | 0.90 | 907-917 | (−) | 1 | 0.903 |
| P$CARM | CA-rich motif | P$CARICH.01 | 0.78 | 908-926 | (−) | 1 | 0.826 |
| P$MYBL | MYB-like proteins | P$NTMYBAS1.01 | 0.96 | 916-932 | (−) | 1 | 0.962 |
| P$MIIG | MYB IIG-type binding sites | P$PALBOXP.01 | 0.81 | 918-932 | (−) | 0.94 | 0.817 |
| P$DOFF | DNA binding with one finger (DOF) | P$DOF1.01 | 0.98 | 929-945 | (−) | 1 | 0.983 |
| P$GTBX | GT-box elements | P$GT1.01 | 0.85 | 933-949 | (+) | 0.97 | 0.854 |
| O$VTBP | Vertebrate TATA binding protein factor | O$LTATA.01 | 0.82 | 944-960 | (+) | 1 | 0.829 |

TABLE 3-continued

Boxes and Motifs identified in the starting sequence of the VfSBP promoter p-VfSBP (nativ)

| Family | Further Family Information | Matrix | Opt. | Position from-to | Strand | Core sim. | Matrix sim. |
|---|---|---|---|---|---|---|---|
| P$AHBP | *Arabidopsis* homeobox protein | P$ATHB9.01 | 0.77 | 959-969 | (+) | 0.75 | 0.816 |
| P$AHBP | *Arabidopsis* homeobox protein | P$ATHB9.01 | 0.77 | 959-969 | (−) | 1 | 0.909 |
| P$AHBP | *Arabidopsis* homeobox protein | P$HAHB4.01 | 0.87 | 970-980 | (+) | 1 | 0.916 |
| P$AHBP | *Arabidopsis* homeobox protein | P$ATHB1.01 | 0.90 | 973-983 | (+) | 1 | 0.989 |
| P$AHBP | *Arabidopsis* homeobox protein | P$HAHB4.01 | 0.87 | 973-983 | (−) | 1 | 0.976 |
| P$IDDF | ID domain factors | P$ID1.01 | 0.92 | 976-988 | (+) | 1 | 0.928 |
| P$IBOX | Plant I-Box sites | P$GATA.01 | 0.93 | 995-1011 | (+) | 1 | 0.96 |
| P$AHBP | *Arabidopsis* homeobox protein | P$HAHB4.01 | 0.87 | 1008-1018 | (+) | 1 | 0.937 |
| P$AHBP | *Arabidopsis* homeobox protein | P$WUS.01 | 0.94 | 1012-1022 | (−) | 1 | 1 |
| P$SPF1 | Sweet potato DNA-binding factor with two WRKY-domains | P$SP8BF.01 | 0.87 | 1029-1041 | (−) | 0.78 | 0.879 |
| P$SUCB | Sucrose box | P$SUCROSE.01 | 0.81 | 1036-1054 | (−) | 1 | 0.822 |
| P$AHBP | *Arabidopsis* homeobox protein | P$ATHB1.01 | 0.90 | 1054-1064 | (+) | 1 | 0.99 |
| P$AHBP | *Arabidopsis* homeobox protein | P$ATHB5.01 | 0.89 | 1054-1064 | (−) | 0.83 | 0.94 |
| P$GTBX | GT-box elements | P$GT3A.01 | 0.83 | 1066-1082 | (+) | 1 | 0.889 |
| O$PTBP | Plant TATA binding protein factor | O$PTATA.02 | 0.90 | 1086-1100 | (+) | 1 | 0.94 |
| O$VTBP | Vertebrate TATA binding protein factor | O$VTATA.01 | 0.90 | 1087-1103 | (+) | 0.89 | 0.927 |
| O$PTBP | Plant TATA binding protein factor | O$PTATA.01 | 0.88 | 1088-1102 | (+) | 1 | 0.958 |
| O$VTBP | Vertebrate TATA binding protein factor | O$VTATA.01 | 0.90 | 1089-1105 | (+) | 1 | 0.971 |
| P$E2FF | E2F-homolog cell cycle regulators | P$E2F.01 | 0.82 | 1117-1131 | (−) | 1 | 0.833 |
| P$PSRE | Pollen-specific regulatory elements | P$GAAA.01 | 0.83 | 1146-1162 | (+) | 1 | 0.908 |
| P$GTBX | GT-box elements | P$S1F.01 | 0.79 | 1153-1169 | (+) | 1 | 0.8 |
| P$GTBX | GT-box elements | P$S1F.01 | 0.79 | 1170-1186 | (−) | 1 | 0.797 |
| P$SUCB | Sucrose box | P$SUCROSE.01 | 0.81 | 1173-1191 | (+) | 1 | 0.813 |
| P$MADS | MADS box proteins | P$AGL2.01 | 0.82 | 1174-1194 | (+) | 1 | 0.9 |
| P$AHBP | *Arabidopsis* homeobox protein | P$BLR.01 | 0.90 | 1189-1199 | (+) | 0.83 | 0.919 |
| P$DOFF | DNA binding with one finger (DOF) | P$PBOX.01 | 0.75 | 1229-1245 | (−) | 0.76 | 0.763 |
| P$MYBL | MYB-like proteins | P$WER.01 | 0.87 | 1234-1250 | (−) | 0.94 | 0.88 |
| O$PTBP | Plant TATA binding protein factor | O$PTATA.01 | 0.88 | 1241-1255 | (+) | 1 | 0.964 |
| O$VTBP | Vertebrate TATA binding protein factor | O$VTATA.01 | 0.90 | 1242-1258 | (+) | 1 | 0.967 |
| P$DOFF | DNA binding with one finger (DOF) | P$PBOX.01 | 0.75 | 1265-1281 | (−) | 0.76 | 0.762 |
| P$GTBX | GT-box elements | P$GT3A.01 | 0.83 | 1265-1281 | (+) | 0.75 | 0.839 |
| P$AHBP | *Arabidopsis* homeobox protein | P$BLR.01 | 0.90 | 1274-1284 | (−) | 1 | 0.928 |
| P$OCSE | Enhancer element first identified in the | P$OCSL.01 | 0.69 | 1278-1298 | (+) | 0.77 | 0.732 |

TABLE 3-continued

Boxes and Motifs identified in the starting sequence of the VfSBP promoter p-VfSBP
(nativ)

| Family | Further Family Information | Matrix | Opt. | Position from-to | Strand | Core sim. | Matrix sim. |
|---|---|---|---|---|---|---|---|
| | promoter of the octopine synthase gene (OCS) of the *Agrobacterium tumefaciens* T-DNA | | | | | | |
| P$MYCL | Myc-like basic helix-loop-helix binding factors | P$MYCRS.01 | 0.93 | 1284-1302 | (−) | 0.86 | 0.963 |
| P$TALE | TALE (3-aa acid loop extension) class homeodomain proteins | P$KN1__KIP.01 | 0.88 | 1289-1301 | (−) | 1 | 1 |
| P$AREF | Auxin response element | P$SEBF.01 | 0.96 | 1292-1304 | (+) | 1 | 0.98 |
| P$MSAE | M-phase-specific activator elements | P$MSA.01 | 0.80 | 1295-1309 | (−) | 0.75 | 0.818 |
| P$DOFF | DNA binding with one finger (DOF) | P$PBOX.01 | 0.75 | 1296-1312 | (−) | 1 | 0.776 |
| P$MYBL | MYB-like proteins | P$WER.01 | 0.87 | 1310-1326 | (−) | 0.94 | 0.876 |
| P$AHBP | *Arabidopsis* homeobox protein | P$BLR.01 | 0.90 | 1319-1329 | (+) | 1 | 0.93 |
| O$VTBP | Vertebrate TATA binding protein factor | O$ATATA.01 | 0.78 | 1323-1339 | (−) | 1 | 0.881 |
| P$LREM | Light responsive element motif, not modulated by different light qualities | P$RAP22.01 | 0.85 | 1327-1337 | (−) | 1 | 0.936 |
| P$GTBX | GT-box elements | P$SBF1.01 | 0.87 | 1338-1354 | (+) | 1 | 0.896 |
| P$SUCB | Sucrose box | P$SUCROSE.01 | 0.81 | 1338-1356 | (−) | 1 | 0.819 |
| P$AHBP | *Arabidopsis* homeobox protein | P$ATHB5.01 | 0.89 | 1345-1355 | (+) | 0.83 | 0.902 |
| P$AHBP | *Arabidopsis* homeobox protein | P$BLR.01 | 0.90 | 1345-1355 | (−) | 1 | 0.998 |
| P$AGP1 | Plant GATA-type zinc finger protein | P$AGP1.01 | 0.91 | 1354-1364 | (−) | 1 | 0.916 |
| O$VTBP | Vertebrate TA-TA binding protein factor | O$VTATA.01 | 0.90 | 1376-1392 | (−) | 1 | 0.949 |
| P$HMGF | High mobility group factors | P$HMG__IY.01 | 0.89 | 1377-1391 | (+) | 1 | 0.952 |
| O$PTBP | Plant TATA binding protein factor | O$PTATA.01 | 0.88 | 1379-1393 | (−) | 1 | 0.883 |
| P$IBOX | Plant I-Box sites | P$IBOX.01 | 0.81 | 1399-1415 | (−) | 0.75 | 0.822 |
| O$VTBP | Vertebrate TATA binding protein factor | O$LTATA.01 | 0.82 | 1417-1433 | (−) | 1 | 0.86 |
| P$IBOX | Plant I-Box sites | P$IBOX.01 | 0.81 | 1419-1435 | (−) | 0.75 | 0.824 |
| P$WBXF | W Box family | P$WRKY.01 | 0.92 | 1429-1445 | (−) | 1 | 0.958 |
| P$MYBL | MYB-like proteins | P$MYBPH3.02 | 0.76 | 1457-1473 | (+) | 0.82 | 0.798 |
| P$ROOT | Root hair-specific cis-elements in angiosperms | P$RHE.02 | 0.77 | 1458-1482 | (+) | 0.75 | 0.786 |
| P$LFYB | LFY binding site | P$LFY.01 | 0.93 | 1486-1498 | (−) | 0.91 | 0.987 |
| P$CAAT | CCAAT binding factors | P$CAAT.01 | 0.97 | 1490-1498 | (−) | 1 | 0.982 |
| P$HEAT | Heat shock factors | P$HSE.01 | 0.81 | 1526-1540 | (+) | 1 | 0.833 |

TABLE 3-continued

Boxes and Motifs identified in the starting sequence of the VfSBP promoter p-VfSBP (nativ)

| Family | Further Family Information | Matrix | Opt. | Position from-to | Strand | Core sim. | Matrix sim. |
|---|---|---|---|---|---|---|---|
| P$AHBP | *Arabidopsis* homeobox protein | P$BLR.01 | 0.90 | 1550-1560 | (−) | 1 | 0.93 |
| P$IDDF | ID domain factors | P$ID1.01 | 0.92 | 1563-1575 | (+) | 1 | 0.952 |
| P$NCS2 | Nodulin consensus sequence 2 | P$NCS2.01 | 0.79 | 1565-1579 | (+) | 0.75 | 0.845 |
| O$VTBP | Vertebrate TATA binding protein factor | O$MTATA.01 | 0.84 | 1570-1586 | (+) | 1 | 0.846 |
| P$DOFF | DNA binding with one finger (DOF) | P$PBF.01 | 0.97 | 1571-1587 | (+) | 1 | 0.988 |
| P$LEGB | Legumin Box family | P$RY.01 | 0.87 | 1572-1598 | (−) | 1 | 0.898 |
| P$MADS | MADS box proteins | P$AGL3.01 | 0.83 | 1637-1657 | (+) | 1 | 0.851 |
| P$MYBL | MYB-like proteins | P$ATMYB77.01 | 0.87 | 1654-1670 | (−) | 1 | 0.909 |
| P$URNA | Upstream sequence element of U-snRNA genes | P$USE.01 | 0.75 | 1659-1675 | (+) | 1 | 0.758 |
| P$AHBP | *Arabidopsis* homeobox protein | P$ATHB1.01 | 0.90 | 1671-1681 | (−) | 1 | 0.989 |
| P$AHBP | *Arabidopsis* homeobox protein | P$HAHB4.01 | 0.87 | 1671-1681 | (+) | 1 | 0.955 |
| P$OCSE | Enhancer element first identified in the promoter of the octopine synthase gene (OCS) of the *Agrobacterium tumefaciens* T-DNA | P$OCSL.01 | 0.69 | 1677-1697 | (+) | 1 | 0.763 |
| P$GBOX | Plant G-box/C-box bZIP proteins | P$GBF1.01 | 0.94 | 1682-1702 | (−) | 1 | 0.968 |
| P$ABRE | ABA response elements | P$ABRE.01 | 0.82 | 1685-1701 | (−) | 1 | 0.855 |
| P$BRRE | Brassinosteroid (BR) response element | P$BZR1.01 | 0.95 | 1696-1712 | (−) | 1 | 0.954 |
| P$GBOX | Plant G-box/C-box bZIP proteins | P$GBF1.01 | 0.94 | 1696-1716 | (−) | 1 | 0.963 |
| P$TEFB | TEF-box | P$TEF1.01 | 0.76 | 1696-1716 | (−) | 0.96 | 0.826 |
| P$OPAQ | Opaque-2 like transcriptional activators | P$O2_GCN4.01 | 0.81 | 1698-1714 | (−) | 0.95 | 0.824 |
| P$DPBF | Dc3 promoter binding factors | P$DPBF.01 | 0.89 | 1700-1710 | (+) | 1 | 0.943 |
| P$LEGB | Legumin Box family | P$RY.01 | 0.87 | 1701-1727 | (−) | 1 | 0.887 |
| P$LEGB | Legumin Box family | P$IDE1.01 | 0.77 | 1708-1734 | (+) | 1 | 0.871 |
| P$MYBS | MYB proteins with single DNA binding repeat | P$TAMYB80.01 | 0.83 | 1727-1743 | (+) | 1 | 0.85 |
| P$ROOT | Root hair-specific cis-elements in angiosperms | P$RHE.02 | 0.77 | 1740-1764 | (+) | 1 | 0.786 |
| P$GBOX | Plant G-box/C-box bZIP proteins | P$EMBP1.01 | 0.84 | 1747-1767 | (−) | 1 | 0.84 |
| P$ABRE | ABA response elements | P$ABRE.01 | 0.82 | 1750-1766 | (−) | 1 | 0.831 |
| O$VTBP | Vertebrate TATA binding protein factor | O$VTATA.01 | 0.90 | 1756-1772 | (+) | 1 | 0.963 |
| P$MYBL | MYB-like proteins | P$MYBPH3.02 | 0.76 | 1765-1781 | (−) | 1 | 0.781 |

TABLE 4

Boxes and Motifs identified in the permutated sequence of the VfSBP promoter. Preferably associated boxes are annotated in line 8, 14, 26, 56, 58, 59, 66, 121, 144, 148, 158, 185, 200, 201, 211, 215, 218, 219, 220, 225, 226, 228 of tables 3 and 4. Essential boxes are annotated in line 130, 132 and 146 of tables 3 and 4.

| | | p-VfSBP__perm | | | | | |
|---|---|---|---|---|---|---|---|
| Family | Further Family Information | Matrix | Opt. | Position from-to | Strand | Core sim. | Matrix sim. |
| P$MYBS | MYB proteins with single DNA binding repeat | P$MYBST1.01 | 0.90 | 12-28 | (+) | 1 | 0.918 |
| P$AGP1 | Plant GATA-type zinc finger protein | P$AGP1.01 | 0.91 | 25-35 | (−) | 1 | 0.914 |
| P$GAGA | GAGA elements | P$BPC.01 | 1.00 | 25-49 | (−) | 1 | 1 |
| P$AGP1 | Plant GATA-type zinc finger protein | P$AGP1.01 | 0.91 | 26-36 | (+) | 1 | 0.914 |
| P$LEGB | Legumin Box family | P$IDE1.01 | 0.77 | 80-106 | (−) | 1 | 0.805 |
| P$GTBX | GT-box elements | P$GT3A.01 | 0.83 | 85-101 | (−) | 1 | 0.843 |
| P$PSRE | Pollen-specific regulatory elements | P$GAAA.01 | 0.83 | 101-117 | (−) | 1 | 0.883 |
| P$GBOX | Plant G-box/C-box bZIP proteins | P$HBP1B.01 | 0.83 | 138-158 | (+) | 1 | 0.834 |
| P$WBXF | W Box family | P$ERE.01 | 0.89 | 154-170 | (−) | 1 | 0.935 |
| P$MYBL | MYB-like proteins | P$MYBPH3.02 | 0.76 | 165-181 | (−) | 0.78 | 0.788 |
| P$NACF | Plant specific NAC [NAM (no apical meristem), ATAF172, CUC2 (cup-shaped cotyledons 2)] transcription factors | P$TANAC69.01 | 0.68 | 173-195 | (−) | 0.81 | 0.728 |
| P$MADS | MADS box proteins | P$AGL1.01 | 0.84 | 174-194 | (−) | 0.98 | 0.856 |
| P$MADS | MADS box proteins | P$AGL1.01 | 0.84 | 175-195 | (+) | 0.98 | 0.844 |
| P$TCPF | DNA-binding proteins with the plant specific TCP-domain | P$ATTCP20.01 | 0.94 | 189-201 | (+) | 1 | 0.968 |
| P$L1BX | L1 box, motif for L1 layer-specific expression | P$ATML1.02 | 0.76 | 194-210 | (−) | 0.89 | 0.795 |
| P$AHBP | *Arabidopsis* homeobox protein | P$BLR.01 | 0.90 | 198-208 | (+) | 0.83 | 0.936 |
| P$EINL | Ethylen insensitive 3 like factors | P$TEIL.01 | 0.92 | 215-223 | (−) | 0.96 | 0.924 |
| P$GBOX | Plant G-box/C-box bZIP proteins | P$HBP1A.01 | 0.88 | 217-237 | (−) | 1 | 0.908 |
| P$GBOX | Plant G-box/C-box bZIP proteins | P$GBF1.01 | 0.94 | 218-238 | (+) | 1 | 0.963 |
| P$GTBX | GT-box elements | P$S1F.01 | 0.79 | 218-234 | (+) | 1 | 0.821 |
| P$ABRE | ABA response elements | P$ABF1.03 | 0.82 | 219-235 | (+) | 1 | 0.825 |
| P$ROOT | Root hair-specific cis-elements in angiosperms | P$RHE.01 | 0.77 | 221-245 | (−) | 1 | 0.803 |
| P$CE1F | Coupling element 1 binding factors | P$SBOX.01 | 0.87 | 222-234 | (−) | 0.78 | 0.916 |
| O$VTBP | Vertebrate TATA binding protein factor | O$VTATA.01 | 0.90 | 233-249 | (−) | 1 | 0.939 |
| P$IBOX | Plant I-Box sites | P$GATA.01 | 0.93 | 245-261 | (−) | 1 | 0.963 |
| P$MYBS | MYB proteins with single DNA binding repeat | P$HVMCB1.01 | 0.93 | 248-264 | (+) | 1 | 0.957 |

TABLE 4-continued

Boxes and Motifs identified in the permutated sequence of the VfSBP promoter. Preferably associated boxes are annotated in line 8, 14, 26, 56, 58, 59, 66, 121, 144, 148, 158, 185, 200, 201, 211, 215, 218, 219, 220, 225, 226, 228 of tables 3 and 4. Essential boxes are annotated in line 130, 132 and 146 of tables 3 and 4.

| Family | Further Family Information | Matrix | Opt. | Position from-to | Strand | Core sim. | Matrix sim. |
|---|---|---|---|---|---|---|---|
| P$AHBP | Arabidopsis homeobox protein | P$ATHB5.01 | 0.89 | 256-266 | (+) | 0.94 | 0.896 |
| P$NCS1 | Nodulin consensus sequence 1 | P$NCS1.01 | 0.85 | 256-266 | (−) | 0.88 | 0.871 |
| O$VTBP | Vertebrate TATA binding protein factor | O$ATATA.01 | 0.78 | 260-276 | (+) | 1 | 0.819 |
| P$LREM | Light responsive element motif, not modulated by different light qualities | P$RAP22.01 | 0.85 | 290-300 | (−) | 1 | 0.931 |
| P$AGP1 | Plant GATA-type zinc finger protein | P$AGP1.01 | 0.91 | 292-302 | (−) | 1 | 0.984 |
| P$AGP1 | Plant GATA-type zinc finger protein | P$AGP1.01 | 0.91 | 293-303 | (+) | 1 | 0.915 |
| P$LREM | Light responsive element motif, not modulated by different light qualities | P$RAP22.01 | 0.85 | 306-316 | (+) | 1 | 0.938 |
| P$MYBL | MYB-like proteins | P$CARE.01 | 0.83 | 308-324 | (−) | 1 | 0.854 |
| P$MYBL | MYB-like proteins | P$ATMYB77.01 | 0.87 | 319-335 | (+) | 1 | 0.87 |
| O$INRE | Core promoter initiator elements | O$DINR.01 | 0.94 | 322-332 | (+) | 1 | 0.969 |
| P$MADS | MADS box proteins | P$AGL15.01 | 0.79 | 345-365 | (+) | 0.85 | 0.825 |
| P$CCAF | Circadian control factors | P$CCA1.01 | 0.85 | 354-368 | (+) | 1 | 0.895 |
| P$HEAT | Heat shock factors | P$HSE.01 | 0.81 | 375-389 | (−) | 1 | 0.861 |
| P$MYBL | MYB-like proteins | P$WER.01 | 0.87 | 392-408 | (−) | 1 | 0.87 |
| P$MYBL | MYB-like proteins | P$WER.01 | 0.87 | 394-410 | (+) | 1 | 0.95 |
| P$MSAE | M-phase-specific activator elements | P$MSA.01 | 0.80 | 395-409 | (−) | 0.75 | 0.808 |
| P$HMGF | High mobility group factors | P$HMG_IY.01 | 0.89 | 402-416 | (−) | 1 | 0.929 |
| P$CCAF | Circadian control factors | P$CCA1.01 | 0.85 | 404-418 | (+) | 1 | 0.871 |
| P$AHBP | Arabidopsis homeobox protein | P$BLR.01 | 0.90 | 407-417 | (−) | 1 | 0.901 |
| P$LREM | Light responsive element motif, not modulated by different light qualities | P$RAP22.01 | 0.85 | 411-421 | (+) | 1 | 0.916 |
| P$HEAT | Heat shock factors | P$HSE.01 | 0.81 | 415-429 | (+) | 1 | 0.811 |
| P$SUCB | Sucrose box | P$SUCROSE.01 | 0.81 | 421-439 | (−) | 0.75 | 0.849 |
| P$DOFF | DNA binding with one finger (DOF) | P$PBOX.01 | 0.75 | 431-447 | (−) | 0.76 | 0.782 |
| P$WBXF | W Box family | P$WRKY.01 | 0.92 | 453-469 | (+) | 1 | 0.958 |
| P$MYBL | MYB-like proteins | P$MYBPH3.02 | 0.76 | 468-484 | (−) | 0.82 | 0.849 |
| P$OPAQ | Opaque-2 like transcriptional activators | P$O2_GCN4.01 | 0.81 | 486-502 | (+) | 1 | 0.818 |
| P$OPAQ | Opaque-2 like transcriptional activators | P$O2.01 | 0.87 | 498-514 | (−) | 1 | 0.919 |
| P$HEAT | Heat shock factors | P$HSE.01 | 0.81 | 512-526 | (−) | 1 | 0.824 |

TABLE 4-continued

Boxes and Motifs identified in the permutated sequence of the VfSBP promoter. Preferably associated boxes are annotated in line 8, 14, 26, 56, 58, 59, 66, 121, 144, 148, 158, 185, 200, 201, 211, 215, 218, 219, 220, 225, 226, 228 of tables 3 and 4. Essential boxes are annotated in line 130, 132 and 146 of tables 3 and 4.

p-VfSBP_perm

| Family | Further Family Information | Matrix | Opt. | Position from-to | Strand | Core sim. | Matrix sim. |
| --- | --- | --- | --- | --- | --- | --- | --- |
| P$NCS2 | Nodulin consensus sequence 2 | P$NCS2.01 | 0.79 | 525-539 | (−) | 0.75 | 0.815 |
| P$WBXF | W Box family | P$WRKY.01 | 0.92 | 533-549 | (−) | 1 | 0.966 |
| P$WBXF | W Box family | P$WRKY.01 | 0.92 | 543-559 | (+) | 1 | 0.966 |
| P$WBXF | W Box family | P$ERE.01 | 0.89 | 562-578 | (+) | 1 | 0.972 |
| P$DOFF | DNA binding with one finger (DOF) | P$PBOX.01 | 0.75 | 614-630 | (+) | 0.76 | 0.766 |
| P$GTBX | GT-box elements | P$S1F.01 | 0.79 | 630-646 | (+) | 1 | 0.819 |
| P$AGP1 | Plant GATA-type zinc finger protein | P$AGP1.01 | 0.91 | 636-646 | (−) | 1 | 0.913 |
| P$AGP1 | Plant GATA-type zinc finger protein | P$AGP1.01 | 0.91 | 637-647 | (+) | 1 | 0.921 |
| P$MYBL | MYB-like proteins | P$GAMYB.01 | 0.91 | 640-656 | (−) | 1 | 0.918 |
| P$HEAT | Heat shock factors | P$HSE.01 | 0.81 | 649-663 | (+) | 0.78 | 0.87 |
| P$HEAT | Heat shock factors | P$HSE.01 | 0.81 | 654-668 | (−) | 1 | 0.815 |
| O$INRE | Core promoter initiator elements | O$DINR.01 | 0.94 | 660-670 | (−) | 1 | 0.944 |
| P$PREM | Motifs of plastid response elements | P$MGPROTORE.01 | 0.77 | 691-721 | (−) | 1 | 0.789 |
| P$GAPB | GAP-Box (light response elements) | P$GAP.01 | 0.88 | 702-716 | (−) | 1 | 0.897 |
| P$GTBX | GT-box elements | P$GT1.01 | 0.85 | 723-739 | (−) | 1 | 0.925 |
| P$AHBP | *Arabidopsis* homeobox protein | P$WUS.01 | 0.94 | 726-736 | (−) | 1 | 1 |
| P$CARM | CA-rich motif | P$CARICH.01 | 0.78 | 731-749 | (+) | 1 | 0.855 |
| P$MYCL | Myc-like basic helix-loop-helix binding factors | P$ICE.01 | 0.95 | 734-752 | (+) | 0.95 | 0.961 |
| P$MYBL | MYB-like proteins | P$GAMYB.01 | 0.91 | 773-789 | (+) | 1 | 0.951 |
| P$GTBX | GT-box elements | P$GT3A.01 | 0.83 | 775-791 | (+) | 1 | 0.899 |
| P$MYBL | MYB-like proteins | P$CARE.01 | 0.83 | 801-817 | (−) | 1 | 0.837 |
| O$VTBP | Vertebrate TATA binding protein factor | O$ATATA.01 | 0.78 | 803-819 | (−) | 1 | 0.811 |
| P$L1BX | L1 box, motif for L1 layer-specific expression | P$PDF2.01 | 0.85 | 814-830 | (−) | 1 | 0.869 |
| P$GTBX | GT-box elements | P$GT1.01 | 0.85 | 815-831 | (−) | 0.97 | 0.854 |
| O$VTBP | Vertebrate TATA binding protein factor | O$ATATA.01 | 0.78 | 819-835 | (−) | 0.75 | 0.874 |
| P$MADS | MADS box proteins | P$AGL15.01 | 0.79 | 828-848 | (+) | 1 | 0.857 |
| P$CCAF | Circadian control factors | P$CCA1.01 | 0.85 | 843-857 | (−) | 1 | 0.883 |
| P$GTBX | GT-box elements | P$SBF1.01 | 0.87 | 844-860 | (−) | 1 | 0.948 |
| P$CARM | CA-rich motif | P$CARICH.01 | 0.78 | 845-863 | (+) | 1 | 0.806 |
| P$MYBL | MYB-like proteins | P$CARE.01 | 0.83 | 849-865 | (−) | 1 | 0.876 |
| P$GTBX | GT-box elements | P$SBF1.01 | 0.87 | 869-885 | (+) | 1 | 0.883 |
| P$RAV5 | 5′-part of bipartite RAV1 binding site | P$RAV1-5.01 | 0.96 | 882-892 | (+) | 1 | 0.96 |
| P$L1BX | L1 box, motif for L1 layer-specific expression | P$PDF2.01 | 0.85 | 884-900 | (−) | 0.85 | 0.853 |
| P$AHBP | *Arabidopsis* homeobox protein | P$WUS.01 | 0.94 | 888-898 | (−) | 1 | 1 |
| P$MYBL | MYB-like proteins | P$ATMYB77.01 | 0.87 | 895-911 | (+) | 1 | 0.962 |
| P$GTBX | GT-box elements | P$SBF1.01 | 0.87 | 897-913 | (+) | 1 | 0.883 |
| P$AHBP | *Arabidopsis* homeobox protein | P$BLR.01 | 0.90 | 906-916 | (+) | 1 | 1 |
| P$AHBP | *Arabidopsis* homeobox protein | P$BLR.01 | 0.90 | 907-917 | (−) | 1 | 0.903 |

TABLE 4-continued

Boxes and Motifs identified in the permutated sequence of the VfSBP promoter. Preferably associated boxes are annotated in line 8, 14, 26, 56, 58, 59, 66, 121, 144, 148, 158, 185, 200, 201, 211, 215, 218, 219, 220, 225, 226, 228 of tables 3 and 4. Essential boxes are annotated in line 130, 132 and 146 of tables 3 and 4.

p-VfSBP_perm

| Family | Further Family Information | Matrix | Opt. | Position from-to | Strand | Core sim. | Matrix sim. |
|---|---|---|---|---|---|---|---|
| P$CARM | CA-rich motif | P$CARICH.01 | 0.78 | 908-926 | (−) | 1 | 0.826 |
| P$MYBL | MYB-like proteins | P$NTMYBAS1.01 | 0.96 | 916-932 | (−) | 1 | 0.962 |
| P$MIIG | MYB IIG-type binding sites | P$PALBOXP.01 | 0.81 | 918-932 | (−) | 0.94 | 0.817 |
| P$SPF1 | Sweet potato DNA-binding factor with two WRKY-domains | P$SP8BF.01 | 0.87 | 931-943 | (−) | 1 | 0.889 |
| P$L1BX | L1 box, motif for L1 layer-specific expression | P$ATML1.01 | 0.82 | 948-964 | (+) | 1 | 0.908 |
| P$AHBP | *Arabidopsis* homeobox protein | P$ATHB9.01 | 0.77 | 959-969 | (+) | 0.75 | 0.816 |
| P$AHBP | *Arabidopsis* homeobox protein | P$ATHB9.01 | 0.77 | 959-969 | (−) | 1 | 0.909 |
| P$AHBP | *Arabidopsis* homeobox protein | P$HAHB4.01 | 0.87 | 970-980 | (+) | 1 | 0.916 |
| P$AHBP | *Arabidopsis* homeobox protein | P$ATHB1.01 | 0.90 | 973-983 | (+) | 1 | 0.989 |
| P$AHBP | *Arabidopsis* homeobox protein | P$HAHB4.01 | 0.87 | 973-983 | (−) | 1 | 0.976 |
| P$IDDF | ID domain factors | P$ID1.01 | 0.92 | 976-988 | (+) | 1 | 0.928 |
| P$AHBP | *Arabidopsis* homeobox protein | P$HAHB4.01 | 0.87 | 985-995 | (+) | 1 | 0.916 |
| P$GTBX | GT-box elements | P$SBF1.01 | 0.87 | 985-1001 | (+) | 1 | 0.891 |
| P$GTBX | GT-box elements | P$SBF1.01 | 0.87 | 986-1002 | (−) | 1 | 0.877 |
| P$AHBP | *Arabidopsis* homeobox protein | P$HAHB4.01 | 0.87 | 992-1002 | (−) | 1 | 0.916 |
| P$IBOX | Plant I-Box sites | P$GATA.01 | 0.93 | 995-1011 | (+) | 1 | 0.935 |
| P$LEGB | Legumin Box family | P$LEGB.01 | 0.65 | 998-1024 | (+) | 0.75 | 0.676 |
| P$AHBP | *Arabidopsis* homeobox protein | P$HAHB4.01 | 0.87 | 1008-1018 | (+) | 1 | 0.937 |
| P$AHBP | *Arabidopsis* homeobox protein | P$WUS.01 | 0.94 | 1012-1022 | (−) | 1 | 1 |
| P$MYBL | MYB-like proteins | P$GAMYB.01 | 0.91 | 1022-1038 | (−) | 1 | 0.925 |
| P$SPF1 | Sweet potato DNA-binding factor with two WRKY-domains | P$SP8BF.01 | 0.87 | 1029-1041 | (−) | 0.78 | 0.879 |
| P$SUCB | Sucrose box | P$SUCROSE.01 | 0.81 | 1036-1054 | (−) | 1 | 0.83 |
| P$AHBP | *Arabidopsis* homeobox protein | P$ATHB1.01 | 0.90 | 1054-1064 | (+) | 1 | 0.99 |
| P$AHBP | *Arabidopsis* homeobox protein | P$ATHB5.01 | 0.89 | 1054-1064 | (−) | 0.83 | 0.94 |
| P$GTBX | GT-box elements | P$GT3A.01 | 0.83 | 1066-1082 | (+) | 1 | 0.889 |
| O$PTBP | Plant TATA binding protein factor | O$PTATA.02 | 0.90 | 1086-1100 | (+) | 1 | 0.94 |
| O$VTBP | Vertebrate TATA binding protein factor | O$VTATA.01 | 0.90 | 1087-1103 | (+) | 0.89 | 0.927 |
| O$PTBP | Plant TATA binding protein factor | O$PTATA.01 | 0.88 | 1088-1102 | (+) | 1 | 0.958 |
| O$VTBP | Vertebrate TATA binding protein factor | O$VTATA.01 | 0.90 | 1089-1105 | (+) | 1 | 0.971 |
| P$DOFF | DNA binding with one finger (DOF) | P$DOF3.01 | 0.99 | 1098-1114 | (+) | 1 | 0.995 |
| P$E2FF | E2F-homolog cell cycle regulators | P$E2F.01 | 0.82 | 1117-1131 | (−) | 1 | 0.833 |
| P$SPF1 | Sweet potato DNA-binding factor with two | P$SP8BF.01 | 0.87 | 1130-1142 | (+) | 1 | 0.881 |

TABLE 4-continued

Boxes and Motifs identified in the permutated sequence of the VfSBP promoter. Preferably associated boxes are annotated in line 8, 14, 26, 56, 58, 59, 66, 121, 144, 148, 158, 185, 200, 201, 211, 215, 218, 219, 220, 225, 226, 228 of tables 3 and 4. Essential boxes are annotated in line 130, 132 and 146 of tables 3 and 4.

p-VfSBP_perm

| Family | Further Family Information | Matrix | Opt. | Position from-to | Strand | Core sim. | Matrix sim. |
|---|---|---|---|---|---|---|---|
| P$PSRE | WRKY-domains Pollen-specific regulatory elements | P$GAAA.01 | 0.83 | 1146-1162 | (+) | 1 | 0.873 |
| P$GTBX | GT-box elements | P$S1F.01 | 0.79 | 1170-1186 | (−) | 1 | 0.797 |
| P$SUCB | Sucrose box | P$SUCROSE.01 | 0.81 | 1173-1191 | (+) | 1 | 0.813 |
| P$MADS | MADS box proteins | P$AGL2.01 | 0.82 | 1174-1194 | (+) | 1 | 0.9 |
| P$AHBP | *Arabidopsis* homeobox protein | P$BLR.01 | 0.90 | 1189-1199 | (+) | 0.83 | 0.919 |
| P$IDDF | ID domain factors | P$ID1.01 | 0.92 | 1205-1217 | (−) | 1 | 0.97 |
| P$DOFF | DNA binding with one finger (DOF) | P$PBOX.01 | 0.75 | 1229-1245 | (−) | 0.76 | 0.763 |
| P$MYBL | MYB-like proteins | P$WER.01 | 0.87 | 1234-1250 | (−) | 0.94 | 0.88 |
| O$PTBP | Plant TATA binding protein factor | O$PTATA.01 | 0.88 | 1241-1255 | (+) | 1 | 0.964 |
| O$VTBP | Vertebrate TATA binding protein factor | O$VTATA.01 | 0.90 | 1242-1258 | (+) | 1 | 0.967 |
| P$DOFF | DNA binding with one finger (DOF) | P$PBOX.01 | 0.75 | 1265-1281 | (−) | 0.76 | 0.762 |
| P$GTBX | GT-box elements | P$GT3A.01 | 0.83 | 1265-1281 | (+) | 0.75 | 0.839 |
| P$AHBP | *Arabidopsis* homeobox protein | P$BLR.01 | 0.90 | 1274-1284 | (−) | 1 | 0.928 |
| O$PTBP | Plant TATA binding protein factor | O$PTATA.01 | 0.88 | 1277-1291 | (+) | 1 | 0.908 |
| O$VTBP | Vertebrate TATA binding protein factor | O$VTATA.01 | 0.90 | 1278-1294 | (+) | 1 | 0.918 |
| P$OCSE | Enhancer element first identified in the promoter of the octopine synthase gene (OCS) of the *Agrobacterium tumefaciens* T-DNA | P$OCSL.01 | 0.69 | 1278-1298 | (+) | 0.77 | 0.712 |
| P$MYCL | Myc-like basic helix-loop-helix binding factors | P$MYCRS.01 | 0.93 | 1284-1302 | (−) | 0.86 | 0.933 |
| P$TALE | TALE (3-aa acid loop extension) class homeodomain proteins | P$KN1_KIP.01 | 0.88 | 1289-1301 | (−) | 1 | 1 |
| P$AREF | Auxin response element | P$SEBF.01 | 0.96 | 1292-1304 | (+) | 1 | 0.98 |
| P$MSAE | M-phase-specific activator elements | P$MSA.01 | 0.80 | 1295-1309 | (−) | 0.75 | 0.803 |
| P$DOFF | DNA binding with one finger (DOF) | P$PBOX.01 | 0.75 | 1296-1312 | (−) | 1 | 0.797 |
| P$MYBL | MYB-like proteins | P$WER.01 | 0.87 | 1310-1326 | (−) | 0.94 | 0.876 |
| P$AHBP | *Arabidopsis* homeobox protein | P$BLR.01 | 0.90 | 1319-1329 | (+) | 1 | 0.93 |
| O$VTBP | Vertebrate TATA binding protein factor | O$ATATA.01 | 0.78 | 1323-1339 | (−) | 1 | 0.833 |
| P$LREM | Light responsive element motif, not modulated by different | P$RAP22.01 | 0.85 | 1327-1337 | (−) | 1 | 0.936 |

TABLE 4-continued

Boxes and Motifs identified in the permutated sequence of the VfSBP promoter. Preferably associated boxes are annotated in line 8, 14, 26, 56, 58, 59, 66, 121, 144, 148, 158, 185, 200, 201, 211, 215, 218, 219, 220, 225, 226, 228 of tables 3 and 4. Essential boxes are annotated in line 130, 132 and 146 of tables 3 and 4.

p-VfSBP_perm

| Family | Further Family Information | Matrix | Opt. | Position from-to | Strand | Core sim. | Matrix sim. |
|---|---|---|---|---|---|---|---|
| P$IBOX | Plant I-Box sites light qualities | P$GATA.01 | 0.93 | 1328-1344 | (+) | 1 | 0.939 |
| P$SUCB | Sucrose box | P$SUCROSE.01 | 0.81 | 1334-1352 | (+) | 1 | 0.816 |
| P$AHBP | Arabidopsis homeobox protein | P$ATHB5.01 | 0.89 | 1335-1345 | (−) | 0.83 | 0.904 |
| P$AHBP | Arabidopsis homeobox protein | P$BLR.01 | 0.90 | 1335-1345 | (+) | 1 | 0.998 |
| P$GTBX | GT-box elements | P$SBF1.01 | 0.87 | 1338-1354 | (+) | 1 | 0.896 |
| P$SUCB | Sucrose box | P$SUCROSE.01 | 0.81 | 1338-1356 | (−) | 1 | 0.819 |
| P$AHBP | Arabidopsis homeobox protein | P$ATHB5.01 | 0.89 | 1345-1355 | (+) | 0.83 | 0.902 |
| P$AHBP | Arabidopsis homeobox protein | P$BLR.01 | 0.90 | 1345-1355 | (−) | 1 | 0.998 |
| P$AGP1 | Plant GATA-type zinc finger protein | P$AGP1.01 | 0.91 | 1354-1364 | (−) | 1 | 0.916 |
| P$AHBP | Arabidopsis homeobox protein | P$HAHB4.01 | 0.87 | 1365-1375 | (−) | 1 | 0.896 |
| O$VTBP | Vertebrate TATA binding protein factor | O$VTATA.01 | 0.90 | 1376-1392 | (−) | 1 | 0.949 |
| P$HMGF | High mobility group factors | P$HMG_IY.01 | 0.89 | 1377-1391 | (+) | 1 | 0.952 |
| O$PTBP | Plant TATA binding protein factor | O$PTATA.01 | 0.88 | 1379-1393 | (−) | 1 | 0.883 |
| P$IDDF | ID domain factors | P$ID1.01 | 0.92 | 1387-1399 | (+) | 1 | 0.926 |
| P$MYBL | MYB-like proteins | P$GAMYB.01 | 0.91 | 1389-1405 | (+) | 1 | 0.939 |
| O$INRE | Core promoter initiator elements | O$DINR.01 | 0.94 | 1392-1402 | (+) | 1 | 0.943 |
| P$IBOX | Plant I-Box sites | P$IBOX.01 | 0.81 | 1399-1415 | (−) | 0.75 | 0.822 |
| P$MYBL | MYB-like proteins | P$WER.01 | 0.87 | 1410-1426 | (+) | 1 | 0.875 |
| P$SPF1 | Sweet potato DNA-binding factor with two WRKY-domains | P$SP8BF.01 | 0.87 | 1412-1424 | (+) | 1 | 0.91 |
| O$VTBP | Vertebrate TATA binding protein factor | O$LTATA.01 | 0.82 | 1417-1433 | (−) | 1 | 0.847 |
| P$IBOX | Plant I-Box sites | P$IBOX.01 | 0.81 | 1419-1435 | (−) | 0.75 | 0.824 |
| P$WBXF | W Box family | P$WRKY.01 | 0.92 | 1429-1445 | (−) | 1 | 0.958 |
| P$MYBL | MYB-like proteins | P$MYBPH3.02 | 0.76 | 1457-1473 | (+) | 0.82 | 0.798 |
| P$ROOT | Root hair-specific cis-elements in angiosperms | P$RHE.02 | 0.77 | 1458-1482 | (+) | 0.75 | 0.786 |
| P$LFYB | LFY binding site | P$LFY.01 | 0.93 | 1486-1498 | (−) | 0.91 | 0.987 |
| P$CAAT | CCAAT binding factors | P$CAAT.01 | 0.97 | 1490-1498 | (−) | 1 | 0.982 |
| P$HEAT | Heat shock factors | P$HSE.01 | 0.81 | 1526-1540 | (+) | 1 | 0.833 |
| P$GTBX | GT-box elements | P$GT1.01 | 0.85 | 1536-1552 | (−) | 0.84 | 0.869 |
| P$WBXF | W Box family | P$ERE.01 | 0.89 | 1537-1553 | (+) | 1 | 0.9 |
| P$SPF1 | Sweet potato DNA-binding factor with two WRKY-domains | P$SP8BF.01 | 0.87 | 1546-1558 | (+) | 1 | 0.919 |
| P$AHBP | Arabidopsis homeobox protein | P$BLR.01 | 0.90 | 1550-1560 | (−) | 1 | 0.93 |
| P$LREM | Light responsive element motif, not modulated | P$RAP22.01 | 0.85 | 1555-1565 | (−) | 1 | 0.882 |

TABLE 4-continued

Boxes and Motifs identified in the permutated sequence of the VfSBP promoter. Preferably associated boxes are annotated in line 8, 14, 26, 56, 58, 59, 66, 121, 144, 148, 158, 185, 200, 201, 211, 215, 218, 219, 220, 225, 226, 228 of tables 3 and 4. Essential boxes are annotated in line 130, 132 and 146 of tables 3 and 4.

| Family | Further Family Information | Matrix | Opt. | Position from-to | Strand | Core sim. | Matrix sim. |
|---|---|---|---|---|---|---|---|
| | by different light qualities | | | | | | |
| P$NCS1 | Nodulin consensus sequence 1 | P$NCS1.01 | 0.85 | 1559-1569 | (−) | 0.8 | 0.855 |
| P$GARP | Myb-related DNA binding proteins (Golden2, ARR, Psr) | P$ARR10.01 | 0.97 | 1560-1568 | (+) | 1 | 0.97 |
| P$IDDF | ID domain factors | P$ID1.01 | 0.92 | 1563-1575 | (+) | 1 | 0.952 |
| P$NCS2 | Nodulin consensus sequence 2 | P$NCS2.01 | 0.79 | 1565-1579 | (+) | 0.75 | 0.845 |
| O$VTBP | Vertebrate TATA binding protein factor | O$MTATA.01 | 0.84 | 1570-1586 | (+) | 1 | 0.846 |
| P$DOFF | DNA binding with one finger (DOF) | P$PBF.01 | 0.97 | 1571-1587 | (+) | 1 | 0.988 |
| P$LEGB | Legumin Box family | P$RY.01 | 0.87 | 1572-1598 | (−) | 1 | 0.898 |
| P$NCS2 | Nodulin consensus sequence 2 | P$NCS2.01 | 0.79 | 1610-1624 | (+) | 1 | 0.867 |
| P$MADS | MADS box proteins | P$AGL3.01 | 0.83 | 1637-1657 | (+) | 1 | 0.851 |
| P$GTBX | GT-box elements | P$GT3A.01 | 0.83 | 1652-1668 | (−) | 1 | 0.854 |
| P$MYBL | MYB-like proteins | P$NTMYBAS1.01 | 0.96 | 1654-1670 | (−) | 1 | 0.971 |
| P$AHBP | *Arabidopsis* homeobox protein | P$HAHB4.01 | 0.87 | 1671-1681 | (+) | 1 | 0.934 |
| P$OCSE | Enhancer element first identified in the promoter of the octopine synthase gene (OCS) of the *Agrobacterium tumefaciens* T-DNA | P$OCSL.01 | 0.69 | 1677-1697 | (+) | 1 | 0.763 |
| P$GBOX | Plant G-box/C-box bZIP proteins | P$GBF1.01 | 0.94 | 1682-1702 | (−) | 1 | 0.968 |
| P$ABRE | ABA response elements | P$ABRE.01 | 0.82 | 1685-1701 | (−) | 1 | 0.855 |
| P$BRRE | Brassinosteroid (BR) response element | P$BZR1.01 | 0.95 | 1696-1712 | (−) | 1 | 0.954 |
| P$GBOX | Plant G-box/C-box bZIP proteins | P$GBF1.01 | 0.94 | 1696-1716 | (−) | 1 | 0.963 |
| P$TEFB | TEF-box | P$TEF1.01 | 0.76 | 1696-1716 | (−) | 0.84 | 0.799 |
| P$DPBF | Dc3 promoter binding factors | P$DPBF.01 | 0.89 | 1700-1710 | (+) | 1 | 0.943 |
| P$EREF | Ethylen respone element factors | P$ANT.01 | 0.81 | 1701-1717 | (+) | 1 | 0.862 |
| P$LEGB | Legumin Box family | P$RY.01 | 0.87 | 1701-1727 | (−) | 1 | 0.925 |
| P$LEGB | Legumin Box family | P$RY.01 | 0.87 | 1704-1730 | (+) | 1 | 0.967 |
| P$LEGB | Legumin Box family | P$IDE1.01 | 0.77 | 1708-1734 | (+) | 1 | 0.888 |
| P$MADS | MADS box proteins | P$MADS.01 | 0.75 | 1722-1742 | (+) | 1 | 0.758 |
| P$MYBS | MYB proteins with single DNA binding repeat | P$TAMYB80.01 | 0.83 | 1727-1743 | (+) | 1 | 0.861 |
| P$URNA | Upstream sequence element of U-snRNA genes | P$USE.01 | 0.75 | 1731-1747 | (+) | 1 | 0.77 |

TABLE 4-continued

Boxes and Motifs identified in the permutated sequence of the VfSBP promoter. Preferably associated boxes are annotated in line 8, 14, 26, 56, 58, 59, 66, 121, 144, 148, 158, 185, 200, 201, 211, 215, 218, 219, 220, 225, 226, 228 of tables 3 and 4. Essential boxes are annotated in line 130, 132 and 146 of tables 3 and 4.

p-VfSBP_perm

| Family | Further Family Information | Matrix | Opt. | Position from-to | Strand | Core sim. | Matrix sim. |
|---|---|---|---|---|---|---|---|
| P$ROOT | Root hair-specific cis-elements in angiosperms | P$RHE.02 | 0.77 | 1740-1764 | (+) | 1 | 0.79 |
| P$GBOX | Plant G-box/C-box bZIP proteins | P$EMBP1.01 | 0.84 | 1747-1767 | (−) | 1 | 0.84 |
| P$ABRE | ABA response elements | P$ABRE.01 | 0.82 | 1750-1766 | (−) | 1 | 0.831 |
| O$VTBP | Vertebrate TATA binding protein factor | O$VTATA.01 | 0.90 | 1756-1772 | (+) | 1 | 0.957 |
| P$MYBL | MYB-like proteins | P$MYBPH3.02 | 0.76 | 1765-1781 | (−) | 1 | 0.781 |

1.2 Vector Construction

Using the Multisite Gateway System (Invitrogen, Carlsbad, Calif., USA), promoter::reporter-gene cassettes were assembled into binary constructs for plant transformation. beta-Glucuronidase (GUS) or uidA gene which encodes an enzyme for which various chromogenic substrates are known, was utilized as reporter protein for determining the expression features of the permutated p-PvArc5_perm (SEQ ID NO2) and p-VfSBP_perm (SEQ ID NO4) promoter sequences. The DNA fragments representing promoters p-PvArc5_perm (SEQ ID NO2) and p-VfSBP_perm (SEQ ID NO4) were generated by gene synthesis. Endonucleolytic restriction sites suitable for cloning the promoter fragments into beta-Glucuronidase reporter gene cassettes were included in the synthesis. The p-PvArc5_perm (SEQ ID NO2) promoter was cloned into a pENTR/A vector harboring the beta-Glucuronidase reporter gene c-GUS (with the prefix c- denoting coding sequence) followed by the t-PvArc (with the prefix t- denoting terminator) transcription terminator sequence using restriction endonucleases FseI and NcoI, yielding construct LJB2012. Similarly, the p-VfSBP_perm (SEQ ID NO4) promoter was cloned into a pENTR/B vector harboring the beta-Glucuronidase reporter gene c-GUS followed by the t-StCatpA transcriptional terminator sequence using restriction endonucleases FseI and NcoI, yielding construct LJB2007.

The complementary pENTR vectors without any expression cassettes were constructed by introduction of a multiple cloning site via KpnI and HindIII restriction sites. By performing a site specific recombination (LR-reaction), the created pENTR/A, pENTR/B and pENTR/C were combined with the pSUN destination vector (pSUN derivative) according to the manufacturers (Invitrogen, Carlsbad, Calif., USA) Multisite Gateway manual. The reactions yielded a binary vector with the p-PvArc5_perm (SEQ ID NO2) promoter, the beta-Glucuronidase coding sequence c-GUS and the t-PvArc terminator, for which the full construct sequence is given (SEQ ID NO7). Accordingly, a binary vector with the p-VfSBP_perm (SEQ ID NO4) promoter, the beta-Glucuronidase reporter gene and the t-StCatpA terminator for which the full construct sequence is given (SEQ ID NO8). The resulting plant transformation vectors are summarized in table 5:

TABLE 5

Plant expression vectors for B. napus transformation

| plant expression vector | Composition of the expression cassette Promoter::reporter gene::terminator | SEQ ID NO |
|---|---|---|
| LJB2045 | p-PvArc5_perm::c-GUS::t-PvArc | 7 |
| LJB2043 | p-VfSBP_perm::c-GUS::t-StCatpA | 8 |

1.3 Generation of Transgenic Rapeseed Plants (amended protocol according to Moloney et al., 1992, Plant Cell Reports, 8: 238-242).

In preparation for the generation of transgenic rapeseed plants, the binary vectors were transformed into Agrobacterium tumefaciens C58C1:pGV2260 (Deblaere et al., 1985, Nucl. Acids. Res. 13: 4777-4788). A 1:50 dilution of an overnight culture of Agrobacteria harboring the respective binary construct was grown in Murashige-Skoog Medium (Murashige and Skoog, 1962, Physiol. Plant 15, 473) supplemented with 3% saccharose (3MS-Medium). For the transformation of rapeseed plants, petioles or hypocotyledons of sterile plants were incubated with a 1:50 Agrobacterium solution for 5-10 minutes followed by a three-day co-incubation in darkness at 25° C. on 3 MS. Medium supplemented with 0.8% bacto-agar. After three days, the explants were transferred to MS-medium containing 500 mg/l Claforan (Cefotaxime-Sodium), 100 nM Imazetapyr, 20 microM Benzylaminopurin (BAP) and 1.6 g/l Glucose in a 16 h light/8 h darkness light regime, which was repeated in weekly periods. Growing shoots were transferred to MS-Medium containing 2% saccharose, 250 mg/l Claforan and 0.8% Bacto-agar. After 3 weeks, the growth hormone 2-Indolbutyl acid was added to the medium to promote root formation. Shoots were transferred to soil following root development, grown for two weeks in a growth chamber and grown to maturity in greenhouse conditions.

Example 2: Expression Profile of the p-PvArc5_Perm and p-VfSBP_Perm Gene Control Elements To demonstrate and analyze the transcription regulating properties of a promoter, it is useful to operably link the promoter or its fragments to a reporter gene, which can be employed to monitor its expression both qualitatively and quantitatively. Preferably bacterial ß-glucuronidase is used (Jefferson 1987). ß-glucuronidase activity can be monitored in planta with chromogenic substrates such as 5-bromo-4-Chloro-ß-indolyl-R-D-glucuronic acid during corresponding activity assays (Jefferson 1987). For determination of promoter activity and tissue specificity, plant tissue is dissected, stained and analyzed as described (e.g., Bäumlein 1991).

The regenerated transgenic T0 rapeseed plants harboring single or double insertions of the transgene deriving from constructs LJB2043 or LJB2045 were used for reporter gene analysis. Table 6 summarizes the reporter gene activity observed in plants harboring transgenes containing SEQ ID NO2 and SEQ ID NO4 in constructs LJB2043 and LJB2045, respectively:

TABLE 6 beta-Glucuronidase reporter gene activity in selected rapeseed plants harboring transgenes with SEQ ID NO2 (p-PvARC5-perm) and SEQ ID NO4 (p-VfSBP-perm) compared to the GUS expression derived from the respective starting sequence in rapeseed (p-VfSBP) or *Phaseolus* and *Arabidopsis* plants (p-PvArc5).

| Tissue | LJB2043 p-VfSBP-perm | p-VfSBP | LJB2045 p-PvArc5_perm | p-PvArc5* |
|---|---|---|---|---|
| leaves | negative | negative | negative | negative |
| stem | negative | negative | negative | negative |
| roots | negative | negative | negative | negative |
| flower | negative | negative | negative | negative |
| silique (without seed) | negative | not analyzed | negative | not assayed |
| embryo (early) | weak | weak | strong | strong, no seperate analyses of different stages |
| embryo (young) | weak | weak | strong | |
| embryo (medium) | strong | strong | strong | |
| embryo (mature) | strong | strong | strong | strong |
| seed shell | weak | not analyzed | strong | strong |

*expression in *Phaseolus* and *Arabidopsis* according to Goossens et al.

Figure 2:
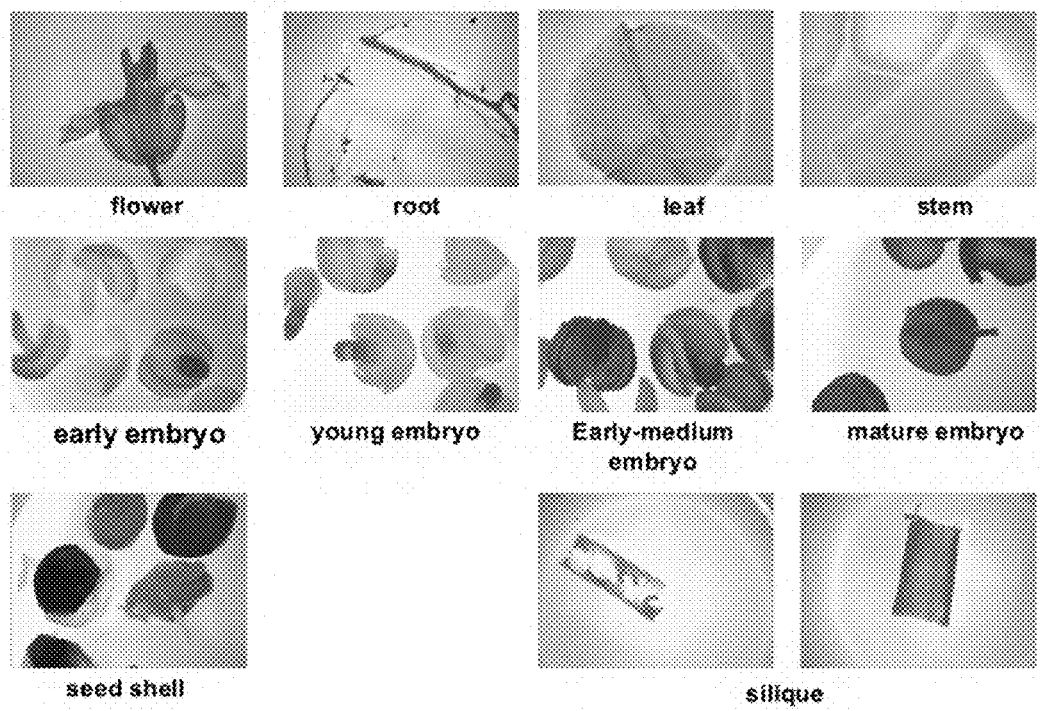
FIG. 2 shows the gene expression activity conferred by p-VfSBP_perm as described in Example 2.

The gene expression activity conferred by p-PvArc5_perm and p-VfSBP_perm is shown exemplary in FIG. 1 (p-PvArc5_perm) and in FIG. 2 (P-VfSBP_perm).

General results for SEQ ID NO2: Strong GUS expression was detected in all stages of embryo development and in seed shells. No activity was found in other tissues analyzed.

General results for SEQ ID NO4: Weak GUS expression was detected in early and young embryo stages, strong GUS expression could be observed in medium and mature embryos. Weak expression was monitored in seed shells. No activity was found in other tissues investigated.

Example 3

3.1 Random Permutation of the Promoter Sequence

Using publicly available data, a promoter showing seed specific expression in plants was selected for analyzing the effects of sequence permutation in periodic intervals throughout the full length of the promoter DNA sequence. The wild type sequences of the *Brassica napus* p-BnNapin promoter was analyzed and annotated for the occurrence of cis-regulatory elements using available literature data (Ellerström et al., Ericson et al., Ezcurra et al.). In the following, the DNA sequence of the promoter was permutated in the region of −1000 to +1 nucleotides with the following criteria to yield p-BnNapin_perm (SEQ ID NO6): DNA permutation was conducted in a way to not affect cis regulatory elements which have been proven previously to be essential for seed specific gene expression and motives essential for gene expression. The remaining promoter sequence was randomly permutated resulting in a promoter sequence with an overall nucleotide homology of 75% to the initial p-BnNapin sequence 3.2 Vector Construction Using the Multisite Gateway System (Invitrogen, Carlsbad, Calif., USA), promoter::reporter-gene cassettes were assembled into binary constructs for plant transformation. Beta-Glucuronidase (GUS) or uidA gene which encodes an enzyme for which various chromogenic substrates are known, was utilized as reporter protein for determining the expression features of the permutated p-BnNapin_perm (SEQ ID NO6) promoter sequences.

The DNA fragments representing promoter p-BnNapin_perm was generated by gene synthesis. Endonucleolytic restriction sites suitable for cloning the promoter fragment into a beta-Glucuronidase reporter gene cassette was included in the synthesis. p-BnNapin_perm (SEQ ID NO6) promoter was cloned into a pENTR/A vector harboring the beta-Glucuronidase reporter gene c-GUS (with the prefix c- denoting coding sequence) followed by the t-nos transcription terminator sequence using restriction endonucleases BamHI and NcoI, yielding pENTR/A LLL1168.

A 1138 bp DNA fragment representing the native promoter p-BnNapin (SEQ ID NO5) was generated by PCR with the following primers.

```
Loy963
                                        SEQ ID NO11
GATATAGGTACCTCTTCATCGGTGATTGATTCCT

Loy964
                                        SEQ ID NO12
GATATACCATGGTCGTGTATGTTTTTAATCTTGTTTG
```

Endonucleolytic restriction sites suitable for cloning the promoter fragment into a beta-Glucuronidase reporter gene cassette were included in the primers. p-BnNapin (SEQ ID NO5) promoter was cloned into a pENTR/A vector harboring the beta-Glucuronidase reporter gene c-GUS (with the prefix c- denoting coding sequence) followed by the t-nos transcription terminator sequence using restriction endonucleases KpnI and NcoI, yielding pENTR/A LLL1166.

By performing a site specific recombination (LR-reaction), the newly created pENTRs/A LLL1168 and LLL1166, were combined with pENTR/B and pENTR/C and the pSUN destination vector (pSUN derivative) according to the manufacturers (Invitrogen, Carlsbad, Calif., USA) Multisite Gateway manual. The reaction yielded binary vector LLL 1184 with the p-BnNapin_perm (SEQ ID NO6) promoter, the beta-Glucuronidase coding sequence c-GUS and the t-nos terminator, and binary vector LLL 1176 with the native p-BnNapin (SEQ ID NO5) promoter, the beta-Glucuronidase coding sequence c-GUS and the t-nos terminator. For both vectors the full construct sequence is given (SEQ ID NO9 and 10). The resulting plant transformation vectors are shown in table 7:

TABLE 7

Plant expression vectors for *A. thaliana* transformation

| plant expression vector | Composition of the expression cassette Promoter::reporter gene::terminator | SEQ ID NO |
|---|---|---|
| LLL1184 | p-BnNapin_perm::c-GUS::t-nos | 9 |
| LLL1176 | p-BnNapin::c-GUS::t-nos | 10 |

3.3 Generation of *Arabidopsis thaliana* Plants

*A. thaliana* plants were grown in soil until they flowered. *Agrobacterium tumefaciens* (strain C58C1 [pMP90]) transformed with the construct of interest was grown in 500 mL in liquid YEB medium (5 g/L Beef extract, 1 g/L Yeast Extract (Duchefa), 5 g/L Peptone (Duchefa), 5 g/L sucrose (Duchefa), 0.49 g/L MgSO$_4$ (Merck)) until the culture reached an OD$_{600}$ 0.8-1.0. The bacterial cells were harvested by centrifugation (15 minutes, 5,000 rpm) and resuspended in 500 mL infiltration solution (5% sucrose, 0.05% SILWET L-77 [distributed by Lehle seeds, Cat.No. VIS-02]). Flowering plants were dipped for 10-20 seconds into the *Agrobacterium* solution. Afterwards the plants were kept in the dark for one day and then in the greenhouse until seeds could be harvested. Transgenic seeds were selected on soil by spraying the seeds directly after sowing with a solution of 0.016 g/1 Imazamox. After 12 to 14 days surviving plants were transferred to pots and grown in the greenhouse.

Example 4: Expression Profile of the Native p-Bn-Napin and the p-BnNapin_Perm Gene Control Elements To demonstrate and analyze the transcription regulating properties of a promoter, it is useful to operably link the promoter or its fragments to a reporter gene, which can be employed to monitor its expression both qualitatively and quantitatively. Preferably bacterial ß-glucuronidase is used (Jefferson 1987). ß-glucuronidase activity can be monitored in planta with chromogenic substrates such as 5-bromo-4-Chloro-3-indolyl-ß-D-glucuronic acid during corresponding activity assays (Jefferson 1987). For determination of promoter activity and tissue specificity, plant tissue is dissected, stained and analyzed as described (e.g., Bäumlein 1991).

The regenerated transgenic T0 *Arabidopsis* plants harboring single or double insertions of the transgene deriving from constructs LLL1184 (SEQ ID NO9) and constructs LLL1176 (SEQ ID NO10) were used for reporter gene analysis. Table 8 summarizes the reporter gene activity observed in plants harboring transgenes containing SEQ ID NO9 and SEQ ID NO10 in constructs LLL1184 and LLL1176, respectively:

TABLE 8 beta-Glucuronidase reporter gene activity in selected *Arabidopsis* plants harboring transgenes with SEQ ID NO 9 or 10 respectively.

| Tissue | LLL1176 | LLL1184 |
|---|---|---|
| leaves | negative | negative |
| Stem | negative | negative |
| Roots | negative | negative |
| Flower | negative | negative |
| Silique | weak | weak |
| Embryo (medium) | strong | strong |
| Embryo (mature) | strong | strong |

Figure 3:
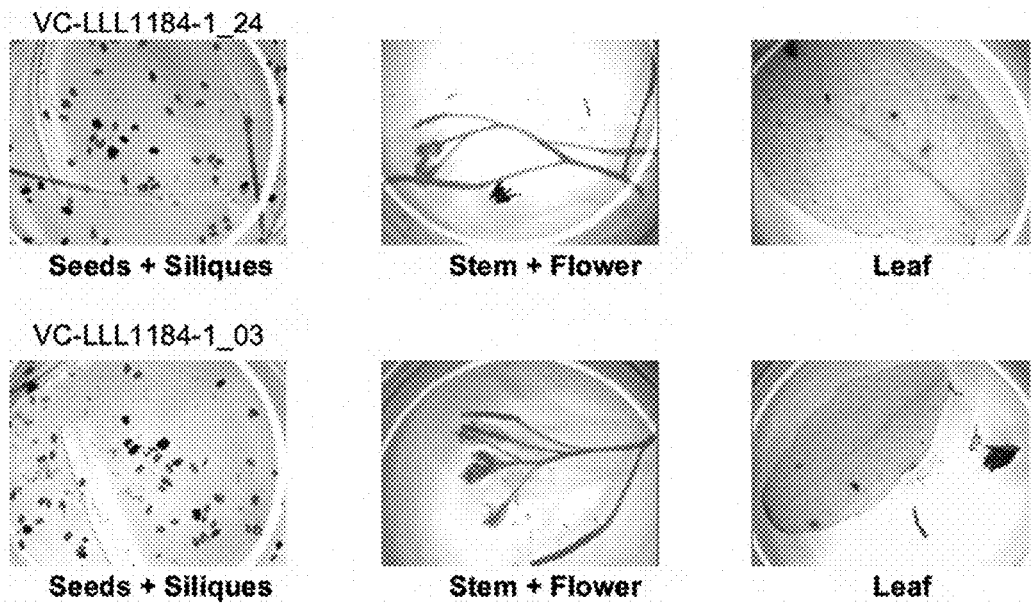
FIG. 3 shows gene expression activity conferred by pBn-Napin and p-BNapin_perm as described in Example 4.

The gene expression activity conferred by pBn-Napin and p-BNapin_perm is shown exemplary in FIG. 3 (p-Bn_napin SEQ ID NO5, p-BnNapin_perm SEQ ID NO6)

General results for SEQ ID NO5 and 6: For both promoters pBn-Napin and p-BNapin_perm strong GUS expression was detected in medium to mature stages of embryo development Weak expression was monitored in seed shells and in siliques. No activity was found in other tissues analyzed.

Example 5: Directed Permutation of a Constitutive Promoter Sequence

Using publicly available data, one promoters showing constitutive expression in plants was selected (de Pater, B. S., van der Mark, F., Rueb, S., Katagiri, F., Chua, N. H., Schilperoort, R. A. and Hensgens, L. A. (1992) The promoter of the rice gene GOS2 is active in various different monocot tissues and binds rice nuclear factor ASF-1 Plant J. 2 (6)) for analyzing the effects of sequence permutation in periodic intervals throughout the full length of the promoter DNA sequence. The wildtype or starting sequence of the *Oryza sativa* p-GOS2 (SEQ ID NO 13) (with the prefix p- denoting promoter) promoter was analyzed and annotated for the occurrence of motives, boxes, cis-regulatory elements using e.g. the GEMS Launcher Software (www.genomatix.de) as described above in example 1.

The promoter p-Gos2 encompasses a 5'UTR sequence with an internal intron. To ensure correct splicing of the intron after permutation, splice sites and putative branching point were not altered. No nucleotide exchanges were introduced into sequences 10 bp up- and downstream of the splice site (5' GT; 3' CAG) and "TNA" sequence elements within the last 100 base pairs of the original p-Gos2 were preserved after permutation.

In the following, the DNA sequence of the promoter was permutated according to the method of the invention to yield p-GOS2_perm1 and p-GOS2_perm2 respectively (SEQ ID NO 14 and 15).

The list of motives, boxes, cis regulatory elements in the p-GOS2 promoters before and after the permutation are shown in Table 9 for the starting sequence of p-GOS2, Table 10 for the p-GOS2_perm1 (SEQ ID NO 14) and Table 11 for the p-GOS2_perm2 sequence (SEQ ID NO 15).

Empty lines resemble motives, boxes, cis regulatory elements not found in one sequence but present in the corresponding sequence, hence, motives, boxes, cis regulatory elements that were deleted from the starting sequence or that were introduced into the permutated sequence.

TABLE 9

Boxes and Motifs identified in the starting sequence of the p-GOS2 promoter

| p-GOS2 | | | | Position | | Core | Matrix |
| | | | | Position | | sim. | sim. |
| Family | Further Family Information | Matrix | Opt. | from-to | | — | — |
| P$NCS1 | Nodulin consensus sequence 1 | P$NCS1.01 | 0.85 | 6 | 16 | 1 | 0.857 |
| P$MSAE | M-phase-specific activator elements | P$MSA.01 | 0.8 | 15 | 29 | 1 | 0.832 |
| P$MYBL | MYB-like proteins | P$GAMYB.01 | 0.91 | 29 | 45 | 1 | 0.927 |
| P$MYBL | MYB-like proteins | P$WER.01 | 0.87 | 33 | 49 | 1 | 0.897 |
| P$MADS | MADS box proteins | P$AGL2.01 | 0.82 | 35 | 55 | 0.79 | 0.82 |

TABLE 9-continued

Boxes and Motifs identified in the starting sequence of the p-GOS2 promoter

| p-GOS2 | | | | Position Position | | Core sim. | Matrix sim. |
|---|---|---|---|---|---|---|---|
| Family | Further Family Information | Matrix | Opt. | from-to | | — | — |
| P$NACF | Plant specific NAC [NAM (no apical meristem), ATAF172, CUC2 (cup-shaped cotyledons 2)] transcription factors | P$IDEF2.01 | 0.96 | 48 | 60 | 1 | 0.96 |
| P$BRRE | Brassinosteroid (BR) response element | P$BZR1.01 | 0.95 | 48 | 64 | 1 | 0.954 |
| O$PTBP | Plant TATA binding protein factor | O$PTATA.01 | 0.88 | 60 | 74 | 1 | 0.883 |
| O$VTBP | Vertebrate TATA binding protein factor | O$VTATA.01 | 0.9 | 61 | 77 | 1 | 0.961 |
| O$INRE | Core promoter initiator elements | O$DINR.01 | 0.94 | 65 | 75 | 0.97 | 0.94 |
| O$VTBP | Vertebrate TATA binding protein factor | O$LTATA.01 | 0.82 | 69 | 85 | 1 | 0.842 |
| O$VTBP | Vertebrate TATA binding protein factor | O$VTATA.01 | 0.9 | 71 | 87 | 0.89 | 0.921 |
| O$YTBP | Yeast TATA binding protein factor | O$SPT15.01 | 0.83 | 74 | 90 | 1 | 0.832 |
| O$YTBP | Yeast TATA binding protein factor | O$SPT15.01 | 0.83 | 75 | 91 | 1 | 0.876 |
| O$VTBP | Vertebrate TATA binding protein factor | O$ATATA.01 | 0.78 | 76 | 92 | 0.75 | 0.781 |
| O$YTBP | Yeast TATA binding protein factor | O$SPT15.01 | 0.83 | 77 | 93 | 0.76 | 0.835 |
| P$MIIG | MYB IIG-type binding sites | P$PALBOXL.01 | 0.8 | 118 | 132 | 0.77 | 0.841 |
| P$DOFF | DNA binding with one finger (DOF) | P$DOF1.01 | 0.98 | 126 | 142 | 1 | 0.99 |
| P$DOFF | DNA binding with one finger (DOF) | P$PBF.01 | 0.97 | 149 | 165 | 1 | 0.989 |
| P$WNAC | Wheat NAC-domain transcription factors | P$TANAC69.01 | 0.68 | 170 | 192 | 0.81 | 0.712 |
| O$VTBP | Vertebrate TATA binding protein factor | O$ATATA.01 | 0.78 | 187 | 203 | 1 | 0.922 |
| P$E2FF | E2F-homolog cell cycle regulators | P$E2F.01 | 0.82 | 193 | 207 | 1 | 0.829 |
| O$INRE | Core promoter initiator elements | O$DINR.01 | 0.94 | 200 | 210 | 0.97 | 0.945 |
| P$AHBP | *Arabidopsis* homeobox protein | P$ATHB5.01 | 0.89 | 207 | 217 | 0.83 | 0.903 |
| P$AHBP | *Arabidopsis* homeobox protein | P$HAHB4.01 | 0.87 | 207 | 217 | 1 | 0.967 |
| P$CNAC | Calcium regulated NAC-factors | P$CBNAC.02 | 0.85 | 215 | 235 | 1 | 0.947 |
| P$MYBS | MYB proteins with single DNA binding repeat | P$PHR1.01 | 0.84 | 217 | 233 | 1 | 0.944 |
| P$OCSE | Enhancer element first identified in the promoter of the octopine synthase gene (OCS) of the *Agrobacterium tumefaciens* T-DNA | P$OCSL.01 | 0.69 | 216 | 236 | 1 | 0.722 |
| P$MYBS | MYB proteins with single DNA binding repeat | P$PHR1.01 | 0.84 | 222 | 238 | 1 | 0.979 |
| P$GTBX | GT-box elements | P$SBF1.01 | 0.87 | 246 | 262 | 1 | 0.901 |
| P$STKM | Storekeeper motif | P$STK.01 | 0.85 | 251 | 265 | 1 | 0.85 |
| P$AHBP | *Arabidopsis* homeobox protein | P$ATHB5.01 | 0.89 | 254 | 264 | 0.83 | 0.904 |
| P$AHBP | *Arabidopsis* homeobox protein | P$BLR.01 | 0.9 | 254 | 264 | 1 | 0.998 |
| P$HEAT | Heat shock factors | P$HSFA1A.01 | 0.75 | 284 | 300 | 1 | 0.757 |
| P$CCAF | Circadian control factors | P$CCA1.01 | 0.85 | 297 | 311 | 1 | 0.953 |
| P$LFYB | LFY binding site | P$LFY.01 | 0.93 | 318 | 330 | 0.91 | 0.945 |
| P$GAGA | GAGA elements | P$BPC.01 | 1 | 329 | 353 | 1 | 1 |
| P$CCAF | Circadian control factors | P$EE.01 | 0.84 | 335 | 349 | 0.75 | 0.865 |
| P$GAGA | GAGA elements | P$BPC.01 | 1 | 331 | 355 | 1 | 1 |
| P$CCAF | Circadian control factors | P$CCA1.01 | 0.85 | 337 | 351 | 1 | 0.968 |
| P$GTBX | GT-box elements | P$SBF1.01 | 0.87 | 341 | 357 | 1 | 0.875 |
| P$MADS | MADS box proteins | P$SQUA.01 | 0.9 | 345 | 365 | 1 | 0.925 |
| P$CCAF | Circadian control factors | P$EE.01 | 0.84 | 363 | 377 | 1 | 0.925 |
| O$VTBP | Vertebrate TATA binding protein factor | O$MTATA.01 | 0.84 | 383 | 399 | 1 | 0.895 |
| P$CARM | CA-rich motif | P$CARICH.01 | 0.78 | 388 | 406 | 1 | 0.785 |
| P$AHBP | *Arabidopsis* homeobox protein | P$HAHB4.01 | 0.87 | 397 | 407 | 1 | 0.902 |

TABLE 9-continued

Boxes and Motifs identified in the starting sequence of the p-GOS2 promoter

| Family | Further Family Information | Matrix | Opt. | Position from-to | | Core sim. | Matrix sim. |
|---|---|---|---|---|---|---|---|
| O$VTBP | Vertebrate TATA binding protein factor | O$LTATA.01 | 0.82 | 395 | 411 | 1 | 0.889 |
| O$VTBP | Vertebrate TATA binding protein factor | O$LTATA.01 | 0.82 | 396 | 412 | 1 | 0.844 |
| O$PTBP | Plant TATA binding protein factor | O$PTATA.01 | 0.88 | 398 | 412 | 1 | 0.892 |
| O$VTBP | Vertebrate TATA binding protein factor | O$ATATA.01 | 0.78 | 397 | 413 | 0.75 | 0.781 |
| P$AHBP | *Arabidopsis* homeobox protein | P$HAHB4.01 | 0.87 | 400 | 410 | 1 | 0.902 |
| O$VTBP | Vertebrate TATA binding protein factor | O$ATATA.01 | 0.78 | 402 | 418 | 0.75 | 0.781 |
| O$VTBP | Vertebrate TATA binding protein factor | O$VTATA.02 | 0.89 | 405 | 421 | 1 | 0.983 |
| O$PTBP | Plant TATA binding protein factor | O$PTATA.02 | 0.9 | 408 | 422 | 1 | 0.917 |
| P$OCSE | Enhancer element first identified in the promoter of the octopine synthase gene (OCS) of the *Agrobacterium tumefaciens* T-DNA | P$OCSTF.01 | 0.73 | 426 | 446 | 1 | 0.784 |
| P$AHBP | *Arabidopsis* homeobox protein | P$HAHB4.01 | 0.87 | 440 | 450 | 1 | 0.926 |
| P$AHBP | *Arabidopsis* homeobox protein | P$WUS.01 | 0.94 | 444 | 454 | 1 | 1 |
| P$OPAQ | Opaque-2 like transcriptional activators | P$O2_GCN4.01 | 0.81 | 447 | 463 | 1 | 0.819 |
| P$SEF4 | Soybean embryo factor 4 | P$SEF4.01 | 0.98 | 472 | 482 | 1 | 0.984 |
| P$GTBX | GT-box elements | P$SBF1.01 | 0.87 | 481 | 497 | 1 | 0.922 |
| P$DOFF | DNA binding with one finger (DOF) | P$DOF1.01 | 0.98 | 482 | 498 | 1 | 0.994 |
| P$GTBX | GT-box elements | P$SBF1.01 | 0.87 | 482 | 498 | 1 | 0.9 |
| P$WBXF | W Box family | P$WRKY11.01 | 0.94 | 493 | 509 | 1 | 0.963 |
| P$SEF4 | Soybean embryo factor 4 | P$SEF4.01 | 0.98 | 504 | 514 | 1 | 0.994 |
| P$IBOX | Plant I-Box sites | P$GATA.01 | 0.93 | 509 | 525 | 1 | 0.961 |
| P$NCS1 | Nodulin consensus sequence 1 | P$NCS1.01 | 0.85 | 515 | 525 | 1 | 0.948 |
| P$GTBX | GT-box elements | P$S1F.01 | 0.79 | 518 | 534 | 0.75 | 0.793 |
| P$LREM | Light responsive element motif, not modulated by different light qualities | P$RAP22.01 | 0.85 | 527 | 537 | 1 | 0.897 |
| P$L1BX | L1 box, motif for L1 layer-specific expression | P$ATML1.01 | 0.82 | 525 | 541 | 0.75 | 0.825 |
| O$VTBP | Vertebrate TATA binding protein factor | O$ATATA.01 | 0.78 | 539 | 555 | 0.75 | 0.782 |
| P$ROOT | Root hair-specific cis-elements in angiosperms | P$RHE.01 | 0.77 | 568 | 592 | 0.75 | 0.772 |
| P$ABRE | ABA response elements | P$ABRE.01 | 0.82 | 591 | 607 | 1 | 0.837 |
| P$ASRC | AS1/AS2 repressor complex | P$AS1_AS2_II.01 | 0.86 | 599 | 607 | 1 | 0.867 |
| P$L1BX | L1 box, motif for L1 layer-specific expression | P$HDG9.01 | 0.77 | 629 | 645 | 1 | 0.89 |
| P$L1BX | L1 box, motif for L1 layer-specific expression | P$HDG9.01 | 0.77 | 631 | 647 | 0.8 | 0.783 |
| P$L1BX | L1 box, motif for L1 layer-specific expression | P$ATML1.01 | 0.82 | 638 | 654 | 1 | 0.877 |
| P$CCAF | Circadian control factors | P$EE.01 | 0.84 | 649 | 663 | 1 | 0.899 |
| P$DOFF | DNA binding with one finger (DOF) | P$PBF.01 | 0.97 | 687 | 703 | 1 | 0.987 |
| P$GTBX | GT-box elements | P$SBF1.01 | 0.87 | 689 | 705 | 1 | 0.888 |
| P$AHBP | *Arabidopsis* homeobox protein | P$BLR.01 | 0.9 | 695 | 705 | 1 | 0.929 |
| P$CCAF | Circadian control factors | P$EE.01 | 0.84 | 694 | 708 | 1 | 0.954 |
| P$LREM | Light responsive element motif, not modulated by different light qualities | P$RAP22.01 | 0.85 | 701 | 711 | 1 | 1 |
| O$VTBP | Vertebrate TATA binding protein factor | O$ATATA.01 | 0.78 | 699 | 715 | 0.75 | 0.822 |
| P$HMGF | High mobility group factors | P$HMG_IY.01 | 0.89 | 711 | 725 | 1 | 0.929 |
| P$AHBP | *Arabidopsis* homeobox protein | P$ATHB1.01 | 0.9 | 716 | 726 | 0.79 | 0.901 |
| P$AHBP | *Arabidopsis* homeobox protein | P$BLR.01 | 0.9 | 716 | 726 | 1 | 0.998 |
| O$VTBP | Vertebrate TATA binding protein factor | O$VTATA.02 | 0.89 | 716 | 732 | 1 | 0.893 |

TABLE 9-continued

Boxes and Motifs identified in the starting sequence of the p-GOS2 promoter

| Family | Further Family Information | Matrix | Opt. | Position from-to | | Core sim. | Matrix sim. |
|---|---|---|---|---|---|---|---|
| P$SUCB | Sucrose box | P$SUCROSE.01 | 0.81 | 715 | 733 | 1 | 0.856 |
| P$DOFF | DNA binding with one finger (DOF) | P$PBOX.01 | 0.75 | 718 | 734 | 0.76 | 0.762 |
| P$HEAT | Heat shock factors | P$HSE.01 | 0.81 | 718 | 734 | 1 | 0.833 |
| P$GAPB | GAP-Box (light response elements) | P$GAP.01 | 0.88 | 733 | 747 | 1 | 0.924 |
| P$MYBL | MYB-like proteins | P$MYBPH3.02 | 0.76 | 744 | 760 | 0.78 | 0.834 |
| O$VTBP | Vertebrate TATA binding protein factor | O$ATATA.01 | 0.78 | 754 | 770 | 0.75 | 0.831 |
| P$TELO | Telo box (plant interstitial telomere motifs) | P$ATPURA.01 | 0.85 | 756 | 770 | 0.75 | 0.869 |
| P$MYCL | Myc-like basic helix-loop-helix binding factors | P$OSBHLH66.01 | 0.85 | 789 | 807 | 1 | 0.851 |
| P$BRRE | Brassinosteroid (BR) response element | P$BZR1.01 | 0.95 | 793 | 809 | 1 | 0.998 |
| P$URNA | Upstream sequence element of U-snRNA genes | P$USE.01 | 0.75 | 812 | 828 | 0.75 | 0.797 |
| P$MADS | MADS box proteins | P$AGL1.01 | 0.84 | 812 | 832 | 1 | 0.895 |
| P$MADS | MADS box proteins | P$AGL1.01 | 0.84 | 813 | 833 | 0.92 | 0.911 |
| P$NCS1 | Nodulin consensus sequence 1 | P$NCS1.01 | 0.85 | 872 | 882 | 0.81 | 0.888 |
| P$LREM | Light responsive element motif, not modulated by different light qualities | P$RAP22.01 | 0.85 | 879 | 889 | 1 | 0.896 |
| P$MSAE | M-phase-specific activator elements | P$MSA.01 | 0.8 | 880 | 894 | 1 | 0.877 |
| P$MYBL | MYB-like proteins | P$NTMYBAS1.01 | 0.96 | 900 | 916 | 0.95 | 0.968 |
| P$GTBX | GT-box elements | P$SBF1.01 | 0.87 | 909 | 925 | 1 | 0.905 |
| P$MYBL | MYB-like proteins | P$AS1__AS2__I.01 | 0.99 | 911 | 927 | 1 | 1 |
| P$LREM | Light responsive element motif, not modulated by different light qualities | P$RAP22.01 | 0.85 | 981 | 991 | 1 | 0.893 |
| O$PTBP | Plant TATA binding protein factor | O$PTATA.02 | 0.9 | 982 | 996 | 1 | 0.951 |
| P$L1BX | L1 box, motif for L1 layer-specific expression | P$PDF2.01 | 0.85 | 982 | 998 | 1 | 0.884 |
| O$VTBP | Vertebrate TATA binding protein factor | O$VTATA.01 | 0.9 | 983 | 999 | 1 | 0.955 |
| P$MADS | MADS box proteins | P$AGL15.01 | 0.79 | 1006 | 1026 | 0.83 | 0.793 |
| P$MYBS | MYB proteins with single DNA binding repeat | P$ZMMRP1.01 | 0.79 | 1008 | 1024 | 0.78 | 0.811 |
| O$PTBP | Plant TATA binding protein factor | O$PTATA.02 | 0.9 | 1010 | 1024 | 1 | 0.91 |
| P$CGCG | Calmodulin binding/CGCG box binding proteins | P$ATSR1.01 | 0.84 | 1051 | 1067 | 1 | 0.859 |
| P$ABRE | ABA response elements | P$ABF1.01 | 0.79 | 1053 | 1069 | 1 | 0.837 |
| P$CE3S | Coupling element 3 sequence | P$CE3.01 | 0.77 | 1052 | 1070 | 1 | 0.893 |
| P$NACF | Plant specific NAC [NAM (no apical meristem), ATAF172, CUC2 (cup-shaped cotyledons 2)] transcription factors | P$ANAC092.01 | 0.92 | 1055 | 1067 | 1 | 0.927 |
| P$DPBF | Dc3 promoter binding factors | P$DPBF.01 | 0.89 | 1057 | 1067 | 1 | 0.908 |
| P$PREM | Motifs of plastid response elements | P$MGPROTORE.01 | 0.77 | 1059 | 1089 | 1 | 0.806 |
| O$MTEN | Core promoter motif ten elements | O$HMTE.01 | 0.88 | 1072 | 1092 | 0.96 | 0.94 |
| P$DREB | Dehydration responsive element binding factors | P$HVDRF1.01 | 0.89 | 1079 | 1093 | 1 | 0.922 |
| P$PREM | Motifs of plastid response elements | P$MGPROTORE.01 | 0.77 | 1077 | 1107 | 1 | 0.805 |
| O$MTEN | Core promoter motif ten elements | O$DMTE.01 | 0.77 | 1097 | 1117 | 0.84 | 0.805 |
| P$OPAQ | Opaque-2 like transcriptional activators | P$O2.02 | 0.87 | 1135 | 1151 | 1 | 0.915 |
| P$SALT | Salt/drought responsive elements | P$ALFIN1.02 | 0.95 | 1136 | 1150 | 1 | 0.954 |
| P$L1BX | L1 box, motif for L1 layer-specific expression | P$PDF2.01 | 0.85 | 1179 | 1195 | 1 | 0.882 |
| P$SBPD | SBP-domain proteins | P$SBP.01 | 0.88 | 1199 | 1215 | 1 | 0.912 |
| P$PALA | Conserved box A in PAL and 4CL gene promoters | P$PALBOXA.01 | 0.84 | 1201 | 1219 | 1 | 0.863 |
| P$MYBS | MYB proteins with single DNA binding repeat | P$ZMMRP1.01 | 0.79 | 1230 | 1246 | 1 | 0.833 |

TABLE 9-continued

Boxes and Motifs identified in the starting sequence of the p-GOS2 promoter

| | p-GOS2 | | | Position Position | | Core sim. | Matrix sim. |
|---|---|---|---|---|---|---|---|
| Family | Further Family Information | Matrix | Opt. | from-to | | — | — |
| P$AHBP | *Arabidopsis* homeobox protein | P$ATHB9.01 | 0.77 | 1244 | 1254 | 1 | 0.867 |
| P$MADS | MADS box proteins | P$AGL2.01 | 0.82 | 1248 | 1268 | 0.97 | 0.828 |
| P$MYBS | MYB proteins with single DNA binding repeat | P$MYBST1.01 | 0.9 | 1262 | 1278 | 1 | 0.953 |
| P$HEAT | Heat shock factors | P$HSE.01 | 0.81 | 1278 | 1294 | 1 | 0.864 |
| P$LEGB | Legumin Box family | P$RY.01 | 0.87 | 1277 | 1303 | 1 | 0.871 |
| P$MYBS | MYB proteins with single DNA binding repeat | P$OSMYBS.01 | 0.82 | 1343 | 1359 | 0.75 | 0.822 |
| O$INRE | Core promoter initiator elements | O$DINR.01 | 0.94 | 1349 | 1359 | 0.97 | 0.955 |
| P$STKM | Storekeeper motif | P$STK.01 | 0.85 | 1355 | 1369 | 1 | 0.95 |
| P$GTBX | GT-box elements | P$GT1.01 | 0.85 | 1403 | 1419 | 0.97 | 0.865 |
| O$VTBP | Vertebrate TATA binding protein factor | O$ATATA.01 | 0.78 | 1439 | 1455 | 0.75 | 0.797 |
| P$OCSE | Enhancer element first identified in the promoter of the octopine synthase gene (OCS) of the *Agrobacterium tumefaciens* T-DNA | P$OCSL.01 | 0.69 | 1437 | 1457 | 0.77 | 0.745 |
| P$HEAT | Heat shock factors | P$HSFA1A.01 | 0.75 | 1478 | 1494 | 1 | 0.764 |
| P$WBXF | W Box family | P$WRKY.01 | 0.92 | 1488 | 1504 | 1 | 0.94 |
| P$TEFB | TEF-box | P$TEF1.01 | 0.76 | 1491 | 1511 | 0.96 | 0.858 |
| P$MYBS | MYB proteins with single DNA binding repeat | P$HVMCB1.01 | 0.93 | 1498 | 1514 | 1 | 0.934 |
| P$MYBS | MYB proteins with single DNA binding repeat | P$TAMYB80.01 | 0.83 | 1509 | 1525 | 0.75 | 0.837 |
| P$MSAE | M-phase-specific activator elements | P$MSA.01 | 0.8 | 1551 | 1565 | 1 | 0.802 |
| P$OPAQ | Opaque-2 like transcriptional activators | P$O2.01 | 0.87 | 1558 | 1574 | 1 | 0.883 |
| P$AHBP | *Arabidopsis* homeobox protein | P$ATHB5.01 | 0.89 | 1569 | 1579 | 0.83 | 0.904 |
| P$AHBP | *Arabidopsis* homeobox protein | P$ATHB5.01 | 0.89 | 1569 | 1579 | 0.94 | 0.978 |
| O$VTBP | Vertebrate TATA binding protein factor | O$ATATA.01 | 0.78 | 1609 | 1625 | 0.75 | 0.781 |
| P$LREM | Light responsive element motif, not modulated by different light qualities | P$RAP22.01 | 0.85 | 1613 | 1623 | 1 | 0.966 |
| P$TEFB | TEF-box | P$TEF1.01 | 0.76 | 1617 | 1637 | 0.84 | 0.812 |
| P$WNAC | Wheat NAC-domain transcription factors | P$TANAC69.01 | 0.68 | 1625 | 1647 | 0.9 | 0.775 |
| P$NACF | Plant specific NAC [NAM (no apical meristem), ATAF172, CUC2 (cup-shaped cotyledons 2)] transcription factors | P$ANAC019.01 | 0.94 | 1632 | 1644 | 0.95 | 0.968 |
| P$GTBX | GT-box elements | P$S1F.01 | 0.79 | 1642 | 1658 | 1 | 0.917 |
| P$PSRE | Pollen-specific regulatory elements | P$GAAA.01 | 0.83 | 1644 | 1660 | 1 | 0.864 |
| P$MYBL | MYB-like proteins | P$MYBPH3.01 | 0.8 | 1647 | 1663 | 1 | 0.938 |
| P$DOFF | DNA binding with one finger (DOF) | P$DOF1.01 | 0.98 | 1694 | 1710 | 1 | 1 |
| P$HEAT | Heat shock factors | P$HSFA1A.01 | 0.75 | 1703 | 1719 | 0.86 | 0.757 |
| P$CCAF | Circadian control factors | P$EE.01 | 0.84 | 1719 | 1733 | 1 | 0.955 |
| P$MADS | MADS box proteins | P$AG.01 | 0.8 | 1717 | 1737 | 0.9 | 0.816 |
| P$GTBX | GT-box elements | P$ASIL1.01 | 0.93 | 1732 | 1748 | 1 | 0.967 |
| O$INRE | Core promoter initiator elements | O$DINR.01 | 0.94 | 1749 | 1759 | 1 | 0.957 |
| P$SUCB | Sucrose box | P$SUCROSE.01 | 0.81 | 1749 | 1767 | 0.75 | 0.837 |
| P$SUCB | Sucrose box | P$SUCROSE.01 | 0.81 | 1754 | 1772 | 0.75 | 0.815 |
| P$L1BX | L1 box, motif for L1 layer-specific expression | P$ATML1.02 | 0.76 | 1757 | 1773 | 0.89 | 0.848 |
| P$AHBP | *Arabidopsis* homeobox protein | P$ATHB9.01 | 0.77 | 1761 | 1771 | 0.75 | 0.815 |
| O$VTBP | Vertebrate TATA binding protein factor | O$VTATA.02 | 0.89 | 1777 | 1793 | 1 | 0.996 |
| P$DOFF | DNA binding with one finger (DOF) | P$DOF3.01 | 0.99 | 1778 | 1794 | 1 | 0.995 |
| O$PTBP | Plant TATA binding protein factor | O$PTATA.02 | 0.9 | 1780 | 1794 | 1 | 0.923 |
| P$IBOX | Plant I-Box sites | P$GATA.01 | 0.93 | 1787 | 1803 | 1 | 0.967 |
| P$MYBS | MYB proteins with single DNA binding repeat | P$MYBST1.01 | 0.9 | 1790 | 1806 | 1 | 0.972 |

TABLE 9-continued

Boxes and Motifs identified in the starting sequence of the p-GOS2 promoter

| p-GOS2 | | | | Position Position | | Core sim. | Matrix sim. |
|---|---|---|---|---|---|---|---|
| Family | Further Family Information | Matrix | Opt. | from | to | — | — |
| O$VTBP | Vertebrate TATA binding protein factor | O$ATATA.01 | 0.78 | 1803 | 1819 | 0.75 | 0.797 |
| P$IBOX | Plant I-Box sites | P$GATA.01 | 0.93 | 1847 | 1863 | 1 | 0.945 |
| P$MYBS | MYB proteins with single DNA binding repeat | P$MYBST1.01 | 0.9 | 1850 | 1866 | 1 | 0.966 |
| P$MADS | MADS box proteins | P$SQUA.01 | 0.9 | 1866 | 1886 | 1 | 0.916 |
| P$GTBX | GT-box elements | P$SBF1.01 | 0.87 | 1872 | 1888 | 1 | 0.905 |
| O$VTBP | Vertebrate TATA binding protein factor | O$LTATA.01 | 0.82 | 1873 | 1889 | 1 | 0.837 |
| P$AHBP | *Arabidopsis* homeobox protein | P$HAHB4.01 | 0.87 | 1878 | 1888 | 1 | 0.902 |
| P$L1BX | L1 box, motif for L1 layer-specific expression | P$ATML1.01 | 0.82 | 1882 | 1898 | 0.75 | 0.824 |
| O$INRE | Core promoter initiator elements | O$DINR.01 | 0.94 | 1886 | 1896 | 0.97 | 0.949 |
| P$EPFF | EPF-type zinc finger factors, two canonical Cys2/His2 zinc finger motifs separated by spacers of various length | P$ZPT22.01 | 0.75 | 1887 | 1909 | 1 | 0.774 |
| P$GAPB | GAP-Box (light response elements) | P$GAP.01 | 0.88 | 1907 | 1921 | 1 | 0.903 |
| P$SUCB | Sucrose box | P$SUCROSE.01 | 0.81 | 1912 | 1930 | 1 | 0.849 |
| P$HMGF | High mobility group factors | P$HMG_IY.01 | 0.89 | 1920 | 1934 | 1 | 0.892 |
| P$SEF4 | Soybean embryo factor 4 | P$SEF4.01 | 0.98 | 1927 | 1937 | 1 | 0.984 |
| P$MYBL | MYB-like proteins | P$ATMYB77.01 | 0.87 | 1973 | 1989 | 1 | 0.9 |
| P$GTBX | GT-box elements | P$ASIL1.01 | 0.93 | 1998 | 2014 | 1 | 0.971 |
| P$OPAQ | Opaque-2 like transcriptional activators | P$O2_GCN4.01 | 0.81 | 2001 | 2017 | 1 | 0.83 |
| P$IBOX | Plant I-Box sites | P$GATA.01 | 0.93 | 2018 | 2034 | 1 | 0.964 |
| P$MYBS | MYB proteins with single DNA binding repeat | P$MYBST1.01 | 0.9 | 2021 | 2037 | 1 | 0.957 |
| P$LREM | Light responsive element motif, not modulated by different light qualities | P$RAP22.01 | 0.85 | 2035 | 2045 | 1 | 0.858 |
| P$MIIG | MYB IIG-type binding sites | P$MYBC1.01 | 0.92 | 2033 | 2047 | 1 | 0.941 |
| P$HEAT | Heat shock factors | P$HSFA1A.01 | 0.75 | 2041 | 2057 | 1 | 0.792 |
| P$MYBL | MYB-like proteins | P$GAMYB.01 | 0.91 | 2054 | 2070 | 1 | 0.918 |
| P$GTBX | GT-box elements | P$GT1.01 | 0.85 | 2056 | 2072 | 1 | 0.876 |
| P$ASRC | AS1/AS2 repressor complex | P$AS1_AS2_II.01 | 0.86 | 2067 | 2075 | 1 | 0.906 |
| P$EINL | Ethylen insensitive 3 like factors | P$TEIL.01 | 0.92 | 2098 | 2106 | 0.96 | 0.926 |
| O$VTBP | Vertebrate TATA binding protein factor | O$LTATA.01 | 0.82 | 2110 | 2126 | 1 | 0.828 |
| P$MYBL | MYB-like proteins | P$MYBPH3.02 | 0.76 | 2110 | 2126 | 1 | 0.807 |

TABLE 10

Boxes and Motifs identified in the permutated sequence of the p-GOS2_perm1 promoter.

| p-GOS2_perm1 | | | | Position Position | | Core sim. | Matrix sim. |
|---|---|---|---|---|---|---|---|
| Family | Further Family Information | Matrix | Opt. | from | to | | |
| P$NCS1 | Nodulin consensus sequence 1 | P$NCS1.01 | 0.85 | 6 | 16 | 1 | 0.857 |
| P$MSAE | M-phase-specific activator elements | P$MSA.01 | 0.8 | 15 | 29 | 1 | 0.832 |
| P$MYBL | MYB-like proteins | P$GAMYB.01 | 0.91 | 29 | 45 | 1 | 0.92 |
| P$MYBL | MYB-like proteins | P$WER.01 | 0.87 | 33 | 49 | 1 | 0.897 |
| P$MADS | MADS box proteins | P$AGL2.01 | 0.82 | 35 | 55 | 0.79 | 0.82 |
| P$NACF | Plant specific NAC [NAM (no apical meristem), ATAF172, CUC2 (cup-shaped cotyledons 2)] transcription factors | P$IDEF2.01 | 0.96 | 48 | 60 | 1 | 0.96 |
| P$BRRE | Brassinosteroid (BR) response element | P$BZR1.01 | 0.95 | 48 | 64 | 1 | 0.954 |
| O$PTBP | Plant TATA binding protein factor | O$PTATA.01 | 0.88 | 60 | 74 | 1 | 0.887 |
| O$VTBP | Vertebrate TATA binding protein factor | O$VTATA.01 | 0.9 | 61 | 77 | 1 | 0.961 |

TABLE 10-continued

Boxes and Motifs identified in the permutated sequence of the p-GOS2_perm1 promoter.

| p-GOS2_perm1 | | | | Position Position from-to | | Core sim. | Matrix sim. |
|---|---|---|---|---|---|---|---|
| Family | Further Family Information | Matrix | Opt. | | | | |
| O$INRE | Core promoter initiator elements | O$DINR.01 | 0.94 | 65 | 75 | 0.97 | 0.94 |
| O$VTBP | Vertebrate TATA binding protein factor | O$LTATA.01 | 0.82 | 69 | 85 | 1 | 0.867 |
| O$VTBP | Vertebrate TATA binding protein factor | O$VTATA.01 | 0.9 | 71 | 87 | 0.89 | 0.92 |
| O$YTBP | Yeast TATA binding protein factor | O$SPT15.01 | 0.83 | 74 | 90 | 1 | 0.832 |
| O$YTBP | Yeast TATA binding protein factor | O$SPT15.01 | 0.83 | 75 | 91 | 1 | 0.877 |
| O$VTBP | Vertebrate TATA binding protein factor | O$ATATA.01 | 0.78 | 76 | 92 | 0.75 | 0.781 |
| O$YTBP | Yeast TATA binding protein factor | O$SPT15.01 | 0.83 | 77 | 93 | 0.76 | 0.835 |
| P$MIIG | MYB IIG-type binding sites | P$PALBOXL.01 | 0.8 | 118 | 132 | 0.77 | 0.841 |
| P$DOFF | DNA binding with one finger (DOF) | P$DOF1.01 | 0.98 | 126 | 142 | 1 | 0.99 |
| P$DOFF | DNA binding with one finger (DOF) | P$PBF.01 | 0.97 | 149 | 165 | 1 | 0.989 |
| P$WNAC | Wheat NAC-domain transcription factors | P$TANAC69.01 | 0.68 | 170 | 192 | 0.81 | 0.712 |
| O$VTBP | Vertebrate TATA binding protein factor | O$ATATA.01 | 0.78 | 187 | 203 | 1 | 0.878 |
| P$E2FF | E2F-homolog cell cycle regulators | P$E2F.01 | 0.82 | 193 | 207 | 1 | 0.826 |
| P$AHBP | *Arabidopsis* homeobox protein | P$ATHB5.01 | 0.89 | 207 | 217 | 0.83 | 0.903 |
| P$AHBP | *Arabidopsis* homeobox protein | P$HAHB4.01 | 0.87 | 207 | 217 | 1 | 0.967 |
| P$CNAC | Calcium regulated NAC-factors | P$CBNAC.02 | 0.85 | 215 | 235 | 1 | 0.937 |
| P$MYBS | MYB proteins with single DNA binding repeat | P$PHR1.01 | 0.84 | 217 | 233 | 1 | 0.944 |
| P$OCSE | Enhancer element first identified in the promoter of the octopine synthase gene (OCS) of the *Agrobacterium tumefaciens* T-DNA | P$OCSL.01 | 0.69 | 216 | 236 | 1 | 0.735 |
| P$MYBS | MYB proteins with single DNA binding repeat | P$PHR1.01 | 0.84 | 222 | 238 | 1 | 0.979 |
| P$GTBX | GT-box elements | P$SBF1.01 | 0.87 | 246 | 262 | 1 | 0.901 |
| P$STKM | Storekeeper motif | P$STK.01 | 0.85 | 251 | 265 | 1 | 0.85 |
| P$AHBP | *Arabidopsis* homeobox protein | P$ATHB5.01 | 0.89 | 254 | 264 | 0.83 | 0.904 |
| P$AHBP | *Arabidopsis* homeobox protein | P$BLR.01 | 0.9 | 254 | 264 | 1 | 0.998 |
| P$HEAT | Heat shock factors | P$HSFA1A.01 | 0.75 | 284 | 300 | 1 | 0.757 |
| P$CCAF | Circadian control factors | P$CCA1.01 | 0.85 | 297 | 311 | 1 | 0.94 |
| P$LFYB | LFY binding site | P$LFY.01 | 0.93 | 318 | 330 | 0.91 | 0.945 |
| P$WBXF | W Box family | P$ERE.01 | 0.89 | 322 | 338 | 1 | 0.893 |
| P$GAGA | GAGA elements | P$BPC.01 | 1 | 329 | 353 | 1 | 1 |
| P$CCAF | Circadian control factors | P$EE.01 | 0.84 | 335 | 349 | 0.75 | 0.865 |
| P$GAGA | GAGA elements | P$BPC.01 | 1 | 331 | 355 | 1 | 1 |
| P$CCAF | Circadian control factors | P$CCA1.01 | 0.85 | 337 | 351 | 1 | 0.968 |
| P$GTBX | GT-box elements | P$SBF1.01 | 0.87 | 341 | 357 | 1 | 0.875 |
| P$MADS | MADS box proteins | P$SQUA.01 | 0.9 | 345 | 365 | 1 | 0.925 |
| P$CCAF | Circadian control factors | P$EE.01 | 0.84 | 363 | 377 | 1 | 0.924 |
| O$VTBP | Vertebrate TATA binding protein factor | O$MTATA.01 | 0.84 | 383 | 399 | 1 | 0.895 |
| P$CARM | CA-rich motif | P$CARICH.01 | 0.78 | 388 | 406 | 1 | 0.8 |
| P$AHBP | *Arabidopsis* homeobox protein | P$HAHB4.01 | 0.87 | 397 | 407 | 1 | 0.902 |
| O$VTBP | Vertebrate TATA binding protein factor | O$LTATA.01 | 0.82 | 395 | 411 | 1 | 0.889 |
| O$VTBP | Vertebrate TATA binding protein factor | O$LTATA.01 | 0.82 | 396 | 412 | 1 | 0.844 |
| O$PTBP | Plant TATA binding protein factor | O$PTATA.01 | 0.88 | 398 | 412 | 1 | 0.892 |
| O$VTBP | Vertebrate TATA binding protein factor | O$ATATA.01 | 0.78 | 397 | 413 | 0.75 | 0.781 |
| P$AHBP | *Arabidopsis* homeobox protein | P$HAHB4.01 | 0.87 | 400 | 410 | 1 | 0.902 |
| O$VTBP | Vertebrate TATA binding protein factor | O$ATATA.01 | 0.78 | 402 | 418 | 0.75 | 0.781 |
| O$VTBP | Vertebrate TATA binding protein factor | O$VTATA.02 | 0.89 | 405 | 421 | 1 | 0.983 |
| O$PTBP | Plant TATA binding protein factor | O$PTATA.02 | 0.9 | 408 | 422 | 1 | 0.917 |
| P$OCSE | Enhancer element first identified in the promoter of the octopine synthase gene | P$OCSTF.01 | 0.73 | 426 | 446 | 1 | 0.762 |

TABLE 10-continued

Boxes and Motifs identified in the permutated sequence of the p-GOS2_perm1 promoter.

| | p-GOS2_perm1 | | | Position Position | | Core | Matrix |
|---|---|---|---|---|---|---|---|
| Family | Further Family Information | Matrix | Opt. | from | to | sim. | sim. |
| | (OCS) of the *Agrobacterium tumefaciens* T-DNA | | | | | | |
| P$AHBP | *Arabidopsis* homeobox protein | P$HAHB4.01 | 0.87 | 440 | 450 | 1 | 0.926 |
| P$AHBP | *Arabidopsis* homeobox protein | P$WUS.01 | 0.94 | 444 | 454 | 1 | 1 |
| P$OPAQ | Opaque-2 like transcriptional activators | P$O2_GCN4.01 | 0.81 | 447 | 463 | 1 | 0.819 |
| P$SEF4 | Soybean embryo factor 4 | P$SEF4.01 | 0.98 | 472 | 482 | 1 | 0.988 |
| P$GTBX | GT-box elements | P$SBF1.01 | 0.87 | 481 | 497 | 1 | 0.922 |
| P$DOFF | DNA binding with one finger (DOF) | P$DOF1.01 | 0.98 | 482 | 498 | 1 | 0.994 |
| P$GTBX | GT-box elements | P$SBF1.01 | 0.87 | 482 | 498 | 1 | 0.9 |
| P$WBXF | W Box family | P$WRKY11.01 | 0.94 | 493 | 509 | 1 | 0.957 |
| P$SEF4 | Soybean embryo factor 4 | P$SEF4.01 | 0.98 | 504 | 514 | 1 | 0.988 |
| P$IBOX | Plant I-Box sites | P$GATA.01 | 0.93 | 509 | 525 | 1 | 0.961 |
| P$NCS1 | Nodulin consensus sequence 1 | P$NCS1.01 | 0.85 | 515 | 525 | 1 | 0.948 |
| P$GTBX | GT-box elements | P$S1F.01 | 0.79 | 518 | 534 | 0.75 | 0.793 |
| P$LREM | Light responsive element motif, not modulated by different light qualities | P$RAP22.01 | 0.85 | 527 | 537 | 1 | 0.897 |
| P$L1BX | L1 box, motif for L1 layer-specific expression | P$HDG9.01 | 0.77 | 525 | 541 | 0.75 | 0.78 |
| O$VTBP | Vertebrate TATA binding protein factor | O$ATATA.01 | 0.78 | 539 | 555 | 0.75 | 0.782 |
| P$ROOT | Root hair-specific cis-elements in angiosperms | P$RHE.01 | 0.77 | 568 | 592 | 0.75 | 0.772 |
| P$ABRE | ABA response elements | P$ABRE.01 | 0.82 | 591 | 607 | 1 | 0.837 |
| P$ASRC | AS1/AS2 repressor complex | P$AS1_AS2_II.01 | 0.86 | 599 | 607 | 1 | 0.867 |
| P$L1BX | L1 box, motif for L1 layer-specific expression | P$HDG9.01 | 0.77 | 629 | 645 | 1 | 0.888 |
| O$VTBP | Vertebrate TATA binding protein factor | O$ATATA.01 | 0.78 | 631 | 647 | 0.75 | 0.831 |
| P$L1BX | L1 box, motif for L1 layer-specific expression | P$HDG9.01 | 0.77 | 631 | 647 | 0.8 | 0.783 |
| P$L1BX | L1 box, motif for L1 layer-specific expression | P$PDF2.01 | 0.85 | 638 | 654 | 1 | 0.861 |
| P$CCAF | Circadian control factors | P$EE.01 | 0.84 | 649 | 663 | 1 | 0.899 |
| P$DOFF | DNA binding with one finger (DOF) | P$PBF.01 | 0.97 | 687 | 703 | 1 | 0.987 |
| P$GTBX | GT-box elements | P$SBF1.01 | 0.87 | 689 | 705 | 1 | 0.888 |
| P$AHBP | *Arabidopsis* homeobox protein | P$BLR.01 | 0.9 | 695 | 705 | 1 | 0.929 |
| P$CCAF | Circadian control factors | P$EE.01 | 0.84 | 694 | 708 | 1 | 0.954 |
| P$LREM | Light responsive element motif, not modulated by different light qualities | P$RAP22.01 | 0.85 | 701 | 711 | 1 | 0.98 |
| P$HMGF | High mobility group factors | P$HMG_IY.01 | 0.89 | 711 | 725 | 1 | 0.929 |
| P$AHBP | *Arabidopsis* homeobox protein | P$ATHB1.01 | 0.9 | 716 | 726 | 0.79 | 0.901 |
| P$AHBP | *Arabidopsis* homeobox protein | P$BLR.01 | 0.9 | 716 | 726 | 1 | 0.998 |
| O$VTBP | Vertebrate TATA binding protein factor | O$VTATA.02 | 0.89 | 716 | 732 | 1 | 0.893 |
| P$SUCB | Sucrose box | P$SUCROSE.01 | 0.81 | 715 | 733 | 1 | 0.856 |
| P$DOFF | DNA binding with one finger (DOF) | P$PBOX.01 | 0.75 | 718 | 734 | 0.76 | 0.762 |
| P$HEAT | Heat shock factors | P$HSE.01 | 0.81 | 718 | 734 | 1 | 0.833 |
| P$GAPB | GAP-Box (light response elements) | P$GAP.01 | 0.88 | 733 | 747 | 1 | 0.917 |
| P$MYBL | MYB-like proteins | P$MYBPH3.02 | 0.76 | 744 | 760 | 0.78 | 0.834 |
| O$VTBP | Vertebrate TATA binding protein factor | O$ATATA.01 | 0.78 | 754 | 770 | 0.75 | 0.831 |
| P$TELO | Telo box (plant interstitial telomere motifs) | P$ATPURA.01 | 0.85 | 756 | 770 | 0.75 | 0.869 |
| P$MYCL | Myc-like basic helix-loop-helix binding factors | P$OSBHLH66.01 | 0.85 | 789 | 807 | 1 | 0.851 |
| P$BRRE | Brassinosteroid (BR) response element | P$BZR1.01 | 0.95 | 793 | 809 | 1 | 0.998 |
| P$URNA | Upstream sequence element of U-snRNA genes | P$USE.01 | 0.75 | 812 | 828 | 0.75 | 0.797 |
| P$MADS | MADS box proteins | P$AGL1.01 | 0.84 | 812 | 832 | 1 | 0.895 |
| P$MADS | MADS box proteins | P$AGL1.01 | 0.84 | 813 | 833 | 0.92 | 0.911 |
| P$NCS1 | Nodulin consensus sequence 1 | P$NCS1.01 | 0.85 | 872 | 882 | 0.81 | 0.888 |
| P$LREM | Light responsive element motif, not modulated by different light qualities | P$RAP22.01 | 0.85 | 879 | 889 | 1 | 0.896 |

TABLE 10-continued

Boxes and Motifs identified in the permutated sequence of the p-GOS2_perm1 promoter.

| p-GOS2_perm1 | | | | Position Position | | Core | Matrix |
|---|---|---|---|---|---|---|---|
| Family | Further Family Information | Matrix | Opt. | from | to | sim. | sim. |
| P$MSAE | M-phase-specific activator elements | P$MSA.01 | 0.8 | 880 | 894 | 1 | 0.877 |
| P$MYBL | MYB-like proteins | P$NTMYBAS1.01 | 0.96 | 900 | 916 | 0.95 | 0.968 |
| P$GTBX | GT-box elements | P$SBF1.01 | 0.87 | 909 | 925 | 1 | 0.905 |
| P$MYBL | MYB-like proteins | P$AS1_AS2_I.01 | 0.99 | 911 | 927 | 1 | 1 |
| P$LREM | Light responsive element motif, not modulated by different light qualities | P$RAP22.01 | 0.85 | 981 | 991 | 1 | 0.893 |
| O$PTBP | Plant TATA binding protein factor | O$PTATA.02 | 0.9 | 982 | 996 | 1 | 0.951 |
| P$L1BX | L1 box, motif for L1 layer-specific expression | P$PDF2.01 | 0.85 | 982 | 998 | 1 | 0.884 |
| O$VTBP | Vertebrate TATA binding protein factor | O$VTATA.01 | 0.9 | 983 | 999 | 1 | 0.955 |
| P$MADS | MADS box proteins | P$AGL15.01 | 0.79 | 1006 | 1026 | 0.83 | 0.8 |
| P$MYBS | MYB proteins with single DNA binding repeat | P$ZMMRP1.01 | 0.79 | 1008 | 1024 | 0.78 | 0.811 |
| O$PTBP | Plant TATA binding protein factor | O$PTATA.02 | 0.9 | 1010 | 1024 | 1 | 0.91 |
| P$CGCG | Calmodulin binding/CGCG box binding proteins | P$ATSR1.01 | 0.84 | 1051 | 1067 | 1 | 0.859 |
| P$ABRE | ABA response elements | P$ABF1.01 | 0.79 | 1053 | 1069 | 1 | 0.837 |
| P$CE3S | Coupling element 3 sequence | P$CE3.01 | 0.77 | 1052 | 1070 | 1 | 0.863 |
| P$NACF | Plant specific NAC [NAM (no apical meristem), ATAF172, CUC2 (cup-shaped cotyledons 2)] transcription factors | P$ANAC092.01 | 0.92 | 1055 | 1067 | 1 | 0.927 |
| P$DPBF | Dc3 promoter binding factors | P$DPBF.01 | 0.89 | 1057 | 1067 | 1 | 0.908 |
| P$PREM | Motifs of plastid response elements | P$MGPROTORE.01 | 0.77 | 1059 | 1089 | 1 | 0.806 |
| O$MTEN | Core promoter motif ten elements | O$HMTE.01 | 0.88 | 1072 | 1092 | 0.96 | 0.94 |
| P$DREB | Dehydration responsive element binding factors | P$HVDRF1.01 | 0.89 | 1079 | 1093 | 1 | 0.917 |
| P$PREM | Motifs of plastid response elements | P$MGPROTORE.01 | 0.77 | 1077 | 1107 | 1 | 0.807 |
| O$MTEN | Core promoter motif ten elements | O$DMTE.01 | 0.77 | 1097 | 1117 | 0.84 | 0.805 |
| P$OPAQ | Opaque-2 like transcriptional activators | P$O2.02 | 0.87 | 1135 | 1151 | 1 | 0.915 |
| P$SALT | Salt/drought responsive elements | P$ALFIN1.02 | 0.95 | 1136 | 1150 | 1 | 0.954 |
| P$L1BX | L1 box, motif for L1 layer-specific expression | P$PDF2.01 | 0.85 | 1179 | 1195 | 1 | 0.882 |
| P$SBPD | SBP-domain proteins | P$SBP.01 | 0.88 | 1199 | 1215 | 1 | 0.912 |
| P$PALA | Conserved box A in PAL and 4CL gene promoters | P$PALBOXA.01 | 0.84 | 1201 | 1219 | 1 | 0.863 |
| P$MYBS | MYB proteins with single DNA binding repeat | P$ZMMRP1.01 | 0.79 | 1230 | 1246 | 1 | 0.833 |
| P$AHBP | *Arabidopsis* homeobox protein | P$ATHB9.01 | 0.77 | 1244 | 1254 | 1 | 0.89 |
| P$AHBP | *Arabidopsis* homeobox protein | P$ATHB9.01 | 0.77 | 1244 | 1254 | 0.75 | 0.777 |
| P$MADS | MADS box proteins | P$AGL2.01 | 0.82 | 1248 | 1268 | 0.97 | 0.835 |
| P$MYBS | MYB proteins with single DNA binding repeat | P$MYBST1.01 | 0.9 | 1262 | 1278 | 1 | 0.953 |
| P$HEAT | Heat shock factors | P$HSE.01 | 0.81 | 1278 | 1294 | 1 | 0.864 |
| P$LEGB | Legumin Box family | P$RY.01 | 0.87 | 1277 | 1303 | 1 | 0.871 |
| P$MYBS | MYB proteins with single DNA binding repeat | P$OSMYBS.01 | 0.82 | 1343 | 1359 | 0.75 | 0.822 |
| O$INRE | Core promoter initiator elements | O$DINR.01 | 0.94 | 1349 | 1359 | 0.97 | 0.955 |
| P$STKM | Storekeeper motif | P$STK.01 | 0.85 | 1355 | 1369 | 1 | 0.927 |
| P$GTBX | GT-box elements | P$GT1.01 | 0.85 | 1403 | 1419 | 0.97 | 0.865 |
| P$OCSE | Enhancer element first identified in the promoter of the octopine synthase gene (OCS) of the *Agrobacterium tumefaciens* T-DNA | P$OCSL.01 | 0.69 | 1437 | 1457 | 0.77 | 0.703 |
| P$HEAT | Heat shock factors | P$HSFA1A.01 | 0.75 | 1478 | 1494 | 1 | 0.764 |
| P$WBXF | W Box family | P$ERE.01 | 0.89 | 1488 | 1504 | 1 | 0.968 |
| P$TEFB | TEF-box | P$TEF1.01 | 0.76 | 1491 | 1511 | 0.96 | 0.852 |
| P$MYBS | MYB proteins with single DNA binding repeat | P$HVMCB1.01 | 0.93 | 1498 | 1514 | 1 | 0.934 |
| P$MYBS | MYB proteins with single DNA binding repeat | P$TAMYB80.01 | 0.83 | 1509 | 1525 | 0.75 | 0.837 |
| P$MSAE | M-phase-specific activator elements | P$MSA.01 | 0.8 | 1551 | 1565 | 1 | 0.82 |

TABLE 10-continued

Boxes and Motifs identified in the permutated sequence of the p-GOS2_perm1 promoter.

| p-GOS2_perm1 | | | | Position | | Core | Matrix |
|---|---|---|---|---|---|---|---|
| Family | Further Family Information | Matrix | Opt. | Position from-to | | sim. | sim. |
| P$OPAQ | Opaque-2 like transcriptional activators | P$O2.01 | 0.87 | 1558 | 1574 | 1 | 0.883 |
| P$AHBP | *Arabidopsis* homeobox protein | P$ATHB5.01 | 0.89 | 1569 | 1579 | 0.83 | 0.904 |
| P$AHBP | *Arabidopsis* homeobox protein | P$ATHB5.01 | 0.89 | 1569 | 1579 | 0.94 | 0.978 |
| O$VTBP | Vertebrate TATA binding protein factor | O$ATATA.01 | 0.78 | 1609 | 1625 | 0.75 | 0.781 |
| P$LREM | Light responsive element motif, not modulated by different light qualities | P$RAP22.01 | 0.85 | 1613 | 1623 | 1 | 0.966 |
| P$TEFB | TEF-box | P$TEF1.01 | 0.76 | 1617 | 1637 | 0.84 | 0.761 |
| P$WNAC | Wheat NAC-domain transcription factors | P$TANAC69.01 | 0.68 | 1625 | 1647 | 0.9 | 0.75 |
| P$NACF | Plant specific NAC [NAM (no apical meristem), ATAF172, CUC2 (cup-shaped cotyledons 2)] transcription factors | P$ANAC019.01 | 0.94 | 1632 | 1644 | 0.95 | 0.968 |
| P$GTBX | GT-box elements | P$S1F.01 | 0.79 | 1642 | 1658 | 1 | 0.882 |
| P$PSRE | Pollen-specific regulatory elements | P$GAAA.01 | 0.83 | 1644 | 1660 | 1 | 0.864 |
| P$MYBL | MYB-like proteins | P$MYBPH3.01 | 0.8 | 1647 | 1663 | 1 | 0.938 |
| P$DOFF | DNA binding with one finger (DOF) | P$DOF1.01 | 0.98 | 1694 | 1710 | 1 | 1 |
| P$HEAT | Heat shock factors | P$HSFA1A.01 | 0.75 | 1703 | 1719 | 0.86 | 0.765 |
| P$CCAF | Circadian control factors | P$EE.01 | 0.84 | 1719 | 1733 | 1 | 0.955 |
| P$MADS | MADS box proteins | P$AG.01 | 0.8 | 1717 | 1737 | 0.9 | 0.816 |
| P$GTBX | GT-box elements | P$ASIL1.01 | 0.93 | 1732 | 1748 | 1 | 0.98 |
| O$INRE | Core promoter initiator elements | O$DINR.01 | 0.94 | 1749 | 1759 | 1 | 0.957 |
| P$SUCB | Sucrose box | P$SUCROSE.01 | 0.81 | 1749 | 1767 | 0.75 | 0.837 |
| P$SUCB | Sucrose box | P$SUCROSE.01 | 0.81 | 1754 | 1772 | 0.75 | 0.815 |
| P$L1BX | L1 box, motif for L1 layer-specific expression | P$ATML1.02 | 0.76 | 1757 | 1773 | 0.89 | 0.848 |
| P$AHBP | *Arabidopsis* homeobox protein | P$ATHB9.01 | 0.77 | 1761 | 1771 | 0.75 | 0.815 |
| P$MADS | MADS box proteins | P$AGL3.01 | 0.83 | 1768 | 1788 | 0.97 | 0.838 |
| O$VTBP | Vertebrate TATA binding protein factor | O$VTATA.02 | 0.89 | 1777 | 1793 | 1 | 0.996 |
| P$DOFF | DNA binding with one finger (DOF) | P$DOF3.01 | 0.99 | 1778 | 1794 | 1 | 0.995 |
| O$PTBP | Plant TATA binding protein factor | O$PTATA.02 | 0.9 | 1780 | 1794 | 1 | 0.923 |
| P$IBOX | Plant I-Box sites | P$GATA.01 | 0.93 | 1787 | 1803 | 1 | 0.967 |
| P$MYBS | MYB proteins with single DNA binding repeat | P$MYBST1.01 | 0.9 | 1790 | 1806 | 1 | 0.972 |
| O$VTBP | Vertebrate TATA binding protein factor | O$ATATA.01 | 0.78 | 1803 | 1819 | 0.75 | 0.797 |
| P$IBOX | Plant I-Box sites | P$GATA.01 | 0.93 | 1847 | 1863 | 1 | 0.945 |
| P$MYBS | MYB proteins with single DNA binding repeat | P$MYBST1.01 | 0.9 | 1850 | 1866 | 1 | 0.966 |
| P$MADS | MADS box proteins | P$SQUA.01 | 0.9 | 1866 | 1886 | 1 | 0.916 |
| P$GTBX | GT-box elements | P$SBF1.01 | 0.87 | 1872 | 1888 | 1 | 0.905 |
| O$VTBP | Vertebrate TATA binding protein factor | O$LTATA.01 | 0.82 | 1873 | 1889 | 1 | 0.837 |
| P$AHBP | *Arabidopsis* homeobox protein | P$HAHB4.01 | 0.87 | 1878 | 1888 | 1 | 0.902 |
| P$L1BX | L1 box, motif for L1 layer-specific expression | P$ATML1.01 | 0.82 | 1882 | 1898 | 0.75 | 0.824 |
| O$INRE | Core promoter initiator elements | O$DINR.01 | 0.94 | 1886 | 1896 | 0.97 | 0.949 |
| P$EPFF | EPF-type zinc finger factors, two canonical Cys2/His2 zinc finger motifs separated by spacers of various length | P$ZPT22.01 | 0.75 | 1887 | 1909 | 1 | 0.752 |
| P$GAPB | GAP-Box (light response elements) | P$GAP.01 | 0.88 | 1907 | 1921 | 1 | 0.903 |
| P$SUCB | Sucrose box | P$SUCROSE.01 | 0.81 | 1912 | 1930 | 1 | 0.849 |
| P$HMGF | High mobility group factors | P$HMG_IY.01 | 0.89 | 1920 | 1934 | 1 | 0.892 |
| P$SEF4 | Soybean embryo factor 4 | P$SEF4.01 | 0.98 | 1927 | 1937 | 1 | 0.984 |
| P$MYBL | MYB-like proteins | P$ATMYB77.01 | 0.87 | 1973 | 1989 | 1 | 0.9 |
| P$GTBX | GT-box elements | P$ASIL1.01 | 0.93 | 1998 | 2014 | 1 | 0.958 |
| P$OPAQ | Opaque-2 like transcriptional activators | P$O2_GCN4.01 | 0.81 | 2001 | 2017 | 1 | 0.875 |
| P$IBOX | Plant I-Box sites | P$GATA.01 | 0.93 | 2018 | 2034 | 1 | 0.964 |
| P$MYBS | MYB proteins with single DNA binding repeat | P$MYBST1.01 | 0.9 | 2021 | 2037 | 1 | 0.957 |

TABLE 10-continued

Boxes and Motifs identified in the permutated sequence of the p-GOS2_perm1 promoter.

| p-GOS2_perm1 | | | | Position Position | | Core | Matrix |
|---|---|---|---|---|---|---|---|
| Family | Further Family Information | Matrix | Opt. | from-to | | sim. | sim. |
| P$LREM | Light responsive element motif, not modulated by different light qualities | P$RAP22.01 | 0.85 | 2035 | 2045 | 1 | 0.868 |
| P$MIIG | MYB IIG-type binding sites | P$MYBC1.01 | 0.92 | 2033 | 2047 | 1 | 0.938 |
| P$HEAT | Heat shock factors | P$HSFA1A.01 | 0.75 | 2041 | 2057 | 1 | 0.792 |
| P$MYBL | MYB-like proteins | P$GAMYB.01 | 0.91 | 2054 | 2070 | 1 | 0.918 |
| P$GTBX | GT-box elements | P$GT1.01 | 0.85 | 2056 | 2072 | 1 | 0.876 |
| P$ASRC | AS1/AS2 repressor complex | P$AS1_AS2_II.01 | 0.86 | 2067 | 2075 | 1 | 0.906 |
| P$ASRC | AS1/AS2 repressor complex | P$AS1_AS2_II.01 | 0.86 | 2075 | 2083 | 1 | 0.906 |
| P$EINL | Ethylen insensitive 3 like factors | P$TEIL.01 | 0.92 | 2098 | 2106 | 0.96 | 0.926 |
| O$VTBP | Vertebrate TATA binding protein factor | O$LTATA.01 | 0.82 | 2110 | 2126 | 1 | 0.828 |
| P$MYBL | MYB-like proteins | P$MYBPH3.02 | 0.76 | 2110 | 2126 | 1 | 0.807 |

TABLE 11

Boxes and Motifs identified in the permutated sequence of the p-GOS2_perm2 promoter.

| p-GOS2_perm2 | | | | Position Position | | Core | Matrix |
|---|---|---|---|---|---|---|---|
| Family | Further Family Information | Matrix | Opt. | from-to | | sim. | sim. |
| P$NCS1 | Nodulin consensus sequence 1 | P$NCS1.01 | 0.85 | 6 | 16 | 1 | 0.857 |
| P$MSAE | M-phase-specific activator elements | P$MSA.01 | 0.8 | 15 | 29 | 1 | 0.832 |
| P$MYBL | MYB-like proteins | P$GAMYB.01 | 0.91 | 29 | 45 | 1 | 0.95 |
| P$MYBL | MYB-like proteins | P$WER.01 | 0.87 | 33 | 49 | 1 | 0.897 |
| P$MADS | MADS box proteins | P$AGL2.01 | 0.82 | 35 | 55 | 0.789 | 0.82 |
| P$NACF | Plant specific NAC [NAM (no apical meristem), ATAF172, CUC2 (cup-shaped cotyledons 2)] transcription factors | P$IDEF2.01 | 0.96 | 48 | 60 | 1 | 0.96 |
| P$BRRE | Brassinosteroid (BR) response element | P$BZR1.01 | 0.95 | 48 | 64 | 1 | 0.954 |
| O$PTBP | Plant TATA binding protein factor | O$PTATA.01 | 0.88 | 60 | 74 | 1 | 0.883 |
| O$VTBP | Vertebrate TATA binding protein factor | O$VTATA.01 | 0.9 | 61 | 77 | 1 | 0.961 |
| O$INRE | Core promoter initiator elements | O$DINR.01 | 0.94 | 65 | 75 | 0.969 | 0.94 |
| O$VTBP | Vertebrate TATA binding protein factor | O$LTATA.01 | 0.82 | 69 | 85 | 1 | 0.867 |
| O$VTBP | Vertebrate TATA binding protein factor | O$VTATA.01 | 0.9 | 71 | 87 | 0.892 | 0.92 |
| O$YTBP | Yeast TATA binding protein factor | O$SPT15.01 | 0.83 | 74 | 90 | 1 | 0.832 |
| O$YTBP | Yeast TATA binding protein factor | O$SPT15.01 | 0.83 | 75 | 91 | 1 | 0.877 |
| O$VTBP | Vertebrate TATA binding protein factor | O$ATATA.01 | 0.78 | 76 | 92 | 0.75 | 0.781 |
| O$YTBP | Yeast TATA binding protein factor | O$SPT15.01 | 0.83 | 77 | 93 | 0.755 | 0.835 |
| P$MIIG | MYB IIG-type binding sites | P$PALBOXL.01 | 0.8 | 118 | 132 | 0.768 | 0.841 |
| P$DOFF | DNA binding with one finger (DOF) | P$DOF1.01 | 0.98 | 126 | 142 | 1 | 0.99 |
| P$DOFF | DNA binding with one finger (DOF) | P$PBF.01 | 0.97 | 149 | 165 | 1 | 0.989 |
| P$WNAC | Wheat NAC-domain transcription factors | P$TANAC69.01 | 0.68 | 170 | 192 | 0.812 | 0.713 |
| O$VTBP | Vertebrate TATA binding protein factor | O$ATATA.01 | 0.78 | 187 | 203 | 1 | 0.869 |
| P$E2FF | E2F-homolog cell cycle regulators | P$E2F.01 | 0.82 | 193 | 207 | 1 | 0.829 |
| O$INRE | Core promoter initiator elements | O$DINR.01 | 0.94 | 200 | 210 | 0.969 | 0.945 |
| P$AHBP | *Arabidopsis* homeobox protein | P$ATHB5.01 | 0.89 | 207 | 217 | 0.83 | 0.903 |
| P$AHBP | *Arabidopsis* homeobox protein | P$HAHB4.01 | 0.87 | 207 | 217 | 1 | 0.967 |

TABLE 11-continued

Boxes and Motifs identified in the permutated sequence of the p-GOS2_perm2 promoter.

| | p-GOS2_perm2 | | | Position Position from-to | | Core sim. | Matrix sim. |
|---|---|---|---|---|---|---|---|
| Family | Further Family Information | Matrix | Opt. | | | | |
| P$CNAC | Calcium regulated NAC-factors | P$CBNAC.02 | 0.85 | 215 | 235 | 1 | 0.95 |
| P$MYBS | MYB proteins with single DNA binding repeat | P$PHR1.01 | 0.84 | 217 | 233 | 1 | 0.975 |
| P$OCSE | Enhancer element first identified in the promoter of the octopine synthase gene (OCS) of the *Agrobacterium tumefaciens* T-DNA | P$OCSL.01 | 0.69 | 216 | 236 | 1 | 0.71 |
| P$MYBS | MYB proteins with single DNA binding repeat | P$PHR1.01 | 0.84 | 222 | 238 | 1 | 0.922 |
| P$GTBX | GT-box elements | P$SBF1.01 | 0.87 | 246 | 262 | 1 | 0.901 |
| P$STKM | Storekeeper motif | P$STK.01 | 0.85 | 251 | 265 | 1 | 0.85 |
| P$AHBP | *Arabidopsis* homeobox protein | P$ATHB5.01 | 0.89 | 254 | 264 | 0.83 | 0.904 |
| P$AHBP | *Arabidopsis* homeobox protein | P$BLR.01 | 0.9 | 254 | 264 | 1 | 0.998 |
| P$HEAT | Heat shock factors | P$HSFA1A.01 | 0.75 | 284 | 300 | 1 | 0.784 |
| P$CCAF | Circadian control factors | P$CCA1.01 | 0.85 | 297 | 311 | 1 | 0.947 |
| P$LFYB | LFY binding site | P$LFY.01 | 0.93 | 318 | 330 | 0.914 | 0.945 |
| P$GAGA | GAGA elements | P$BPC.01 | 1 | 329 | 353 | 1 | 1 |
| P$CCAF | Circadian control factors | P$EE.01 | 0.84 | 335 | 349 | 0.75 | 0.865 |
| P$GAGA | GAGA elements | P$BPC.01 | 1 | 331 | 355 | 1 | 1 |
| P$CCAF | Circadian control factors | P$CCA1.01 | 0.85 | 337 | 351 | 1 | 0.968 |
| P$GTBX | GT-box elements | P$SBF1.01 | 0.87 | 341 | 357 | 1 | 0.875 |
| P$MADS | MADS box proteins | P$SQUA.01 | 0.9 | 345 | 365 | 1 | 0.925 |
| P$CCAF | Circadian control factors | P$EE.01 | 0.84 | 363 | 377 | 1 | 0.925 |
| O$VTBP | Vertebrate TATA binding protein factor | O$MTATA.01 | 0.84 | 383 | 399 | 1 | 0.91 |
| P$CARM | CA-rich motif | P$CARICH.01 | 0.78 | 388 | 406 | 1 | 0.785 |
| P$AHBP | *Arabidopsis* homeobox protein | P$HAHB4.01 | 0.87 | 397 | 407 | 1 | 0.902 |
| O$VTBP | Vertebrate TATA binding protein factor | O$LTATA.01 | 0.82 | 395 | 411 | 1 | 0.889 |
| O$VTBP | Vertebrate TATA binding protein factor | O$LTATA.01 | 0.82 | 396 | 412 | 1 | 0.844 |
| O$PTBP | Plant TATA binding protein factor | O$PTATA.01 | 0.88 | 398 | 412 | 1 | 0.892 |
| O$VTBP | Vertebrate TATA binding protein factor | O$ATATA.01 | 0.78 | 397 | 413 | 0.75 | 0.781 |
| P$NCS2 | *Arabidopsis* homeobox protein | P$HAHB4.01 | 0.87 | 400 | 410 | 1 | 0.902 |
| P$MSAE | Vertebrate TATA binding protein factor | O$ATATA.01 | 0.78 | 402 | 418 | 0.75 | 0.781 |
| P$MYBL | Vertebrate TATA binding protein factor | O$VTATA.02 | 0.89 | 405 | 421 | 1 | 0.983 |
| P$MYBL | Plant TATA binding protein factor | O$PTATA.02 | 0.9 | 408 | 422 | 1 | 0.917 |
| P$OCSE | Enhancer element first identified in the promoter of the octopine synthase gene (OCS) of the *Agrobacterium tumefaciens* T-DNA | P$OCSTF.01 | 0.73 | 426 | 446 | 1 | 0.733 |
| P$AHBP | *Arabidopsis* homeobox protein | P$HAHB4.01 | 0.87 | 440 | 450 | 1 | 0.921 |
| P$AHBP | *Arabidopsis* homeobox protein | P$WUS.01 | 0.94 | 444 | 454 | 1 | 1 |
| P$OPAQ | Opaque-2 like transcriptional activators | P$O2_GCN4.01 | 0.81 | 447 | 463 | 1 | 0.819 |
| P$SEF4 | Soybean embryo factor 4 | P$SEF4.01 | 0.98 | 472 | 482 | 1 | 0.987 |
| P$GTBX | GT-box elements | P$SBF1.01 | 0.87 | 481 | 497 | 1 | 0.922 |
| P$DOFF | DNA binding with one finger (DOF) | P$DOF1.01 | 0.98 | 482 | 498 | 1 | 0.994 |
| P$GTBX | GT-box elements | P$SBF1.01 | 0.87 | 482 | 498 | 1 | 0.9 |
| P$WBXF | W Box family | P$WRKY11.01 | 0.94 | 493 | 509 | 1 | 0.957 |
| P$SEF4 | Soybean embryo factor 4 | P$SEF4.01 | 0.98 | 504 | 514 | 1 | 0.998 |
| P$IBOX | Plant I-Box sites | P$GATA.01 | 0.93 | 509 | 525 | 1 | 0.986 |
| P$NCS1 | Nodulin consensus sequence 1 | P$NCS1.01 | 0.85 | 515 | 525 | 1 | 0.948 |
| P$GTBX | GT-box elements | P$S1F.01 | 0.79 | 518 | 534 | 0.75 | 0.793 |
| P$LREM | Light responsive element motif, not modulated by different light qualities | P$RAP22.01 | 0.85 | 527 | 537 | 1 | 0.897 |

TABLE 11-continued

Boxes and Motifs identified in the permutated sequence of the p-GOS2_perm2 promoter.

| p-GOS2_perm2 | | | | Position Position from-to | | Core sim. | Matrix sim. |
|---|---|---|---|---|---|---|---|
| Family | Further Family Information | Matrix | Opt. | | | | |
| P$L1BX | L1 box, motif for L1 layer-specific expression | P$ATML1.01 | 0.82 | 525 | 541 | 0.75 | 0.825 |
| O$VTBP | Vertebrate TATA binding protein factor | O$ATATA.01 | 0.78 | 539 | 555 | 0.75 | 0.782 |
| P$ROOT | Root hair-specific cis-elements in angiosperms | P$RHE.01 | 0.77 | 568 | 592 | 0.75 | 0.787 |
| P$ABRE | ABA response elements | P$ABRE.01 | 0.82 | 591 | 607 | 1 | 0.837 |
| P$ASRC | AS1/AS2 repressor complex | P$AS1_AS2_II.01 | 0.86 | 599 | 607 | 1 | 0.867 |
| P$L1BX | L1 box, motif for L1 layer-specific expression | P$HDG9.01 | 0.77 | 629 | 645 | 1 | 0.883 |
| P$L1BX | L1 box, motif for L1 layer-specific expression | P$HDG9.01 | 0.77 | 631 | 647 | 0.797 | 0.776 |
| P$L1BX | L1 box, motif for L1 layer-specific expression | P$ATML1.01 | 0.82 | 638 | 654 | 1 | 0.886 |
| P$CCAF | Circadian control factors | P$EE.01 | 0.84 | 649 | 663 | 1 | 0.891 |
| P$DOFF | DNA binding with one finger (DOF) | P$PBF.01 | 0.97 | 687 | 703 | 1 | 0.987 |
| P$GTBX | GT-box elements | P$SBF1.01 | 0.87 | 689 | 705 | 1 | 0.888 |
| P$AHBP | *Arabidopsis* homeobox protein | P$BLR.01 | 0.9 | 695 | 705 | 1 | 0.929 |
| P$CCAF | Circadian control factors | P$EE.01 | 0.84 | 694 | 708 | 1 | 0.954 |
| P$LREM | Light responsive element motif, not modulated by different light qualities | P$RAP22.01 | 0.85 | 701 | 711 | 1 | 1 |
| P$MADS | MADS box proteins | P$RIN.01 | 0.77 | 699 | 719 | 1 | 0.776 |
| P$HMGF | High mobility group factors | P$HMG_IY.01 | 0.89 | 711 | 725 | 1 | 0.924 |
| P$AHBP | *Arabidopsis* homeobox protein | P$ATHB1.01 | 0.9 | 716 | 726 | 0.789 | 0.901 |
| P$AHBP | *Arabidopsis* homeobox protein | P$BLR.01 | 0.9 | 716 | 726 | 1 | 0.998 |
| O$VTBP | Vertebrate TATA binding protein factor | O$VTATA.02 | 0.89 | 716 | 732 | 1 | 0.893 |
| P$SUCB | Sucrose box | P$SUCROSE.01 | 0.81 | 715 | 733 | 1 | 0.856 |
| P$DOFF | DNA binding with one finger (DOF) | P$PBOX.01 | 0.75 | 718 | 734 | 0.761 | 0.762 |
| P$HEAT | Heat shock factors | P$HSE.01 | 0.81 | 718 | 734 | 1 | 0.833 |
| P$GAPB | GAP-Box (light response elements) | P$GAP.01 | 0.88 | 733 | 747 | 1 | 0.885 |
| P$MYBL | MYB-like proteins | P$MYBPH3.02 | 0.76 | 744 | 760 | 0.779 | 0.834 |
| O$VTBP | Vertebrate TATA binding protein factor | O$ATATA.01 | 0.78 | 754 | 770 | 0.75 | 0.831 |
| P$TELO | Telo box (plant interstitial telomere motifs) | P$ATPURA.01 | 0.85 | 756 | 770 | 0.75 | 0.869 |
| P$MYCL | Myc-like basic helix-loop-helix binding factors | P$OSBHLH66.01 | 0.85 | 789 | 807 | 1 | 0.851 |
| P$BRRE | Brassinosteroid (BR) response element | P$BZR1.01 | 0.95 | 793 | 809 | 1 | 0.998 |
| P$URNA | Upstream sequence element of U-snRNA genes | P$USE.01 | 0.75 | 812 | 828 | 0.75 | 0.797 |
| P$MADS | MADS box proteins | P$AGL1.01 | 0.84 | 812 | 832 | 1 | 0.895 |
| P$MADS | MADS box proteins | P$AGL1.01 | 0.84 | 813 | 833 | 0.915 | 0.911 |
| P$NCS1 | Nodulin consensus sequence 1 | P$NCS1.01 | 0.85 | 872 | 882 | 0.805 | 0.888 |
| P$LREM | Light responsive element motif, not modulated by different light qualities | P$RAP22.01 | 0.85 | 879 | 889 | 1 | 0.896 |
| P$MSAE | M-phase-specific activator elements | P$MSA.01 | 0.8 | 880 | 894 | 1 | 0.877 |
| P$MYBL | MYB-like proteins | P$NTMYBAS1.01 | 0.96 | 900 | 916 | 0.949 | 0.968 |
| P$GTBX | GT-box elements | P$SBF1.01 | 0.87 | 909 | 925 | 1 | 0.905 |
| P$MYBL | MYB-like proteins | P$AS1_AS2_I.01 | 0.99 | 911 | 927 | 1 | 1 |
| P$LREM | Light responsive element motif, not modulated by different light qualities | P$RAP22.01 | 0.85 | 981 | 991 | 1 | 0.893 |
| O$PTBP | Plant TATA binding protein factor | O$PTATA.02 | 0.9 | 982 | 996 | 1 | 1 |
| P$L1BX | L1 box, motif for L1 layer-specific expression | P$PDF2.01 | 0.85 | 982 | 998 | 1 | 0.884 |
| O$VTBP | Vertebrate TATA binding protein factor | O$VTATA.01 | 0.9 | 983 | 999 | 1 | 0.973 |
| P$MADS | MADS box proteins | P$AGL15.01 | 0.79 | 1006 | 1026 | 0.825 | 0.793 |
| P$MYBS | MYB proteins with single DNA binding repeat | P$ZMMRP1.01 | 0.79 | 1008 | 1024 | 0.778 | 0.811 |

TABLE 11-continued

Boxes and Motifs identified in the permutated sequence of the p-GOS2_perm2 promoter.

| p-GOS2_perm2 | | | | Position Position | | Core | Matrix |
|---|---|---|---|---|---|---|---|
| Family | Further Family Information | Matrix | Opt. | from | to | sim. | sim. |
| O$PTBP | Plant TATA binding protein factor | O$PTATA.02 | 0.9 | 1010 | 1024 | 1 | 0.91 |
| P$CGCG | Calmodulin binding/ CGCG box binding proteins | P$ATSR1.01 | 0.84 | 1051 | 1067 | 1 | 0.859 |
| P$ABRE | ABA response elements | P$ABF1.01 | 0.79 | 1053 | 1069 | 1 | 0.797 |
| P$CE3S | Coupling element 3 sequence | P$CE3.01 | 0.77 | 1052 | 1070 | 1 | 0.874 |
| P$NACF | Plant specific NAC [NAM (no apical meristem), ATAF172, CUC2 (cup-shaped cotyledons 2)] transcription factors | P$ANAC092.01 | 0.92 | 1055 | 1067 | 1 | 0.924 |
| P$DPBF | Dc3 promoter binding factors | P$DPBF.01 | 0.89 | 1057 | 1067 | 1 | 0.908 |
| P$PREM | Motifs of plastid response elements | P$MGPROTORE.01 | 0.77 | 1059 | 1089 | 1 | 0.806 |
| O$MTEN | Core promoter motif ten elements | O$HMTE.01 | 0.88 | 1072 | 1092 | 0.961 | 0.94 |
| P$DREB | Dehydration responsive element binding factors | P$HVDRF1.01 | 0.89 | 1079 | 1093 | 1 | 0.922 |
| P$PREM | Motifs of plastid response elements | P$MGPROTORE.01 | 0.77 | 1077 | 1107 | 1 | 0.784 |
| O$MTEN | Core promoter motif ten elements | O$DMTE.01 | 0.77 | 1097 | 1117 | 0.844 | 0.802 |
| P$OPAQ | Opaque-2 like transcriptional activators | P$O2.02 | 0.87 | 1135 | 1151 | 1 | 0.915 |
| P$SALT | Salt/drought responsive elements | P$ALFIN1.02 | 0.95 | 1136 | 1150 | 1 | 0.954 |
| P$L1BX | L1 box, motif for L1 layer-specific expression | P$PDF2.01 | 0.85 | 1179 | 1195 | 1 | 0.882 |
| P$SBPD | SBP-domain proteins | P$SBP.01 | 0.88 | 1199 | 1215 | 1 | 0.912 |
| P$PALA | Conserved box A in PAL and 4CL gene promoters | P$PALBOXA.01 | 0.84 | 1201 | 1219 | 1 | 0.863 |
| P$MYBS | MYB proteins with single DNA binding repeat | P$ZMMRP1.01 | 0.79 | 1230 | 1246 | 1 | 0.838 |
| P$AHBP | *Arabidopsis* homeobox protein | P$ATHB9.01 | 0.77 | 1244 | 1254 | 1 | 0.777 |
| P$MADS | MADS box proteins | P$AGL2.01 | 0.82 | 1248 | 1268 | 0.969 | 0.828 |
| P$MYBS | MYB proteins with single DNA binding repeat | P$MYBST1.01 | 0.9 | 1262 | 1278 | 1 | 0.953 |
| P$HEAT | Heat shock factors | P$HSE.01 | 0.81 | 1278 | 1294 | 1 | 0.864 |
| P$LEGB | Legumin Box family | P$RY.01 | 0.87 | 1277 | 1303 | 1 | 0.871 |
| P$MYBS | MYB proteins with single DNA binding repeat | P$OSMYBS.01 | 0.82 | 1343 | 1359 | 0.75 | 0.822 |
| O$INRE | Core promoter initiator elements | O$DINR.01 | 0.94 | 1349 | 1359 | 0.969 | 0.955 |
| P$STKM | Storekeeper motif | P$STK.01 | 0.85 | 1355 | 1369 | 1 | 0.95 |
| P$GTBX | GT-box elements | P$GT1.01 | 0.85 | 1403 | 1419 | 0.969 | 0.85 |
| O$VTBP | Vertebrate TATA binding protein factor | O$ATATA.01 | 0.78 | 1439 | 1455 | 0.75 | 0.797 |
| P$OCSE | Enhancer element first identified in the promoter of the octopine synthase gene (OCS) of the *Agrobacterium tumefaciens* T-DNA | P$OCSL.01 | 0.69 | 1437 | 1457 | 0.769 | 0.734 |
| P$HEAT | Heat shock factors | P$HSFA1A.01 | 0.75 | 1478 | 1494 | 1 | 0.764 |
| P$WBXF | W Box family | P$WRKY.01 | 0.92 | 1488 | 1504 | 1 | 0.94 |
| P$TEFB | TEF-box | P$TEF1.01 | 0.76 | 1491 | 1511 | 0.957 | 0.859 |
| P$MYBS | MYB proteins with single DNA binding repeat | P$HVMCB1.01 | 0.93 | 1498 | 1514 | 1 | 0.934 |
| P$MYBS | MYB proteins with single DNA binding repeat | P$TAMYB80.01 | 0.83 | 1509 | 1525 | 0.75 | 0.845 |
| P$MSAE | M-phase-specific activator elements | P$MSA.01 | 0.8 | 1551 | 1565 | 1 | 0.807 |
| P$OPAQ | Opaque-2 like transcriptional activators | P$O2.01 | 0.87 | 1558 | 1574 | 1 | 0.883 |
| P$AHBP | *Arabidopsis* homeobox protein | P$ATHB5.01 | 0.89 | 1569 | 1579 | 0.83 | 0.904 |
| P$AHBP | *Arabidopsis* homeobox protein | P$ATHB5.01 | 0.89 | 1569 | 1579 | 0.936 | 0.978 |
| O$VTBP | Vertebrate TATA binding protein factor | O$ATATA.01 | 0.78 | 1609 | 1625 | 0.75 | 0.781 |
| P$LREM | Light responsive element motif, not modulated by different light qualities | P$RAP22.01 | 0.85 | 1613 | 1623 | 1 | 0.966 |

TABLE 11-continued

Boxes and Motifs identified in the permutated sequence of the p-GOS2_perm2 promoter.

| p-GOS2_perm2 | | | | Position | | | |
|---|---|---|---|---|---|---|---|
| Family | Further Family Information | Matrix | Opt. | Position from-to | | Core sim. | Matrix sim. |
| P$TEFB | TEF-box | P$TEF1.01 | 0.76 | 1617 | 1637 | 0.839 | 0.812 |
| P$WNAC | Wheat NAC-domain transcription factors | P$TANAC69.01 | 0.68 | 1625 | 1647 | 0.896 | 0.811 |
| P$NACF | Plant specific NAC [NAM (no apical meristem), ATAF172, CUC2 (cup-shaped cotyledons 2)] transcription factors | P$ANAC019.01 | 0.94 | 1632 | 1644 | 0.953 | 0.968 |
| P$GTBX | GT-box elements | P$S1F.01 | 0.79 | 1642 | 1658 | 1 | 0.917 |
| P$PSRE | Pollen-specific regulatory elements | P$GAAA.01 | 0.83 | 1644 | 1660 | 1 | 0.864 |
| P$MYBL | MYB-like proteins | P$MYBPH3.01 | 0.8 | 1647 | 1663 | 1 | 0.938 |
| P$DOFF | DNA binding with one finger (DOF) | P$DOF1.01 | 0.98 | 1694 | 1710 | 1 | 1 |
| P$HEAT | Heat shock factors | P$HSFA1A.01 | 0.75 | 1703 | 1719 | 0.857 | 0.757 |
| P$CCAF | Circadian control factors | P$EE.01 | 0.84 | 1719 | 1733 | 1 | 0.953 |
| P$MADS | MADS box proteins | P$AG.01 | 0.8 | 1717 | 1737 | 0.902 | 0.813 |
| P$GTBX | GT-box elements | P$ASIL1.01 | 0.93 | 1732 | 1748 | 1 | 0.967 |
| O$INRE | Core promoter initiator elements | O$DINR.01 | 0.94 | 1749 | 1759 | 1 | 0.965 |
| P$SUCB | Sucrose box | P$SUCROSE.01 | 0.81 | 1749 | 1767 | 0.75 | 0.83 |
| P$SUCB | Sucrose box | P$SUCROSE.01 | 0.81 | 1754 | 1772 | 0.75 | 0.822 |
| P$L1BX | L1 box, motif for L1 layer-specific expression | P$ATML1.02 | 0.76 | 1757 | 1773 | 0.89 | 0.848 |
| P$AHBP | Arabidopsis homeobox protein | P$ATHB9.01 | 0.77 | 1761 | 1771 | 0.75 | 0.815 |
| O$VTBP | Vertebrate TATA binding protein factor | O$VTATA.02 | 0.89 | 1777 | 1793 | 1 | 0.996 |
| P$DOFF | DNA binding with one finger (DOF) | P$DOF3.01 | 0.99 | 1778 | 1794 | 1 | 0.995 |
| O$PTBP | Plant TATA binding protein factor | O$PTATA.02 | 0.9 | 1780 | 1794 | 1 | 0.923 |
| P$IBOX | Plant I-Box sites | P$GATA.01 | 0.93 | 1787 | 1803 | 1 | 0.967 |
| P$MYBS | MYB proteins with single DNA binding repeat | P$MYBST1.01 | 0.9 | 1790 | 1806 | 1 | 0.972 |
| O$VTBP | Vertebrate TATA binding protein factor | O$ATATA.01 | 0.78 | 1803 | 1819 | 0.75 | 0.812 |
| P$IBOX | Plant I-Box sites | P$GATA.01 | 0.93 | 1847 | 1863 | 1 | 0.945 |
| P$MYBS | MYB proteins with single DNA binding repeat | P$MYBST1.01 | 0.9 | 1850 | 1866 | 1 | 0.966 |
| P$MADS | MADS box proteins | P$SQUA.01 | 0.9 | 1866 | 1886 | 1 | 0.916 |
| P$GTBX | GT-box elements | P$SBF1.01 | 0.87 | 1872 | 1888 | 1 | 0.905 |
| O$VTBP | Vertebrate TATA binding protein factor | O$LTATA.01 | 0.82 | 1873 | 1889 | 1 | 0.837 |
| P$AHBP | Arabidopsis homeobox protein | P$HAHB4.01 | 0.87 | 1878 | 1888 | 1 | 0.902 |
| P$L1BX | L1 box, motif for L1 layer-specific expression | P$ATML1.01 | 0.82 | 1882 | 1898 | 0.75 | 0.824 |
| O$INRE | Core promoter initiator elements | O$DINR.01 | 0.94 | 1886 | 1896 | 0.969 | 0.949 |
| P$EPFF | EPF-type zinc finger factors, two canonical Cys2/His2 zinc finger motifs separated by spacers of various length | P$ZPT22.01 | 0.75 | 1887 | 1909 | 1 | 0.755 |
| P$GAPB | GAP-Box (light response elements) | P$GAP.01 | 0.88 | 1907 | 1921 | 1 | 0.903 |
| P$SUCB | Sucrose box | P$SUCROSE.01 | 0.81 | 1912 | 1930 | 1 | 0.849 |
| P$HMGF | High mobility group factors | P$HMG_IY.01 | 0.89 | 1920 | 1934 | 1 | 0.892 |
| P$SEF4 | Soybean embryo factor 4 | P$SEF4.01 | 0.98 | 1927 | 1937 | 1 | 0.984 |
| P$MYBL | MYB-like proteins | P$ATMYB77.01 | 0.87 | 1973 | 1989 | 1 | 0.894 |
| P$GTBX | GT-box elements | P$ASIL1.01 | 0.93 | 1998 | 2014 | 1 | 0.971 |
| P$OPAQ | Opaque-2 like transcriptional activators | P$O2_GCN4.01 | 0.81 | 2001 | 2017 | 1 | 0.83 |
| P$IBOX | Plant I-Box sites | P$GATA.01 | 0.93 | 2018 | 2034 | 1 | 0.964 |
| P$MYBS | MYB proteins with single DNA binding repeat | P$MYBST1.01 | 0.9 | 2021 | 2037 | 1 | 0.957 |
| P$LREM | Light responsive element motif, not modulated by different light qualities | P$RAP22.01 | 0.85 | 2035 | 2045 | 1 | 0.858 |
| P$MIIG | MYB IIG-type binding sites | P$MYBC1.01 | 0.92 | 2033 | 2047 | 1 | 0.941 |
| P$HEAT | Heat shock factors | P$HSFA1A.01 | 0.75 | 2041 | 2057 | 1 | 0.801 |
| P$MYBL | MYB-like proteins | P$GAMYB.01 | 0.91 | 2054 | 2070 | 1 | 0.918 |

TABLE 11-continued

Boxes and Motifs identified in the permutated sequence of the p-GOS2_perm2 promoter.

| | p-GOS2_perm2 | | | Position Position from-to | | Core sim. | Matrix sim. |
|---|---|---|---|---|---|---|---|
| Family | Further Family Information | Matrix | Opt. | | | | |
| P$GTBX | GT-box elements | P$GT1.01 | 0.85 | 2056 | 2072 | 1 | 0.876 |
| P$ASRC | AS1/AS2 repressor complex | P$AS1_AS2_II.01 | 0.86 | 2067 | 2075 | 1 | 0.906 |
| P$EINL | Ethylen insensitive 3 like factors | P$TEIL.01 | 0.92 | 2098 | 2106 | 0.964 | 0.926 |
| O$VTBP | Vertebrate TATA binding protein factor | O$LTATA.01 | 0.82 | 2110 | 2126 | 1 | 0.828 |
| P$MYBL | MYB-like proteins | P$MYBPH3.02 | 0.76 | 2110 | 2126 | 1 | 0.807 |

5.2 Vector Construction

The DNA fragments representing promoter p-GOS2_perm1 (SEQ ID NO14) and p-GOS2_perm2 (SEQ ID NO15), respectively, were generated by gene synthesis. Endonucleolytic restriction sites suitable for cloning the promoter fragments were included in the synthesis.

The p-GOS2_perm1 (SEQ ID NO14) and p-GOS2_perm2 (SEQ ID NO15) promoters are cloned into destination vectors compatible with the Multisite Gateway System upstream of an attachment site and a terminator using SwaI restriction endonuclease.

beta-Glucuronidase (GUS) or uidA gene which encodes an enzyme for which various chromogenic substrates are known, is utilized as reporter protein for determining the expression features of the permutated p-GOS2_perm (SEQ ID NO14) and p-GOS2_perm2 (SEQ ID NO15) promoter sequences.

A pENTR/A vector harboring the beta-Glucuronidase reporter gene c-GUS (with the prefix c- denoting coding sequence) is constructed using site specific recombination (BP-reaction).

By performing a site specific recombination (LR-reaction), the created pENTR/A is combined with the destination vector according to the manufacturers (Invitrogen, Carlsbad, Calif., USA) Multisite Gateway manual. The reaction yields a binary vector with the p-GOS2_perm1 promoter (SEQ ID NO14) or the p-Gos2_perm2 promoter (SEQ ID NO 15), respectively, the beta-Glucuronidase coding sequence c-GUS and a terminator.

5.3 Generation do Transgenic Rice Plants

The *Agrobacterium* containing the respective expression vector is used to transform *Oryza* sativa plants. Mature dry seeds of the rice *japonica* cultivar Nipponbare are dehusked. Sterilization is carried out by incubating for one minute in 70% ethanol, followed by 30 minutes in 0.2% $HgCl_2$, followed by a 6 times 15 minutes wash with sterile distilled water. The sterile seeds are then germinated on a medium containing 2.4-D (callus induction medium). After incubation in the dark for four weeks, embryogenic, scutellum-derived calli are excised and propagated on the same medium. After two weeks, the calli are multiplied or propagated by subculture on the same medium for another 2 weeks. Embryogenic callus pieces are sub-cultured on fresh medium 3 days before co-cultivation (to boost cell division activity).

*Agrobacterium* strain LBA4404 containing the respective expression vector is used for co-cultivation. *Agrobacterium* is inoculated on AB medium with the appropriate antibiotics and cultured for 3 days at 28° C. The bacteria are then collected and suspended in liquid co-cultivation medium to a density ($OD_{600}$) of about 1. The suspension is then transferred to a Petri dish and the calli immersed in the suspension for 15 minutes. The callus tissues are then blotted dry on a filter paper and transferred to solidified, co-cultivation medium and incubated for 3 days in the dark at 25° C. Co-cultivated calli are grown on 2.4-D-containing medium for 4 weeks in the dark at 28° C. in the presence of a selection agent During this period, rapidly growing resistant callus islands developed. After transfer of this material to a regeneration medium and incubation in the light, the embryogenic potential is released and shoots developed in the next four to five weeks. Shoots are excised from the calli and incubated for 2 to 3 weeks on an auxin-containing medium from which they are transferred to soil. Hardened shoots are grown under high humidity and short days in a greenhouse.

The primary transformants are transferred from a tissue culture chamber to a greenhouse. After a quantitative PCR analysis to verify copy number of the T-DNA insert, only single copy transgenic plants that exhibit tolerance to the selection agent are kept for harvest of T1 seed. Seeds are then harvested three to five months after transplanting. The method yields single locus transformants at a rate of over 50% (Aldemita and Hodges 1996, Chan et al. 1993, Hiei et al. 1994).

Example 6: Expression Profile of the p-GOS2_perm1 (SEQ ID NO14) and p-GOS2_perm2 (SEQ ID NO15) Control Elements To demonstrate and analyze the transcription regulating properties of a promoter, it is useful to operably link the promoter or its fragments to a reporter gene, which can be employed to monitor its expression both qualitatively and quantitatively. Preferably bacterial ß-glucuronidase is used (Jefferson 1987). ß-glucuronidase activity can be monitored in planta with chromogenic substrates such as 5-bromo-4-Chloro-3-indolyl-ß-D-glucuronic acid during corresponding activity assays (Jefferson 1987). For determination of promoter activity and tissue specificity, plant tissue is dissected, stained and analyzed as described (e.g., Bäumlein 1991).

The regenerated transgenic T0 rice plants are used for reporter gene analysis.

General results for SEQ ID NO14: Medium-strong GUS expression is detected in all plant tissues analyzed.

General results for SEQ ID NO15: Medium-strong GUS expression is detected in all plant tissues analyzed.

General results for SEQ ID NO13: Medium-strong GUS expression is detected in all plant tissues analyzed.

The invention claimed is:

1. A synthetic promoter comprising SEQ ID NO: 4.
2. An expression construct comprising the synthetic promoter of claim 1 operably linked to a nucleotide sequence of interest.
3. A vector comprising the expression construct of claim 2.
4. A host cell comprising the synthetic promoter of claim 1.
5. The host cell of claim 4, wherein said host cell is a plant cell.
6. A plant or plant part comprising the synthetic promoter of claim 1.
7. A plant seed comprising the synthetic promoter of claim 1.
8. A method of making a transgenic plant or plant cell, the method comprising:
   a) transforming a plant or plant cell with a construct comprising SEQ ID NO: 4 operably linked to a sequence of interest to produce a transgenic plant or plant cell; and, optionally,
   b) regenerating a transgenic plant from said transformed plant cell.
9. The method of claim 8, further comprising producing seed from said transgenic plant and collecting said seed.

* * * * *

SEQUENCE LISTING

<160> NUMBER OF SEQ ID NOS: 15

<210> SEQ ID NO 1
<211> LENGTH: 1151
<212> TYPE: DNA
<213> ORGANISM: Phaseolus vulgaris
<220> FEATURE:
<221> NAME/KEY: Promoter
<222> LOCATION: (1)..(1151)
<223> OTHER INFORMATION: p-PvArc

<400> SEQUENCE: 1

| | | | | | |
|---|---|---|---|---|---|
| ttctatagaa | aatgtgttat | ttcctcatca | ccagacaaag | gggcaacagt | taacaaaaca | 60 |
| aatttatgtt | tcatttgaga | ttaaggaagg | taaggaagaa | aaaagattaa | aaaaaatgtc | 120 |
| cttatctctt | tgtttctgta | ataataatat | aagagactta | aactttaat | ataataattg | 180 |
| taattaggtt | ttctagtcat | gagcaccact | cagagacaag | atttcaagaa | acaattttg | 240 |
| ttaaacatct | tattagaaac | ttttagttaa | gtcttgaagt | tagaattaaa | caaaaaaag | 300 |
| tacacacgag | aaacacaata | aacccactac | cgtcaggtta | tcataaggat | gaaatgtttt | 360 |
| gatatcatta | aatataacac | acacaaaaat | acatctaatt | ataacaatat | atgttataca | 420 |
| tatattttg | taaaaactta | gagttttttca | aaacattcta | atacatgatt | agagtttata | 480 |
| gaaatacaaa | tatttaaaaa | atataattt | aaaaaaacat | tctaaagtca | ttcagatcct | 540 |
| ctcacacctg | tgtgatcatt | tagtcatgta | tgtagtacaa | tcattgtagt | tcacaacaga | 600 |
| gtaaaataaa | taaggataaa | ctagggaata | tatataat | atacaattaa | ataaaaaagg | 660 |
| gaaaatcaaa | ttagaatttt | agattcccca | catgacacaa | ctcaccatgc | acgctgccac | 720 |
| ctcagctccc | tcctctccac | acatgtctca | tgtcactttc | gactttggtt | ttttcactat | 780 |
| gacacaactc | gccatgcatg | ttgccacgtg | agctccttcc | tcttcccatg | atgacaccac | 840 |
| tgggcatgca | tgctgccacc | tcagctccca | cctcttctca | ttatgagcct | actggccatg | 900 |
| cacactgcca | cctcagcact | cctctcactt | cccattgcta | cctgccaaac | cgcttctctc | 960 |
| cataaatatc | tatttaaatt | taaactaatt | atttcatata | ctttttgat | gacgtggatg | 1020 |
| cattgccatc | gttgtttaat | aattgttaat | ttggagttga | ataataaaat | gaaagaaaaa | 1080 |
| agttggaaag | attttgcatt | tgttgttgta | taaatagaga | agagagtgat | ggttaatgca | 1140 |
| tgaatgcatg | a | | | | | 1151 |

<210> SEQ ID NO 2
<211> LENGTH: 1151
<212> TYPE: DNA
<213> ORGANISM: Artificial Sequence
<220> FEATURE:
<223> OTHER INFORMATION: Promoter
<220> FEATURE:
<221> NAME/KEY: Promoter
<222> LOCATION: (1)..(1151)
<223> OTHER INFORMATION: p-PvArc-perm

<400> SEQUENCE: 2

| | | | | | |
|---|---|---|---|---|---|
| tactatagaa | aatgtgttat | atcgacatga | ccagacaaag | gggcaacagt | taacaaaaca | 60 |
| attaattctt | tcatttgaga | ttaaggaagg | taaggtacta | aaaagattaa | aaaaaatgag | 120 |
| cttatctctt | tgtttctgta | ataataatat | aagtgtgata | aactttaat | ataataattg | 180 |
| taattaggtt | ttctacagat | gagcaccact | cagagacaag | ataagaagaa | acaattttg | 240 |
| ttaaacatga | ttatagaaac | ttttagttaa | gtcttgaagt | atcaatataa | caaaaaaag | 300 |
| tacacacgac | tatgacaata | aacccactac | cgtcaggtta | tcatttcgat | gaaatgtttt | 360 |

```
gatatcatta aatataacag tcacaaaaaa tcatctaatt ataacaatat aacttataca        420
tatatttaac taaaaactta gagtttttgt aatgattcta attgatgatt agagtttata        480
gaaatacaat taaataaaaa atataatttt aaaaaaacat agtaaagtca atgagatcct        540
ctctgacctc agtgatcatt tagtcatgta tgtacaacaa tcattgttca tcacatgact        600
gtaaaataaa taaggataaa cttgggaata tatataatat attgtattaa ataaaaaagg        660
gaaatacaaa tatcaatttt agattcccga gttgacacaa ctcaccatgc acgctgccac        720
ctcagctccc agctctcgtc acatgtctca tgtcagttag gtctttggtt tttagtcttt        780
gacacaactc gccatgcatg ttgccacgtg agctcgttcc tcttcccatg atctcaccac        840
tgggcatgca tgctgccacc tcagctggca cctcttctct atatgtccct agaggccatg        900
cacagtgcca cctcagcact cctctcagaa cccatacgta cctgccaatc ggcttctctc        960
cataaatatc tatttaaatt ataactaatt atttcatata cttaattgat gacgtggatg       1020
cattgccatc gttgtttaat aattgttaat tacgacatga taaataaaat gaaagtaaaa       1080
agtacgaaag atttccatt tgttgttgta aaatagaga agtgagtgat gcataatgca         1140
tgaatgcatg a                                                            1151
```

<210> SEQ ID NO 3
<211> LENGTH: 1799
<212> TYPE: DNA
<213> ORGANISM: Vicia faba
<220> FEATURE:
<221> NAME/KEY: Promoter
<222> LOCATION: (1)..(1799)
<223> OTHER INFORMATION: p-VfSBP

<400> SEQUENCE: 3

```
tcgacggccc ggactgtatc caacttctga tctttgaatc tctctgttcc aacatgttct         60
gaaggagttc taagactttt cagaaagctt gtaacatgct ttgtagactt tctttgaatt        120
actcttgcaa actctgattg aacctacgtg aaaactgctc cagaagttct aaccaaattc        180
cgtcttggga aggcccaaaa tttattgagt acttcagttt catggacgtg tcttcaaaga        240
tttataactt gaaatcccat cattttttaag agaagttctg ttccgcaatg tcttagatct        300
cattgaaatc tacaactctt gtgtcagaag ttcttccaga atcaacttgc atcatggtga        360
aaatctggcc agaagttctg aacttgtcat atttcttaac agttagaaaa atttctaagt        420
gtttagaatt ttgacttttc caaagcaaac ttgacttttg actttcttaa taaaacaaac        480
ttcatattct aacatgtctt gatgaaatgt gattcttgaa atttgatgtt gatgcaaaag        540
tcaaagtttg acttttcagt gtgcaattga ccatttgct cttgtgccaa ttccaaacct        600
aaattgatgt atcagtgctg caaacttgat gtcatggaag atcttatgag aaaattcttg        660
aagactgaga ggaaaaattt tgtagtacaa cacaaagaat cctgtttttc atagtcggac        720
tagacacatt aacataaaac accacttcat tcgaagagtg attgaagaag gaaatgtgca        780
gttacctttc tgcagttcat aagagcaact tacagacact tttactaaaa tactacaaag        840
aggaagattt taacaactta gagaagtaat gggagttaaa gagcaacaca ttaaggggga        900
gtgttaaaat taatgtgttg taaccaccac tacctttagt aagtattata agaaaattgt        960
aatcatcaca ttataattat tgtccttatt taaaattatg ataaagttgt atcattaaga       1020
ttgagaaaac caaatagtcc tcgtcttgat ttttgaatta ttgttttcta tgttactttg       1080
cttcaagcct atataaaaac tttgtaatgc taaattgtat gctggaaaaa aatgtgtaat       1140
```

```
gaattgaata gaaattatgg tatttcaaag tccaaaatcc atcaatagaa atttagtaca     1200
aaacgtaact caaaaatatt ctcttatttt aaattttaca acaatataaa aatattctct     1260
tattttaaat tttacaataa tataatttat cacctgtcac ctttagaata ccaccaacaa     1320
tattaatact tagatatttt attcttaata attttgagat ctctcaatat atctgatatt     1380
tattttatat ttgtgtcata ttttcttatg ttttagagtt aacccttata tcttggtcaa     1440
actagtaatt caatatatga gtttgtgaag gacacattga catcttgaaa cattggtttt     1500
aaccttgttg gaatgttaaa ggtaataaaa cattcagaat tatgaccatc tattaatata     1560
cttcctttgt cttttaaaaa agtgtgcatg aaaatgctct atggtaagct agagtgtctt     1620
gctggcctgt gtatatcaat tccatttcca gatggtagaa actgccacta cgaataatta     1680
gtcataagac acgtatgtta acacacgtcc ccttgcatgt ttttgccat atattccgtc      1740 tctttctttt tcttcacgta taaacaatg aactaattaa tagagcgatc aagctgaac      1799
```

```
<210> SEQ ID NO 4
<211> LENGTH: 1799
<212> TYPE: DNA
<213> ORGANISM: Artificial Sequence
<220> FEATURE:
<223> OTHER INFORMATION: Promoter
<220> FEATURE:
<221> NAME/KEY: Promoter
<222> LOCATION: (1)..(1799)
<223> OTHER INFORMATION: p-VfSBP-perm

<400> SEQUENCE: 4
```

```
tgctcggccc ggactgtatc caacttgaga tctttgaatc tctctgttcc ttgatgttct      60
gaaggagttc taagtgtaat cagaaagctt gtaacatgct ttgtagactt tcttttgatat     120 actcttgcaa tgactgattg aacctacgtg aaaactgctg gtcaagttct aaccaaattc     180
cgtctacgga aggcccaaaa tttattgaca tcttcagttt catggacgtg tcttcaaagt     240
tttataactt cttatcccat cattttttaag tctagttctg ttccgcatag tcttagatct     300
caaacaaatc tacaactctt gtgtcagttc ttcttccaga atcaacttgc tacatggtga     360
aaatctggcg tcaagttctg aacttgtcaa ttttcttaac agttagaaaa taatctaagt     420
gtttagaata ttgactttc caaagcaaag aagactttg actttcttaa taaaacaaac       480
ttctaattct aacatgtctt gatgaaatgt cttttcttgaa atttgatcaa gatgcaaaag    540
tcaaagtttg actttcaga ctgcaattga ccattttgca gaagtgccaa ttccaaacca      600
aaattgatga tacagtgctg caaacttgat gtcatggaag atcttaacag aaaattcttg    660
aagactgaga gcaaaaattt tcatgtacaa cacaaacttt cctgttttc atagtcgctg      720 tagacacatt aacataaac acctgatcat tcgaagagtg attcttgaag gaaatgtgca     780
gttacctttg tgcagaactt aagagcaact tacagactca tttactaaaa tactacaatc     840
aggaagattt taacaactta cagaagtatt cggagttaaa gagcaacaca ttaagggcga    900
cagttaaaat taatgtgttg taaccaccac tacgaatagt aagtattata agttaaatgt    960
aatcatcaca ttataattat tgtccttata attaattatg ataaacatgt atcattaaga    1020
ttgtcataac caaatagtcc tcgacttgat ttttgaatta ttgtattcta tgttactttt    1080
cttgtagcct atataaaaac tttgtaaagc ataattgtat gctggaaaaa atactgtaat    1140
gaattgaata gaaattatgg tatttcattc tccaaaatcc atcaatagaa atttagtaca    1200
aatcgaaaga caaaaatatt gacttatttt aaattttaca acaatataaa aatattgact    1260
tattttaaat tttacaataa tataaatttt cacctgtcac ctttagaaat ccaccaacaa    1320
```

```
tattaattct tagataaatt attcttaata attttgagat ctctgtaatt atctgatatt    1380
tattttatat ttgtcagtta ttttcttatg ttttactgtt aacccttata tcttggtcaa    1440
actagaataa gtaaatatga gtttgtgaag gacacattga caagatgaaa cattggtttt    1500
ttccttcttc gaatgttaaa ggtaataaaa cattcagaat attgacctac tattaatata    1560
gatcctttgt cttttaaaaa agtgtgcatg aaaatgctct taggtaagct agtgtctctt    1620
gcagggctgt gtatatcaat tccatttcca gatggttgta actgccacta cctataatta    1680
gtcataagac acgtatgtta acacacgtcc ccatgcatgt ttttgccat atattcccac     1740 actttctttt tcttcacgta taaaacattg aactaattaa tagtccgatc aagctgaac     1799
```

<210> SEQ ID NO 5
<211> LENGTH: 1138
<212> TYPE: DNA
<213> ORGANISM: Vicia faba
<220> FEATURE:
<221> NAME/KEY: Promoter
<222> LOCATION: (1)..(1138)
<223> OTHER INFORMATION: p-VfNapin

<400> SEQUENCE: 5

```
tcttcatcgg tgattgattc ctttaaagac ttatgtttct tatcttgctt ctgaggcaag     60
tattcagtta ccagttacca cttatattct ggactttctg actgcatcct cattttccca    120
acatttaaaa tttcactatt ggctgaatgc ttcttctttg aggaagaaac aattcagatg    180
gcagaaatgt atcaaccaat gcatatatac aaatgtacct cttgttctca aaacatctat    240
cggatggttc catttgcttt gtcatccaat tagtgactac tttatattat tcactcctct    300
ttattactat tttcatgcga ggttgccatg tacattatat ttgtaaggat tgacgctatt    360
gagcgttttt cttcaatttt ctttatttta gacatgggta tgaaatgtgt gttagagttg    420
ggttgaatga gatatacgtt caagtgaatg gcataccgtt ctcgagtaag gatgacctac    480
ccattcttga gacaaatgtt acattttagt atcagagtaa aatgtgtacc tataactcaa    540
attcgattga catgtatcca ttcaacataa aattaaacca gcctgcacct gcatccacat    600
ttcaagtatt ttcaaaccgt tcggctccta tccaccgggt gtaacaagac ggattccgaa    660
tttggaagat tttgactcaa attcccaatt tatattgacc gtgactaaat caactttaac    720
ttctataatt ctgattaagc tcccaattta tattcccaac ggcactacct ccaaaattta    780
tagactctca tccccttta aaccaactta gtaaacgttt ttttttttaa ttttatgaag     840
ttaagttttt accttgtttt taaaagaat cgttcataag atgccatgcc agaacattag     900
ctacacgtta cacatagcat gcagccgcgg agaattgttt tcttcgcca cttgtcactc    960 ccttcaaaca cctaagagct tctctctcac agcacacaca tacaatcaca tgcgtgcatg   1020
cattattaca cgtgatcgcc atgcaaatct cctttatagc ctataaatta actcatccgc   1080
ttcactcttt actcaaacca aaactcatca atacaaacaa gattaaaaac atacacga     1138
```

<210> SEQ ID NO 6
<211> LENGTH: 990
<212> TYPE: DNA
<213> ORGANISM: Artificial Sequence
<220> FEATURE:
<223> OTHER INFORMATION: Promoter
<220> FEATURE:
<221> NAME/KEY: Promoter
<222> LOCATION: (1)..(990)
<223> OTHER INFORMATION: p-VfNapin-perm

<400> SEQUENCE: 6

```
cccggggata tcaagcttaa acaatacagg tggctgaaat atataaacca attcatgtct    60
acaaatgtac cctttgcact taaaaaattt atcggaggga tccactcgca ttggaagtca   120
atcaaggact attggttatt agtctgtccg ttatttgaat atgataacgc aaggtttccg   180
tgtacaatat atgtgcatgg aatgccgctg ttgagcgttt aacctgaatt ttcatgattt   240
gaggcatggg gctgtattgc ttgttagcgt tggggtgaat gaaatttagc ttcaacctaa   300
tgagatacag ttcccgggtc aggatgatct aatcattcct catacaaatg tctcattttt   360
caattagagt aatatgtgtc catatgtctc gatttcgatt gacttacatc cattcaagat   420
aaaattgcgc aatcttgcac ttcccttaac attttcataa gtttcatacc tatcactacc   480
tatacacccg ggataacaca tcgtgttcgg gtgttggaag attttgactc aaattcctaa   540
tttacattgc tcctaactat attagcttta acttctgtac tgctggtaaa gctgccaacc   600
gttatcacca taggccatac ttccatcggt tatagactct catcccctt  tagaccagct   660
tagtcaacgt tctgtctttt aattctaaga cgttatgaac ttagatggtt ttcaaaaaaa   720
atcgtgatga gaatgccttg ccaggacatt agctacacgt tacacatacc atgcaatcca   780
ggagaatatt atttcttcgc cacttgtcac tcccttcaaa cacctaagac cttatctctc   840
acatcagccg catacattca catgcgtgca tgcattatta cacgtgatcg ccatgcaaat   900
cttcattaaa gtgtataaaa gtacccatcc gattcaggct tgaatctacc gatacctgag   960
caacacaaac acggtcaaaa acatacacga                                    990
```

<210> SEQ ID NO 7
<211> LENGTH: 14944
<212> TYPE: DNA
<213> ORGANISM: Artificial Sequence
<220> FEATURE:
<223> OTHER INFORMATION: Transformation Vector

<400> SEQUENCE: 7

```
tggcaggata tattgtggtg taaacaaatt gacgcttaga caacttaata acacattgcg    60
gacgtcttta atgtactgaa tttagttact gatcactgat taagtactgc gatcgcctcg   120
acatattgtt tttgtttcac ataaatgtcg ttttggatta ttcatgtaat attttaaact   180
aaagtacaat ttttgactac tttagtttac tagttaagct tttatttttt tgactaacca   240
ttgaatgatg aagagatcaa cgcatcatat ttacaactta catagtcttt tggaagtgta   300
aattgctaat actacctaaa atatatctat aattaactaa tattttttcg tcaattataa   360
tagatcaatt aaaaggctat caaaaggaaa aaaatgaaat ccacatcctg ccatcataac   420
ctcatgctgg aaaagaaat  gaaaaaatat aaaaaatttc ttttgtttat taaatttaca   480
actttaatac tagtttcttt tctatttttt aaaagctttt gtcacttact taaaaaaaaa   540
aaacttttg  aaatattcct acttccaatg tctgattagt gcttctggat ttccttttg    600
gatcatgtga atcctaaatc agaaaaattc atataatacc caattcagta tatttttcata  660
cttcaattta caagagttct ctatgttttt agcttctttc ttttaagcca aatgttttaa   720
gcatcttttta tacattaaaa taatttagtg ttgagttgag atttttttttt tttttttttg   780
gatttacttg ttcaaaatct gaaaaaatgt ttacagaagg ttaaaatgaa ccaaaaggca   840
tatcaagcta gattttgaat taccctattt catcgtatac acaaaactga taatgtggac   900
acagttgatt ttacttctcg atgacatcgt agttttattt aatttggaaa ccacggccca   960
tatgagcaca tttcaattaa aaaccaatgg taagagcatt ttccatgcaa gattcgagag  1020
```

```
atattaaccc agtgactgtt aaaacagctt agaaccctaa taacgaattt caattactca    1080
atttaccatt cgcatttcgc aataaccaaa ctgagccagt cacaaggagt aaaccgaacc    1140
ggattattta tttataaaat gaaagaaagg aaaccaaaca acaacagcag tagtagtctg    1200
acgtaaacca aaaagcaggc agatcaacaa ctaaaagaaa ctcaaattac aaaacaaac     1260 aggaaattgc aaactaagtt tttttaccat atgcatacaa agaccataaa aggttctgat    1320
aatcaccggt ttcatctcgt cgagattacc ctgttatccc tatcagtatt taatccggcc   1380
atctccttcc gttatgacat cgttgaaagt gccaccattc gggatcatcg gcaacacatg   1440
ttcttggtgc ggacaaatca catccaacag gtaaggtcct ggtgtatcca gcattgtctg   1500
aatagcttct cggagatctg cttttctttgt caccctcgcc gctggaatcc cgcaagctgc  1560
tgcaaacagc aacatgttcg ggaatatctc gtcctcctga gccggatccc cgagaaatgt   1620
gtgagctcgg ttagctttgt agaaccgatc ttcccattgc ataaccatgc caagatgctg   1680
gttgtttaat aaaagtacct tcactggaag attctctaca cgaatagtgg ctagctcttg   1740
cacattcatt ataaagcttc catctccgtc aatatccaca actatcgcat cagggttagc   1800
aacagacgct ccaatcgcag caggaagtcc aaatcccata gctccaaggc ctcctgatga   1860
tagccactgc cttggtttct tgtaattgta gaactgcgcc gcccacattt gatgttgccc   1920
gacaccagta cttattatgg cttttccatc agtcaactca tcaaggacct taatcgcata   1980
ctgtggagga atagcttccc caaacgtctt aaagctcaac ggaaacttct gtttctgtac    2040
gttcaactca ttcctccaaa ctccaaaatc aagcttaagc cctccgctc ggttctcaag    2100 aaccttattc atcccttgca aagccagctt aacatcacca cacacagaca catgaggagt   2160
cttattcttc ccaatctcag ccgagtcaat atcaatatga acaatcttag ccctactagc   2220
aaaagcctca agcttacccg tgacacgatc atcaaacctt accccaaacg ccaacaacaa   2280
atcactatgc tccacagcgt aatttgcata cacagtccca tgcattccaa gcatatgtaa   2340
cgacaactca tcatcacaag gataagatcc cagccccatc aacgtactcg caacagggat   2400
ccccgtaagc tcaacaaacc tacccaattc atcgctagaa ttcaaacaac caccaccaac   2460
atacaacaca ggcttcttag actcagaaat caacctaaca atctgctcca aatgagaatc   2520
ttccggaggt ttaggcatcc tagacatata accaggtaat ctcatagcct gttcccaatt   2580
aggaatcgca agctgttgtt gaatatcttt aggaacatca accaaaacag gtccaggtct   2640
accagaagta gctaaaaaga aagcttcctc aataatccta gggatatctt caacatccat   2700
cacaagatag ttatgcttcg taatcgaacg cgttacctca acaatcggag tctcttgaaa   2760
cgcatctgta ccaatcatac gacgagggac ttgtcctgtg attgctacaa gaggaacact   2820
atctaacaac gcatcggcta atccgctaac gagatttgta gctccgggac ctgaagtggc   2880
tatacagata cctggtttac ctgaggatcg agcgtatcct tctgctgcga atacacctcc   2940
ttgttcgtga cgaggaagga cgttacggat tgaggaagag cgggttaagg cttggtgaat   3000
ctccattgat gtacctccag ggtaagcgaa tacggtttct acgccttgac gttctaaagc   3060
ttcgacgagg atatcagcgc ctttgcgggg ttgatctgga gcgaatcggg agatgaatgt   3120
ttcgggtttg gtaggtttgg ttggagaggg agtggttgtg acattggtgg ttgtgttgag   3180
cacggcggag atggaggagg gagagctgga tttgataccg cggcggcggg aggaggagga   3240
tgatttgttg gggtttaggg agaatgggag ggagaatctg gagattggta atggtgatt    3300 ggaggaggaa ggagatggtt tggtggagaa ggagatcgaa gaagatgttg ttgttgttgt   3360
```

```
tgttgccgcc gccatggttc agctgcacat acataacata tcaagatcag aacacacata   3420
tacacacaca aatacaatca agtcaacaac tccaaaaagt ccagatctac atatatacat   3480
acgtaaataa caaaatcatg taaataatca caatcatgta atccagatct atgcacatat   3540
atatatacac aattaataaa aaaaatgata taacagatct atatctatgt atgtaacaac   3600
acaatcagat gagagaagtg atgttttcag atctgtatac atacaaacac aaacagatga   3660
acaattgata cgtagatcca tatgtatacg tacaattagc tacacgatta aatgaaaaaa   3720
atcaacgatt tcggattggt acacacaaac gcaacaatat gaagaaattc atatctgatt   3780
agatataaac ataaccacgt gtagatacac agtcaaatca acaaatttat agcttctaaa   3840
cggatgagat gaacaagata aagatattca cataaggcat acataagata agcagattaa   3900
caaactagca ataatacata cctaattaaa acaaggaata acagagagag agagagagag   3960
agagatttac cttgaaaatg aagaggagaa gagaggattt cttaaaattg ggggtagaga   4020
aagaaagatg atgaattgtg agaaggaga gatagaaggg ggggttgtat ataggctg    4080 tagaagatta ttttgtgtt tgaggcggtg aaggaagagg ggatctgact atgacacgtt   4140
tgcggttacg tatttcgata ggagtctttc aacgcttaac gccgttactc tatatgaccg   4200
tttgggccgt aacggggccg tttgttaacg ctgatgttga ttcttttctt tctttctttc   4260 ttccttttt aaagaagcaa ttgtacaatc gttgctagct gtcaaacgga taattcggat   4320
acggatatgc ctatattcat atccgtaatt tttggattcg aattttcccc tctaggata   4380 acagggtaat ggatctatat tgttttttgtt tcacataaat gtcgttttgg attattcatg   4440
taatatttta aactaaagta caattttttga ctacttttagt ttactagtta agcttttatt   4500
tttttgacta accattgaat gatgaagaga tcaacgcatc atatttacaa cttacatagt   4560
cttttggaag tgtaaattgc taatactacc taaaatatat ctataattaa ctaatatttt   4620
ttcgtcaatt ataatagatc aattaaaagg ctatcaaaag gaaaaaaatg aaatccacat   4680
cctgccatca taacctcatg ctggaaaaag aaatgaaaaa atataaaaaa tttcttttgt   4740
ttattaaatt tacaacttta atactagttt cttttctatt ttttaaaagc ttttgtcact   4800
tacttaaaaa aaaaaaactt tttgaaatat tcctacttcc aatgtctgat tagtgcttct   4860
ggatttcctt tttggatcat gtgaatccta atcagaaaa attcatataa tacccaattc   4920
agtatatttt catacttcaa tttacaagag ttctctatgt ttttagcttc tttcttttaa   4980
gccaaatgtt ttaagcatct tttatacatt aaaataattt agtgttgagt tgagattttt   5040
tttttttttt tttggattta cttgttcaaa atctgaaaaa atgttacag aaggttaaaa   5100 tgaaccaaaa ggcatatcaa gctagatttt gaattaccct atttcatcgt atacacaaaa   5160
ctgataatgt ggacacagtt gattttactt ctcgatgaca tcgtagtttt atttaatttg   5220
gaaaccacgg cccatatgag cacatttcaa ttaaaaacca atggtaagag catttttccat   5280 gcaagattcg agagatatta acccagtgac tgttaaaaca gcttagaacc ctaataacga   5340
atttcaatta ctcaatttac cattcgcatt tcgcaataac caaactgagc cagtcacaag   5400
gagtaaaccg aaccggatta tttatttata aaatgaaaga aaggaaacca aacaacaaca   5460
gcagtagtag tctgacgtaa accaaaaagc aggcagatca acaactaaaa gaaactcaaa   5520
ttaccaaaac aaacaggaaa ttgcaaacta agttttttta ccatatgcat acaaagacca   5580
taaaaggttc tgataatcac cggtttcatc tcagatccgc gatcgccaat tgacgcgtac   5640
tagtgtacaa gcttgcggcc gcgaattcgg tacatccggc cagtgaatta tcaactatgt   5700
ataataaagt tgggtaccgg cctattaggc cacggtccgt acagtgttta aacgattgac   5760
```

```
ctgcaggata caagtgcgca cagactagcg gccgctaatc ccgggaatta ccggtagtag   5820
gcgcctactt tggccggcct agtagattta aattggcctt agtggccaag cttggcgtaa   5880
tcatggccac tttgtacaag aaagctgggt ggtaccggcc tattaggcca cggtccgtac   5940
agtgtttaaa cgattgacct gcaggataca agtgcgcaca gactagcggc cgctaatccc   6000
gggaattacc ggtagtaggc gcctactttg gccggcctag tagatttaaa ttggccttag   6060
tggccaagct tggcgtaatc atggagcctg ctttttttgta caaacttggg taccggccta   6120
ttaggccacg gtccgtacag tgtttaaacg attgacctgc aggatacaag tgcgcacaga   6180
ctagcggccg ctaatcccgg gaattaccgg tagtaggcgc cttgttttag actgaatata   6240
acacaacgat tatatagccg ctgtctttgt ttgaagagaa tggactacat gctgaaaaat   6300
agtgatacaa gaatcgttgt tttaatgcta aaatgaccat ctcgtgattt aacttttctg   6360
gaccaatgat tgtaaagttt ttttttagaga ggtggtgata acatatatt gattttttgaa   6420 atgaatagag ttagaaagta agaaaaatac aataaaaatg ttaaataatg ttgtagaaat   6480
agaaatggaa gagaagtgta agaaatttta aataaaaatt agatgggaga gtaagttagt   6540
ttatattgat ttgttttgtg gttagtttat ctatgttata cttttaactt ataataatcc   6600
tttccatcat taagcaattt ttaaaaatga cataatttta aaattatgaa gtaataattg   6660
gcatggtgaa taatagacag tgtaaatggt gtaaatatat gagctcccat tttatttatt   6720
gctcccattt tatttatttt agtttgtgtg acagatgaac attattagga ggaaaggtat   6780
aagcagggtt taactgtcac agggaaggtg gttttgggag tcttagttaa ttaatcattg   6840
tttgcctccc tgctgcggtt tttcaccgaa gttcatgcca gtccagcgtt tttgcagcag   6900
aaaagccgcc gacttcggtt tgcggtcgcg agtgaagatc cctttcttgt taccgccaac   6960
gcgcaatatg ccttgcgagg tcgcaaaatc ggcgaaattc catacctgtt caccgacgac   7020
ggcgctgacg cgatcaaaga cgcggtgata catatccagc catgcacact gatactcttc   7080
actccacatg tcggtgtaca ttgagtgcag cccggctaac gtatccacgc cgtattcggt   7140
gatgataatc ggctgatgca gtttctcctg ccaggccaga agttctttttt ccagtacctt   7200 ctctgccgtt tccaaatcgc cgctttggac ataccatccg taataacggt tcaggcacag   7260
cacatcaaag agatcgctga tggtatcggt gtgagcgtcg cagaacatta cattgacgca   7320
ggtgatcgga cgcgtcgggt cgagtttacg cgttgcttcc gccagtggcg cgaaatattc   7380
ccgtgcacct tgcggacggg tatccggttc gttggcaata ctccacatca ccacgcttgg   7440 gtggttttttg tcacgcgcta tcagctcttt aatcgcctgt aagtgcgctt gctgagtttc   7500
cccgttgact gcctcttcgc tgtacagttc tttcggcttg ttgcccgctt cgaaaccaat   7560
gcctaaagag aggttaaagc cgacagcagc agtttcatca atcaccacga tgccatgttc   7620
atctgcccag tcgagcatct cttcagcgta agggtaatgc gaggtacggt aggagttggc   7680
cccaatccag tccattaatg cgtggtcgtg caccatcagc acgttatcga atcctttgcc   7740
acgcaagtcc gcatcttcat gacgaccaaa gccagtaaag tagaacggtt tgtggttaat   7800
caggaactgt tcgcccttca ctgccactga ccggatgccg acgcgaagcg ggtagatatc   7860
acactctgtc tggcttttgg ctgtgacgca cagttcatag agataacctt cacccggttg   7920
ccagaggtgc ggattcacca cttgcaaagt cccgctagtg ccttgtccag ttgcaaccac   7980
ctgttgatcc gcatcacgca gttcaacgct gacatcacca ttggccacca cctgccagtc   8040
aacagacgcg tggttacagt cttgcgcgac atgcgtcacc acggtgatat cgtccaccca   8100
```

```
ggtgttcggc gtggtgtaga gcattacgct gcgatggatt ccggcatagt taaagaaatc    8160
atggaagtaa gactgctttt tcttgccgtt ttcgtcggta atcaccattc ccggcgggat    8220
agtctgccag ttcagttcgt tgttcacaca acggtgata  cctgcacatc aacaaatttt    8280
ggtcatatat tagaaaagtt ataaattaaa atatacacac ttataaacta cagaaaagca    8340
attgctatat actacattct tttattttga aaaaaatatt tgaaatatta tattactact    8400
aattaatgat aattattata tatatatcaa aggtagaagc agaaacttac gtacactttt    8460
cccggcaata acatacggcg tgacatcggc ttcaaatggc gtatagccgc cctgatgctc    8520
catcacttcc tgattattga cccacacttt gccgtaatga gtgaccgcat cgaaacgcag    8580
cacgatacgc tggcctgccc aacctttcgg tataaagact cgcgctgat  accagacgtt    8640
gcccgcataa ttacgaatat ctgcatcggc gaactgatcg ttaaaactgc ctggcacagc    8700
aattgcccgg ctttcttgta acgcgctttc ccaccaacgc tgaccaattc cacagttttc    8760
gcgatccaga ctgaatgccc acaggccgtc gagttttttg atttcacggg ttggggtttc    8820
tacaggacgt accatggtca tgcattcatg cattatgcat cactcacttc tctatttata    8880
caacaacaaa tggaaaatct ttcgtacttt ttactttcat tttatttatc atgtcgtaat    8940
taacaattat taaacaacga tggcaatgca tccacgtcat caattaagta tatgaaataa    9000
ttagttataa tttaaataga tatttatgga gagaagccga ttggcaggta cgtatgggtt    9060
ctgagaggag tgctgaggtg gcactgtgca tggcctctag gacatatag  agaagaggtg    9120
ccagctgagg tggcagcatg catgcccagt ggtgagatca tgggaagagg aacgagctca    9180
cgtggcaaca tgcatggcga gttgtgtcaa agactaaaaa ccaaagacct aactgacatg    9240
agacatgtga cgagagctgg gagctgaggt ggcagcgtgc atggtgagtt gtgtcaactc    9300
gggaatctaa aattgatatt tgtatttccc tttttttatt taatacaatat attatatata    9360
ttcccaagtt tatccttatt tattttacag tcatgtgatg aacaatgatt gttgtacata    9420
catgactaaa tgatcactga ggtcagagag gatctcattg actttactat gttttttaa    9480
aattatatt  tttattaat  tgtatttcta taaactctaa tcatcaatta gaatcattac    9540
aaaaactcta agttttagt  taaatatatg tataagttat attgttataa ttagatgatt    9600
ttttgtgact gttatattta atgatatcaa aacatttcat cgaaatgata acctgacggt    9660
agtgggttta ttgtcatagt cgtgtgtact ttttttttgtt atattgatac ttcaagactt    9720
aactaaaagt ttctataatc atgtttaaca aaattgtttt cttcttatct tgtctctgag    9780
tggtgctcat ctgtagaaaa cctaattaca attattatat taaagttta  tcacacttat    9840
attattatta cagaaacaaa gagataagct cattttttt  aatctttta  gtaccttacc    9900
ttccttaatc tcaaatgaaa gaattaattg ttttgttaac tgttgccccct ttgtctggtc    9960
atgtcgatat aacacatttt ctatagtagg ccggcctagt agatttaaat tggccttagt   10020
ggccaagctt ggcgtaatca tggcaacttt tctatacaaa gttgatagct tggcgtaatc   10080
gatgtaccga tatcaatta  aattggccgg ccgagctccc tgcaggggc  ccggcgcgcc   10140
tctagattaa ttaaaggcct tagttactaa tcagtgatca gattgtcgtt tcccgccttc   10200
agtttaaact atcagtgttt gacaggatat attggcgggt aaacctaaga gaaaagagcg   10260
tttattagaa taatcggata tttaaagggg cgtgaaaagg tttatccgtt cgtccatttg   10320
tatgtcaata tccatgataa gtcgcgctgt atgtgtttgt ttgaatattc atggaacgca   10380
gtggcggttt tcatgcttg  ttatgactgt tttttttgggg tacagtctat gcctcggca    10440
tccaagcagc aagcgcgtta cgccgtgggt cgatgtttga tgttatggag cagcaacgat   10500
```

```
gttacgcagc agggcagtcg ccctaaaaca aagttaaaca tcatgggtga agcggtcatc   10560
gccgaggtgt ccacccagct gtcggaagtc gtgggtgtca tcgagcgcca cctcgaaccg   10620
accctcctcg ccgtgcatct gtatggtagc gccgttgacg gcggccttaa gccccattcg   10680
gacatcgacc tgcttgtcac cgttaccgtc cgtctcgacg agaccacgcg ccgcgcgctt   10740
atcaacgacc ttctggaaac gtccgcctcc cccggcgaga gcgaaatcct gcgcgcggtt   10800
gaggtgacga ttgtggtgca cgatgacatc atcccctggc gctatccggc caaacgcgaa   10860
ctccagttcg gcgaatggca gcgtaatgat attctggcgg gtatctttga accggccacc   10920
atcgacattg atctggcgat cctgctcacc aaggcccggg agcatagcgt ggccctcgtc   10980
ggccccgcgg ccgaggaact tttcgacccg gtgccggaac aggatctgtt cgaagcactg   11040
aacgagacgc tgaccctgtg gaactccccg ccggattggg cggcgatga gcgcaatgtg    11100 gtccttacgc tgagccggat ttggtactcg gcggttaccg gcaagatcgc gccgaaggat   11160
gtcgccgccg actgggcgat ggagcgcctt ccggcgcaat accagcccgt gatcctcgaa   11220
gcgcgccaag cctatctggg ccaagaagaa gaccgtctcg cgtcccgggc cgaccagctc   11280
gaagaatttg tccactatgt caagggcgag atcacgaagg tcgttggcaa ataatgtcta   11340
gctagaaatt cgttcaagcc gacgccgctt cgcggcgcgg cttaactcaa gcgttagatg   11400
cactaagcac ataattgctc acagccaaac tatcgatgag ttgaaggacc ccgtagaaaa   11460
gatcaaagga tcttcttgag atccttttt tctgcgcgta atctgctgct tgcaaacaaa    11520
aaaaccaccg ctaccagcgg tggtttgttt gccggatcaa gagctaccaa ctcttttcc    11580 gaaggtaact ggcttcagca gagcgcagat accaaatact gtccttctag tgtagccgta   11640
gttaggccac cacttcaaga actctgtagc accgcctaca tacctcgctc tgctaatcct   11700
gttaccagtg gctgctgcca gtggcgataa gtcgtgtctt accgggttgg actcaagacg   11760
atagttaccg gataaggcgc agcggtcggg ctgaacgggg ggttcgtgca cacagcccag   11820
cttggagcga acgacctaca ccgaactgag atacctacag cgtgagctat gagaaagcgc   11880
cacgcttccc gaagggagaa aggcggacag gtatccggta agcggcaggg tcggaacagg   11940
agagcgcacg agggagcttc caggggaaac gcctggtat ctttatagtc ctgtcgggtt     12000
tcgccaccct tgacttgagc gtcgattttt tgtgatgctcg tcaggggggc ggagcctatg   12060
gaaaaacgcc agcaacgcgg ccttttttacg gttcctggcc ttttgctggc cttttgctca   12120
catgttcttt cctgcgttat cccctgattc tgtggataac cgtattaccg cctttgagtg   12180
agctgatacc gctcgccgca gccgaacgac cgagcgcagc gagtcagtga gcgaggaagc   12240
ggaagagcgc ctgatgcggt attttctcct tacgcatctg tgcggtattt cacaccgcat   12300
aggccgcgat aggccgacgc gaagcggcgg ggcgtaggga gcgcagcgac cgaagggtag   12360 gcgcttttttg cagctcttcg gctgtgcgct ggccagacag ttatgcacag gccaggcggg   12420
ttttaagagt tttaataagt tttaaagagt tttaggcgga aaaatcgcct ttttctctt    12480 ttatatcagt cacttacatg tgtgaccggt tcccaatgta cggctttggg ttcccaatgt   12540
acgggttccg gttcccaatg tacggctttg ggttcccaat gtacgtgcta tccacaggaa   12600
agagaccttt tcgacctttt tcccctgcta gggcaatttg ccctagcatc tgctccgtac   12660
attaggaacc ggcggatgct tcgccctcga tcaggttgcg gtagcgcatg actaggatcg   12720
ggccagcctg ccccgcctcc tccttcaaat cgtactccgg caggtcattt gacccgatca   12780
gcttgcgcac ggtgaaacag aacttcttga actctccggc gctgccactg cgttcgtaga   12840
```

```
tcgtcttgaa caaccatctg gcttctgcct tgcctgcggc gcggcgtgcc aggcggtaga    12900
gaaaacggcc gatgccgggg tcgatcaaaa agtaatcggg gtgaaccgtc agcacgtccg    12960
ggttcttgcc ttctgtgatc tcgcggtaca tccaatcagc aagctcgatc tcgatgtact    13020
ccggccgccc ggtttcgctc tttacgatct tgtagcggct aatcaaggct tcaccctcgg    13080
ataccgtcac caggcggccg ttcttggcct tcttggtacg ctgcatggca acgtgcgtgg    13140
tgtttaaccg aatgcaggtt tctaccaggt cgtctttctg ctttccgcca tcggctcgcc    13200
ggcagaactt gagtacgtcc gcaacgtgtg gacggaacac gcggccgggc ttgtctccct    13260
tcccttcccg gtatcggttc atggattcgg ttagatggga aaccgccatc agtaccaggt    13320
cgtaatccca cacactggcc atgccggcgg ggcctgcgga aacctctacg tgcccgtctg    13380
gaagctcgta gcggatcacc tcgccagctc gtcggtcacg cttcgacaga cggaaaacgg    13440
ccacgtccat gatgctgcga ctatcgcggg tgcccacgtc atagagcatc ggaacgaaaa    13500
aatctggttg ctcgtcgccc ttgggcggct tcctaatcga cggcgcaccg gctgccggcg    13560
gttgccggga ttctttgcgg attcgatcag cggccccttg ccacgattca ccggggcgtg    13620
cttctgcctc gatgcgttgc cgctgggcgg cctgcgcggc cttcaacttc tccaccaggt    13680
catcacccag cgccgcgccg atttgtaccg ggccggatgg tttgcgaccg ctcacgccga    13740
ttcctcgggc ttgggggttc cagtgccatt gcagggccgg cagacaaccc agccgcttac    13800
gcctggccaa ccgcccgttc ctccacacat ggggcattcc acggcgtcgg tgcctggttg    13860
ttcttgattt tccatgccgc ctcctttagc cgctaaaatt catctactca tttattcatt    13920
tgctcattta ctctggtagc tgcgcgatgt attcagatag cagctcggta atggtcttgc    13980
cttggcgtac cgcgtacatc ttcagcttgg tgtgatcctc cgccggcaac tgaaagttga    14040
cccgcttcat ggctggcgtg tctgccaggc tggccaacgt tgcagccttg ctgctgcgtg    14100
cgctcggacg gccggcactt agcgtgtttg tgcttttgct cattttctct ttacctcatt    14160
aactcaaatg agttttgatt taatttcagc ggccagcgcc tggacctcgc gggcagcgtc    14220
gccctcgggt tctgattcaa gaacggttgt gccggcggcg gcagtgcctg ggtagctcac    14280
gcgctgcgtg atacgggact caagaatggg cagctcgtac ccggccagcg cctcggcaac    14340
ctcaccgccg atgcgcgtgc cttttgatcgc ccgcgacacg acaaaggccg cttgtagcct    14400
tccatccgtg acctcaatgc gctgcttaac cagctccacc aggtcggcgg tgcccaaat    14460 gtcgtaaggg cttggctgca ccggaatcag cacgaagtcg gctgccttga tcgcggacac    14520
agccaagtcc gccgcctggg gcgctccgtc gatcactacg aagtcgcgcc ggccgatggc    14580
cttcacgtcg cggtcaatcg tcgggcggtc gatgccgaca acggttagcg gttgatcttc    14640
ccgcacggcc gcccaatcgc gggcactgcc ctggggatcg gaatcgacta acagaacatc    14700
ggccccggcg agttgcaggg cgcgggctag atgggttgcg atggtcgtct tgcctgaccc    14760
gcctttctgg ttaagtacag cgataaccdt catgcgttcc ccttgcgtat ttgtttattt    14820
actcatcgca tcatatacgc agcgaccgca tgacgcaagc tgttttactc aaatacacat    14880
caccttttta gatgatcagt gattttgtgc cgagctgccg gtcggggagc tgttggctgg    14940
ctgg                                                                14944

<210> SEQ ID NO 8
<211> LENGTH: 15242
<212> TYPE: DNA
<213> ORGANISM: Artificial Sequence
<220> FEATURE:
<223> OTHER INFORMATION: Transformation vector
```

<400> SEQUENCE: 8

```
tggcaggata tattgtggtg taaacaaatt gacgcttaga caacttaata acacattgcg    60
gacgtcttta atgtactgaa tttagttact gatcactgat taagtactgc gatcgcctcg   120
acatattgtt tttgtttcac ataaatgtcg ttttggatta ttcatgtaat attttaaact   180
aaagtacaat ttttgactac tttagtttac tagttaagct tttattttt tgactaacca    240
ttgaatgatg aagagatcaa cgcatcatat ttacaactta catagtcttt tggaagtgta   300
aattgctaat actacctaaa atatatctat aattaactaa tatttttcg tcaattataa    360
tagatcaatt aaaaggctat caaaggaaa aaatgaaat ccacatcctg ccatcataac     420
ctcatgctgg aaaagaaat gaaaaaatat aaaaaatttc ttttgtttat taaatttaca    480
actttaatac tagtttcttt tctattttt aaaagcttt gtcacttact taaaaaaaaa     540
aaactttttg aaatattcct acttccaatg tctgattagt gcttctggat ttccttttg    600
gatcatgtga atcctaaatc agaaaaattc atataatacc caattcagta tattttcata   660
cttcaattta caagagttct ctatgttttt agcttctttc ttttaagcca aatgttttaa   720
gcatctttta tacattaaaa taatttagtg ttgagttgag attttttttt tttttttttg   780
gatttacttg ttcaaaatct gaaaaaatgt ttacagaagg ttaaaatgaa ccaaaaggca   840
tatcaagcta gattttgaat taccctattt catcgtatac acaaaactga taatgtggac   900
acagttgatt ttacttctcg atgacatcgt agttttattt aatttggaaa ccacggccca   960
tatgagcaca tttcaattaa aaaccaatgg taagagcatt ttccatgcaa gattcgagag  1020
atattaaccc agtgactgtt aaaacagctt agaaccctaa taacgaattt caattactca  1080
atttaccatt cgcatttcgc aataaccaaa ctgagccagt cacaaggagt aaaccgaacc  1140
ggattattta tttataaaat gaaagaaagg aaaccaaaca acaacagcag tagtagtctg  1200
acgtaaacca aaaagcaggc agatcaacaa ctaaaagaaa ctcaaattac caaaacaaac  1260
aggaaattgc aaactaagtt ttttaccat atgcatacaa agaccataaa aggttctgat   1320
aatcaccggt ttcatctcgt cgagattacc ctgttatccc tatcagtatt taatccggcc  1380
atctccttcc gttatgacat cgttgaaagt gccaccattc gggatcatcg gcaacacatg  1440
ttcttggtgc ggacaaatca catccaacag gtaaggtcct ggtgtatcca gcattgtctg  1500
aatagcttct cggagatctg ctttctttgt caccctcgcc gctggaatcc cgcaagctgc  1560
tgcaaacagc aacatgttcg ggaatatctc gtcctcctga gccggatccc cgagaaatgt  1620
gtgagctcgg ttagctttgt agaaccgatc ttcccattgc ataaccatgc caagatgctg  1680
gttgtttaat aaaagtacct tcactggaag attctctaca cgaatagtgg ctagctcttg  1740
cacattcatt ataaagcttc catctccgtc aatatccaca actatcgcat cagggttagc  1800
aacagacgct ccaatcgcag caggaagtcc aaatcccata gctccaaggc ctcctgatga  1860
tagccactgc cttggtttct tgtaattgta gaactgcgcc gcccacattt gatgttgccc  1920
gacaccagta cttattatgg cttttccatc agtcaactca tcaaggacct taatcgcata  1980
ctgtggagga atagcttccc caaacgtctt aaagctcaac ggaaacttct gtttctgtac  2040
gttcaactca ttcctccaaa ctccaaaatc aagcttaagc tcctccgctc ggttctcaag  2100
aaccttattc atcccttgca aagccagctt aacatcacca cacacagaca catgaggagt  2160
cttattcttc ccaatctcag ccgagtcaat atcaatatga acaatcttag ccctactagc  2220
aaaagcctca agcttacccg tgacacgatc atcaaacctt accccaaacg ccaacaacaa  2280
```

```
atcactatgc tccacagcgt aatttgcata cacagtccca tgcattccaa gcatatgtaa   2340
cgacaactca tcatcacaag gataagatcc cagccccatc aacgtactcg caacagggat   2400
ccccgtaagc tcaacaaacc tacccaattc atcgctagaa ttcaaacaac caccaccaac   2460
atacaacaca ggcttcttag actcagaaat caacctaaca atctgctcca aatgagaatc   2520
ttccggaggt ttaggcatcc tagacatata accaggtaat ctcatagcct gttcccaatt   2580
aggaatcgca agctgttgtt gaatatcttt aggaacatca accaaaacag gtccaggtct   2640
accagaagta gctaaaaaga aagcttcctc aataatccta gggatatctt caacatccat   2700
cacaagatag ttatgcttcg taatcgaacg cgttacctca acaatcggag tctcttgaaa   2760
cgcatctgta ccaatcatac gacgagggac ttgtcctgtg attgctacaa gaggaacact   2820
atctaacaac gcatcggcta atccgctaac gagatttgta gctccgggac ctgaagtggc   2880
tatacagata cctggtttac ctgaggatcg agcgtatcct tctgctgcga atacacctcc   2940
ttgttcgtga cgaggaagga cgttacggat tgaggaagag cgggttaagg cttggtgaat   3000
ctccattgat gtacctccag ggtaagcgaa tacggtttct acgccttgac gttctaaagc   3060
ttcgacgagg atatcagcgc ctttgcgggg ttgatctgga gcgaatcggg agatgaatgt   3120
ttcgggtttg gtaggtttgg ttggagaggg agtggttgtg acattggtgg ttgtgttgag   3180
cacggcggag atggaggagg gagagctgga tttgataccg cggcggcggg aggaggagga   3240
tgatttgttg gggtttaggg agaatgggag ggagaatctg gagattggta atggtgattt   3300
ggaggaggaa ggagatggtt tggtggagaa ggagatcgaa gaagatgttg ttgttgttgt   3360
tgttgccgcc gccatggttc agctgcacat acataacata tcaagatcag aacacacata   3420
tacacacaca aatacaatca agtcaacaac tccaaaaagt ccagatctac atatatacat   3480
acgtaaataa caaaatcatg taaataatca caatcatgta atccagatct atgcacatat   3540
atatatacac aattaataaa aaaaatgata taacagatct atatctatgt atgtaacaac   3600
acaatcagat gagagaagtg atgttttcag atctgtatac atacaaacac aaacagatga   3660
acaattgata cgtagatcca tatgtatacg tacaattagc tacacgatta aatgaaaaaa   3720
atcaacgatt tcggattggt acacacaaac gcaacaatat gaagaaattc atatctgatt   3780
agatataaac ataaccacgt gtagatacac agtcaaatca acaaatttat agcttctaaa   3840
cggatgagat gaacaagata aagatattca cataaggcat acataagata agcagattaa   3900
caaactagca ataatacata cctaattaaa acaaggaata acagagagag agagagagag   3960
agagatttac cttgaaaatg aagaggaaa gagaggattt cttaaaattg ggggtagaga   4020
aagaaagatg atgaattgtg agaaaggaga gatagaaggg ggggttgtat atataggctg   4080
tagaagatta tttttgtgtt tgaggcggtg aaggaagagg ggatctgact atgcacgtt    4140
tgcggttacg tatttcgata ggagtctttc aacgcttaac gccgttactc tatatgaccg   4200
tttgggccgt aacggggccg tttgttaacg ctgatgttga ttcttttctt tctttctttc   4260
ttcctttttt aaagaagcaa ttgtacaatc gttgctagct gtcaaacgga taattcggat   4320
acggatatgc ctatattcat atccgtaatt tttggattcg aatttccccc tctagggata   4380
acagggtaat ggatctatat tgttttgtt tcacataaat gtcgttttgg attattcatg    4440
taatatttta aactaaagta caattttga ctactttagt ttactagtta agcttttatt    4500
ttttgacta accattgaat gatgaagaga tcaacgcatc atatttacaa cttacatagt    4560
cttttggaag tgtaaattgc taatactacc taaaatatat ctataattaa ctaatatttt   4620
ttcgtcaatt ataatagatc aattaaaagg ctatcaaaag gaaaaaaatg aaatccacat   4680
```

```
cctgccatca taacctcatg ctggaaaaag aaatgaaaaa atataaaaaa tttcttttgt    4740
ttattaaatt tacaacttta atactagttt cttttctatt ttttaaaagc ttttgtcact    4800
tacttaaaaa aaaaaaactt tttgaaatat tcctacttcc aatgtctgat tagtgcttct    4860
ggatttcctt tttggatcat gtgaatccta aatcagaaaa attcatataa tacccaattc    4920
agtatatttt catacttcaa tttacaagag ttctctatgt ttttagcttc tttcttttaa    4980
gccaaatgtt ttaagcatct tttatacatt aaaataattt agtgttgagt tgagattttt    5040 ttttttttt tttggattta cttgttcaaa atctgaaaaa atgtttacag aaggttaaaa    5100
tgaaccaaaa ggcatatcaa gctagatttt gaattaccct atttcatcgt atacacaaaa    5160
ctgataatgt ggacacagtt gattttactt ctcgatgaca tcgtagtttt atttaatttg    5220
gaaaccacgg cccatatgag cacatttcaa ttaaaaacca atggtaagag cattttccat    5280
gcaagattcg agagatatta acccagtgac tgttaaaaca gcttagaacc ctaataacga    5340
atttcaatta ctcaatttac cattcgcatt tcgcaataac caaactgagc cagtcacaag    5400
gagtaaaccg aaccggatta tttatttata aaatgaaaga aaggaaacca aacaacaaca    5460
gcagtagtag tctgacgtaa accaaaaagc aggcagatca acaactaaaa gaaactcaaa    5520
ttaccaaaac aaacaggaaa ttgcaaacta agttttttta ccatatgcat acaaagacca    5580
taaaaggttc tgataatcac cggtttcatc tcagatccgc gatcgccaat tgacgcgtac    5640
tagtgtacaa gcttgcggcc gcgaattcgg tacatccggc cagtgaatta tcaactatgt    5700
ataataaagt tgggtaccgg cctattaggc cacggtccgt acagtgttta aacgattgac    5760
ctgcaggata caagtgcgca cagactagcg gccgctaatc ccgggaatta ccggtagtag    5820
gcgcctactt tggccggcct agtagattta aattggcctt agtggccaag cttggcgtaa    5880
tcatggccac tttgtacaag aaagctgggt ggtaccggcc tattaggcca cggtccgtac    5940 agtgttttaaa cgattgacct gcaggataca agtgcgcaca gactagcggc cgctaatccc    6000
gggaattacc ggtagtaggc gcccccccact ccgccctaca ctcgtatata tatgcctaaa    6060
cctgccccgt tcctcatatg tgatattatt atttcattat taggtataag atagtaaacg    6120
ataaggaaag acaatttatt gagaaagcca tgctaaaata tagatagata taccttagca    6180
ggtgtttatt ttacaacata acataacata gtagctagcc agcaggcagg ctaaaacata    6240
gtatagtcta tctgcagggg gtacggtcga ggcggcctta attaatcatt gtttgcctcc    6300
ctgctgcggt ttttcaccga agttcatgcc agtccagcgt ttttgcagca gaaaagccgc    6360
cgacttcggt ttgcggtcgc gagtgaagat ccctttcttg ttaccgccaa cgcgcaatat    6420
gccttgcgag gtcgcaaaat cggcgaaatt ccatacctgt tcaccgacga cggcgctgac    6480
gcgatcaaag acgcggtgat acatatccag ccatgcacac tgatactctt cactccacat    6540
gtcggtgtac attgagtgca gcccggctaa cgtatccacg ccgtattcgg tgatgataat    6600
cggctgatgc agtttctcct gccaggccag aagttctttt tccagtacct tctctgccgt    6660
ttccaaatcg ccgctttgga cataccatcc gtaataacgg ttcaggcaca gcacatcaaa    6720
gagatcgctg atggtatcgg tgtgagcgtc gcagaacatt acattgacgc aggtgatcgg    6780
acgcgtcggg tcgagtttac gcgttgcttc cgccagtggc gcgaaatatt cccgtgcacc    6840
ttgcggacgg gtatccggtt cgttggcaat actccacatc accacgcttg gtggtttttt    6900
gtcacgcgct atcagctctt taatcgcctg taagtgcgct tgctgagttt ccccgttgac    6960
tgcctcttcg ctgtacagtt ctttcggctt gttgcccgct tcgaaaccaa tgcctaaaga    7020
```

```
gaggttaaag ccgacagcag cagtttcatc aatcaccacg atgccatgtt catctgccca    7080
gtcgagcatc tcttcagcgt aagggtaatg cgaggtacgg taggagttgg ccccaatcca    7140
gtccattaat gcgtggtcgt gcaccatcag cacgttatcg aatcctttgc cacgcaagtc    7200
cgcatcttca tgacgaccaa agccagtaaa gtagaacggt ttgtggttaa tcaggaactg    7260
ttcgcccttc actgccactg accggatgcc gacgcgaagc gggtagatat cacactctgt    7320
ctggcttttg gctgtgacgc acagttcata gagataacct tcacccggtt gccagaggtg    7380
cggattcacc acttgcaaag tcccgctagt gccttgtcca gttgcaacca cctgttgatc    7440
cgcatcacgc agttcaacgc tgacatcacc attggccacc acctgccagt caacagacgc    7500
gtggttacag tcttgcgcga catgcgtcac cacggtgata tcgtccaccc aggtgttcgg    7560
cgtggtgtag agcattacgc tgcgatggat tccggcatag ttaaagaaat catgcaagta    7620
agactgcttt ttcttgccgt tttcgtcggt aatcaccatt cccggcggga tagtctgcca    7680
gttcagttcg ttgttcacac aaacggtgat acctgcacat caacaaattt tggtcatata    7740
ttagaaaagt tataaattaa aatatacaca cttataaact acagaaaagc aattgctata    7800
tactacattc ttttattttg aaaaaaatat ttgaaatatt atattactac taattaatga    7860
taattattat atatatatca aaggtagaag cagaaacttc cgtacacttt tcccggcaat    7920
aacatacggc gtgacatcgg cttcaaatgg cgtatagccg ccctgatgct ccatcacttc    7980
ctgattattg acccacactt tgccgtaatg agtgaccgca tcgaaacgca gcacgatacg    8040
ctggcctgcc caacctttcg gtataaagac ttcgcgctga taccagacgt tgcccgcata    8100
attacgaata tctgcatcgg cgaactgatc gttaaaactg cctggcacag caattgcccg    8160
gctttcttgt aacgcgcttt cccaccaacg ctgaccaatt ccacagtttt cgcgatccag    8220
actgaatgcc cacaggccgt cgagtttttt gatttcacgg gttggggttt ctacaggacg    8280
taccatggtg ttcagcttga tcggactatt aattagttca atgttttata cgtgaagaaa    8340
aagaaagtgt gggaatatat ggcaaaaaac atgcatgggg acgtgtgtta acatacgtgt    8400
cttatgacta attataggta gtggcagtta caaccatctg gaaatggaat tgatatacac    8460
agccctgcaa gagacactag cttacctaag agcattttca tgcacacttt tttaaaagac    8520
aaaggatcta tattaatagt aggtcaatat tctgaatgtt ttattacctt taacattcga    8580
agaaggaaaa aaccaatgtt tcatcttgtc aatgtgtcct tcacaaactc atatttactt    8640
attctagttt gaccaagata taagggttaa cagtaaaaca taagaaaata actgacaaat    8700
ataaaataaa tatcagataa ttacagagat ctcaaaatta ttaagaataa tttatctaag    8760
aattaatatt gttggtggat ttctaaaggt gacaggtgaa aatttatatt attgtaaaat    8820
ttaaataagt caatattttt tatattgttg taaaatttaa aataagtcaa tattttgtc     8880 tttcgatttg tactaaattt ctattgatgg attttggaga atgaaatacc ataatttcta    8940
ttcaattcat tacagtattt tttccagcat acaattatgc tttacaaagt ttttatatag    9000
gctacaagaa aagtaacata gaatacaata attcaaaaat caagtcgagg actatttggt    9060
tatgacaatc ttaatgatac atgtttatca taattaatta taaggacaat aattataatg    9120
tgatgattac atttaactta taatacttac tattcgtagt ggtggttaca acacattaat    9180
tttaactgtc gcccttaatg tgttgctctt taactccgaa tacttctgta agttgttaaa    9240
atcttcctga ttgtagtatt ttagtaaatg agtctgtaag ttgctcttaa gttctgcaca    9300
aaggtaactg cacatttcct tcaagaatca ctcttcgaat gatcaggtgt tttatgttaa    9360
tgtgtctaca gcgactatga aaaacaggaa agtttgtgtt gtacatgaaa attttgctc     9420
```

```
tcagtcttca agaatttttct gttaagatct tccatgacat caagtttgca gcactgtatc   9480
atcaattttg gtttggaatt ggcacttctg caaaatggtc aattgcagtc tgaaaagtca   9540
aactttgact tttgcatctt gatcaaattt caagaaagac atttcatcaa gacatgttag   9600
aattagaagt ttgttttatt aagaaagtca aagtcttct ttgctttgga aaagtcaata   9660
ttctaaacac ttagattatt ttctaactgt taagaaaatt gacaagttca gaacttgacg   9720
ccagattttc accatgtagc aagttgattc tggaagaaga actgacacaa gagttgtaga   9780
tttgtttgag atctaagact atgcggaaca gaactagact taaaaatgat gggataagaa   9840
gttataaaac tttgaagaca cgtccatgaa actgaagatg tcaataaatt ttgggccttc   9900
cgtagacgga atttggttag aacttgacca gcagttttca cgtaggttca atcagtcatt   9960
gcaagagtat atcaaagaaa gtctacaaag catgttacaa gctttctgat tacacttaga  10020
actccttcag aacatcaagg aacagagaga ttcaaagatc tcaagttgga tacagtccgg  10080
gccgagcagg ccggcctagt agatttaaat tggccttagt ggccaagctt ggcgtaatca  10140
tggagcctgc tttttgtac aaacttgggt accggcctat taggccacgg tccgtacagt  10200
gtttaaacga ttgacctgca ggatacaagt gcgcacagac tagcggccgc taatcccggg  10260
aattaccggt agtaggcgcc tactttggcc ggcctagtag atttaaattg gccttagtgg  10320
ccaagcttgg cgtaatcatg gcaacttttc tatacaaagt tgatagcttg gcgtaatcga  10380
tgtaccgata tcaatttaaa ttggccggcc gagctccctg caggggccc ggcgcgcctc  10440
tagattaatt aaaggcctta gttactaatc agtgatcaga ttgtcgtttc ccgccttcag  10500
tttaaactat cagtgtttga caggatatat tggcgggtaa acctaagaga aaagagcgtt  10560
tattagaata tcggatatt taaagggcg tgaaaaggtt tatccgttcg tccatttgta  10620
tgtcaatatc catgataagt cgcgctgtat gtgtttgttt gaatattcat ggaacgcagt  10680
ggcggttttc atggcttgtt atgactgttt ttttggggta cagtctatgc ctcgggcatc  10740
caagcagcaa gcgcgttacg ccgtgggtcg atgtttgatg ttatggagca gcaacgatgt  10800
tacgcagcag ggcagtcgcc ctaaaacaaa gttaaacatc atgggtgaag cggtcatcgc  10860
cgaggtgtcc acccagctgt cggaagtcgt gggtgtcatc gagcgccacc tcgaaccgac  10920
cctcctcgcc gtgcatctgt atggtagcgc cgttgacggc ggccttaagc cccattcgga  10980
catcgacctg cttgtcaccg ttaccgtccg tctcgacgag accacgcgcc gcgcgcttat  11040
caacgacctt ctggaaacgt ccgcctcccc cggcgagagc gaaatcctgc gcgcggttga  11100
ggtgacgatt gtggtgcacg atgacatcat cccctggcgc tatccggcca acgcgcgaact  11160
ccagttcggc gaatggcagc gtaatgatat tctggcgggt atctttgaac cggccaccat  11220
cgacattgat ctgcgatcc tgctcaccaa ggcccgggag catagcgtgg ccctcgtcgg  11280
ccccgcggcc gaggaacttt tcgacccggt gccggaacag gatctgttcg aagcactgaa  11340
cgagacgctg accctgtgga actccccgcc ggattgggcg ggcgatgagc gcaatgtggt  11400
ccttacgctg agccggattt ggtactcggc ggttaccggc aagatcgcgc gaaggatgt  11460
cgccgccgac tgggcgatgg agcgccttcc ggcgcaatac cagcccgtga tcctcgaagc  11520
gcgccaagcc tatctgggcc aagaagaaga ccgtctcgcg tcccgggccg accagctcga  11580
agaatttgtc cactatgtca agggcgagat cacgaaggtc gttggcaaat aatgtctagc  11640
tagaaattcg ttcaagccga cgccgcttcg cggcgcggct taactcaagc gttagatgca  11700
ctaagcacat aattgctcac agccaaacta tcgatgagtt gaaggacccc gtagaaaaga  11760
```

```
tcaaaggatc ttcttgagat cctttttttc tgcgcgtaat ctgctgcttg caaacaaaaa    11820
aaccaccgct accagcggtg gtttgtttgc cggatcaaga gctaccaact cttttttccga   11880 aggtaactgg cttcagcaga gcgcagatac caaatactgt ccttctagtg tagccgtagt   11940
taggccacca cttcaagaac tctgtagcac cgcctacata cctcgctctg ctaatcctgt   12000
taccagtggc tgctgccagt ggcgataagt cgtgtcttac cgggttggac tcaagacgat   12060
agttaccgga taaggcgcag cggtcgggct gaacggggggg ttcgtgcaca cagcccagct   12120
tggagcgaac gacctacacc gaactgagat acctacagcg tgagctatga gaaagcgcca   12180
cgcttcccga agggagaaag gcggacaggt atccggtaag cggcagggtc ggaacaggag   12240
agcgcacgag ggagcttcca gggggaaacg cctggtatct ttatagtcct gtcgggtttc   12300
gccacctctg acttgagcgt cgatttttgt gatgctcgtc aggggggcgg agcctatgga   12360
aaaacgccag caacgcggcc ttttacggt tcctggcctt ttgctggcct tttgctcaca    12420
tgttctttcc tgcgttatcc cctgattctg tggataaccg tattaccgcc tttgagtgag   12480
ctgataccgc tcgccgcagc cgaacgaccg agcgcagcga gtcagtgagc gaggaagcgg   12540
aagagcgcct gatgcggtat tttctcctta cgcatctgtg cggtatttca caccgcatag   12600
gccgcgatag gccgacgcga agcggcgggg cgtagggagc gcagcgaccg aagggtaggc   12660 gcttttttgca gctcttcggc tgtgcgctgg ccagacagtt atgcacaggc caggcgggtt   12720
ttaagagttt taataagttt taaagagttt taggcggaaa aatcgccttt tttctctttt    12780
atatcagtca cttacatgtg tgaccggttc ccaatgtacg gctttgggtt cccaatgtac   12840
gggttccggt tcccaatgta cggctttggg ttcccaatgt acgtgctatc cacaggaaag   12900
agaccttttc gacctttttc ccctgctagg gcaatttgcc ctagcatctg ctccgtacat    12960
taggaaccgg cggatgcttc gccctcgatc aggttgcggt agcgcatgac taggatcggg   13020
ccagcctgcc ccgcctcctc cttcaaatcg tactccggca ggtcatttga cccgatcagc    13080
ttgcgcacgg tgaaacagaa cttcttgaac tctccggcgc tgccactgcg ttcgtagatc   13140
gtcttgaaca accatctggc ttctgccttg cctgcggcgc ggcgtgccag cggtagaga    13200 aaacggccga tgccggggtc gatcaaaaag taatcgggggt gaaccgtcag cacgtccggg   13260
ttcttgcctt ctgtgatctc gcggtacatc caatcagcaa gctcgatctc gatgtactcc    13320
ggccgcccgg tttcgctctt tacgatcttg tagcggctaa tcaaggcttc accctcggat   13380
accgtcacca ggcggccgtt cttggccttc ttggtacgct gcatggcaac gtgcgtggtg   13440
tttaaccgaa tgcaggtttc taccaggtcg tctttctgct ttccgccatc ggctcgccgg    13500
cagaacttga gtacgtccgc aacgtgtgga cggaacacgc ggccgggctt gtctcccttc    13560
ccttcccggt atcggttcat ggattcggtt agatgggaaa ccgccatcag taccaggtcg   13620
taatcccaca cactggccat gccggcgggg cctgcggaaa cctctacgtg cccgtctgga    13680
agctcgtagc ggatcacctc gccagctcgt cggtcacgct tcgacagacg gaaaacggcc   13740
acgtccatga tgctgcgact atcgcgggtg cccacgtcat agagcatcgg aacgaaaaaa   13800
tctggttgct cgtcgcccttt gggcggcttc ctaatcgacg gcgcaccggc tgccggcggt    13860
tgccgggatt ctttgcggat tcgatcagcg gcccccttgcc acgattcacc ggggcgtgct   13920
tctgcctcga tgcgttgccg ctgggcggcc tgcgcggcct tcaacttctc caccaggtca   13980
tcacccagcg ccgcgccgat ttgtaccggg ccggatggtt tgcgaccgct cacgccgatt   14040
cctcgggctt gggggttcca gtgccattgc agggccggca gacaacccag ccgcttacgc   14100
ctggccaacc gcccgttcct ccacacatgg ggcattccac ggcgtcggtg cctggttgtt   14160
```

```
cttgattttc catgccgcct cctttagccg ctaaaattca tctactcatt tattcatttg    14220
ctcatttact ctggtagctg cgcgatgtat tcagatagca gctcggtaat ggtcttgcct    14280
tggcgtaccg cgtacatctt cagcttggtg tgatcctccg ccggcaactg aaagttgacc    14340
cgcttcatgg ctggcgtgtc tgccaggctg gccaacgttg cagccttgct gctgcgtgcg    14400
ctcggacggc cggcacttag cgtgtttgtg cttttgctca ttttctcttt acctcattaa    14460
ctcaaatgag ttttgattta atttcagcgg ccagcgcctg gacctcgcgg gcagcgtcgc    14520
cctcgggttc tgattcaaga acggttgtgc cggcggcggc agtgcctggg tagctcacgc    14580
gctgcgtgat acgggactca agaatgggca gctcgtaccc ggccagcgcc tcggcaacct    14640
caccgccgat gcgcgtgcct ttgatcgccc gcgacacgac aaaggccgct tgtagccttc    14700
catccgtgac ctcaatgcgc tgcttaacca gctccaccag gtcggcggtg gcccaaatgt    14760
cgtaagggct tggctgcacc ggaatcagca cgaagtcggc tgccttgatc gcggacacag    14820
ccaagtccgc cgcctggggc gctccgtcga tcactacgaa gtcgcgccgg ccgatggcct    14880
tcacgtcgcg gtcaatcgtc gggcggtcga tgccgacaac ggttagcggt tgatcttccc    14940
gcacggccgc ccaatcgcgg gcactgccct ggggatcgga atcgactaac agaacatcgg    15000
ccccggcgag ttgcagggcg cgggctagat gggttgcgat ggtcgtcttg cctgacccgc    15060
ctttctggtt aagtacagcg ataaccttca tgcgttcccc ttgcgtattt gtttatttac    15120
tcatcgcatc atatacgcag cgaccgcatg acgcaagctg ttttactcaa atacacatca    15180 ccttttttaga tgatcagtga ttttgtgccg agctgccggt cggggagctg ttggctggct    15240
gg                                                                   15242
```

<210> SEQ ID NO 9
<211> LENGTH: 15405
<212> TYPE: DNA
<213> ORGANISM: Artificial Sequence
<220> FEATURE:
<223> OTHER INFORMATION: Transformation vector

<400> SEQUENCE: 9

```
gacatacaaa tggacgaacg gataaacctt ttcacgccct tttaaatatc cgattattct      60
aataaacgct cttttctctt aggtttaccc gccaatatat cctgtcaaac actgatagtt     120
taaactgaag gcgggaaacg acaatcagat ctagtaggaa acagctatga ccatgattac     180
gccaagctat cgattacgcc aagctatcaa ctttgtatag aaaagttggg tacccccggg     240
gatatcaagc ttaaacaata caggtggctg aaatatataa accaattcat gtctacaaat     300
gtaccctttg cacttaaaaa atttatcgga gggatccact cgcattggaa gtcaatcaag     360
gactattggt tattagtctg tccgttattt gaatatgata acgcaaggtt tccgtgtaca     420
atatatgtgc atggaatgcc gctgttgagc gtttaacctg aattttcatg atttgaggca     480
tggggctgta ttgcttgtta gcgttggggt gaatgaaatt tagcttcaac ctaatgagat     540
acagttcccg ggtcaggatg atctaatcat tcctcataca aatgtctcat ttttcaatta     600
gagtaatatg tgtccatatg tctcgatttc gattgactta catccattca agataaaatt     660
gcgcaatctt gcacttccct taacatttc ataagtttca tacctatcac tacctataca     720
cccgggataa cacatcgtgt tcgggtgttg aagatttg actcaaattc ctaatttaca     780
ttgctcctaa ctatattagc tttaacttct gtactgctgg taaagctgcc aaccgttatc     840
accataggcc atacttccat cggttataga ctctcatccc cttttagacc agcttagtca     900
```

```
acgttctgtc ttttaattct aagacgttat gaacttagat ggttttcaaa aaaaatcgtg    960
atgagaatgc cttgccagga cattagctac acgttacaca taccatgcaa tccaggagaa   1020
tattatttct tcgccacttg tcactcccttc aaacaccta agaccttatc tctcacatca   1080
```
gccgcataca ttcacatgcg tgcatgcatt attacacgtg atcgccatgc aaatcttcat   1140
taaagtgtat aaaagtaccc atccgattca ggcttgaatc taccgatacc tgagcaacac   1200
aaacacggtc aaaaacatac acgaaccatg gtacgtcctg tagaaacccc aacccgtgaa   1260
atcaaaaaac tcgacggcct gtgggcattc agtctggatc gcgaaaactg tggaattggt   1320
cagcgttggt gggaaagcgc gttacaagaa agccgggcaa ttgctgtgcc aggcagtttt   1380
aacgatcagt tcgccgatgc agatattcgt aattatgcgg caacgtctg gtatcagcgc    1440
gaagtcttta taccgaaagg ttgggcaggc cagcgtatcg tgctgcgttt cgatgcggtc   1500
actcattacg gcaaagtgtg ggtcaataat caggaagtga tggagcatca gggcggctat   1560
acgccatttg aagccgatgt cacgccgtat gttattgccg ggaaaagtgt acgtaagttt   1620
ctgcttctac ctttgatata tataataa ttatcattaa ttagtagtaa tataatattt    1680
caaatatttt tttcaaaata aaagaatgta gtatatagca attgcttttc tgtagtttat   1740
aagtgtgtat attttaattt ataactttc taatatatga ccaaaatttg ttgatgtgca   1800
ggtatcaccg tttgtgtgaa caacgaactg aactggcaga ctatcccgcc gggaatggtg   1860
attaccgacg aaaacggcaa gaaaaagcag tcttacttcc atgatttctt taactatgcc   1920
ggaatccatc gcagcgtaat gctctacacc acgccgaaca cctgggtgga cgatatcacc   1980
gtggtgacgc atgtcgcgca agactgtaac cacgcgtctg ttgactggca ggtggtggcc   2040
aatggtgatg tcagcgttga actgcgtgat gcggatcaac aggtggttgc aactggacaa   2100
ggcactagcg ggactttgca agtggtgaat ccgcacctct ggcaaccggg tgaaggttat   2160
ctctatgaac tgtgcgtcac agccaaaagc cagacagagt gtgatatcta cccgcttcgc   2220
gtcggcatcc ggtcagtggc agtgaagggc gaacagttcc tgattaacca caaaccgttc   2280
tactttactg gctttggtcg tcatgaagat gcggacttgc gtggcaaagg attcgataac   2340
gtgctgatgg tgcacgacca cgcattaatg gactggattg ggccaactc ctaccgtacc   2400
tcgcattacc cttacgctga agagatgctc gactgggcag atgaacatgg catcgtggtg   2460
attgatgaaa ctgctgctgt cggctttaac ctctcttag gcattggttt cgaagcgggc   2520
aacaagccga agaactgta cagcgaagag gcagtcaacg gggaaactca gcaagcgcac   2580
ttacaggcga ttaaagagct gatagcgcgt gacaaaaacc acccaagcgt ggtgatgtgg   2640
agtattgcca acgaaccgga tacccgtccg caaggtgcac gggaatattt cgcgccactg   2700
gcggaagcaa cgcgtaaact cgacccgacg cgtccgatca cctgcgtcaa tgtaatgttc   2760
tgcgacgctc acaccgatac catcagcgat ctctttgatg tgctgtgcct gaaccgttat   2820
tacgatggt atgtccaaag cggcgatttg gaaacggcag agaaggtact ggaaaaagaa   2880
cttctggcct ggcaggagaa actgcatcag ccgattatca tcaccgaata cggcgtggat   2940
acgttagccg ggctgcactc aatgtacacc gacatgtgga gtgaagagta tcagtgtgca   3000
tggctggata tgtatcaccg cgtctttgat cgcgtcagcg ccgtcgtcgg tgaacaggta   3060
tggaatttcg ccgattttgc gacctcgcaa ggcatattgc gcgttggcgg taacaagaaa   3120
gggatcttca ctcgcgaccg caaaccgaag tcggcggctt ttctgctgca aaaacgctgg   3180
actggcatga acttcggtga aaaaccgcag cagggaggca acaatgaat caacaactct   3240
cctggcgcac catcgtcggc tacagcctcg ggaattgcta ccgagtaagg ccgcctcgag   3300

```
catatgggct cgaatttccc cgatcgttca aacatttggc aataaagttt cttaagattg    3360
aatcctgttg ccggtcttgc gatgattatc atataaattc tgttgaatta cgttaagcat    3420
gtaataatta acatgtaatg catgacgtta tttatgagat gggttttat gattagagtc     3480 ccgcaattat acatttaata cgcgatagaa aacaaaatat agcgcgcaaa ctaggataaa    3540
ttatcgcgcg cggtgtcatc tatgttacta gatcgggaat tcaagcttgg cgtaatcatg    3600
gcaagtttgt acaaaaaagc aggctggtac ccggggatcc tctaggtcga ccagatctga    3660
tatctgcggc cgcctcgagc atatgggcat gcaagcttgg cgtaatcatg acccagctt     3720 tcttgtacaa agtggggtac caattcgaat ccaaaaatta cggatatgaa tataggcata    3780
tccgtatccg aattatccgt ttgacagcta gcaacgattg tacaattgct tctttaaaaa    3840
aggaagaaag aaagaaagaa aagaatcaac atcagcgtta acaaacggcc ccgttacggc    3900
ccaaacggtc atatagagta acggcgttaa gcgttgaaag actcctatcg aaatacgtaa    3960
ccgcaaacgt gtcatagtca gatccctct tccttcaccg cctcaaacac aaaaataatc     4020
ttctacagcc tatatataca acccccctt ctatctctcc tttctcacaa ttcatcatct     4080
ttctttctct accccaatt ttaagaaatc ctctcttctc ctcttcattt tcaaggtaaa     4140
tctctctctc tctctctctc tctgttattc cttgttttaa ttaggtatgt attattgcta    4200
gtttgttaat ctgcttatct tatgtatgcc ttatgtgaat atctttatct tgttcatctc    4260
atccgtttag aagctataaa tttgttgatt tgactgtgta tctacacgtg ttatgttta     4320 tatctaatca gatatgaatt tcttcatatt gttgcgtttg tgtgtaccaa tccgaaatcg    4380
ttgatttttt tcatttaatc gtgtagctaa ttgtacgtat acatatggat ctacgtatca    4440
attgttcatc tgtttgtgtt tgtatgtata cagatctgaa aacatcactt ctctcatctg    4500
attgtgttgt tacatacata gatatagatc tgttatatca tttttttat taattgtgta    4560 tatatatatg tgcatagatc tggattacat gattgtgatt atttacatga ttttgttatt    4620
tacgtatgta tatatgtaga tctggacttt ttggagttgt tgacttgatt gtatttgtgt    4680
gtgtatatgt gtgttctgat cttgatatgt tatgtatgtg cagctgaacc atggcggcgg    4740
caacaacaac aacaacaaca tcttcttcga tctccttctc caccaaacca tctccttcct    4800
cctccaaatc accattacca atctccagat tctccctccc attctcccta aaccccaaca    4860
aatcatcctc ctcctcccgc cgccgcggta tcaaatccag ctctcccctcc tccatctccg    4920 ccgtgctcaa cacaaccacc aatgtcacaa ccactccctc tccaaccaaa cctaccaaac    4980
ccgaaacatt catctcccga ttcgctccag atcaaccccg caaggcgct gatatcctcg     5040 tcgaagcttt agaacgtcaa ggcgtagaaa ccgtattcgc ttaccctgga ggtacatcaa    5100
tggagattca ccaagcctta acccgctctt cctcaatccg taacgtcctt cctcgtcacg    5160
aacaaggagg tgtattcgca gcagaaggat acgctcgatc ctcaggtaaa ccaggtatct    5220
gtatagccac ttcaggtccc ggagctacaa atctcgttag cggattagcc gatgcgttgt    5280
tagatagtgt tcctcttgta gcaatcacag gacaagtccc tcgtcgtatg attggtacag    5340
atgcgtttca agagactccg attgttgagg taacgcgttc gattacgaag cataactatc    5400
ttgtgatgga tgttgaagat atccctagga ttattgagga agctttcttt ttagctactt    5460
ctggtagacc tggacctgtt ttggttgatg ttcctaaaga tattcaacaa cagcttgcga    5520
ttcctaattg ggaacaggct atgagattac ctgttatat gtctaggatg cctaaacctc     5580
cggaagattc tcatttggag cagattgtta ggttgatttc tgagtctaag aagcctgtgt    5640
```

```
tgtatgttgg tggtggttgt ttgaattcta gcgatgaatt gggtaggttt gttgagctta    5700
cggggatccc tgttgcgagt acgttgatgg ggctgggatc ttatccttgt gatgatgagt    5760
tgtcgttaca tatgcttgga atgcatggga ctgtgtatgc aaattacgct gtggagcata    5820
gtgatttgtt gttggcgttt ggggtaaggt ttgatgatcg tgtcacgggt aagcttgagg    5880
cttttgctag tagggctaag attgttcata ttgatattga ctcggctgag attgggaaga    5940
ataagactcc tcatgtgtct gtgtgtggtg atgttaagct ggctttgcaa gggatgaata    6000
aggttcttga gaaccgagcg gaggagctta agcttgattt tggagtttgg aggaatgagt    6060
tgaacgtaca gaaacagaag tttccgttga gctttaagac gtttggggaa gctattcctc    6120
cacagtatgc gattaaggtc cttgatgagt tgactgatgg aaaagccata ataagtactg    6180
gtgtcgggca acatcaaatg tgggcggcgc agttctacaa ttacaagaaa ccaaggcagt    6240
ggctatcatc aggaggcctt ggagctatgg gatttggact tcctgctgcg attggagcgt    6300
ctgttgctaa ccctgatgcg atagttgtgg atattgacgg agatggaagc tttataatga    6360
atgtgcaaga gctagccact attcgtgtag agaatcttcc agtgaaggta ctttttattaa    6420 acaaccagca tcttggcatg ttatgcaat gggaagatcg gttctacaaa gctaaccgag    6480
ctcacacatt tctcggggat ccggctcagg aggacgagat attcccgaac atgttgctgt    6540
ttgcagcagc ttgcgggatt ccagcggcga gggtgacaaa gaaagcagat ctccgagaag    6600
ctattcagac aatgctggat acaccaggac cttacctgtt ggatgtgatt tgtccgcacc    6660
aagaacatgt gttgccgatg atcccgaatg gtggcacttt caacgatgtc ataacggaag    6720
gagatggccg gattaaatac tgagagatga accggtgat tatcagaacc ttttatggtc    6780
tttgtatgca tatggtaaaa aaacttagtt tgcaattttcc tgtttgtttt ggtaatttga    6840
gtttctttta gttgttgatc tgcctgcttt ttggtttacg tcagactact actgctgttg    6900
ttgtttggtt tcctttcttt cattttataa ataaataatc cggttcggtt tactccttgt    6960
gactggctca gtttggttat tgcgaaatgc gaatggtaaa ttgagtaatt gaaattcgtt    7020
attagggttc taagctgttt taacagtcac tgggttaata tctctcgaat cttgcatgga    7080
aaatgctctt accattggtt tttaattgaa atgtgctcat atgggccgtg gtttccaaat    7140
taaataaaac tacgatgtca tcgagaagta aaatcaactg tgtccacatt atcagttttg    7200
tgtatacgat gaaataggt aattcaaaat ctagcttgat atgccttttg gttcatttta    7260
accttctgta aacattttt cagattttga acaagtaaat ccaaaaaaaa aaaaaaaaa    7320 tctcaactca acactaaatt attttaatgt ataaagatg cttaaaacat ttggcttaaa    7380
agaaagaagc taaaaacata gagaactctt gtaaattgaa gtatgaaaat atactgaatt    7440
gggtattata tgaattttc tgatttagga ttcacatgat ccaaaaagga aatccagaag    7500
cactaatcag acattggaag taggaatatt tcaaaaagtt ttttttttt aagtaagtga    7560 caaaagcttt taaaaatag aaagaaact agtattaaag ttgtaaattt aataaacaaa    7620
agaaattttt tatattttt catttctttt tccagcatga ggttatgatg gcaggatgtg    7680
gatttcattt ttttcctttt gatagccttt taattgatct attataattg acgaaaaaat    7740
attagttaat tatagatata ttttaggtag tattagcaat ttacacttcc aaagactat    7800 gtaagttgta aatatgatgc gttgatctct tcatcattca atggttagtc aaaaaaataa    7860
aagcttaact agtaaactaa agtagtcaaa aattgtactt tagtttaaaa tattacatga    7920
ataatccaaa acgacattta tgtgaaacaa aaacaatatc tagagtcgac ttaattaaac    7980
tagtggcgcg ccaattgact agtaggccta tcgattaatt aaggccgcct cgagcatatg    8040
```

```
ggcatgcaag cttggcgtaa tcatggcaac tttattatac atagttgata attcactggc   8100
cggataattc actggccgtc gttttacaac gactcaggat cctgtcaaac actgatagtt   8160
taaactgaag gcgggaaacg acaatctgat catgagcgga gaattaaggg agtcacgtta   8220 tgaccccgc cgatgacgcg ggacaagccg ttttacgttt ggaactgaca gaaccgcaac    8280
gttgaaggag ccactcagcc gcgggtttct ggagtttaat gagctaagca catacgtcag   8340
aaaccattat tgcgcgttca aaagtcgcct aaggtcacta tcagctagca aatatttctt   8400
gtcaaaaatg ctccactgac gttccataaa ttcccctcgg tatccaatta gagtctcata   8460
ttcactctca atccaaataa tctgcaccgg atctggatcg tttcgcatga ttgaacaaga   8520
tggattgcac gcaggttctc cggccgcttg ggtggagagg ctattcggct atgactgggc   8580
acaacagaca atcggctgct ctgatgccgc cgtgttccgg ctgtcagcgc aggggcgccc   8640
ggttcttttt gtcaagaccg acctgtccgg tgccctgaat gaactgcagg acgaggcagc   8700
gcggctatcg tggctggcca cgacgggcgt tccttgcgca gctgtgctcg acgttgtcac   8760
tgaagcggga agggactggc tgctattggg cgaagtgccg gggcaggatc tcctgtcatc   8820
tcaccttgct cctgccgaga aagtatccat catggctgat gcaatgcggc ggctgcatac   8880
gcttgatccg gctacctgcc cattcgacca ccaagcgaaa catcgcatcg agcgagcacg   8940
tactcggatg gaagccggtc ttgtcgatca ggatgatctg gacgaagagc atcaggggct   9000
cgcgccagcc gaactgttcg ccaggctcaa ggcgcgcatg cccgacggcg aggatctcgt   9060
cgtgacccat ggcgatgcct gcttgccgaa tatcatggtg gaaaatggcc gcttttctgg   9120
attcatcgac tgtggccggc tgggtgtggc ggaccgctat caggacatag cgttggctac   9180
ccgtgatatt gctgaagagc ttggcggcga atgggctgac cgcttcctcg tgctttacgg   9240
tatcgccgct cccgattcgc agcgcatcgc cttctatcgc cttcttgacg agttcttctg   9300
agcgggaccc aagctctaga tcttgctgcg ttcggatatt ttcgtggagt tcccgccaca   9360
gacccggatg atccccgatc gttcaaacat ttggcaataa agtttcttaa gattgaatcc   9420
tgttgccggt cttgcgatga ttatcatata atttctgttg aattacgtta agcatgtaat   9480
aattaacatg taatgcatga cgttatttat gagatgggtt tttatgatta gagtcccgca   9540
attatacatt taatacgcga tagaaaacaa aatatagcgc gcaaactagg ataaattatc   9600
gcgcgcggtg tcatctatgt tactagatcg ggcctcctgt caagtctgtc ttggtaataa   9660
ttgtcattag attgttttta tgcatagatg cactcgaaat cagccaattt tagacaagta   9720
tcaaacggat gttaattcag tacattaaag acgtccgcaa tgtgttatta agttgtctaa   9780
gcgtcaattt gtttacacca caatatatcc tgccaccagc cagccaacag ctccccgacc   9840
ggcagctcgg cacaaaatca ccacgcgtta ccaccacgcc ggccggccgc atggtgttga   9900
ccgtgttcgc cggcattgcc gagttcgagc gttccctaat catcgaccgc acccggagcg   9960
ggcgcgaggc cgccaaggcc cgaggcgtga agtttggccc cgccctacc ctcacccgg   10020 cacagatcgc gcacgcccgc gagctgatcg accaggaagg ccgcaccgtg aaagaggcgg   10080
ctgcactgct ggccgtgcat cgctcgaccc tgtaccgcgc acttgagcgc agcgaggaag   10140 tgacgccac cgaggccagg cggcgcggtg ccttccgtga ggacgcattg accgaggccg   10200
acgccctggc ggccgccgag aatgaacgcc aagaggaaca agcatgaaac cgcaccagga   10260
cggccaggac gaaccgttttt tcattaccga agagatcgag gcggagatga tcgcggccgg   10320
gtacgtgttc gagccgcccg cgcacgtctc aaccgtgcgg ctgcatgaaa tcctggccgg   10380
```

```
tttgtctgat gccaagctgg cggcctggcc ggccagcttg gccgctgaag aaaccgagcg   10440
ccgccgtcta aaaaggtgat gtgtatttga gtaaaacagc ttgcgtcatg cggtcgctgc   10500
gtatatgatg cgatgagtaa ataaacaaat acgcaagggg aacgcatgaa ggttatcgct   10560
gtacttaacc agaaaggcgg gtcaggcaag acgaccatcg caacccatct agcccgcgcc   10620
ctgcaactcg ccggggccga tgttctgtta gtcgattccg atccccaggg cagtgcccgc   10680
gattgggcgg ccgtgcggga agatcaaccg ctaaccgttg tcggcatcga ccgcccgacg   10740
attgaccgcg acgtgaaggc catcggccgg cgcgacttcg tagtgatcga cggagcgccc   10800
caggcggcgg acttggctgt gtccgcgatc aaggcagccg acttcgtgct gattccggtg   10860
cagccaagcc cttacgacat atgggccacc gccgacctgg tggagctggt taagcagcgc   10920
attgaggtca cggatggaag gctacaagcg gcctttgtcg tgtcgcgggc gatcaaaggc   10980
acgcgcatcg gcggtgaggt tgccgaggcg ctggccgggt acgagctgcc cattcttgag   11040
tcccgtatca cgcagcgcgt gagctaccca ggcactgccg ccgccggcac aaccgttctt   11100
gaatcagaac ccgagggcga cgctgcccgc gaggtccagg cgctggccgc tgaaattaaa   11160
tcaaaactca tttgagttaa tgaggtaaag agaaaatgag caaaagcaca aacacgctaa   11220
gtgccggccg tccgagcgca cgcagcagca aggctgcaac gttggccagc ctggcagaca   11280
cgccagccat gaagcgggtc aactttcagt tgccggcgga ggatcacacc aagctgaaga   11340
tgtacgcggt acgccaaggc aagaccatta ccgagctgct atctgaatac atcgcgcagc   11400
taccagagta aatgagcaaa tgaataaatg agtagatgaa ttttagcggc taaaggaggc   11460
ggcatggaaa atcaagaaca accaggcacc gacgccgtgg aatgccccat gtgtggagga   11520
acgggcggtt ggccaggcgt aagcggctgg gttgtctgcc ggccctgcaa tggcactgga   11580 accccaagc ccgaggaatc ggcgtgagcg gtcgcaaacc atccggcccg gtacaaatcg   11640
gcgcggcgct gggtgatgac ctggtggaga agttgaaggc cgcgcaggcc gcccagcggc   11700
aacgcatcga ggcagaagca cgccccggtg aatcgtggca agcggccgct gatcgaatcc   11760
gcaaagaatc ccggcaaccg ccggcagccg gtgcgccgtc gattaggaag ccgcccaagg   11820
gcgacgagca accagatttt ttcgttccga tgctctatga cgtgggcacc cgcgatagtc   11880
gcagcatcat ggacgtggcc gttttccgtc tgtcgaagcg tgaccgacga gctggcgagg   11940
tgatccgcta cgagcttcca gacgggcacg tagaggtttc cgcagggccg ccggcatgg   12000 ccagtgtgtg ggattacgac ctggtactga tggcggtttc ccatctaacc gaatccatga   12060
accgataccg ggaagggaag ggagacaagc ccggccgcgt gttccgtcca cacgttgcgg   12120
acgtactcaa gttctgccgg cgagccgatg gcggaaagca gaaagacgac ctggtagaaa   12180
cctgcattcg gttaaacacc acgcacgttg ccatgcagcg tacgaagaag gccaagaacg   12240
gccgcctggt gacggtatcc gagggtgaag ccttgattag ccgctacaag atcgtaaaga   12300
gcgaaaccgg gcggccggag tacatcgaga tcgagctagc tgattggatg taccgcgaga   12360
tcacagaagg caagaacccg gacgtgctga cggttcaccc cgattacttt ttgatcgatc   12420
ccggcatcgg ccgttttctc taccgcctgg cacgccgcgc cgcaggcaag gcagaagcca   12480
gatggttgtt caagacgatc tacgaacgca gtggcagcgc cggagagttc aagaagttct   12540
gtttcaccgt gcgcaagctg atcgggtcaa atgacctgcc ggagtacgat ttgaaggagg   12600
aggcggggca ggctggcccg atcctagtca tgcgctaccg caacctgatc gagggcgaag   12660
catccgccgg ttcctaatgt acggagcaga tgctagggca aattgcccta gcaggggaaa   12720
aaggtcgaaa aggtctcttt cctgtggata gcacgtacat tgggaaccca aagccgtaca   12780
```

```
ttgggaaccg gaacccgtac attgggaacc caaagccgta cattgggaac cggtcacaca  12840
tgtaagtgac tgatataaaa gagaaaaaag gcgattttc cgcctaaaac tctttaaaac   12900
ttattaaaac tcttaaaacc cgcctggcct gtgcataact gtctggccag cgcacagccg   12960
aagagctgca aaaagcgcct acccttcggt cgctgcgctc cctacgcccc gccgcttcgc   13020
gtcggcctat cgcggccgct ggccgctcaa aaatggctgg cctacggcca ggcaatctac   13080
cagggcgcgg acaagccgcg ccgtcgccac tcgaccgccg gcgcccacat caaggcaccc   13140
tgcctcgcgc gtttcggtga tgacggtgaa aacctctgac acatgcagct cccggagacg   13200
gtcacagctt gtctgtaagc ggatgccggg agcagacaag cccgtcaggg gcgtcagcg    13260 ggtgttggcg ggtgtcgggg cgcagccatg acccagtcac gtagcgatag cggagtgtat   13320
actggcttaa ctatgcggca tcagagcaga ttgtactgag agtgcaccat atgcggtgtg   13380
aaataccgca cagatgcgta aggagaaaat accgcatcag gcgctcttcc gcttcctcgc   13440
tcactgactc gctgcgctcg gtcgttcggc tgcggcgagc ggtatcagct cactcaaagg   13500
cggtaatacg gttatccaca gaatcagggg ataacgcagg aaagaacatg tgagcaaaag   13560
gccagcaaaa ggccaggaac cgtaaaaagg ccgcgttgct ggcgtttttc cataggctcc   13620
gcccccctga cgagcatcac aaaaatcgac gctcaagtca gaggtggcga acccgacag    13680 gactataaag ataccaggcg tttccccctg gaagctccct cgtgcgctct cctgttccga   13740
ccctgccgct taccggatac ctgtccgcct ttctcccttc gggaagcgtg gcgctttctc   13800
atagctcacg ctgtaggtat ctcagttcgg tgtaggtcgt tcgctccaag ctgggctgtg   13860
tgcacgaacc cccgttcag cccgaccgct gcgccttatc cggtaactat cgtcttgagt    13920
ccaacccggt aagacacgac ttatcgccac tggcagcagc cactggtaac aggattagca   13980
gagcgaggta tgtaggcggt gctacagagt tcttgaagtg gtggcctaac tacggctaca   14040
ctagaaggac agtatttggt atctgcgctc tgctgaagcc agttaccttc ggaaaaagag   14100
ttggtagctc ttgatccggc aaacaaacca ccgctggtag cggtggtttt tttgtttgca   14160
agcagcagat tacgcgcaga aaaaaaggat ctcaagaaga tcctttgatc ttttctacgg   14220
ggtctgacgc tcagtggaac gaaaactcac gttaagggat tttggtcatg catgatatat   14280
ctcccaattt gtgtagggct tattatgcac gcttaaaaat aataaaagca gacttgacct   14340
gatagtttgg ctgtgagcaa ttatgtgctt agtgcatcta acgcttgagt taagccgcgc   14400
cgcgaagcgg cgtcggcttg aacgaatttc tagctagaca ttatttgccg actaccttgg   14460
tgatctcgcc tttcacgtag tggacaaatt cttccaactg atctgcgcgc gaggccaagc   14520
gatcttcttc ttgtccaaga taagcctgtc tagcttcaag tatgacgggc tgatactggg   14580
ccggcaggcg ctccattgcc cagtcggcag cgacatcctt cggcgcgatt ttgccggtta   14640
ctgcgctgta ccaaatgcgg gacaacgtaa gcactacatt tcgctcatcg ccagcccagt   14700
cgggcggcga gttccatagc gttaaggttt catttagcgc ctcaaataga tcctgttcag   14760
gaaccggatc aaagagttcc tccgccgctg gacctaccaa ggcaacgcta tgttctcttg   14820
cttttgtcag caagatagcc agatcaatgt cgatcgtggc tggctcgaag atacctgcaa   14880
gaatgtcatt gcgctgccat tctccaaatt gcagttcgcg cttagctgga taacgccacg   14940
gaatgatgtc gtcgtgcaca acaatggtga cttctacagc gcggagaatc tcgctctctc   15000
caggggaagc cgaagtttcc aaaaggtcgt tgatcaaagc tcgccgcgtt gtttcatcaa   15060
gccttacggt caccgtaacc agcaaatcaa tatcactgtg tggcttcagg ccgccatcca   15120
```

```
ctgcggagcc gtacaaatgt acggccagca acgtcggttc gagatggcgc tcgatgacgc    15180
caactacctc tgatagttga gtcgatactt cggcgatcac cgcttccccc atgatgttta    15240
actttgtttt agggcgactg ccctgctgcg taacatcgtt gctgctccat aacatcaaac    15300
atcgacccac ggcgtaacgc gcttgctgct tggatgcccg aggcatagac tgtaccccaa    15360
aaaaacagtc ataacaagcc atgaaaaccg ccactgcgtt ccatg                    15405
```

```
<210> SEQ ID NO 10
<211> LENGTH: 15552
<212> TYPE: DNA
<213> ORGANISM: Artificial Sequence
<220> FEATURE:
<223> OTHER INFORMATION: Transformation vector

<400> SEQUENCE: 10
ggacatacaa atggacgaac ggataaacct tttcacgccc ttttaaatat ccgattattc      60
taataaacgc tcttttctct taggtttacc cgccaatata tcctgtcaaa cactgatagt     120
ttaaactgaa ggcgggaaac gacaatcaga tctagtagga aacagctatg accatgatta    180
cgccaagcta tcgattacgc caagctatca actttgtata gaaaagttgg gtacctcttc    240
atcggtgatt gattccttta aagacttatg tttcttatct tgcttctgag gcaagtattc    300
agttaccagt taccacttat attctggact ttctgactgc atcctcattt ttccaacatt    360
ttaaatttca ctattggctg aatgcttctt ctttgaggaa gaaacaattc agatggcaga    420
aatgtatcaa ccaatgcata tatacaaatg tacctcttgt tctcaaaaca tctatcggat    480
ggttccattt gctttgtcat ccaattagtg actactttat attattccact cctctttatt    540 actattttca tgcgaggttg ccatgtacat tatatttgta aggattgacg ctattgagcg    600 ttttttcttca attttcttta ttttagacat gggtatgaaa tgtgtgttag agttgggttg    660
aatgagatat acgttcaagt gaatggcata ccgttctcga gtaaggatga cctacccatt    720
cttgagacaa atgttacatt ttagtatcag agtaaaatgt gtacctataa ctcaaattcg    780
attgacatgt atccattcaa cataaaatta aaccagcctg cacctgcatc cacatttcaa    840
gtattttcaa accgttcggc tcctatccac cgggtgtaac aagacggatt ccgaatttgg    900
aagattttga ctcaaattcc caatttatat tgaccgtgac taaatcaact ttaacttcta    960
taattctgat taagctccca atttatattc ccaacggcac tacctccaaa atttatagac   1020
tctcatcccc ttttaaacca acttagtaaa cgtttttttt tttaatttta tgaagttaag   1080 ttttttacctt gttttttaaaa agaatcgttc ataagatgcc atgccagaac attagctaca   1140
cgttacacat agcatgcagc cgcggagaat tgttttctt cgccacttgt cactcccttc    1200
aaacacctaa gagcttctct ctcacagcac acacatacaa tcacatgcgt gcatgcatta   1260
ttacacgtga tcgccatgca aatctccttt atagcctata aattaactca tccgcttcac   1320
tctttactca aaccaaaact catcaataca aacaagatta aaacataca cgaccatggt    1380 acgtcctgta gaaaccccaa cccgtgaaat caaaaaactc gacggcctgt gggcattcag    1440
tctggatcgc gaaaactgtg gaattggtca gcgttggtgg gaaagcgcgt tacaagaaag    1500
ccgggcaatt gctgtgccag gcagttttaa cgatcagttc gccgatgcag atattcgtaa    1560
ttatgcgggc aacgtctggt atcagcgcga agtctttata ccgaaaggtt gggcaggcca    1620
gcgtatcgtg ctgcgtttcg atgcggtcac tcattacggc aaagtgtggg tcaataatca    1680
ggaagtgatg gagcatcagg gcggctatac gccatttgaa gccgatgtca cgccgtatgt    1740
tattgccggg aaaagtgtac gtaagtttct gcttctacct tgatatata tataataatt    1800
```

```
atcattaatt agtagtaata taatatttca aatattttt tcaaaataaa agaatgtagt    1860
atatagcaat tgcttttctg tagtttataa gtgtgtatat tttaatttat aacttttcta    1920
atatatgacc aaaatttgtt gatgtgcagg tatcaccgtt tgtgtgaaca acgaactgaa    1980
ctggcagact atcccgccgg gaatggtgat taccgacgaa aacggcaaga aaaagcagtc    2040
ttacttccat gatttcttta actatgccgg aatccatcgc agcgtaatgc tctacaccac    2100
gccgaacacc tgggtggacg atatcaccgt ggtgacgcat gtcgcgcaag actgtaacca    2160
cgcgtctgtt gactggcagg tggtggccaa tggtgatgtc agcgttgaac tgcgtgatgc    2220
ggatcaacag gtggttgcaa ctggacaagg cactagcggg actttgcaag tggtgaatcc    2280
gcacctctgg caaccgggtg aaggttatct ctatgaactg tgcgtcacag ccaaaagcca    2340
gacagagtgt gatatctacc cgcttcgcgt cggcatccgg tcagtggcag tgaagggcga    2400
acagttcctg attaaccaca aaccgttcta ctttactggc tttggtcgtc atgaagatgc    2460
ggacttgcgt ggcaaaggat tcgataacgt gctgatggtg cacgaccacg cattaatgga    2520
ctggattggg gccaactcct accgtacctc gcattaccct tacgctgaag agatgctcga    2580
ctgggcagat gaacatggca tcgtggtgat tgatgaaact gctgctgtcg gctttaacct    2640
ctctttaggc attggtttcg aagcgggcaa caagccgaaa gaactgtaca gcgaagaggc    2700
agtcaacggg gaaactcagc aagcgcactt acaggcgatt aaagagctga tagcgcgtga    2760
caaaaaccac ccaagcgtgg tgatgtggag tattgccaac gaaccggata cccgtccgca    2820
aggtgcacgg gaatatttcg cgccactggc ggaagcaacg cgtaaactcg acccgacgcg    2880
tccgatcacc tgcgtcaatg taatgttctg cgacgctcac accgatacca tcagcgatct    2940
ctttgatgtg ctgtgcctga accgttatta cggatggtat gtccaaagcg gcgatttgga    3000
aacggcagag aaggtactgg aaaaagaact tctggcctgg caggagaaac tgcatcagcc    3060
gattatcatc accgaatacg gcgtggatac gttagccggg ctgcactcaa tgtacaccga    3120
catgtggagt gaagagtatc agtgtgcatg gctggatatg tatcaccgcg tctttgatcg    3180
cgtcagcgcc gtcgtcggtg aacaggtatg gaatttcgcc gattttgcga cctcgcaagg    3240
catattgcgc gttggcggta acaagaaagg gatcttcact cgcgaccgca aaccgaagtc    3300
ggcggcttt ctgctgcaaa aacgctggac tggcatgaac ttcggtgaaa aaccgcagca    3360
gggaggcaaa caatgaatca acaactctcc tggcgcacca tcgtcggcta cagcctcggg    3420
aattgctacc gagtaaggcc gcctcgagca tatgggctcg aatttccccg atcgttcaaa    3480
catttggcaa taaagtttct taagattgaa tcctgttgcc ggtcttgcga tgattatcat    3540
ataatttctg ttgaattacg ttaagcatgt aataattaac atgtaatgca tgacgttatt    3600
tatgagatgg gtttttatga ttagagtccc gcaattatac atttaatacg cgatagaaaa    3660
caaaatatag cgcgcaaact aggataaatt atcgcgcgcg gtgtcatcta tgttactaga    3720
tcgggaattc aagcttggcg taatcatggc aagtttgtac aaaaaagcag gctggtaccc    3780
ggggatcctc taggtcgacc agatctgata tctgcggccg cctcgagcat atgggcatgc    3840
aagcttggcg taatcatgga cccagctttc ttgtacaaag tggggtacca attcgaatcc    3900
aaaaattacg gatatgaata taggcatatc cgtatccgaa ttatccgttt gacagctagc    3960
aacgattgta caattgcttc tttaaaaaag gaagaaagaa agaaagaaaa gaatcaacat    4020
cagcgttaac aaacggcccc gttacggccc aaacggtcat atagagtaac ggcgttaagc    4080
gttgaaagac tcctatcgaa atacgtaacc gcaaacgtgt catagtcaga tcccctcttc    4140
```

```
cttcaccgcc tcaaacacaa aaataatctt ctacagccta tatatacaac cccccttct    4200 atctctcctt tctcacaatt catcatcttt cttctctac ccccaatttt aagaaatcct    4260
ctcttctcct cttcattttc aaggtaaatc tctctctc tctctctctc tgttattcct    4320
tgttttaatt aggtatgtat tattgctagt ttgttaatct gcttatctta tgtatgcctt    4380
atgtgaatat ctttatcttg ttcatctcat ccgtttagaa gctataaatt tgttgatttg    4440
actgtgtatc tacacgtggt tatgtttata tctaatcaga tatgaatttc ttcatattgt    4500
tgcgtttgtg tgtaccaatc cgaaatcgtt gatttttttc atttaatcgt gtagctaatt    4560
gtacgtatac atatggatct acgtatcaat tgttcatctg tttgtgtttg tatgtataca    4620
gatctgaaaa catcacttct ctcatctgat tgtgttgtta catacataga tatagatctg    4680
ttatatcatt ttttttatta attgtgtata tatatgtg catagatctg gattacatga    4740
ttgtgattat ttacatgatt ttgttatta cgtatgtata tatgtagatc tggactttt    4800 ggagttgttg acttgattgt atttgtgtgt gtatatgtgt gttctgatct tgatatgtta    4860
tgtatgtgca gctgaaccat ggcggcggca acaacaacaa caacaacatc ttcttcgatc    4920
tccttctcca ccaaaccatc tccttcctcc tccaaatcac cattaccaat ctccagattc    4980
tccctcccat tctccctaaa ccccaacaaa tcatcctcct cctcccgccg ccgcggtatc    5040
aaatccagct ctccctcctc catctccgcc gtgctcaaca caaccaccaa tgtcacaacc    5100
actccctctc caaccaaacc taccaaaccc gaaacattca tctcccgatt cgctccagat    5160
caaccccgca aaggcgctga tatcctcgtc gaagctttag aacgtcaagg cgtagaaacc    5220
gtattcgctt accctggagg tacatcaatg gagattcacc aagccttaac ccgctcttcc    5280
tcaatccgta acgtccttcc tcgtcacgaa caaggaggtg tattcgcagc agaaggatac    5340
gctcgatcct caggtaaacc aggtatctgt atagccactt caggtcccgg agctacaaat    5400
ctcgttagcg gattagccga tgcgttgtta gatagtgttc ctcttgtagc aatcacagga    5460
caagtccctc gtcgtatgat tggtacagat gcgtttcaag agactccgat tgttgaggta    5520
acgcgttcga ttacgaagca taactatctt gtgatggatg ttgaagatat ccctaggatt    5580
attgaggaag ctttctttt agctacttct ggtagacctg gacctgtttt ggttgatgtt    5640
cctaaagata ttcaacaaca gcttgcgatt cctaattggg aacaggctat gagattacct    5700
ggttatatgt ctaggatgcc taaacctccg gaagattctc atttggagca gattgttagg    5760
ttgatttctg agtctaagaa gcctgtgttg tatgttggtg gtggttgttt gaattctagc    5820
gatgaattgg gtaggtttgt tgagcttacg gggatccctg ttgcgagtac gttgatgggg    5880
ctgggatctt atccttgtga tgatgagttg tcgttacata tgcttggaat gcatgggact    5940
gtgtatgcaa attacgctgt ggagcatagt gatttgttgt tggcgtttgg ggtaaggttt    6000
gatgatcgtg tcacgggtaa gcttgaggct tttgctagta gggctaagat tgttcatatt    6060
gatattgact cggctgagat tgggaagaat aagactcctc atgtgtctgt gtgtggtgat    6120
gttaagctgg ctttgcaagg gatgaataag gttcttgaga accgagcgga ggagcttaag    6180
cttgattttg gagtttggag gaatgagttg aacgtacaga aacagaagtt tccgttgagc    6240
tttaagacgt tggggaagc tattcctcca cagtatgcga ttaaggtcct tgatgagttg    6300
actgatggaa aagccataat aagtactggt gtcgggcaac atcaaatgtg ggcggcgcag    6360
ttctacaatt acaagaaacc aaggcagtgg ctatcatcag gaggccttgg agctatggga    6420
tttggacttc ctgctgcgat tggagcgtct gttgctaacc ctgatgcgat agttgtggat    6480
attgacggag atggaagctt tataatgaat gtgcaagagc tagccactat tcgtgtagag    6540
```

```
aatcttccag tgaaggtact tttattaaac aaccagcatc ttggcatggt tatgcaatgg    6600
gaagatcggt tctacaaagc taaccgagct cacacatttc tcgggatccg gctcaggag    6660 gacgagatat tcccgaacat gttgctgttt gcagcagctt gcgggattcc agcggcgagg    6720
gtgacaaaga aagcagatct ccgagaagct attcagacaa tgctggatac accaggacct    6780
tacctgttgg atgtgatttg tccgcaccaa gaacatgtgt tgccgatgat cccgaatggt    6840
ggcactttca acgatgtcat aacggaagga gatggccgga ttaaatactg agagatgaaa    6900
ccggtgatta tcagaacctt ttatggtctt tgtatgcata tggtaaaaaa acttagtttg    6960
caatttcctg tttgttttgg taatttgagt ttcttttagt tgttgatctg cctgcttttt    7020
ggtttacgtc agactactac tgctgttgtt gtttggtttc ctttctttca ttttataaat    7080
aaataatccg gttcggttta ctccttgtga ctggctcagt ttggttattg cgaaatgcga    7140
atggtaaatt gagtaattga aattcgttat tagggttcta agctgtttta acagtcactg    7200
ggttaatatc tctcgaatct tgcatggaaa atgctcttac cattggtttt taattgaaat    7260
gtgctcatat gggccgtggt ttccaaatta aataaaacta cgatgtcatc gagaagtaaa    7320
atcaactgtg tccacattat cagttttgtg tatacgatga aatagggtaa ttcaaaatct    7380
agcttgatat gccttttggt tcattttaac cttctgtaaa cattttttca gattttgaac    7440
aagtaaatcc aaaaaaaaaa aaaaaaaatc tcaactcaac actaaattat tttaatgtat    7500
aaaagatgct taaaacattt ggcttaaaag aaagaagcta aaaacataga gaactcttgt    7560
aaattgaagt atgaaaatat actgaattgg gtattatatg aattttttctg atttaggatt    7620 cacatgatcc aaaaaggaaa tccagaagca ctaatcagac attggaagta ggaatatttc    7680
aaaaagtttt ttttttttaa gtaagtgaca aaagcttttta aaaatagaa aagaaactag    7740 tattaaagtt gtaaatttaa taaacaaaag aaatttttta tatttttca tttcttttc    7800 cagcatgagg ttatgatggc aggatgtgga tttcatttttt ttccttttga tagccttta    7860 attgatctat tataattgac gaaaaaatat tagttaatta tagatatatt ttaggtagta    7920
ttagcaattt acacttccaa aagactatgt aagttgtaaa tatgatgcgt tgatctcttc    7980
atcattcaat ggttagtcaa aaaaataaaa gcttaactag taaactaaag tagtcaaaaa    8040
ttgtacttta gtttaaaata ttacatgaat aatccaaaac gacatttatg tgaaacaaaa    8100
acaatatcta gagtcgactt aattaaacta gtggcgcgcc aattgactag taggcctatc    8160
gattaattaa ggccgcctcg agcatatggg catgcaagct tggcgtaatc atggcaactt    8220
tattatacat agttgataat tcactggccg ataattcac tggccgtcgt tttcaacga     8280 ctcaggatcc tgtcaaacac tgatagttta aactgaaggc gggaaacgac aatctgatca    8340
tgagcggaga attaagggag tcacgttatg acccccgccg atgacgcggg acaagccgtt    8400
ttacgtttgg aactgacaga accgcaacgt tgaaggagcc actcagccgc gggtttctgg    8460
agtttaatga gctaagcaca tacgtcagaa accattattg cgcgttcaaa agtcgcctaa    8520
ggtcactatc agctagcaaa tatttcttgt caaaaatgct ccactgacgt tccataaatt    8580
cccctcggta tccaattaga gtctcatatt cactctcaat ccaaataatc tgcaccggat    8640
ctggatcgtt tcgcatgatt gaacaagatg gattgcacgc aggttctccg gccgcttggg    8700
tggagaggct attcggctat gactgggcac aacagacaat cggctgctct gatgccgccg    8760
tgttccggct gtcagcgcag gggcgcccgg ttcttttttgt caagaccgac ctgtccggtg    8820
ccctgaatga actgcaggac gaggcagcgc ggctatcgtg gctggccacg acgggcgttc    8880
```

```
cttgcgcagc tgtgctcgac gttgtcactg aagcgggaag ggactggctg ctattgggcg    8940
aagtgccggg gcaggatctc ctgtcatctc accttgctcc tgccgagaaa gtatccatca    9000
tggctgatgc aatgcggcgg ctgcatacgc ttgatccggc tacctgccca ttcgaccacc    9060
aagcgaaaca tcgcatcgag cgagcacgta ctcggatgga agccggtctt gtcgatcagg    9120
atgatctgga cgaagagcat caggggctcg cgccagccga actgttcgcc aggctcaagg    9180
cgcgcatgcc cgacggcgag gatctcgtcg tgacccatgg cgatgcctgc ttgccgaata    9240
tcatggtgga aaatggccgc ttttctggat tcatcgactg tggccggctg ggtgtggcgg    9300
accgctatca ggacatagcg ttggctaccc gtgatattgc tgaagagctt ggcggcgaat    9360
gggctgaccg cttcctcgtg ctttacggta tcgccgctcc cgattcgcag cgcatcgcct    9420
tctatcgcct tcttgacgag ttcttctgag cgggacccaa gctctagatc ttgctgcgtt    9480
cggatatttt cgtggagttc cgccacagac ccggatgat ccccgatcgt tcaaacattt    9540
ggcaataaag tttcttaaga ttgaatcctg ttgccggtct tgcgatgatt atcatataat    9600
ttctgttgaa ttacgttaag catgtaataa ttaacatgta atgcatgacg ttatttatga    9660
gatgggtttt tatgattaga gtcccgcaat tatacattta atacgcgata gaaaacaaaa    9720
tatagcgcgc aaactaggat aaattatcgc gcgcggtgtc atctatgtta ctagatcggg    9780
cctcctgtca agctctgctt ggtaataatt gtcattagat tgtttttatg catagatgca    9840
ctcgaaatca gccaatttta gacaagtatc aaacggatgt taattcagta cattaaagac    9900
gtccgcaatg tgttattaag ttgtctaagc gtcaatttgt ttacaccaca atatatcctg    9960
ccaccagcca gccaacagct ccccgaccgg cagctcggca caaatcacc acgcgttacc    10020 accacgccgg ccggccgcat ggtgttgacc gtgttcgccg gcattgccga gttcgagcgt    10080
tccctaatca tcgaccgcac ccggagcggg cgcgaggccg ccaaggcccg aggcgtgaag    10140
tttggccccc gccctaccct caccccggca cagatcgcgc acgcccgcga gctgatcgac    10200
caggaaggcc gcaccgtgaa agaggcggct gcactgcttg gcgtgcatcg ctcgaccctg    10260
taccgcgcac ttgagcgcag cgaggaagtg acgcccaccg aggccaggcg gcgcggtgcc    10320
ttccgtgagg acgcattgac cgaggccgac gccctggcgg ccgccgagaa tgaacgccaa    10380
gaggaacaag catgaaaccg caccaggacg gccaggacga accgtttttc attaccgaag    10440
agatcgaggc ggagatgatc gcggccgggt acgtgttcga gccgcccgcg cacgtctcaa    10500
ccgtgcggct gcatgaaatc ctggccggtt tgtctgatgc caagctggcg gcctggccgg    10560
ccagcttggc cgctgaagaa accgagcgcc gccgtctaaa aaggtgatgt gtatttgagt    10620
aaaacagctt gcgtcatgcg gtcgctgcgt atatgatgcg atgagtaaat aaacaaatac    10680
gcaaggggaa cgcatgaagg ttatcgctgt acttaaccag aaaggcgggt caggcaagac    10740
gaccatcgca acccatctag cccgcgccct gcaactcgcc ggggccgatg ttctgttagt    10800
cgattccgat cccagggca gtgcccgcga ttgggcggcc gtgcgggaag atcaaccgct    10860
aaccgttgtc ggcatcgacc gcccgacgat tgaccgcgac gtgaaggcca tcggccggcg    10920
cgacttcgta gtgatcgacg gagcgcccca ggcggcggac ttggctgtgt ccgcgatcaa    10980
ggcagccgac ttcgtgctga ttccggtgca gccaagccct tacgacatat gggccaccgc    11040
cgacctggtg gagctggtta agcagcgcat tgaggtcacg gatggaaggc tacaagcggc    11100
ctttgtcgtg tcgcgggcga tcaaggcac gcgcatcggc ggtgaggttg ccgaggcgct    11160
ggccgggtac gagctgccca ttcttgagtc ccgtatcacg cagcgcgtga gctacccagg    11220
cactgccgcc gccggcacaa ccgttcttga atcagaaccc gagggcgacg ctgccgcga    11280
```

```
ggtccaggcg ctggccgctg aaattaaatc aaaactcatt tgagttaatg aggtaaagag   11340
aaaatgagca aaagcacaaa cacgctaagt gccggccgtc cgagcgcacg cagcagcaag   11400
gctgcaacgt tggccagcct ggcagacacg ccagccatga agcgggtcaa ctttcagttg   11460
ccggcggagg atcacaccaa gctgaagatg tacgcggtac gccaaggcaa gaccattacc   11520
gagctgctat ctgaatacat cgcgcagcta ccagagtaaa tgagcaaatg aataaatgag   11580
tagatgaatt ttagcggcta aaggaggcgg catggaaaat caagaacaac caggcaccga   11640
cgccgtggaa tgccccatgt gtggaggaac gggcggttgg ccaggcgtaa gcggctgggt   11700
tgtctgccgg ccctgcaatg gcactggaac ccccaagccc gaggaatcgg cgtgagcggt   11760
cgcaaaccat ccggcccggt acaaatcggc gcggcgctgg gtgatgacct ggtggagaag   11820
ttgaaggccg cgcaggccgc ccagcggcaa cgcatcgagg cagaagcacg ccccggtgaa   11880
tcgtggcaag cggccgctga tcgaatccgc aaagaatccc ggcaaccgcc ggcagccggt   11940
gcgccgtcga ttaggaagcc gcccaagggc gacgagcaac cagattttt cgttccgatg   12000 ctctatgacg tgggcacccg cgatagtcgc agcatcatgg acgtggccgt tttccgtctg   12060
tcgaagcgtg accgacgagc tggcgaggtg atccgctacg agcttccaga cgggcacgta   12120
gaggtttccg cagggccggc cggcatggcc agtgtgtggg attacgacct ggtactgatg   12180
gcggtttccc atctaaccga atccatgaac cgataccggg aagggaaggg agacaagccc   12240
ggccgcgtgt tccgtccaca cgttgcggac gtactcaagt tctgccggcg agccgatggc   12300
ggaaagcaga aagacgacct ggtagaaacc tgcattcggt taaacaccac gcacgttgcc   12360
atgcagcgta cgaagaaggc caagaacggc cgcctggtga cggtatccga gggtgaagcc   12420
ttgattagcc gctacaagat cgtaaagagc gaaaccgggc ggccggagta catcgagatc   12480
gagctagctg attggatgta ccgcgagatc acagaaggca agaacccgga cgtgctgacg   12540
gttcaccccg attactttt gatcgatccc ggcatcggcc gttttctcta ccgcctggca   12600
cgccgcgccg caggcaaggc agaagccaga tggttgttca agacgatcta cgaacgcagt   12660
ggcagcgccg gagagttcaa gaagttctgt ttcaccgtgc gcaagctgat cgggtcaaat   12720
gacctgccgg agtacgattt gaaggaggag gcggggcagg ctggcccgat cctagtcatg   12780
cgctaccgca acctgatcga gggcgaagca tccgccggtt cctaatgtac ggagcagatg   12840
ctagggcaaa ttgccctagc aggggaaaaa ggtcgaaaag gtctctttcc tgtggatagc   12900
acgtacattg gaacccaaa gccgtacatt gggaaccgga acccgtacat tgggaaccca   12960
aagccgtaca ttgggaaccg gtcacacatg taagtgactg atataaaga gaaaaaaggc   13020 gattttccg cctaaaactc tttaaaactt attaaaactc ttaaacccg cctggcctgt   13080 gcataactgt ctggcagcg cacagccgaa gagctgcaaa aagcgcctac ccttcggtcg   13140
ctgcgctccc tacgcccgc cgcttcgcgt cggcctatcg cggccgctgg ccgctcaaaa   13200
atggctggcc tacggccagg caatctacca gggcgcggac aagccgcgcc gtcgccactc   13260
gaccgccggc gcccacatca aggcaccctg cctcgcgcgt ttcggtgatg acggtgaaaa   13320
cctctgacac atgcagctcc cggagacggt cacagcttgt ctgtaagcgg atgccgggag   13380
cagacaagcc cgtcagggcg cgtcagcggg tgttggcggg tgtcggggcg cagccatgac   13440
ccagtcacgt agcgatagcg gagtgtatac tggcttaact atgcggcatc agagcagatt   13500
gtactgagag tgcaccatat gcggtgtgaa ataccgcaca gatgcgtaag gagaaaatac   13560
cgcatcaggc gctcttccgc ttcctcgctc actgactcgc tgcgctcggt cgttcggctg   13620
```

```
cggcgagcgg tatcagctca ctcaaaggcg gtaatacggt tatccacaga atcaggggat   13680
aacgcaggaa agaacatgtg agcaaaaggc cagcaaaagg ccaggaaccg taaaaaggcc   13740
gcgttgctgg cgtttttcca taggctccgc ccccctgacg agcatcacaa aaatcgacgc   13800
tcaagtcaga ggtggcgaaa cccgacagga ctataaagat accaggcgtt tccccctgga   13860
agctccctcg tgcgctctcc tgttccgacc ctgccgctta ccggatacct gtccgccttt   13920
ctcccttcgg gaagcgtggc gctttctcat agctcacgct gtaggtatct cagttcggtg   13980
taggtcgttc gctccaagct gggctgtgtg cacgaacccc ccgttcagcc cgaccgctgc   14040
gccttatccg gtaactatcg tcttgagtcc aacccggtaa gacacgactt atcgccactg   14100
gcagcagcca ctggtaacag gattagcaga gcgaggtatg taggcggtgc tacagagttc   14160
ttgaagtggt ggcctaacta cggctacact agaaggacag tatttggtat ctgcgctctg   14220
ctgaagccag ttaccttcgg aaaaagagtt ggtagctctt gatccggcaa acaaaccacc   14280
gctggtagcg gtggtttttt tgtttgcaag cagcagatta cgcgcagaaa aaaggatct   14340 caagaagatc ctttgatctt ttctacgggg tctgacgctc agtggaacga aaactcacgt   14400
taagggattt tggtcatgca tgatatatct cccaatttgt gtagggctta ttatgcacgc   14460
ttaaaaataa taaaagcaga cttgacctga tagtttggct gtgagcaatt atgtgcttag   14520
tgcatctaac gcttgagtta agccgcgccg cgaagcggcg tcggcttgaa cgaatttcta   14580
gctagacatt atttgccgac taccttggtg atctcgcctt tcacgtagtg acaaattct   14640 tccaactgat ctgcgcgcga ggccaagcga tcttcttctt gtccaagata agcctgtcta   14700
gcttcaagta tgacgggctg atactgggcc ggcaggcgct ccattgccca gtcggcagcg   14760
acatccttcg gcgcgatttt gccggttact gcgctgtacc aaatgcggga caacgtaagc   14820
actacatttc gctcatcgcc agcccagtcg ggcggcgagt tccatagcgt taaggttca   14880 tttagcgcct caaatagatc ctgttcagga accggatcaa agagttcctc cgccgctgga   14940
cctaccaagg caacgctatg ttctcttgct tttgtcagca agatagccag atcaatgtcg   15000
atcgtggctg gctcgaagat acctgcaaga atgtcattgc gctgccattc tccaaattgc   15060
agttcgcgct tagctggata acgccacgga atgatgtcgt cgtgcacaac aatggtgact   15120
tctacagcgc ggagaatctc gctctctcca ggggaagccg aagtttccaa aaggtcgttg   15180
atcaaagctc gccgcgttgt ttcatcaagc cttacggtca ccgtaaccag caaatcaata   15240
tcactgtgtg gcttcaggcc gccatccact gcggagccgt acaaatgtac ggccagcaac   15300
gtcggttcga gatggcgctc gatgacgcca actacctctg atagttgagt cgatacttcg   15360
gcgatcaccg cttcccccat gatgtttaac tttgttttag ggcgactgcc ctgctgcgta   15420
acatcgttgc tgctccataa catcaaacat cgacccacgg cgtaacgcgc ttgctgcttg   15480
gatgcccgag gcatagactg tacccccaaaa aaacagtcat aacaagccat gaaaaccgcc   15540
actgcgttcc at                                                       15552
```

<210> SEQ ID NO 11
<211> LENGTH: 34
<212> TYPE: DNA
<213> ORGANISM: Artificial Sequence
<220> FEATURE:
<223> OTHER INFORMATION: Primer

<400> SEQUENCE: 11
gatataggta cctcttcatc ggtgattgat tcct                               34

<210> SEQ ID NO 12
<211> LENGTH: 37
<212> TYPE: DNA
<213> ORGANISM: Artificial Sequence
<220> FEATURE:
<223> OTHER INFORMATION: Primer

<400> SEQUENCE: 12

| gatataccat ggtcgtgtat gtttttaatc ttgtttg | 37 |

<210> SEQ ID NO 13
<211> LENGTH: 2194
<212> TYPE: DNA
<213> ORGANISM: Oryza sativa
<220> FEATURE:
<221> NAME/KEY: Promoter
<222> LOCATION: (1)..(2194)
<223> OTHER INFORMATION: p-GOS2

<400> SEQUENCE: 13

| aatccgaaaa gtttctgcac cgttttcacc ccctaactaa caatataggg aacgtgtgct | 60 |
| aaatataaaa tgagacctta tatgtagc gctgataact agaactatgc aagaaaaact | 120 |
| catccaccta ctttagtggc aatcgggcta aataaaaaag agtcgctaca ctagtttcgt | 180 |
| tttccttagt aattaagtgg gaaaatgaaa tcattattgc ttagaatata cgttcacatc | 240 |
| tctgtcatga agttaaatta ttcgaggtag ccataattgt catcaaactc ttcttgaata | 300 |
| aaaaaatctt tctagctgaa ctcaatgggt aaagagagag atttttttta aaaaaataga | 360 |
| atgaagatat tctgaacgta ttggcaaaga tttaaacata taattatata attttatagt | 420 |
| ttgtgcattc gtcatatcgc acatcattaa ggacatgtct tactccatcc caattttat | 480 |
| ttagtaatta aagacaattg acttattttt attatttatc ttttttcgat tagatgcaag | 540 |
| gtacttacgc acacactttg tgctcatgtg catgtgtgag tgcacctcct caatacacgt | 600 |
| tcaactagca acacatctct aatatcactc gcctatttaa tacatttagg tagcaatatc | 660 |
| tgaattcaag cactccacca tcaccagacc acttttaata atatctaaaa tacaaaaaat | 720 |
| aattttacag aatagcatga aaagtatgaa acgaactatt taggtttttc acatacaaaa | 780 |
| aaaaaaagaa ttttgctcgt gcgcgagcgc caatctccca tattgggcac acaggcaaca | 840 |
| acagagtggc tgcccacaga acaacccaca aaaacgatg atctaacgga ggacagcaag | 900 |
| tccgcaacaa cctttaaca gcaggctttg cggccaggag agaggaggag aggcaaagaa | 960 |
| aaccaagcat cctccttctc ccatctataa attcctcccc cctttccccc tctctatata | 1020 |
| ggaggcatcc aagccaagaa gagggagagc accaaggaca cgcgactagc agaagccgag | 1080 |
| cgaccgcctt ctcgatccat atcttccggt cgagttcttg gtcgatctct tccctcctcc | 1140 |
| acctcctcct cacagggtat gtgcctccct tcggttgttc ttggatttat tgttctaggt | 1200 |
| tgtgtagtac gggcgttgat gttaggaaag gggatctgta tctgtgatga ttcctgttct | 1260 |
| tggatttggg atagaggggt tcttgatgtt gcatgttatc ggttcggttt gattagtagt | 1320 |
| atggttttca atcgtctgga gagctctatg gaaatgaaat ggtttaggga tcggaatctt | 1380 |
| gcgatttgt gagtaccttt tgtttgaggt aaaatcagag caccggtgat tttgcttggt | 1440 |
| gtaataaagt acggttgttt ggtcctcgat tctggtagtg atgcttctcg atttgacgaa | 1500 |
| gctatccttt gtttattccc tattgaacaa aaataatcca actttgaaga cggtcccgtt | 1560 |
| gatgagattg aatgattgat tcttaagcct gtccaaaatt tcgcagctgg cttgtttaga | 1620 |
| tacagtagtc cccatcacga aattcatgga aacagttata atcctcagga acaggggatt | 1680 |

| | |
|---|---|
| ccctgttcttccgatttgctttagtcccagaattttttttcccaaatatcttaaaaagtc | 1740 |
| actttctggttcagttcaatgaattgattgctacaaataatgcttttatagcgttatcct | 1800 |
| agctgtagttcagttaatagGtaatacccctatagtttagtcaggagaagaacttatccg | 1860 |
| atttctgatctccatttttaattatatgaaatgaactgtagcataagcagtattcatttg | 1920 |
| gattattttttttattagctctcaccccttcattattctgagctgaaagtctggcatgaa | 1980 |
| ctgtcctcaattttgttttcaaattcacatcgattatctatgcattatcctcttgtatct | 2040 |
| acctgtagaagtttctttttggttattccttgactgcttgattacagaaagaaatttatg | 2100 |
| aagctgtaatcgggatagttatactgcttgttcttatgattcatttccttgtgcagttc | 2160 |
| ttggtgtagcttgccactttcaccagcaaagttc | 2194 |

<210> SEQ ID NO 14
<211> LENGTH: 2194
<212> TYPE: DNA
<213> ORGANISM: Artificial Sequence
<220> FEATURE:
<223> OTHER INFORMATION: Promoter
<220> FEATURE:
<221> NAME/KEY: Promoter
<222> LOCATION: (1)..(2194)
<223> OTHER INFORMATION: p-GOS2_perm1

<400> SEQUENCE: 14

| | |
|---|---|
| aatccgaaaagtttctgcaccgttttcactccctaactaacaatatagggaacgtgtgct | 60 |
| gaatataaaatgagagcttatatatgtagcgctgataactagaactatgaagaaaaact | 120 |
| catccacctactttagtggcaacagggctaataaaaaagagtcgcaacactagtttcgt | 180 |
| tttccttagtaaataagtgggaaaacgaaatcattattgcttagaatatacgtccacatc | 240 |
| tctgtcatgaagttaaattattcgaggcagccataattgtcatcaaactcttcttgaata | 300 |
| ataaaatctttctagctgaactcaatgggtcaagagagagattttttttaaaaaaataga | 360 |
| atggagatattctgaacgtattggcaaagttttaaacataaattatataattttatagg | 420 |
| ttgtgcattcgtcatattgcacatcattaaggacatgtcttactccatccgatttttat | 480 |
| ttagtaattaaagacaattgacttctttttattatttatctttttttcgattagatgcagg | 540 |
| gtacttacgcacacactttgtgctcatgtgcatctgtgagtgcacctcctcaatacacgt | 600 |
| tcaactatcaacacatctctaatatcactcgcctatttaattcatttaggtagcaatatc | 660 |
| tgaattcaagcactcgaccatcaccagaccacttttaataatatctaaactacaaaaaat | 720 |
| aattttacagaatagcatgaaaaatatgaaacgaactatttaggttttttcacatacacaa | 780 |
| aaaaaaagaattttgctcgtgcgcgagcgctaatctcccatattgggcacacaggcaaaa | 840 |
| acagagtggctgcccacagaacaacccacataaaacgatgatctaacggaggacagtaag | 900 |
| tccgcaacaaccttttaacagcaggctgtgcggccaggagagaggaggagaacgaaagaa | 960 |
| aaccaagcatcctccttctccgatctataaattcctcctccttttccccctctctatata | 1020 |
| ggaaacatccaagccaagaagagggagagggaccatggacacgcgactagcagaagccgag | 1080 |
| cgaccgcccctctcgatccatatcttccggtcgagttcttgtcgctctctccttcctcc | 1140 |
| acctcctcctcacagggtatgtgcctcgctctcggttgttcttggatttattgttctggtt | 1200 |
| tgtgtagtacgggcgttgatgttaagaaaggggatctgtatctgtgatgattgctgttct | 1260 |
| tggatttgggatagagcggttcttgatgttgcatgttatcggctcgatttgattagtagt | 1320 |
| atggttttcaatactctggagagctctatggaaatgaaatagtttagggatcggaatctt | 1380 |
| gcgattttgtgagttcctttgttgaggtaaaatcagagcaccgctgatttgcttgga | 1440 |

```
ctaataaagt acggttgttt ggccctcgat tctggttgtg atgcttctcg atttgaccag    1500
gctatccttt gtttattccc tgttgaacaa aaataatcca actttgaaga gcttcccgtt    1560
gatgagattg aatgattgaa tcttaagcct gtccaaaact tcgcagctgg cttgtttaga    1620
tacagtagtc gccatcacga aagtcatgga aacagttata atcctctgga acaggggatt    1680
ccgagttctt ccgatttgct ttagtccaag aattttttttt cccaaatatc ttaaaaaatc   1740
actttctggt tcagttcaat gaattgattg ctccaaataa tgcttttata gcgttatcct    1800
aggtgtagtt cagttaatag gtaataccccc tatagtctag tcaggagaag aacttatccg   1860
atttctgatg accattttta attatatgaa atgaactgta gcatgagcag tattcatttg    1920
gattattttt tttattagcc ctcaccccctt cattattctg agctgaaagt ctcgcatgaa   1980
ctgtcctcaa ttttgttttc aaactcacat ggtttatcta tgcattatcc tcttgtatct    2040
accactagaa gtttcttttt ggttattcct tgactccttg attacagaaa gaaatttatg    2100
aagctgtatt cgggatagtt atactgcctg ttcttatgat tcattacctt tgtgcagttc    2160
ttggtgtagc atcccaattt caccagcaaa gttc                                2194

<210> SEQ ID NO 15
<211> LENGTH: 2194
<212> TYPE: DNA
<213> ORGANISM: Artificial
<220> FEATURE:
<223> OTHER INFORMATION: Promoter
<220> FEATURE:
<221> NAME/KEY: Promoter
<222> LOCATION: (1)..(2194)
<223> OTHER INFORMATION: p-GOS2_perm2

<400> SEQUENCE: 15
actccgaaaa gtttctgcac cgttttcacc cgctaactaa caatataggg aacgtgtgtt     60
aaatataaaa tgagagctta tatatgtagc gctgaaaact agaactatac aagaaaaact    120
catccaccta ctttagtggc aataaggcta aataaaaaag agtcgctaca ccagtttcgt    180
tttccttagt aattaagggg gaaaatgaaa tcattattgc ttagcatata cgttcacagc    240
tctgtcatga agttaaatta ttcgaggtag ccttaattgt catcaaactc ttcttgaatc    300
aaaaaatctt tctagctgaa ctcaatgggt acagagagag attttttttta aaaaaataga   360 atcaagatat tctgaacgta ttggcagaga tttaaacata taattatata attttatagt    420
tcgtgcattc gtcatatcgc agatcattaa ggacatgtct tactccatcc cagtttttat    480
ttagtaatta aagacaattg acttgttttt attacttatc tttttttcgat tagatgcaag   540 gtacttacgc ccacactttg tgctcatgtg catgtgtgag cgcacctcct caatacacgt    600
tcaactagcc acacatctct aatatcactc gccgatttaa tacatttagg cagcaatatc    660
tgaattcaag cactccaaca tcaccagacc acttttaata atatctaaaa tagaaaaaat   720
aattttacag aatagcatga aaagtctgaa acgaactatt taggttttttc acatacaaat   780 aaaaaaagaa ttttgctcgt gcgcgagcgg caatctccca tattgggcac acaggcacca    840
acagagtggc tgcccacaga acaacccaaa aaaaacgatg atctaacgga ggacagccag    900
tccgcaacaa ccttttaaca gcaggctatg cggccaggag agaggaggag aggcaaagaa    960
atccaagcat cctccttctc ccatctataa atacctcccc ccttttcccc tctctatata   1020
ggaggcctcc aagccaagaa gagggagagc accaaagaca cgcgactagc agaagccgag   1080
cgaccgcctt ttcgatccct atcttccggt cgagttcttg gtcgatctct tgcctcctcc   1140
```

```
acctcctcct cacagggtat gtgcctctct tcggttgttc ttggatttat tgttctagtt    1200
tgtgtagtac gggcgttgat gttaggaatg gggatctgta tctctgatga ttcctgttct    1260
tggatttggg atagaggcgt tcttgatgtt gcatgttatc gcatcggttt gattagttgt    1320
atggttttca atcgtctgga gaactctatg gaaatgaaat ggtttaggga tcgtaatctt    1380
gcgattttgt gagtaccttt tgtttcaggt aaaatcagag caccggtgat tttgcttgga    1440
gtaataaagt acggttgttt ggtcctcgat tctgatagtg atgcttctcg atttgacgaa    1500
ggtatccttt gtttattccc cattgaacaa aaataatcca actttgaaga cgggcccgtt    1560
gatgagattg aatgattgat tcttaagctt gtccaaaatt tcgcagctag cttgtttaga    1620
tacagtagtc cccatcacga aactcatgga aacagttata atcctcagga acagggaatt    1680
ccctgttctt ccgatttgct ttagtcctag aattttttt cccaaatatc tcaaaaagtc    1740
actttctggt tcagttcagt gaattgattg cttcaaataa tgcttttata gcgttatcct    1800
agctgtactt cagttaatag gtaatacccc tatagtatag tcaggagaag aacttatccg    1860
atttctgatc gccatttta attatatgaa atgaactgta gcagaagcag tattcatttg    1920
gattattttt tttattaact ctcacccctt cattattctg agctgaaagt caggcatgaa    1980
ctgtcttcaa ttttgttttc aaattcacat cgattatctc tgcattatcc tcttgtatct    2040
acctgaagaa gtttcttttt ggttattcct tgacttcttg attacagaaa gaaatttatg    2100
aagctataat cgggatagtt atactacttg ttcttatgat tcattccctt tgtgcagttc    2160
ttggtgtagc ttgtcacttt caccagcaaa gttc                                2194
```